United States Patent
Heffernan et al.

(10) Patent No.: US 10,196,399 B2
(45) Date of Patent: Feb. 5, 2019

(54) METABOTROPHIC GLUTAMATE RECEPTOR 5 MODULATORS AND METHODS USE THEREOF

(71) Applicant: SUNOVION PHARMACEUTICALS INC., Marlborough, MA (US)

(72) Inventors: Michele L. R. Heffernan, Worcester, MA (US); Larry Wendell Hardy, Sturbridge, MA (US); Frank Xinhe Wu, Shrewsbury, MA (US); Lakshmi D. Saraswat, Sudbury, MA (US); Kerry L. Spear, Concord, MA (US)

(73) Assignee: Sunovion Pharmaceuticals Inc., Marlborough, MA (US)

( * ) Notice: Subject to any disclaimer, the term of this patent is extended or adjusted under 35 U.S.C. 154(b) by 0 days.

(21) Appl. No.: 15/625,604

(22) Filed: Jun. 16, 2017

(65) Prior Publication Data
US 2018/0037585 A1 Feb. 8, 2018

Related U.S. Application Data

(60) Continuation of application No. 15/013,741, filed on Feb. 2, 2016, now Pat. No. 9,708,331, which is a division of application No. 14/124,455, filed as application No. PCT/US2012/041595 on Jun. 8, 2012, now Pat. No. 9,260,452.

(60) Provisional application No. 61/494,731, filed on Jun. 8, 2011.

(51) Int. Cl.
| | | |
|---|---|---|
| *C07D 487/04* | (2006.01) | |
| *C07D 471/04* | (2006.01) | |
| *C07D 471/14* | (2006.01) | |
| *C07D 471/20* | (2006.01) | |
| *C07D 487/14* | (2006.01) | |
| *C07D 487/18* | (2006.01) | |
| *C07D 491/147* | (2006.01) | |
| *C07D 491/20* | (2006.01) | |
| *C07D 491/22* | (2006.01) | |
| *C07D 498/04* | (2006.01) | |
| *C07D 487/10* | (2006.01) | |

(52) U.S. Cl.
CPC .......... *C07D 487/04* (2013.01); *C07D 471/04* (2013.01); *C07D 471/14* (2013.01); *C07D 471/20* (2013.01); *C07D 487/10* (2013.01); *C07D 487/14* (2013.01); *C07D 487/18* (2013.01); *C07D 491/147* (2013.01); *C07D 491/20* (2013.01); *C07D 491/22* (2013.01); *C07D 498/04* (2013.01)

(58) Field of Classification Search
None
See application file for complete search history.

(56) References Cited

PUBLICATIONS

Kumar, Anil. Frontiers in Neuroscience (2015) 9 article 215.*
Matosin, Natalie. J. Psychiatry Neurosci (2014) 39(6).*
Neurological Disorders and Stroke. NIH. National Institute of Neurological Disorders and Stroke. Disorders Index. (2016). Web: <http://www.ninds.nih.gov/disorders/disorder_index.htm>.*
UCSF. University of California, San Francisco. Creutzfeldt-Jakob Disease. (2016). Web<http://memory.ucsf.edu/cjd/overview>.*

* cited by examiner

*Primary Examiner* — Deepak R Rao
*Assistant Examiner* — Laura M Daniel

(57) ABSTRACT

Compounds that modulate GluR5 activity and methods of using the same are disclosed.

9 Claims, No Drawings

METABOTROPHIC GLUTAMATE RECEPTOR 5 MODULATORS AND METHODS USE THEREOF

RELATED APPLICATIONS

This application claims priority to and is a continuation of pending U.S. patent application Ser. No. 15/013,741, filed Feb. 2, 2016, and which claims the benefit of a divisional U.S. patent application Ser. No. 14/124,455, filed Mar. 11, 2014, and issued as U.S. Pat. No. 9,260,452, on Feb. 16, 2016; which is a 371 National Filing of PCT International Application No. PCT/US2012/041595, filed Jun. 8, 2012, and which claim benefit of Provisional U.S. Patent Application Ser. No. 61/494,731, filed Jun. 8, 2011, which are hereby incorporated by reference in all of their entireties.

BACKGROUND

The amino acid L-glutamate (which herein is referred to simply as glutamate) is the principal excitatory neurotransmitter in the brain and other elements of the central nervous system of mammals. Glutamate binds to neurons and activates cell surface receptors. Glutamate has significant roles in motor control, cognitive function, sensory perception, and acts as a mediator of persistent changes in the strength of synaptic signaling (synaptic plasticity), thereby modulating long term potentiation (LTP) and long term depression (LTD), which form the basis of learning and memory. Many neurological and neuropsychiatric disorders, including, but not limited to, psychosis spectrum disorders, schizophrenia and other cognitive deficits, are associated with aberrations in the function of (or the regulation by, or the regulation of) glutamate signaling systems.

Glutamate mediates its effect via two distinct types of receptors, the ionotropic receptors and the metabotropic receptors. The family of the metabotropic receptors (mGlu or mGluR) consists of eight different subtypes, which are further classified into three subgroups based on sequence homology, effector coupling and pharmacology. In particular, group I mGlu receptors (mGluR1 and mGluR5) are positively coupled to phospholipase C, while group II mGlu receptors (mGluR2 and mGluR3) and group III receptors (mGluR4, mGluR6, mGluR7, and mGluR8) are negatively coupled to adenylate cyclase (Conn et al. *Annu. Rev. Pharmacol. Toxicol.* 1997; 37:205-37).

mGluR5, which is widely expressed in the central nervous system, has at least two discrete allosteric binding sites, in addition to the orthosteric site, and has been implicated in a range of physiological functions, including phosphoinositide hydrolysis responses, modulation of potassium and voltage dependent calcium channels, modulation of ligand-gated ion channels and acting as a presynaptic autoreceptor at glutamatergic synapses, thereby modulating glutamate release (Conn et al., supra). Accordingly, development of therapeutic agents that modulate mGluR5 via direct agonism or antagonism or by positive or negative allosteric modulation may prove useful for treatment of disorders influenced by the forgoing physiological functions, such as neurological disorders, neuropsychiatric disorders, GERD, drug addiction and alcohol addiction.

SUMMARY

The present invention is based, at least in part, on the discovery that the compounds as disclosed herein are allosteric modulators of mGluR5, for example, negative or positive allosteric modulators.

In various embodiments, a compound of formula (I) or a pharmaceutically acceptable salt thereof is provided:

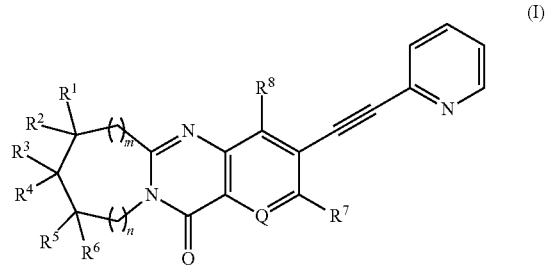

wherein
Q is $CR^9$ or N;
m and n are each independently 0 or 1;
X is F, Cl, Br, or I;
$R^1$, $R^2$, $R^3$, $R^4$, $R^5$, $R^6$, $R^7$, and $R^8$ are each independently hydrogen, X, alkyl, heteroalkyl, cycloalkyl, or alkenyl; or any two of $R^1$, $R^2$, $R^3$, $R^4$, $R^5$ and $R^6$ together with the atoms to which they are attached, form a cycloalkyl ring; and
$R^9$ is hydrogen or alkyl;
provided that
at least one of $R^1$, $R^2$, $R^3$, $R^4$, $R^5$, $R^6$, $R^7$, and $R^8$ is either X, or alkyl or heteroalkyl substituted with at least one X; or a cycloalkyl ring formed by any two of $R^1$, $R^2$, $R^3$, $R^4$, $R^5$ and $R^6$ together with the atoms to which they are attached is substituted with at least one X;
at least one of $R^3$ and $R^4$ is not hydrogen;
when m and n are both 1, Q is CH, and $R^1$, $R^2$, $R^4$, $R^5$, and $R^6$ are all H, then $R^3$ is not $CF_3$ or F;
when m and n are both 1, Q is CH, and $R^1$, $R^2$, $R^5$, and $R^6$ are all H, then $R^3$ and $R^4$ are not both F;
when m and n are both 1, Q is CH, $R^1$, $R^2$, $R^5$, and $R^6$ are all H, and $R^3$ is unsubstituted alkyl, then $R^4$ is not F; and
when m is 1, n is 0, Q is CH, $R^1$, $R^2$, $R^5$, and $R^6$ are all H, and $R^3$ is H or F, then $R^4$ is not F.

In various embodiments, a compound of formula (II) or a pharmaceutically acceptable salt thereof is provided:

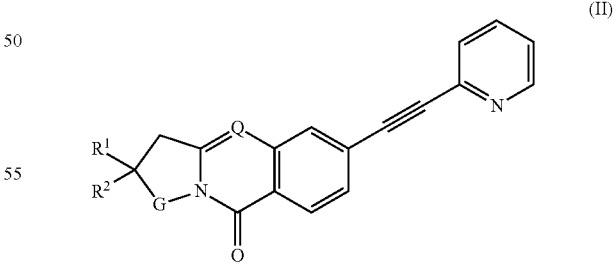

wherein
Q is $CR^7$ or N;
G is $CH_2$ or O
$R^1$ and $R^2$ are independently hydrogen, alkyl, cyano, or heteroalkyl; or $R^1$ and $R^2$ together with the atom to which they are attached form a cycloalkyl or heterocycloalkyl ring; and $R^7$ is selected from hydrogen and alkyl provided that when Q is N and G is $CH_2$, then at least one of $R^1$ and $R^2$ is not hydrogen;

when Q is N, G is $CH_2$, and one of $R^1$ and $R^2$ is methyl, then the other of $R^1$ and $R^2$ is not hydrogen or methyl;

when Q is N, G is $CH_2$, and one of $R^1$ and $R^2$ is hydroxymethyl or methoxymethyl, then the other of $R^1$ and $R^2$ is not hydrogen; and when Q is N, G is $CH_2$, and $R^1$ and $R^2$ together with the atom to which they are attached form a heterocycloalkyl ring, then $R^1$ and $R^2$ together are not $—(CH_2)_2O(CH_2)_2—$.

In various embodiments, a compound of formula (III) or a pharmaceutically acceptable salt thereof is provided:

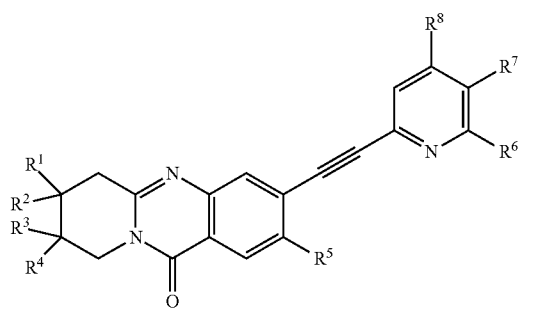

(III)

wherein $R^1$, $R^2$, $R^3$, and $R^4$ are each independently hydrogen, alkyl, hydroxyl, alkenyl, heteroalkyl, or cyano; or $R^1$ and $R^2$ or $R^3$ and $R^4$ together with the atom to which they are attached form a cycloalkyl or heterocycloalkyl ring; or $R^2$ and $R^3$ together with the atoms to which they are attached form a cycloalkyl ring;

$R^5$ is hydrogen or alkyl;

$R^6$, $R^7$, and $R^8$ are each independently hydrogen, CN, heteroalkyl, alkyl, or X; and X is F, Cl, Br, or I;

provided that $R^3$ and $R^4$ cannot together form $=CH_2$;

when $R^1$, $R^2$, $R^3$, and $R^4$ are all hydrogen, then at least one of $R^5$, $R^6$, $R^7$, and $R^8$ is not hydrogen;

when both $R^1$ and $R^2$ are methyl, then at least one of $R^3$, $R^4$, $R^5$, $R^6$, $R^7$, and $R^8$ is other than hydrogen;

when both $R^3$ and $R^4$ are methyl, then at least one of $R^1$, $R^2$, $R^5$, $R^6$, $R^7$, and $R^8$ is not hydrogen;

when one of $R^1$, $R^2$, $R^3$, and $R^4$ is methyl, and the other three of $R^1$, $R^2$, $R^3$, and $R^4$ are all hydrogen, then at least one of $R^5$, $R^6$, $R^7$, and $R^8$ is not hydrogen;

when one of $R^1$ and $R^2$ is hydroxymethyl or methoxymethyl and the other of $R^1$ and $R^2$ is hydrogen, then at least one of $R^3$, $R^4$, $R^5$, $R^6$, $R^7$, and $R^8$ is not hydrogen;

when one of $R^3$ and $R^4$ is hydroxymethyl, hydroxy, methoxy, methoxymethyl, or fluoro, and the other of $R^3$ and $R^4$ is hydrogen, then at least one of $R^1$, $R^2$, $R^5$, $R^6$, $R^7$, and $R^8$ is not hydrogen;

when one of $R^3$ and $R^4$ is methyl and the other of $R^3$ and $R^4$ is hydroxyl or methoxy, then at least one of $R^1$, $R^2$, $R^5$, $R^6$, $R^7$, and $R^8$ is not hydrogen;

when $R^3$ and $R^4$ are both F, then at least one of $R^1$, $R^2$, $R^5$, $R^6$, $R^7$, and $R^8$ is not hydrogen.

In various embodiments, a compound of formula (IV) or a pharmaceutically acceptable salt thereof is provided:

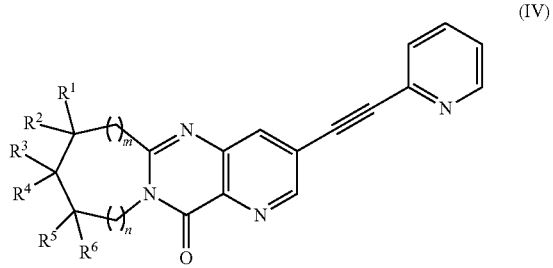

(IV)

wherein m and n are each independently 0 or 1;

$R^1$, $R^2$, $R^3$, $R^4$, $R^5$, and $R^6$ are each independently hydrogen, alkyl, or heteroalkyl; or $R^1$ and $R^2$, $R^3$ and $R^4$, or $R^5$ and $R^6$ together with the atom to which they are bonded form a cycloalkyl or heterocycloalkyl ring;

provided that at least one of $R^1$, $R^2$, $R^3$, $R^4$, $R^5$, and $R^6$ is not hydrogen;

when m and n are both 1 or both m and n are 0, one of $R^3$ and $R^4$ is methyl, and the other of $R^3$ and $R^4$ is hydrogen, then at least one of $R^1$, $R^2$, $R^5$, and $R^6$ is not hydrogen;

when m is 0, n is 1, and both $R^5$ and $R^6$ are methyl, then at least one of $R^1$, $R^2$, $R^3$, and $R^4$ is not hydrogen;

when m is 1, n is 0, and both $R^3$ and $R^4$ are methyl, then at least one of $R^1$, $R^2$, $R^5$, and $R^6$ is not hydrogen;

when m and n are both 0 and both $R^3$ and $R^4$ are methyl, then at least one of $R^1$, $R^2$, $R^5$ and $R^6$ is not hydrogen; and when m and n are both 0, one of $R^5$ and $R^6$ is hydroxymethyl or methoxymethyl, and the other of $R^5$ and $R^6$ is hydrogen, then at least one of $R^1$, $R^2$, $R^3$, and $R^4$ is not hydrogen.

In various embodiments, a compound of formula (V) or a pharmaceutically acceptable salt thereof is provided:

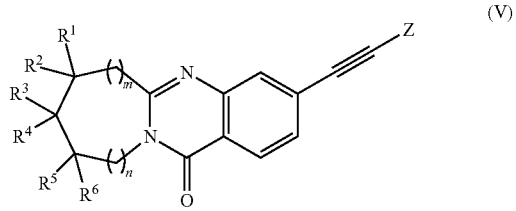

(V)

wherein m and n are independently 0 or 1;

Z is

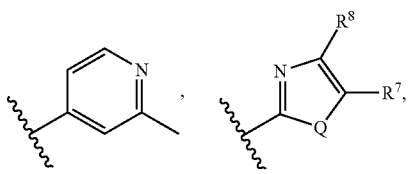

-continued

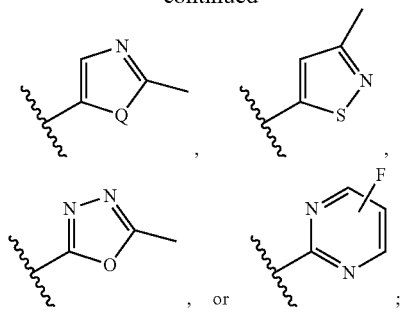

R¹, R², R³, R⁴, R⁵, and R⁶ are each independently hydrogen or alkyl;
Q is O or S;
R⁷ and R⁸ are hydrogen or alkyl; or R⁷ and R⁸ together with the atoms to which they are attached form a cycloalkyl, heterocycloalkyl, aryl, or heteroaryl ring;
provided that
when m is 1, n is 1, Z is

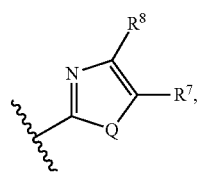

Q is S, R⁷ is methyl and R⁸ is hydrogen, one of R³ and R⁴ is methyl, and the other of R³ and R⁴ is hydrogen, then at least one of R¹, R², R⁵ and R⁶ is not hydrogen.

In various embodiments, a compound of formula (VI) or a pharmaceutically acceptable salt thereof is vided:

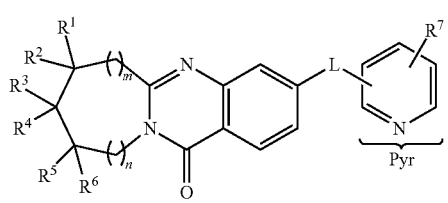

(VI)

wherein
m and n are independently 0 or 1;
L is —R⁸C=CR⁸—, —OC(R⁹)₂—, C(O)NR¹⁰—, or —NR¹⁰C(O)—;
X is F, Cl, Br, or I;
R¹, R², R³, R⁴, R⁵, and R⁶ are each independently hydrogen, alkyl, or X;
R⁷ is hydrogen or cyano;
each R⁸ is hydrogen or X;
R⁹ and R¹⁰ are each independently hydrogen or alkyl;
provided that
when m is 0, n is 0, L is —HC=CH—, one of R³ and R⁴ is methyl, the other of R³ and R⁴ is hydrogen, R¹, R², R⁵, and R⁶ are all hydrogen, and R⁷ is hydrogen, then Pyr is not 2-pyridyl;
when m is 0, n is 1, L is —HC=CH—, R¹, R², R³, and R⁴ are all hydrogen, R⁵ and R⁶ are both methyl, and R⁷ is hydrogen or cyano, then Pyr is not

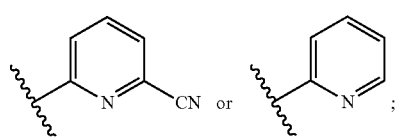 [SMILES: *c1cccc(C#N)n1 ; *c1ccccn1]

when m is 1, n is 0, L is —HC=CH—, R¹, R², R⁵, and R⁶ are all hydrogen, R³ and R⁴ are both methyl, and R⁷ is hydrogen or cyano, then Pyr is not when m is 0, n is 1, L is —HC=CH—, R¹, R², R⁵, and R⁶ are all hydrogen, R³ and R⁴ are both methyl, and R⁷ is hydrogen or cyano, then Pyr is not when m is 1, n is 0, L is —HC=CH—, R³, R⁴, R⁵, and R⁶ are all hydrogen, R¹ and R² are both methyl, and R⁷ is hydrogen or cyano, then Pyr is not when m is 1, n is 1, L is —HC=CH—, one of R³ and R⁴ is methyl, the other of R³ and R⁴ is hydrogen, R¹, R², R⁵, and R⁶ are all hydrogen, and R⁷ is hydrogen or cyano, then Pyr is not and
when m is 1, n is 1, L is —HC=CH—, R¹, R², R³, R⁴, R⁵, R⁶, and R⁷ are all hydrogen, then Pyr is not 2-pyridyl.

In various embodiments, a compound of formula (VII) or a pharmaceutically acceptable salt thereof is provided:

(VII)
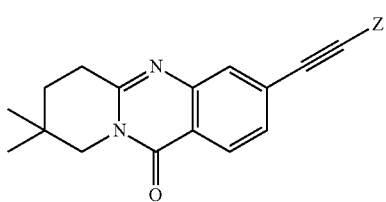
wherein Z is
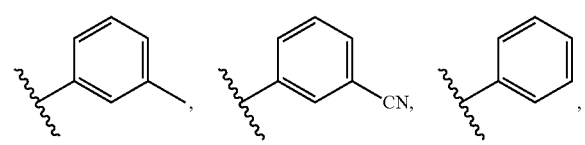
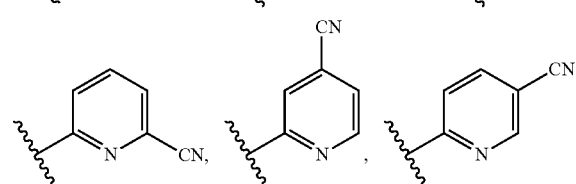
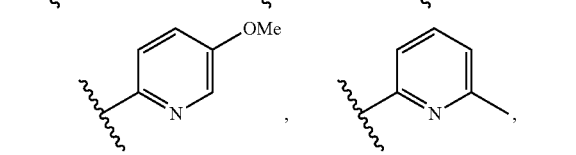
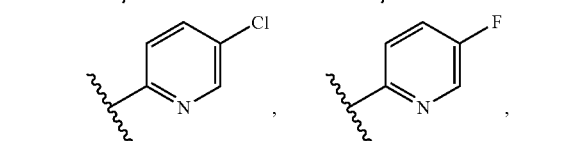
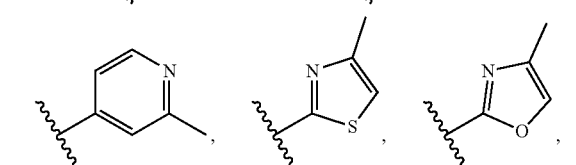
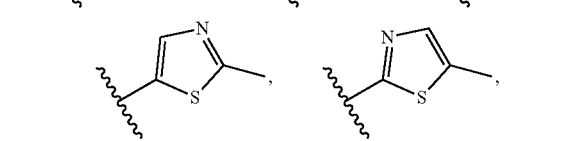
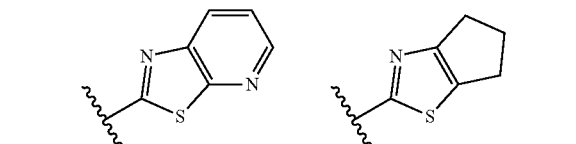
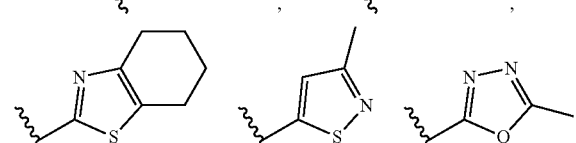
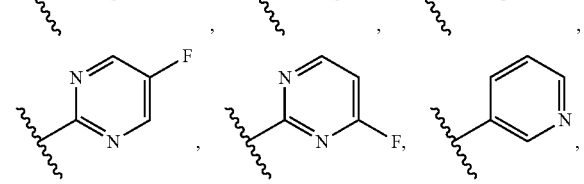
-continued
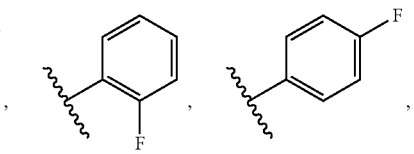

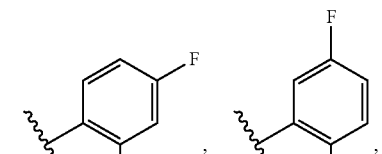
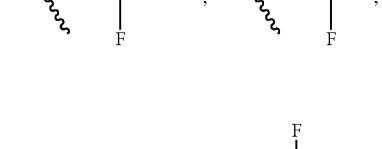
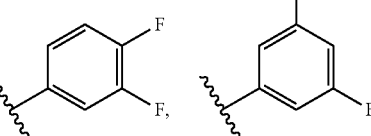
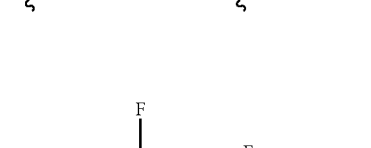
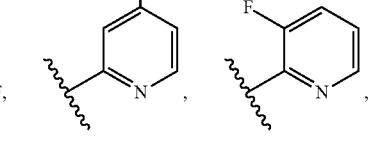
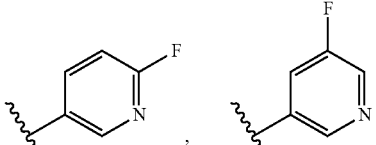
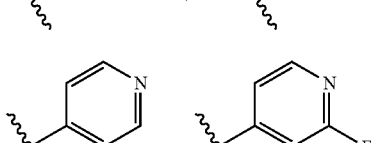
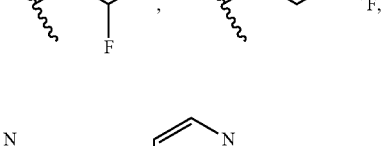
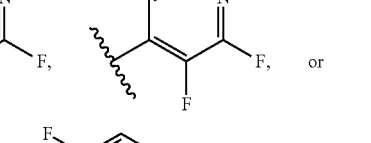 or
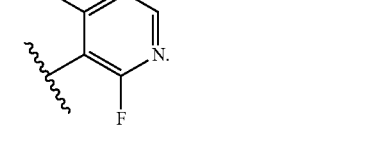
In various embodiments, a compound of formula (VIII) or a pharmaceutically acceptable salt thereof is provided:

(VIII)

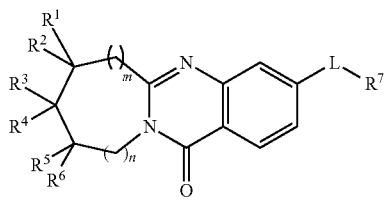

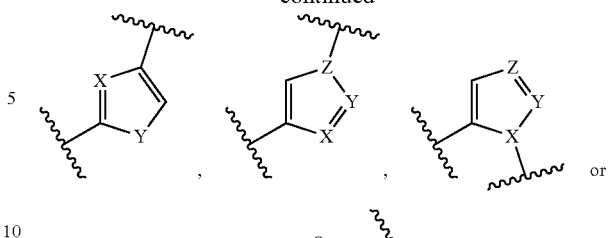

wherein m and n are independently 0 or 1;

$R^1$, $R^2$, $R^3$, $R^4$, $R^5$, and $R^6$ are each independently hydrogen, alkyl, or heteroalkyl; or $R^1$ and $R^2$, $R^3$ and $R^4$, or $R^5$ and $R^6$ together with the atom to which they are bonded form a cycloalkyl or heterocycloalkyl ring;

$R^7$ is

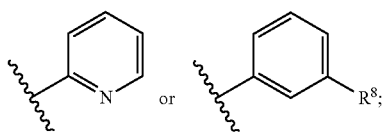

$R^8$ is H, F, Cl, Br, or I;

L is O, NH, —CH$_2$CH(CH$_3$)—, —CH$_2$O—, —CH=C(CH$_3$)—, —C(O)CH$_2$—, —C(O)CH(CH$_3$)—, —(CH$_2$)$_3$—, —CH$_2$OCH$_2$—, —NHC(O)NH—, —C(O)NHNHC(O)—,

X, Y, and Z are independently O, N, or S;

each Q is independently CH or N;

provided that at least two occurrences of Q are CH; and when m is 1, n is 1, and $R^1$, $R^2$, $R^3$, $R^4$, $R^5$, $R^6$, and $R^8$ are all hydrogen, then $R^7$ is not

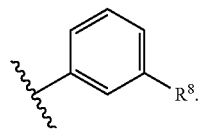

In various embodiments, a compound of the following formulae or a pharmaceutically acceptable salt thereof is provided:

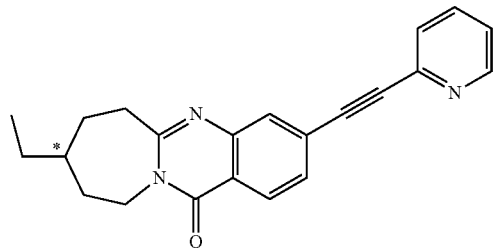

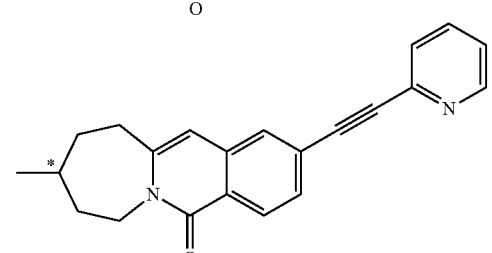

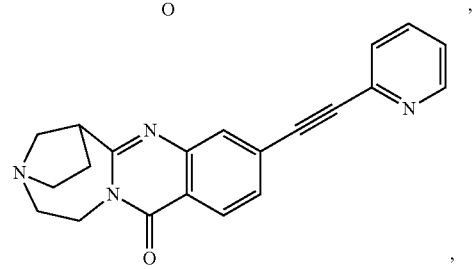

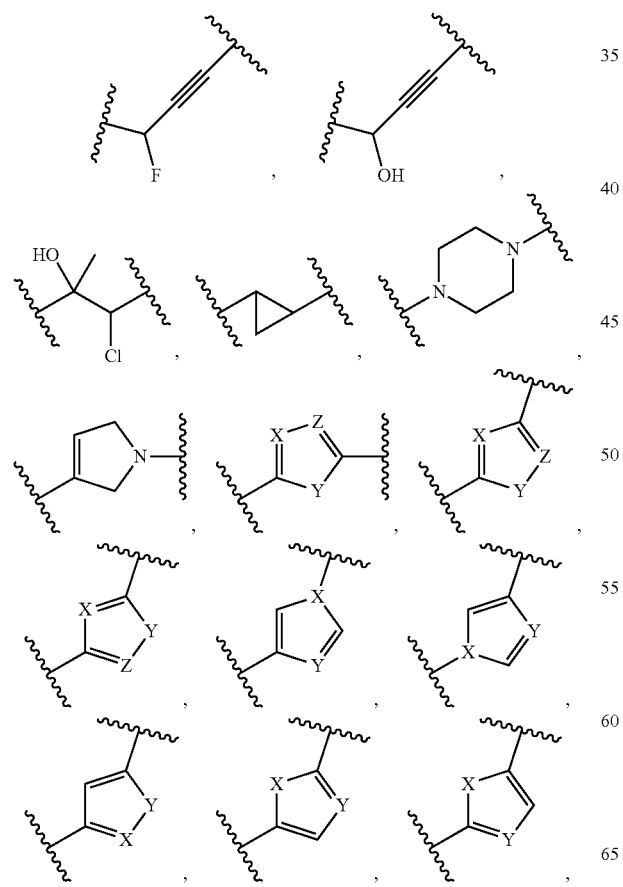

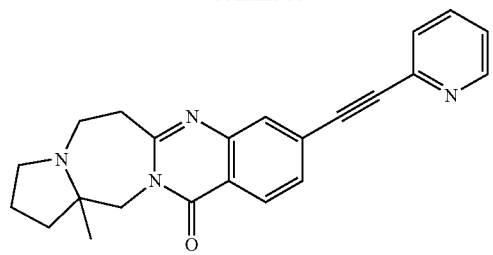,
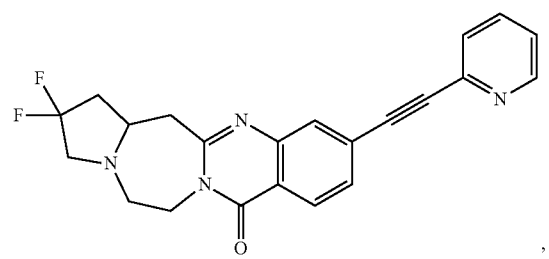,
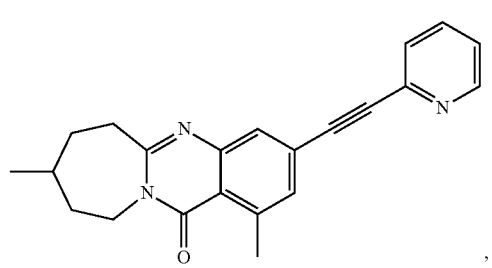,
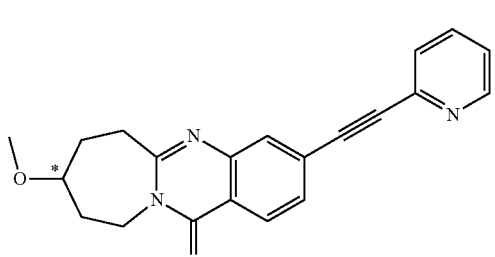,
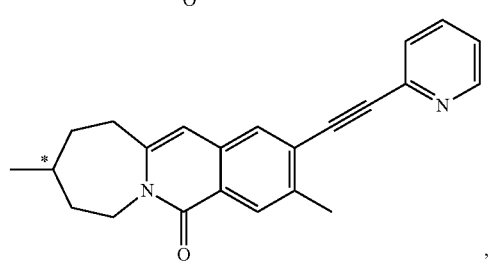,
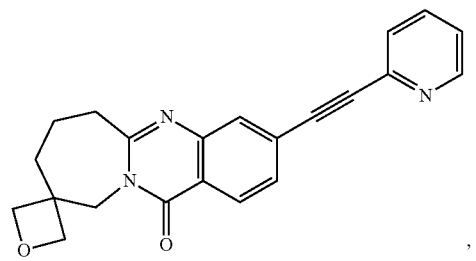,
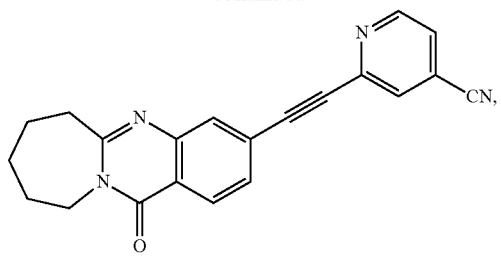,
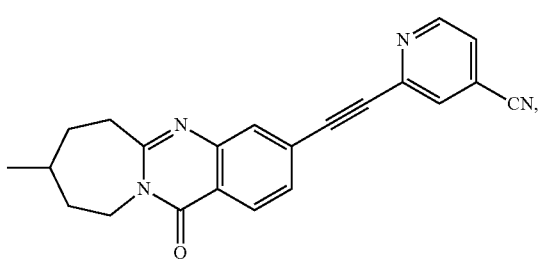,
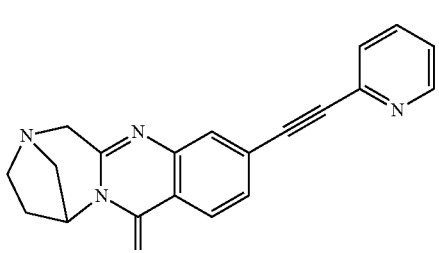,
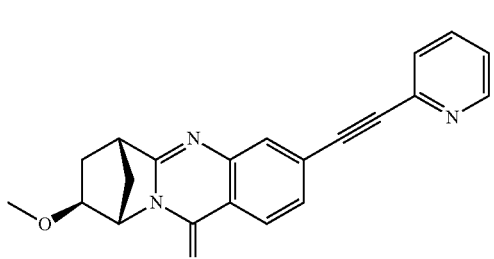,
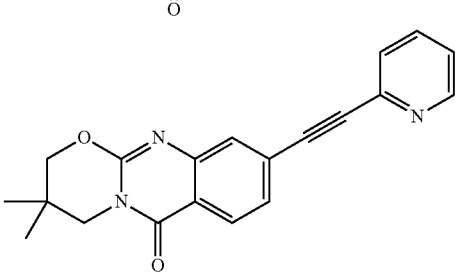,
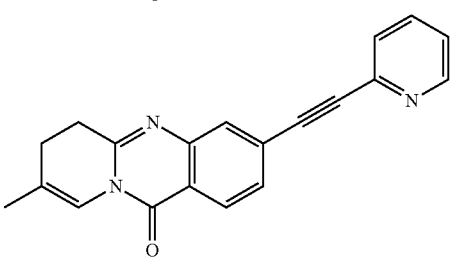, -continued
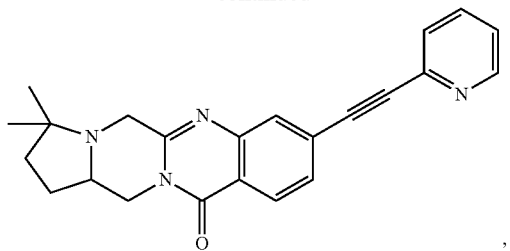,
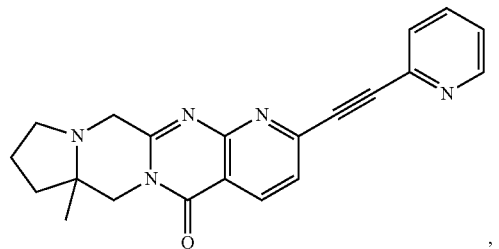,
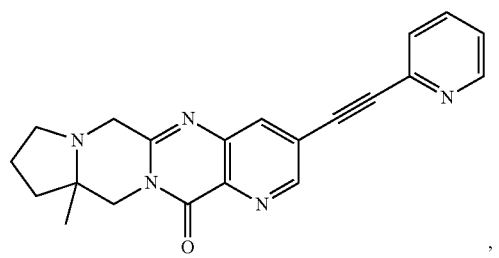,
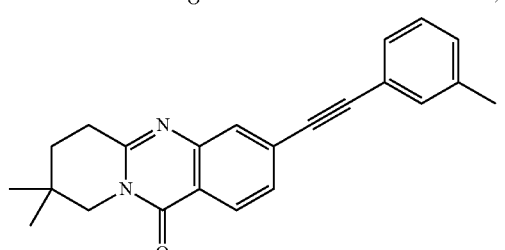,
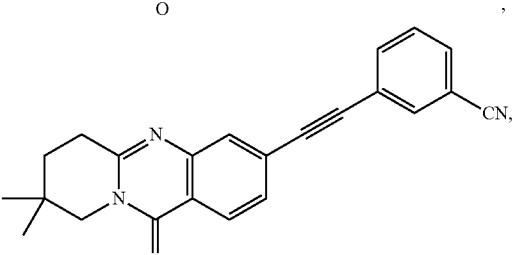,
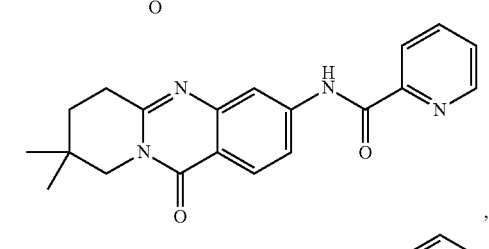,
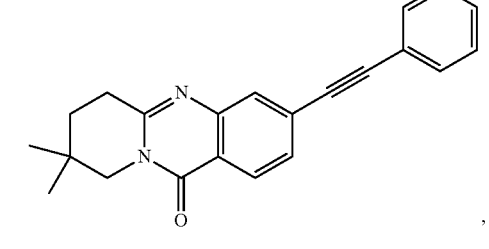,
-continued
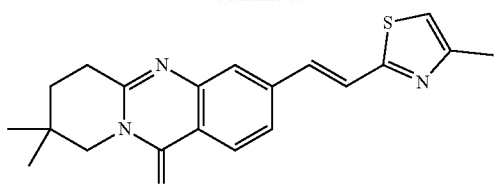,
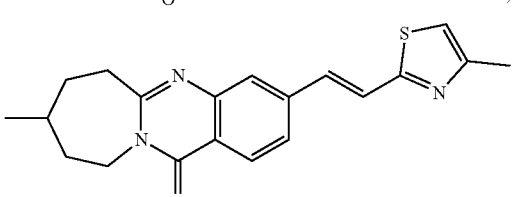,
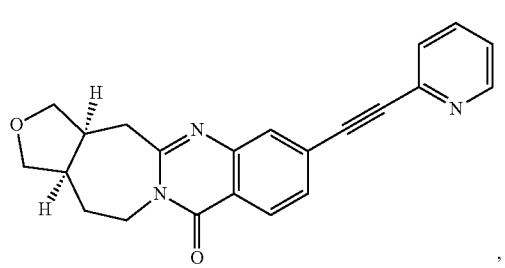,
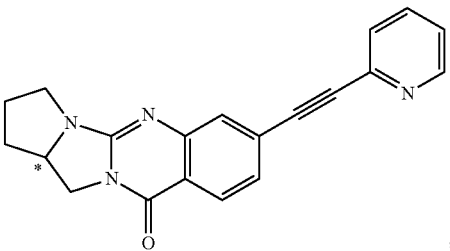,
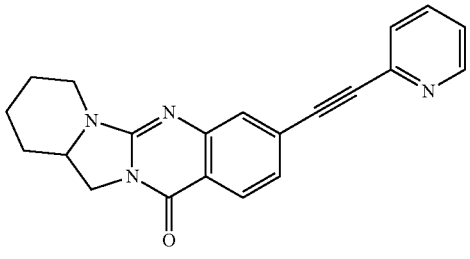,
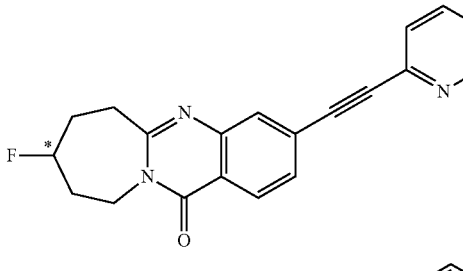,
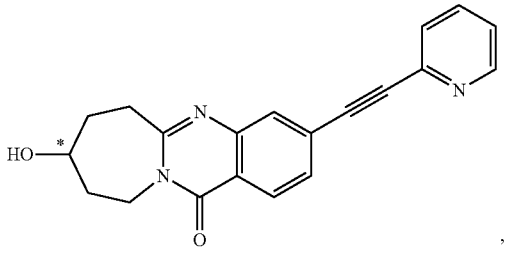, 15
-continued
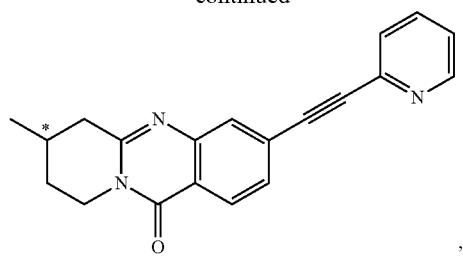
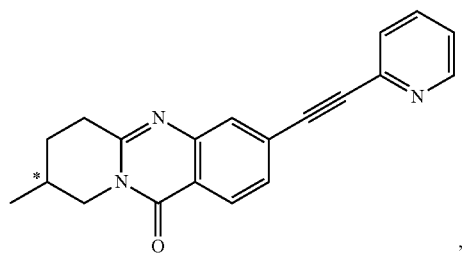
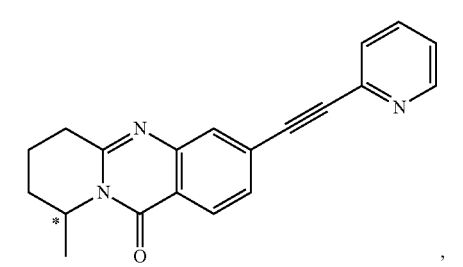
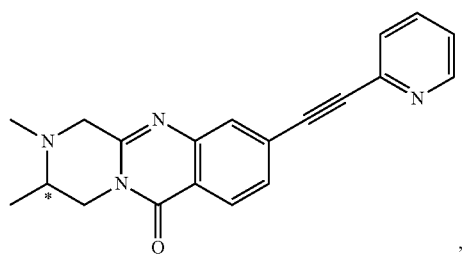
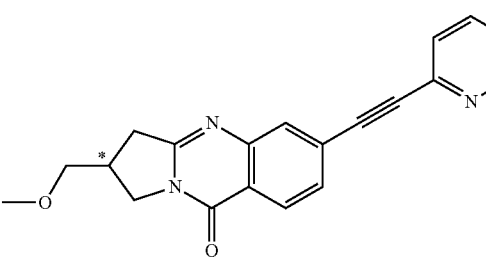
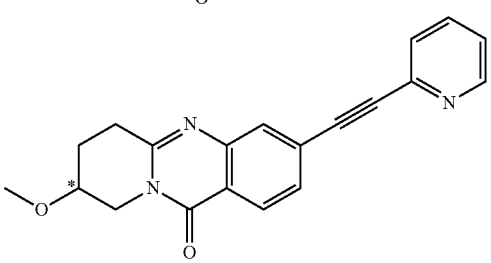
16
-continued
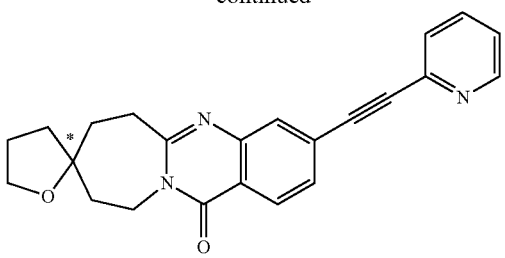
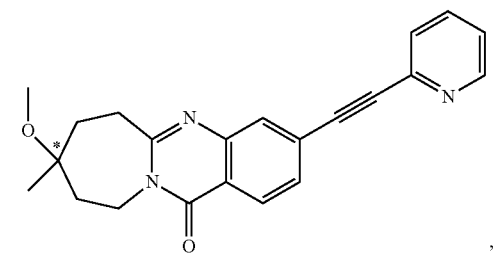
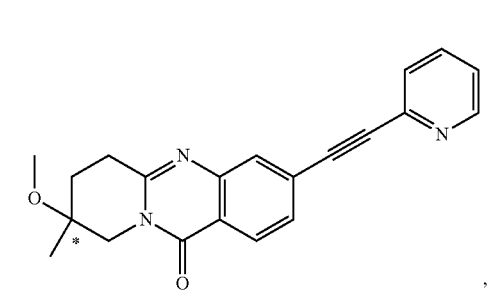
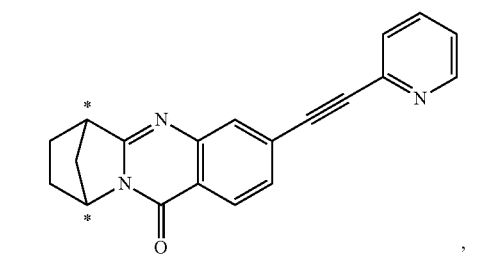
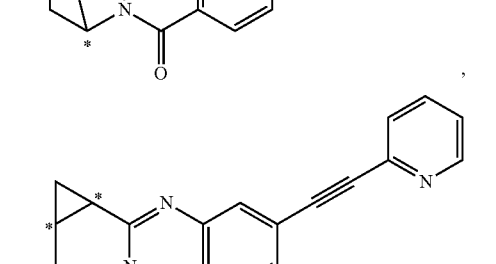
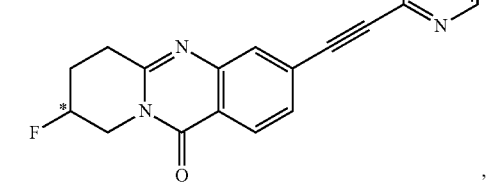

-continued

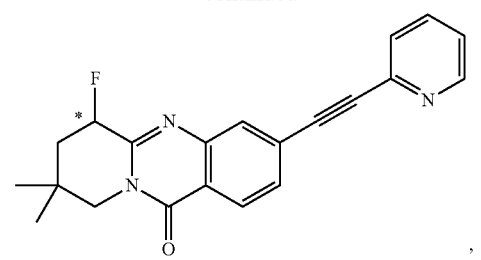

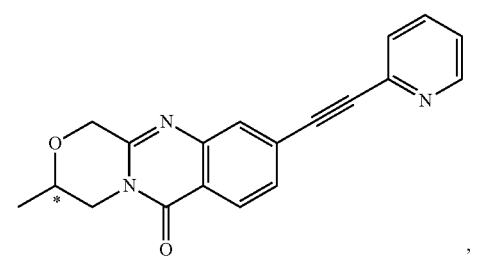

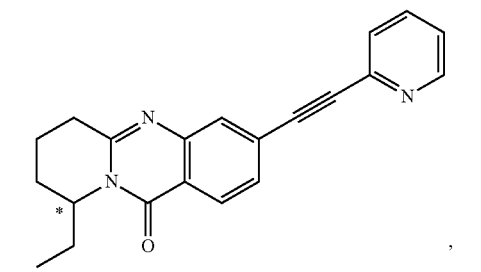

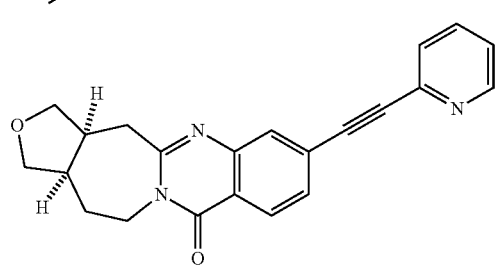

relative stereochemistry

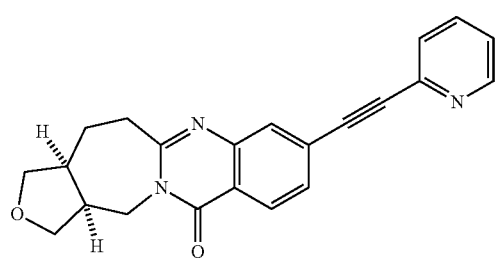

relative stereochemistry

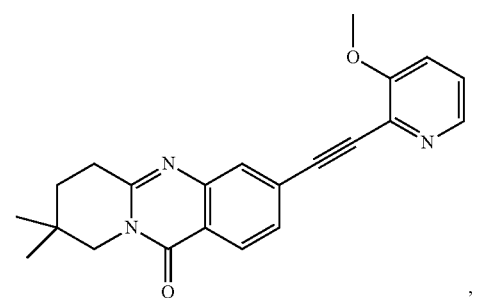

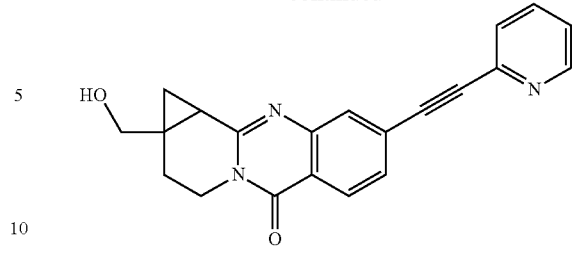

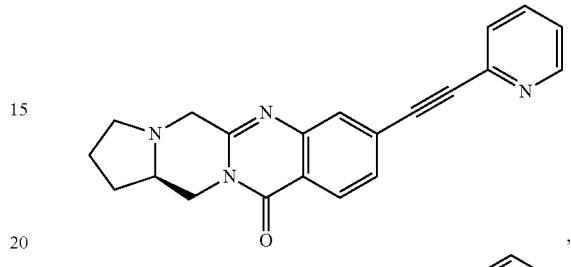


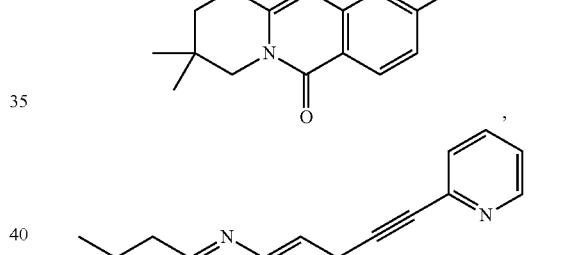

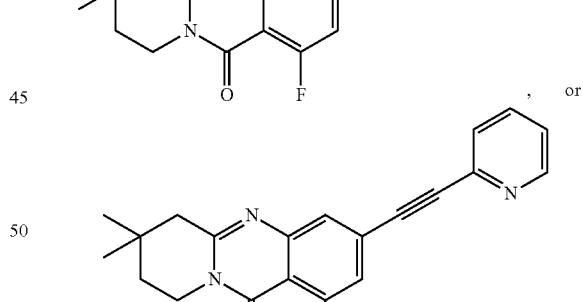

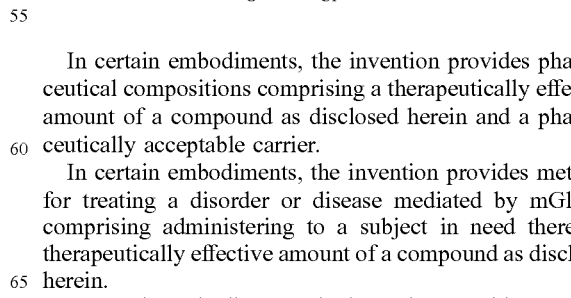, or

In certain embodiments, the invention provides pharmaceutical compositions comprising a therapeutically effective amount of a compound as disclosed herein and a pharmaceutically acceptable carrier.

In certain embodiments, the invention provides methods for treating a disorder or disease mediated by mGluR5, comprising administering to a subject in need thereof a therapeutically effective amount of a compound as disclosed herein.

In certain embodiments, the invention provides methods for treating neurological disorders, such as neurodegenerative diseases, neuropsychiatric diseases, affective disorders, loss of cognitive function, and learning and memory disorders, comprising administering to a subject in need thereof a therapeutically effective amount of a compound as disclosed herein.

In certain embodiments, methods are provided for treating psychosis, comprising administering to a subject in need thereof a therapeutically effective amount of a compound as disclosed herein.

In certain embodiments, methods are provided for treating schizophrenia, comprising administering to a subject in need thereof a therapeutically effective amount of a compound as disclosed herein.

In certain embodiments, methods are provided for treating Alzheimer's disease, comprising administering to a subject in need thereof a therapeutically effective amount of a compound as disclosed herein.

In certain embodiments, methods are provided for treating cognitive disorders, comprising administering to a subject in need thereof a therapeutically effective amount of a compound as disclosed herein.

In certain embodiments, methods are provided for treating cognitive impairment associated with schizophrenia, comprising administering to a subject in need thereof a therapeutically effective amount of a compound as disclosed herein.

In certain embodiments, methods are provided for treating tubular sclerosis.

In certain embodiments, the invention provides methods for modulating mGluR5 in a subject by administering to the subject a therapeutically effective amount of a compound as disclosed herein.

In certain embodiments, the invention provides methods for modulating mGluR5 in a cell by contacting the cell with an effective amount of a compound as disclosed herein.

DETAILED DESCRIPTION OF THE INVENTION

Various embodiments of the invention are described herein. It will be recognized that features specified in each embodiment may be combined with other specified features to provide further embodiments.

As used herein, the articles "a" and "an" mean "one or more" or "at least one," unless otherwise indicated. That is, reference to any element of the present invention by the indefinite article "a" or "an" does not exclude the possibility that more than one of the element is present.

The use of any and all examples, or exemplary language (e.g., "such as") provided herein is intended merely to better illuminate the invention and is not intended to limit the scope of the invention.

Compounds

In certain embodiments, a compound of formula (I) or a pharmaceutically acceptable salt thereof is provided:

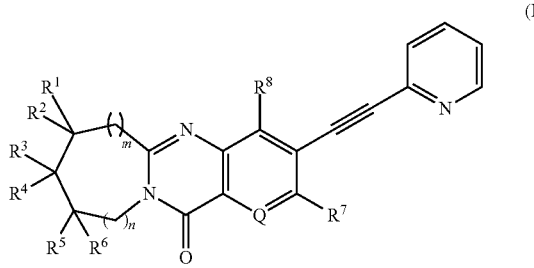

(I)

wherein
Q is $CR^9$ or N;
m and n are each independently 0 or 1;
X is F, Cl, Br, or I;
$R^1$, $R^2$, $R^3$, $R^4$, $R^5$, $R^6$, $R^7$, and $R^8$ are each independently hydrogen, X, alkyl, heteroalkyl, cycloalkyl, or alkenyl; or any two of $R^1$, $R^2$, $R^3$, $R^4$, $R^5$ and $R^6$ together with the atoms to which they are attached, form a cycloalkyl ring; and
$R^9$ is hydrogen or alkyl;
provided that
at least one of $R^1$, $R^2$, $R^3$, $R^4$, $R^5$, $R^6$, $R^7$, and $R^8$ is either X, or alkyl or heteroalkyl substituted with at least one X; or a cycloalkyl ring formed by any two of $R^1$, $R^2$, $R^3$, $R^4$, $R^5$ and $R^6$ together with the atoms to which they are attached is substituted with at least one X;
at least one of $R^3$ and $R^4$ is not hydrogen;
when m and n are both 1, Q is CH, and $R^1$, $R^2$, $R^4$, $R^5$, and $R^6$ are all H, then $R^3$ is not $CF_3$ or F;
when m and n are both 1, Q is CH, and $R^1$, $R^2$, $R^5$, and $R^6$ are all H, then $R^3$ and $R^4$ are not both F;
when m and n are both 1, Q is CH, $R^1$, $R^2$, $R^5$, and $R^6$ are all H, and $R^3$ is unsubstituted alkyl, then $R^4$ is not F; and
when m is 1, n is 0, Q is CH, $R^1$, $R^2$, $R^5$, and $R^6$ are all H, and $R^3$ is H or F, then $R^4$ is not F.

In certain embodiments, $R^1$, $R^2$, $R^3$, $R^4$, $R^5$ $R^6$, $R^7$, and $R^8$ are each independently hydrogen, X, alkyl, heteroalkyl, or alkenyl; or any two of $R^1$, $R^2$, $R^3$, $R^4$, $R^5$ and $R^6$ together with the atoms to which they are attached, form a cycloalkyl ring In certain embodiments, Q is $CR^9$. In certain embodiments, Q is N. In certain embodiments, Q is CH or N. In certain embodiments, Q is CH.

In certain embodiments, m is 0. In certain embodiments, m is 1. In certain embodiments, n is 0. In certain embodiments, n is 1.

In certain embodiments, X is F. In certain embodiments, X is Cl. In certain embodiments, X is Br. In certain embodiments, X is I.

In certain embodiments, $R^1$ is hydrogen. In certain embodiments, $R^1$ is X. In certain embodiments, $R^1$ is alkyl. In certain embodiments, $R^1$ is heteroalkyl. In certain embodiments, $R^1$ is alkenyl.

In certain embodiments, $R^2$ is hydrogen. In certain embodiments, $R^2$ is X. In certain embodiments, $R^2$ is alkyl. In certain embodiments, $R^2$ is heteroalkyl. In certain embodiments, $R^2$ is alkenyl.

In certain embodiments, $R^3$ is hydrogen. In certain embodiments, $R^3$ is X. In certain embodiments, $R^3$ is alkyl. In certain embodiments, $R^3$ is heteroalkyl. In certain embodiments, $R^3$ is alkenyl.

In certain embodiments, $R^4$ is hydrogen. In certain embodiments, $R^4$ is X. In certain embodiments, $R^4$ is alkyl. In certain embodiments, $R^4$ is heteroalkyl. In certain embodiments, $R^4$ is alkenyl.

In certain embodiments, $R^5$ is hydrogen. In certain embodiments, $R^5$ is X. In certain embodiments, $R^5$ is alkyl. In certain embodiments, $R^5$ is heteroalkyl. In certain embodiments, $R^5$ is alkenyl.

In certain embodiments, $R^6$ is hydrogen. In certain embodiments, $R^6$ is X. In certain embodiments, $R^6$ is alkyl. In certain embodiments, $R^6$ is heteroalkyl. In certain embodiments, $R^6$ is alkenyl.

In certain embodiments, $R^7$ is hydrogen. In certain embodiments, $R^7$ is X. In certain embodiments, $R^7$ is alkyl. In certain embodiments, $R^7$ is heteroalkyl. In certain embodiments, $R^7$ is alkenyl.

In certain embodiments, R⁸ is hydrogen. In certain embodiments, R⁸ is X. In certain embodiments, R⁸ is alkyl. In certain embodiments, R⁸ is heteroalkyl. In certain embodiments, R⁸ is alkenyl.

In certain embodiments, R¹ and R² together with the atoms to which they are attached, form a cycloalkyl ring. In certain embodiments, R¹ and R³ together with the atoms to which they are attached, form a cycloalkyl ring. In certain embodiments, R¹ and R⁴ together with the atoms to which they are attached, form a cycloalkyl ring. In certain embodiments, R¹ and R⁵ together with the atoms to which they are attached, form a cycloalkyl ring. In certain embodiments, R¹ and R⁶ together with the atoms to which they are attached, form a cycloalkyl ring. In some embodiments, R¹ and R⁷ together with the atoms to which they are attached, form a cycloalkyl ring. In some embodiments, R¹ and R⁸ together with the atoms to which they are attached, form a cycloalkyl ring.

In certain embodiments, R² and R³ together with the atoms to which they are attached, form a cycloalkyl ring. In certain embodiments, R² and R⁴ together with the atoms to which they are attached, form a cycloalkyl ring. In certain embodiments, R² and R⁵ together with the atoms to which they are attached, form a cycloalkyl ring. In certain embodiments, R² and R⁶ together with the atoms to which they are attached, form a cycloalkyl ring. In certain embodiments, R² and R⁷ together with the atoms to which they are attached, form a cycloalkyl ring. In certain embodiments, R² and R⁸ together with the atoms to which they are attached, form a cycloalkyl ring.

In certain embodiments, R³ and R⁴ together with the atoms to which they are attached, form a cycloalkyl ring. In certain embodiments, R³ and R⁵ together with the atoms to which they are attached, form a cycloalkyl ring. In certain embodiments, R³ and R⁶ together with the atoms to which they are attached, form a cycloalkyl ring. In certain embodiments, R³ and R⁷ together with the atoms to which they are attached, form a cycloalkyl ring. In certain embodiments, R³ and R⁸ together with the atoms to which they are attached, form a cycloalkyl ring.

In certain embodiments, R⁴ and R⁵ together with the atoms to which they are attached, form a cycloalkyl ring. In certain embodiments, R⁴ and R⁶ together with the atoms to which they are attached, form a cycloalkyl ring. In certain embodiments, R⁴ and R⁷ together with the atoms to which they are attached, form a cycloalkyl ring. In certain embodiments, R⁴ and R⁸ together with the atoms to which they are attached, form a cycloalkyl ring.

In certain embodiments, R⁵ and R⁶ together with the atoms to which they are attached, form a cycloalkyl ring. In certain embodiments, R⁵ and R⁷ together with the atoms to which they are attached, form a cycloalkyl ring. In certain embodiments, R⁵ and R⁸ together with the atoms to which they are attached, form a cycloalkyl ring.

In certain embodiments, R⁶ and R⁷ together with the atoms to which they are attached, form a cycloalkyl ring. In certain embodiments, R⁶ and R⁸ together with the atoms to which they are attached, form a cycloalkyl ring.

In certain embodiments, R⁷ and R⁸ together with the atoms to which they are attached, form a cycloalkyl ring.

In certain embodiments, a compound of Formula (I) is

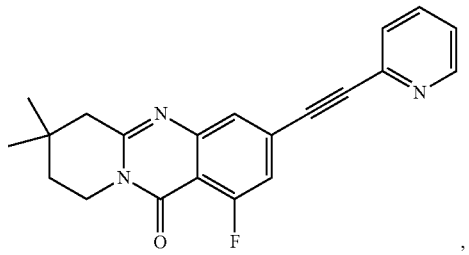

,

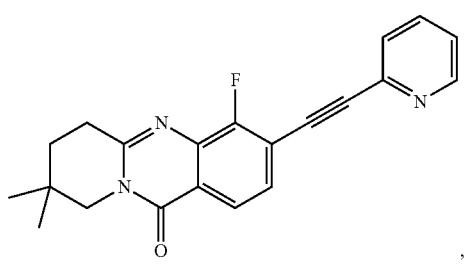

,

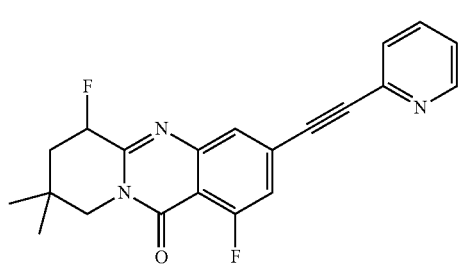

,

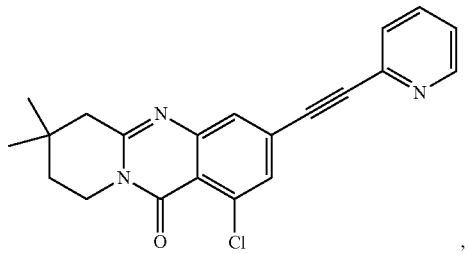

,

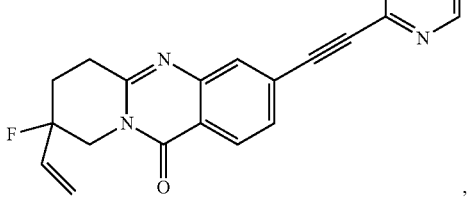

,

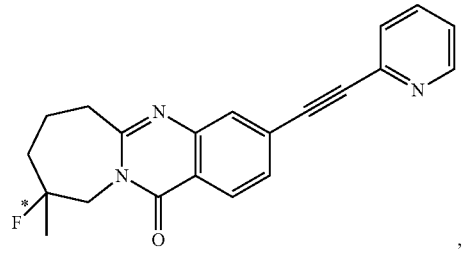

,

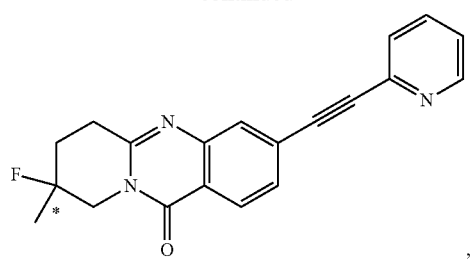
,
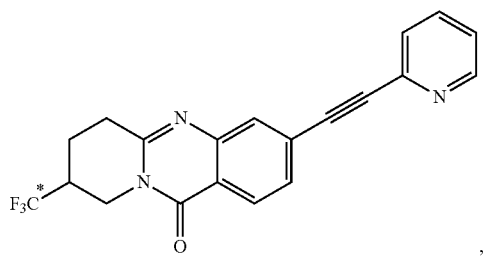
,
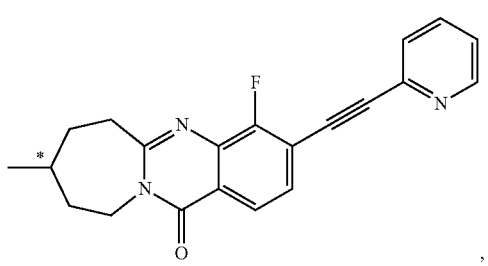
,
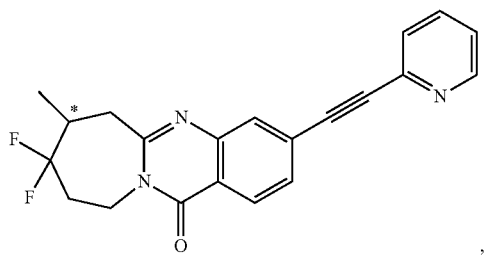
,
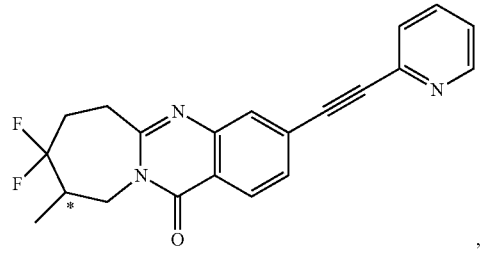
,
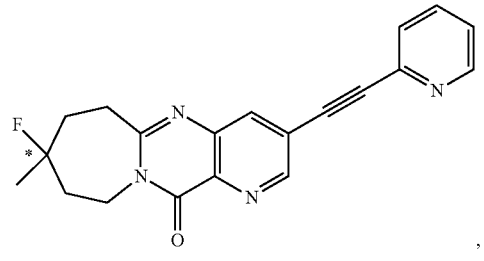
,
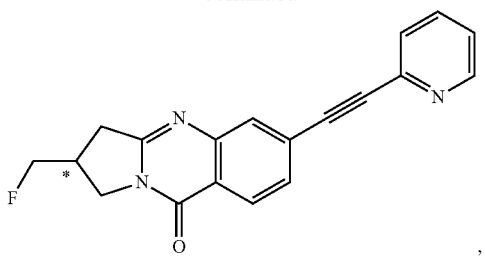
,
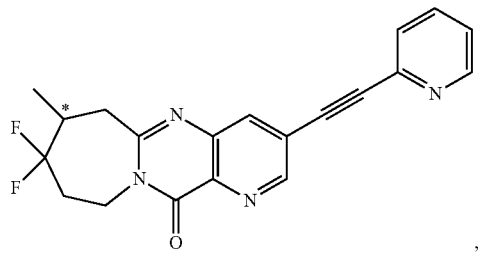
,
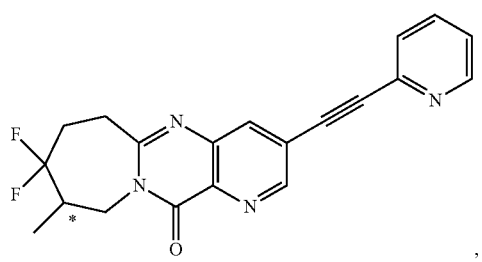
,
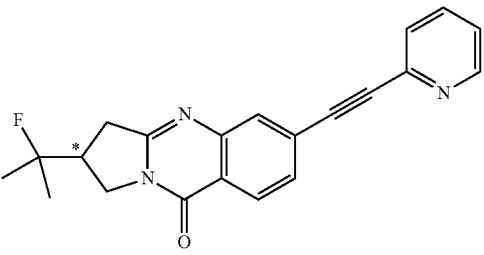
,
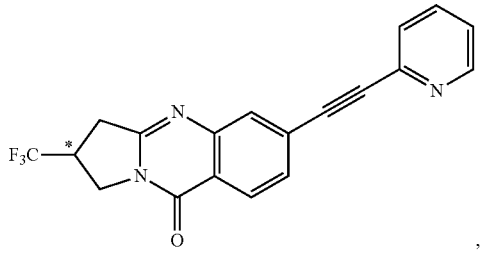
,
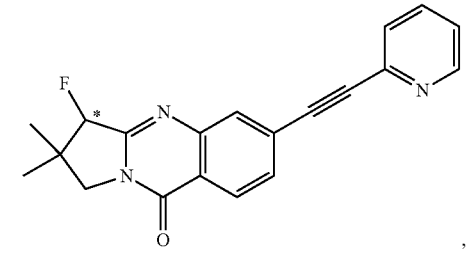
,

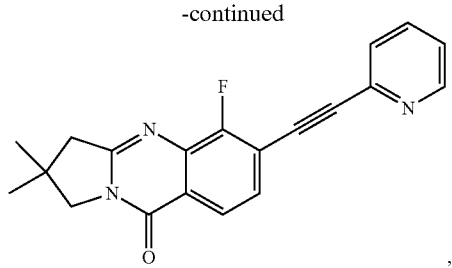,
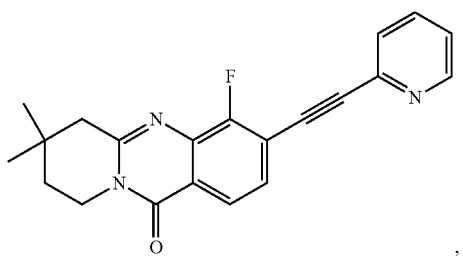,
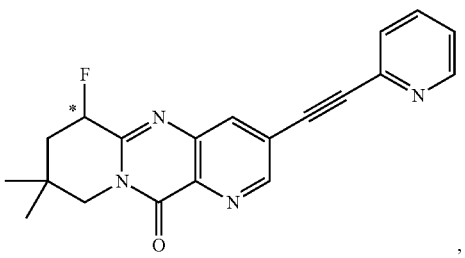,
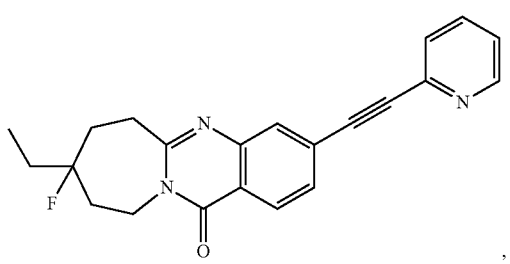,
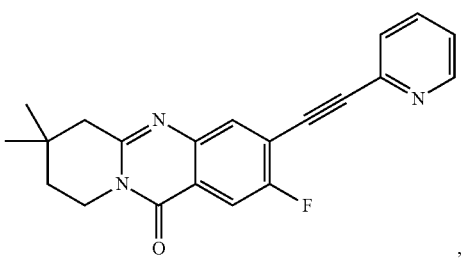,
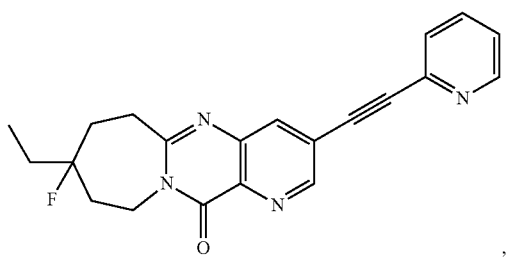,
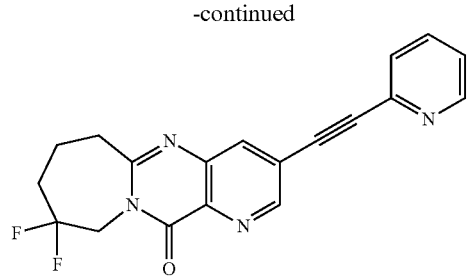,
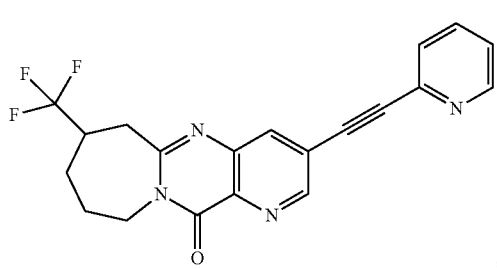,
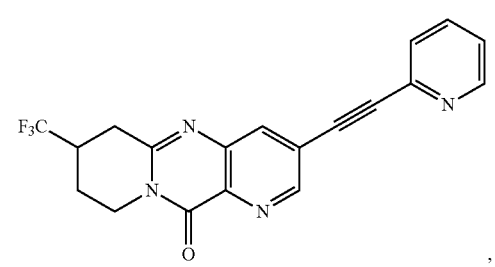,
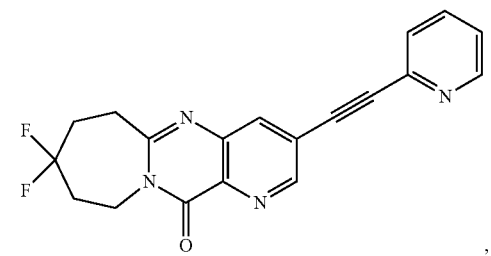,
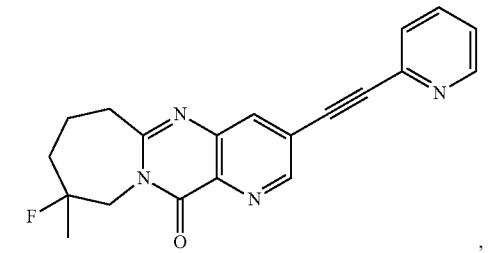,
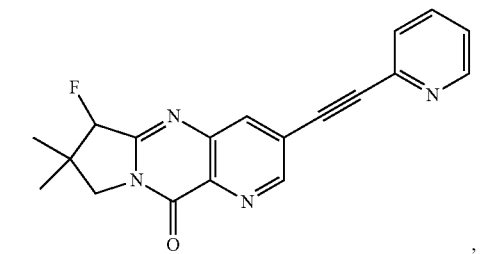,

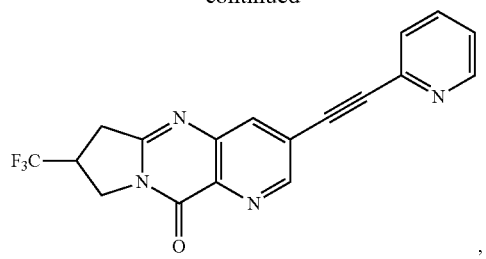
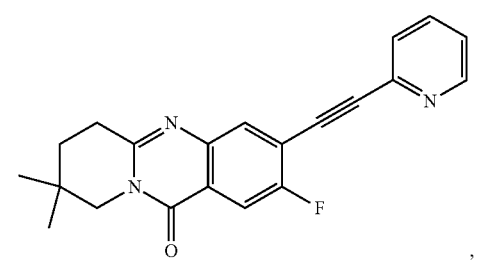
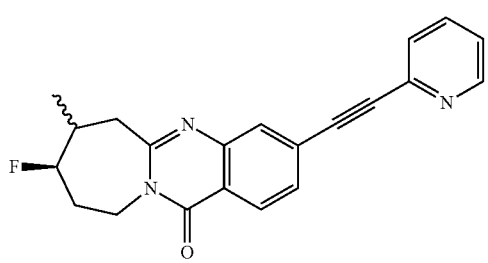
relative stereochemistry
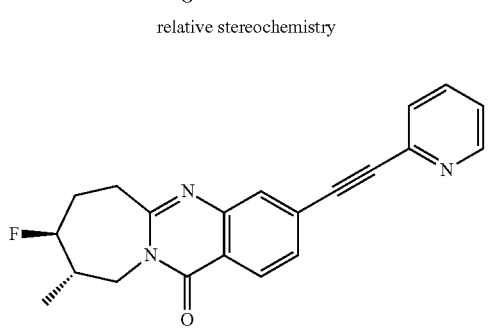
relative stereochemistry
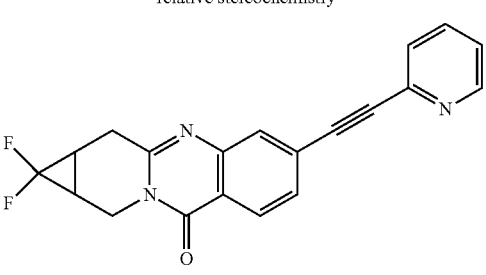
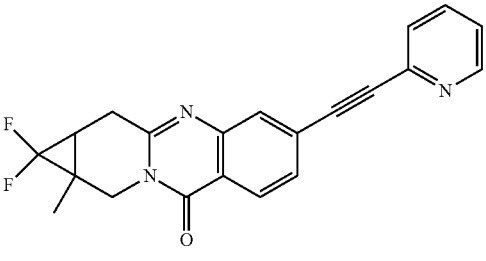
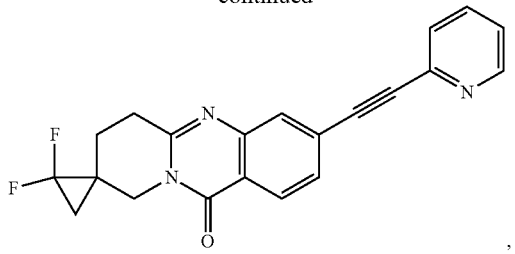
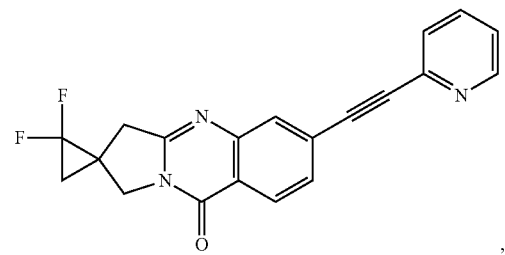
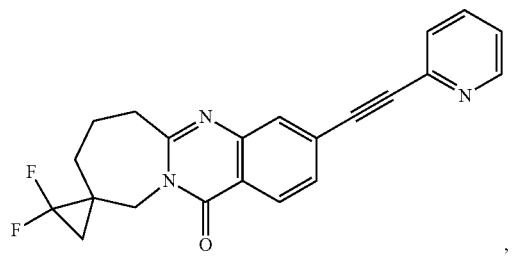
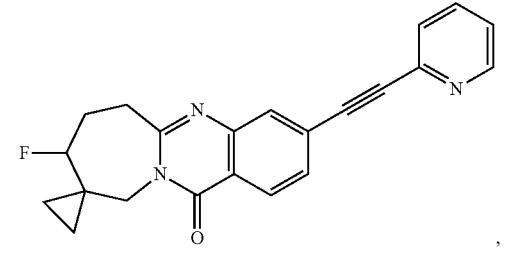
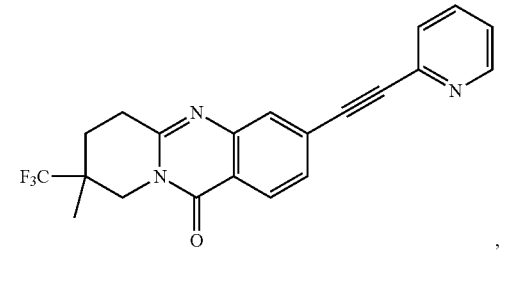
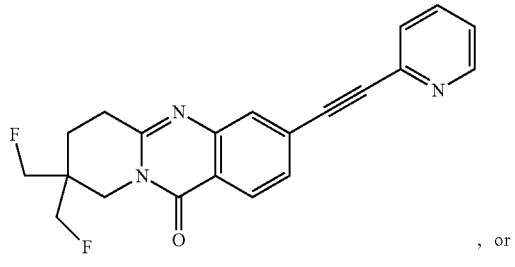
, or -continued

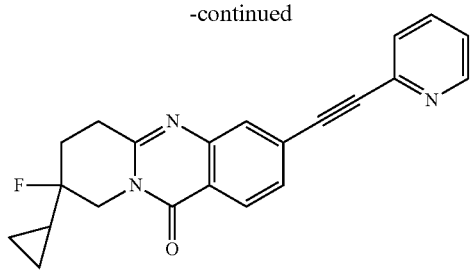

or a pharmaceutically acceptable salt thereof.

In certain embodiments, a compound of Formula (I) is

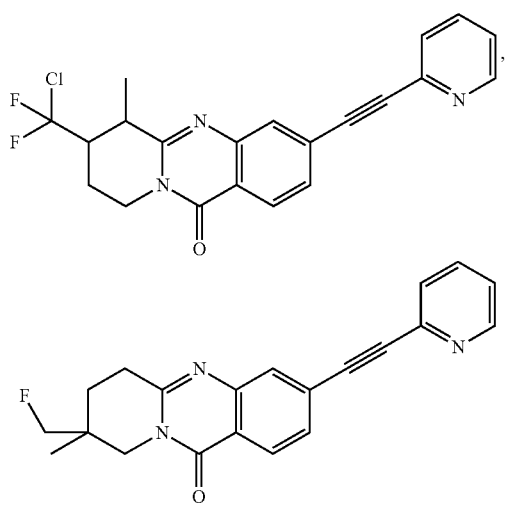

or a pharmaceutically acceptable salt thereof.

As used herein "*" is used to denote a compound having at least one stereocenter, wherein the stereoisomers have been separated, but the absolute stereochemistry has not been determined.

In certain embodiments, a compound of formula (II) or a pharmaceutically acceptable salt thereof is provided:

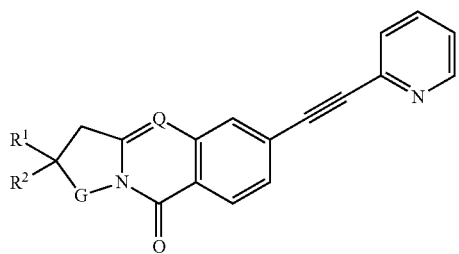
(II)

wherein
Q is $CR^7$ or N;
G is $CH_2$ or O
$R^1$ and $R^2$ are independently hydrogen, alkyl, cyano, or heteroalkyl; or $R^1$ and $R^2$ together with the atom to which they are attached form a cycloalkyl or heterocycloalkyl ring; and
$R^7$ is selected from hydrogen and alkyl
provided that
when Q is N and G is $CH_2$, then at least one of $R^1$ and $R^2$ is not hydrogen;

when Q is N, G is $CH_2$, and one of $R^1$ and $R^2$ is methyl, then the other of $R^1$ and $R^2$ is not hydrogen or methyl;

when Q is N, G is $CH_2$, and one of $R^1$ and $R^2$ is hydroxymethyl or methoxymethyl, then the other of $R^1$ and $R^2$ is not hydrogen; and when Q is N, G is $CH_2$, and $R^1$ and $R^2$ together with the atom to which they are attached form a heterocycloalkyl ring, then $R^1$ and $R^2$ together are not —$(CH_2)_2O(CH_2)_2$—.

In certain embodiments, Q is $CR^7$. In certain embodiments, Q is N.

In certain embodiments, G is $CH_2$. In certain embodiments, G is O.

In certain embodiments, $R^1$ is hydrogen. In certain embodiments, $R^1$ is alkyl. In certain embodiments, $R^1$ is cyano. In certain embodiments, $R^1$ is heteroalkyl.

In certain embodiments, $R^2$ is hydrogen. In certain embodiments, $R^2$ is alkyl. In certain embodiments, $R^2$ is cyano. In certain embodiments, $R^2$ is heteroalkyl.

In certain embodiments, $R^1$ and $R^2$ together with the atom to which they are attached form a cycloalkyl ring. In certain embodiments, $R^1$ and $R^2$ together with the atom to which they are attached form a heterocycloalkyl ring.

In certain embodiments, $R^7$ is hydrogen. In certain embodiments, $R^7$ is alkyl.

In certain embodiments, a compound of Formula (II) is

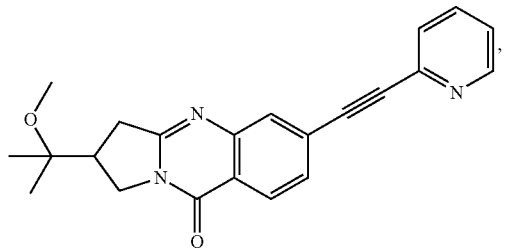

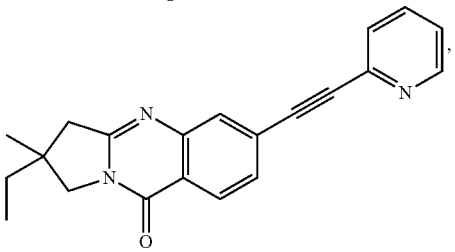

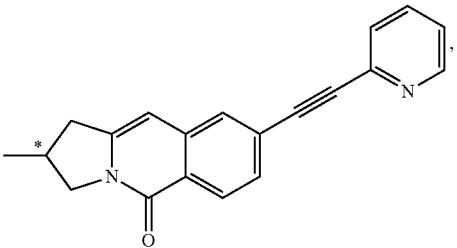

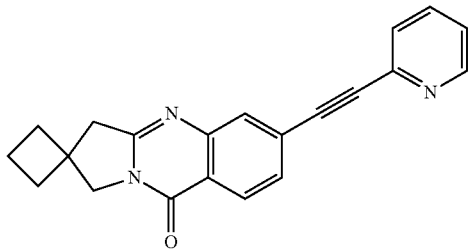

31

-continued

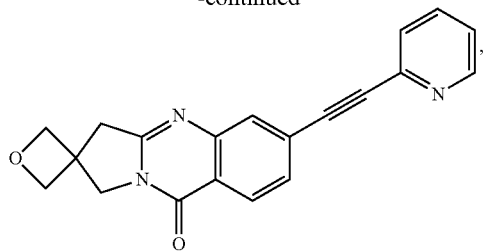

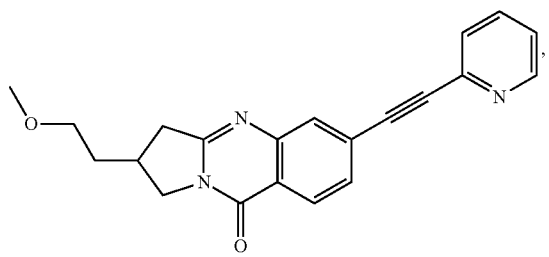

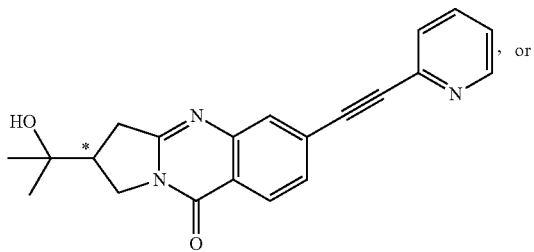

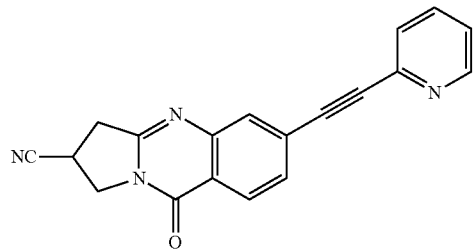

or

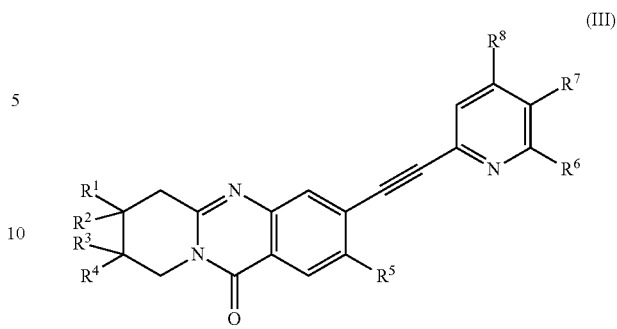

or a pharmaceutically acceptable salt thereof.

In certain embodiments, a compound of formula (III) or a pharmaceutically acceptable salt thereof is provided:

wherein $R^1$, $R^2$, $R^3$, and $R^4$ are each independently hydrogen, alkyl, hydroxyl, alkenyl, heteroalkyl, or cyano; or $R^1$ and $R^2$ or $R^3$ and $R^4$ together with the atom to which they are attached form a cycloalkyl or heterocycloalkyl ring; or $R^2$ and $R^3$ together with the atoms to which they are attached form a cycloalkyl ring;

$R^5$ is hydrogen or alkyl;

$R^6$, $R^7$, and $R^8$ are each independently hydrogen, CN, heteroalkyl, alkyl, or X; and X is F, Cl, Br, or I;

provided that $R^3$ and $R^4$ cannot together form =$CH_2$;

when $R^1$, $R^2$, $R^3$, and $R^4$ are all hydrogen, then at least one of $R^5$, $R^6$, $R^7$, and $R^8$ is not hydrogen;

when both $R^1$ and $R^2$ are methyl, then at least one of $R^3$, $R^4$, $R^5$, $R^6$, $R^7$, and $R^8$ is other than hydrogen;

when both $R^3$ and $R^4$ are methyl, then at least one of $R^1$, $R^2$, $R^5$, $R^6$, $R^7$, and $R^8$ is not hydrogen;

when one of $R^1$, $R^2$, $R^3$, and $R^4$ is methyl, and the other three of $R^1$, $R^2$, $R^3$, and $R^4$ are all hydrogen, then at least one of $R^5$, $R^6$, $R^7$, and $R^8$ is not hydrogen;

when one of $R^1$ and $R^2$ is hydroxymethyl or methoxymethyl and the other of $R^1$ and $R^2$ is hydrogen, then at least one of $R^3$, $R^4$, $R^5$, $R^6$, $R^7$, and $R^8$ is not hydrogen;

when one of $R^3$ and $R^4$ is hydroxymethyl, hydroxy, methoxy, methoxymethyl, or fluoro, and the other of $R^3$ and $R^4$ is hydrogen, then at least one of $R^1$, $R^2$, $R^5$, $R^6$, $R^7$, and $R^8$ is not hydrogen;

when one of $R^3$ and $R^4$ is methyl and the other of $R^3$ and $R^4$ is hydroxyl or methoxy, then at least one of $R^1$, $R^2$, $R^5$, $R^6$, $R^7$, and $R^8$ is not hydrogen;

when $R^3$ and $R^4$ are both F, then at least one of $R^1$, $R^2$, $R^5$, $R^6$, $R^7$, and $R^8$ is not hydrogen.

In certain embodiments, $R^6$, $R^7$, and $R^8$ are all hydrogen.

In certain embodiments, $R^1$ is hydrogen. In certain embodiments, $R^1$ is alkyl. In certain embodiments, $R^1$ is hydroxyl. In certain embodiments, $R^1$ is alkenyl. In certain embodiments, $R^1$ is heteroalkyl. In certain embodiments, $R^1$ is cyano.

In certain embodiments, $R^2$ is hydrogen. In certain embodiments, $R^2$ is alkyl. In certain embodiments, $R^2$ is hydroxyl. In certain embodiments, $R^2$ is alkenyl. In certain embodiments, $R^2$ is heteroalkyl. In certain embodiments, $R^2$ is cyano.

In certain embodiments, $R^3$ is hydrogen. In certain embodiments, $R^3$ is alkyl. In certain embodiments, $R^3$ is hydroxyl. In certain embodiments, $R^3$ is alkenyl. In certain embodiments, $R^3$ is heteroalkyl. In certain embodiments, $R^3$ is cyano.

In certain embodiments, $R^4$ is hydrogen. In certain embodiments, $R^4$ is alkyl. In certain embodiments, $R^4$ is hydroxyl. In certain embodiments, $R^4$ is alkenyl. In certain embodiments, $R^4$ is heteroalkyl. In certain embodiments, $R^4$ is cyano.

In certain embodiments, $R^1$ and $R^2$ together with the atom to which they are attached form a cycloalkyl ring. In certain embodiments, $R^1$ and $R^2$ together with the atom to which they are attached form a heterocycloalkyl ring.

In certain embodiments, $R^3$ and $R^4$ together with the atom to which they are attached form a cycloalkyl ring. In certain embodiments, $R^3$ and $R^4$ together with the atom to which they are attached form a heterocycloalkyl ring.

In certain embodiments, $R^2$ and $R^3$ together with the atoms to which they are attached form a cycloalkyl ring.

In certain embodiments, $R^5$ is hydrogen. In certain embodiments, $R^5$ is alkyl.

In certain embodiments, $R^6$ is hydrogen. In certain embodiments, $R^6$ is CN. In certain embodiments, $R^6$ is heteroalkyl. In certain embodiments, $R^6$ is alkyl. In certain embodiments, $R^6$ is X.

In certain embodiments, $R^7$ is hydrogen. In certain embodiments, $R^7$ is CN. In certain embodiments, $R^7$ is heteroalkyl. In certain embodiments, $R^7$ is alkyl. In certain embodiments, $R^7$ is X.

In certain embodiments, $R^8$ is hydrogen. In certain embodiments, $R^8$ is CN. In certain embodiments, $R^8$ is heteroalkyl. In certain embodiments, $R^8$ is alkyl. In certain embodiments, $R^8$ is X.

In certain embodiments, X is F. In certain embodiments, X is Cl. In certain embodiments, X is Br. In certain embodiments, X is I.

In certain embodiments, a compound of formula (III) is

-continued

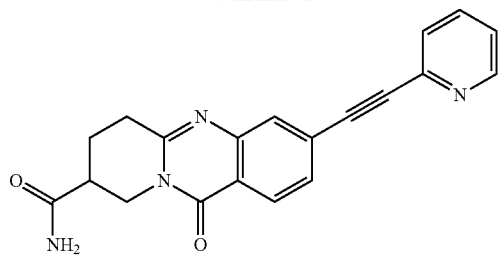

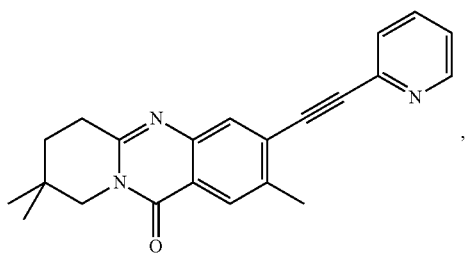

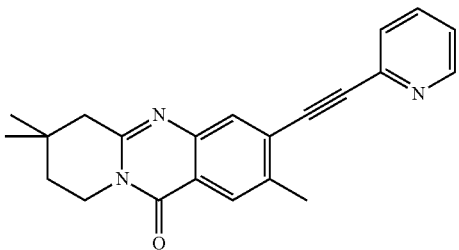

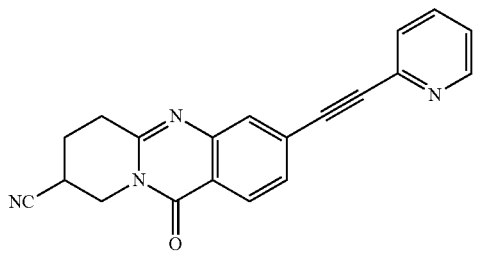

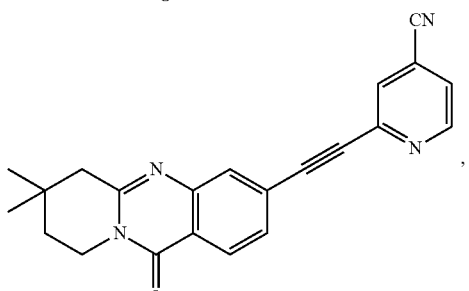

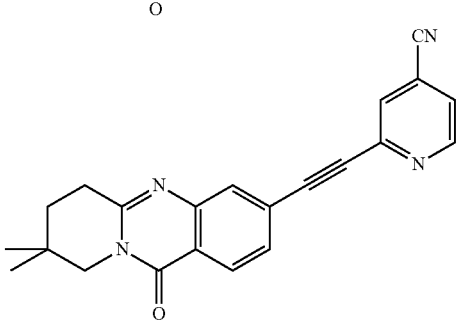

-continued
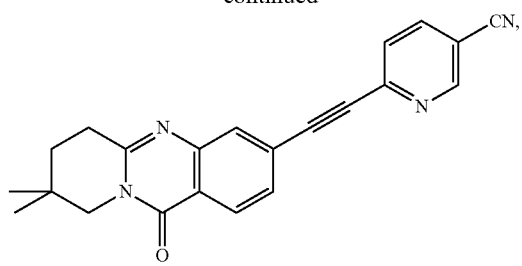
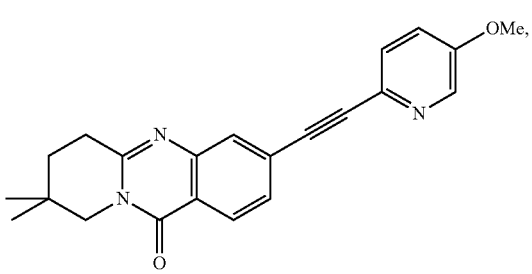
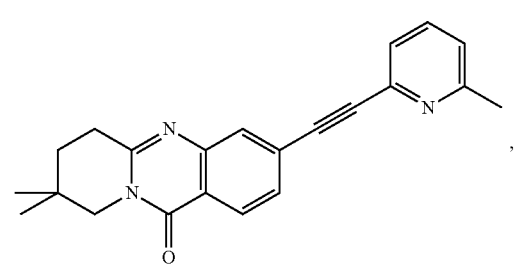
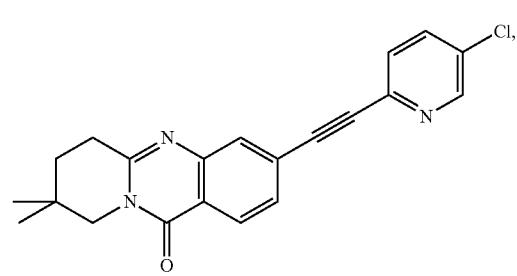
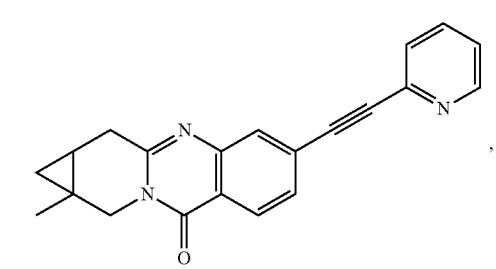
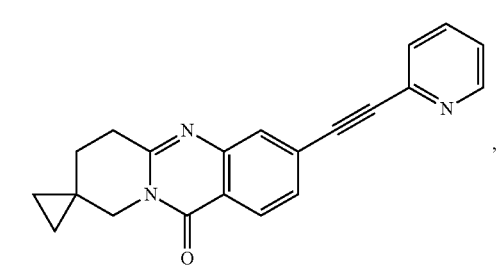
-continued
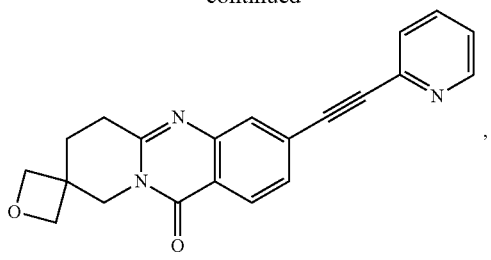
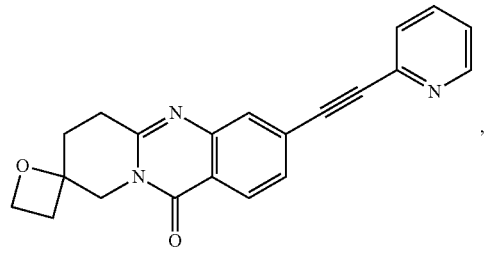
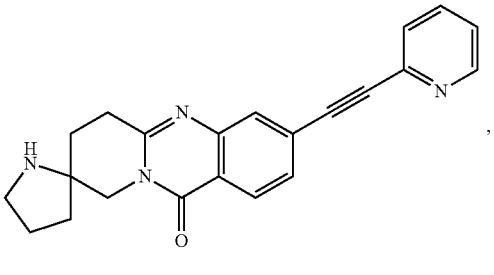
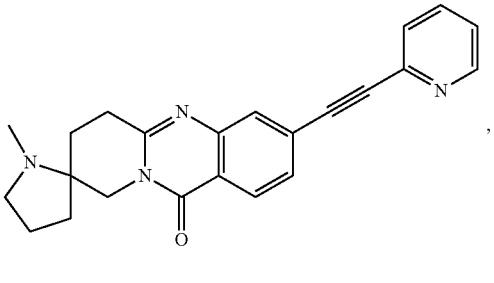
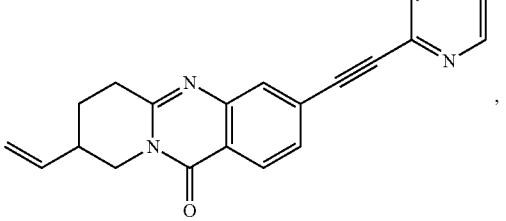, or
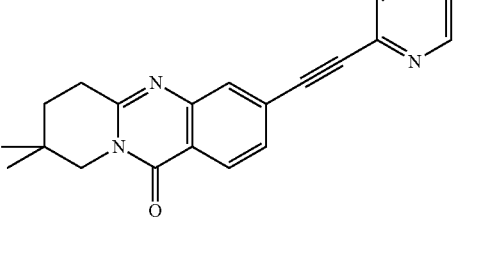
or a pharmaceutically acceptable salt thereof.

In certain embodiments, a compound of formula (III) is

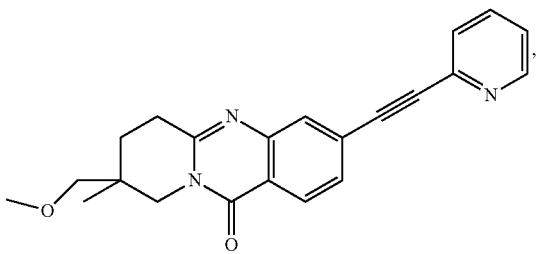,

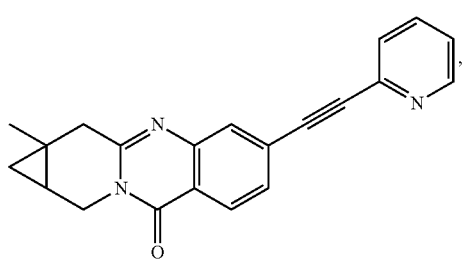,

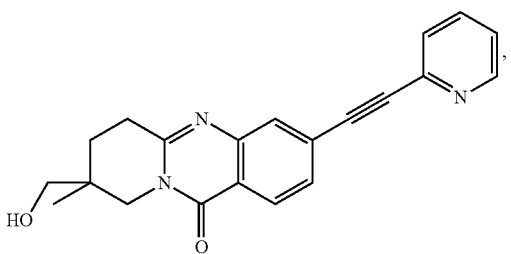,

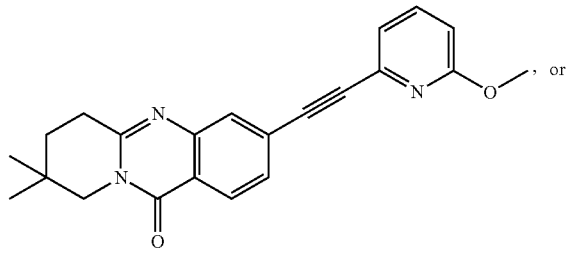, or

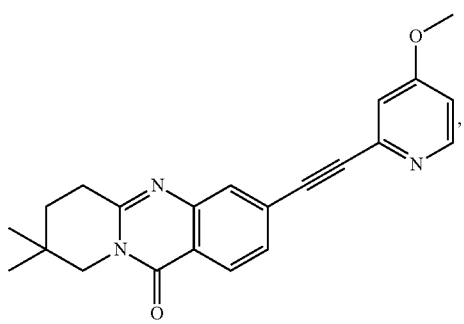, or a pharmaceutically acceptable salt thereof.

In certain embodiments, a compound of formula (IV) or a pharmaceutically acceptable salt thereof is provided:

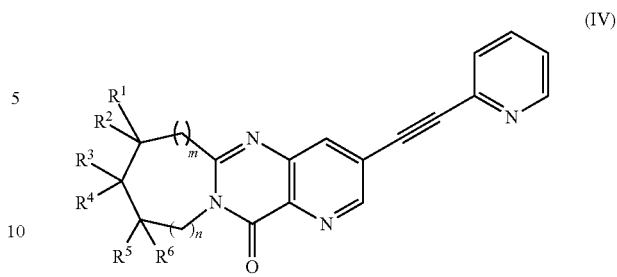

wherein
m and n are each independently 0 or 1;
$R^1$, $R^2$, $R^3$, $R^4$, $R^5$, and $R^6$ are each independently hydrogen, alkyl, or heteroalkyl; or
$R^1$ and $R^2$, $R^3$ and $R^4$, or $R^5$ and $R^6$ together with the atom to which they are bonded form a cycloalkyl or heterocycloalkyl ring;
provided that
at least one of $R^1$, $R^2$, $R^3$, $R^4$, $R^5$, and $R^6$ is not hydrogen;
when in and n are both 1 or both m and n are 0, one of $R^3$ and $R^4$ is methyl, and the other of $R^3$ and $R^4$ is hydrogen, then at least one of $R^1$, $R^2$, $R^5$, and $R^6$ is not hydrogen;
when m is 0, n is 1, and both $R^5$ and $R^6$ are methyl, then at least one of $R^1$, $R^2$, $R^3$, and $R^4$ is not hydrogen;
when m is 1, n is 0, and both $R^3$ and $R^4$ are methyl, then at least one of $R^1$, $R^2$, $R^5$, and $R^6$ is not hydrogen;
when m and n are both 0 and both $R^3$ and $R^4$ are methyl, then at least one of $R^1$, $R^2$, $R^5$ and $R^6$ is not hydrogen; and
when m and n are both 0, one of $R^5$ and $R^6$ is hydroxymethyl or methoxymethyl, and the other of $R^5$ and $R^6$ is hydrogen, then at least one of $R^1$, $R^2$, $R^3$, and $R^4$ is not hydrogen.

In certain embodiments, $R^1$, $R^2$, $R^3$, $R^4$, $R^5$, and $R^6$ do not comprise any halogen atoms.

In certain embodiments, m is 0. In certain embodiments, m is 1. In certain embodiments, n is 0. In certain embodiments, n is 1.

In certain embodiments, $R^1$ is hydrogen. In certain embodiments, $R^1$ is alkyl. In certain embodiments, $R^1$ is heteroalkyl.

In certain embodiments, $R^2$ is hydrogen. In certain embodiments, $R^2$ is alkyl. In certain embodiments, $R^2$ is heteroalkyl.

In certain embodiments, $R^3$ is hydrogen. In certain embodiments, $R^3$ is alkyl. In certain embodiments, $R^3$ is heteroalkyl.

In certain embodiments, $R^4$ is hydrogen. In certain embodiments, $R^4$ is alkyl. In certain embodiments, $R^4$ is heteroalkyl.

In certain embodiments, $R^5$ is hydrogen. In certain embodiments, $R^5$ is alkyl. In certain embodiments, $R^5$ is heteroalkyl.

In certain embodiments, $R^6$ is hydrogen. In certain embodiments, $R^6$ is alkyl. In certain embodiments, $R^6$ is heteroalkyl.

In certain embodiments, $R^1$ and $R^2$ together with the atom to which they are bonded form a cycloalkyl ring. In certain embodiments, $R^1$ and $R^2$ together with the atom to which they are bonded form a heterocycloalkyl ring.

In certain embodiments, $R^3$ and $R^4$ together with the atom to which they are bonded form a cycloalkyl ring. In certain embodiments, $R^3$ and $R^4$ together with the atom to which they are bonded form a heterocycloalkyl ring.

In certain embodiments, $R^5$ and $R^6$ together with the atom to which they are bonded form a cycloalkyl ring. In certain embodiments, $R^5$ and $R^6$ together with the atom to which they are bonded form a heterocycloalkyl ring.

In certain embodiments, a compound of Formula (IV) is

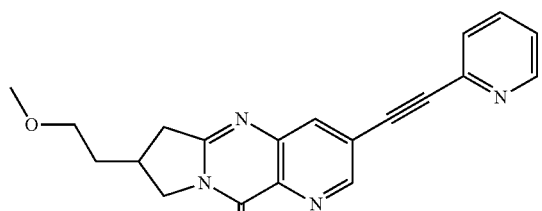,

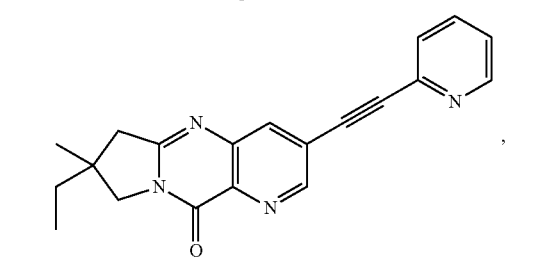,

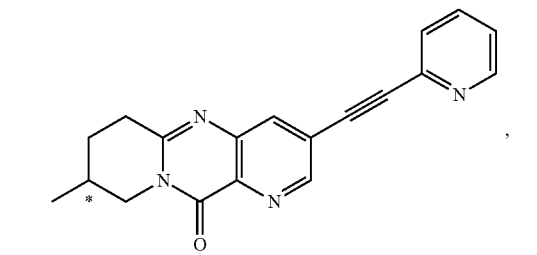,

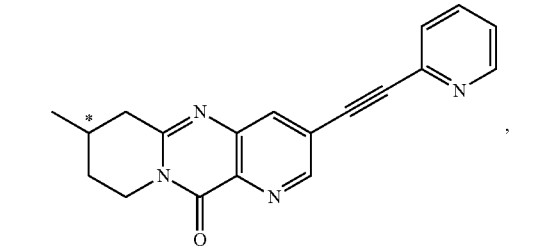,

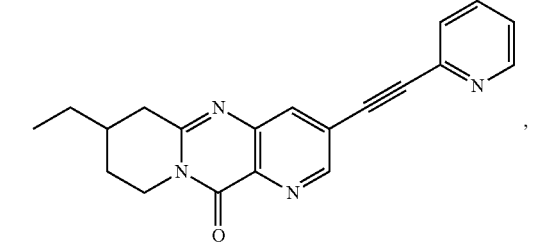,

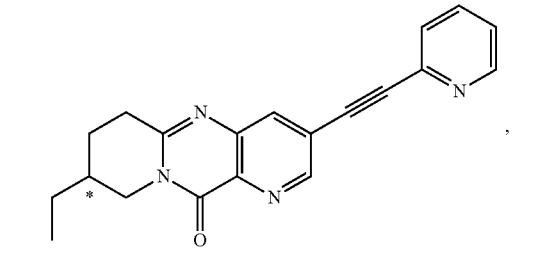,

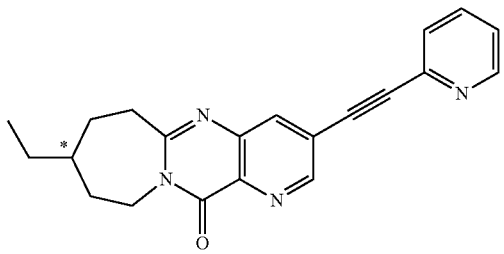,

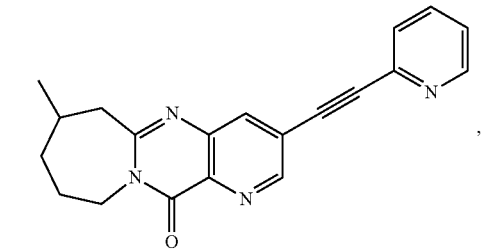,

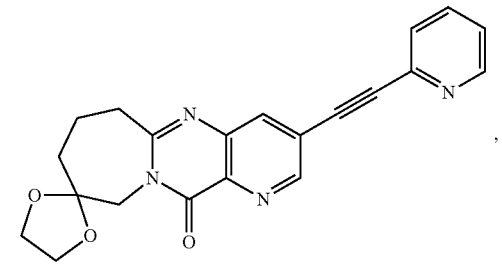,

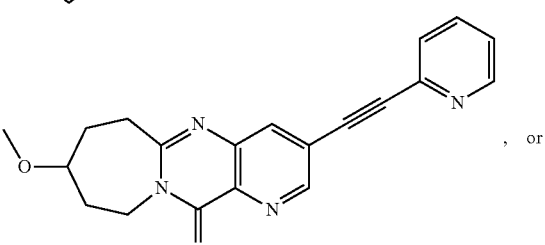,

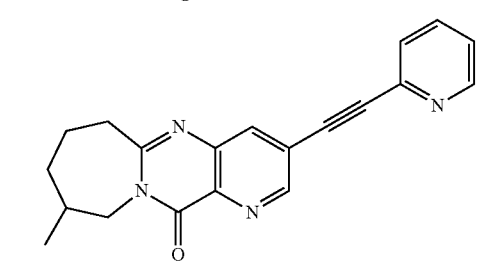, or

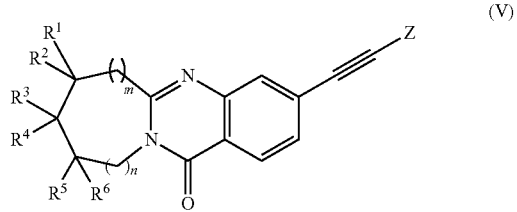

or a pharmaceutically acceptable salt thereof.

In certain embodiments, a compound of formula (V) or a pharmaceutically acceptable salt thereof is provided:

$$\text{(V)}$$

wherein
m and n are independently 0 or 1;
Z is

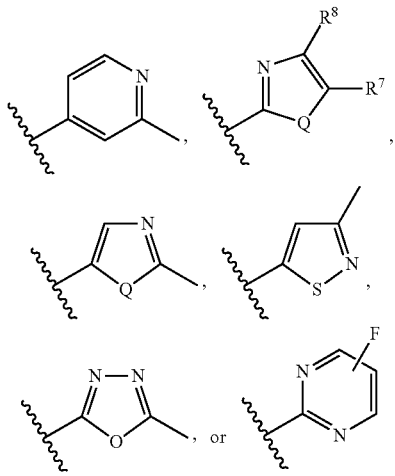

$R^1$, $R^2$, $R^3$, $R^4$, $R^5$, and $R^6$ are each independently hydrogen or alkyl;

Q is O or S;

$R^7$ and $R^8$ are hydrogen or alkyl; or $R^7$ and $R^8$ together with the atoms to which they are attached form a cycloalkyl, heterocycloalkyl, aryl, or heteroaryl ring; provided that when m is 1, n is 1, Z is

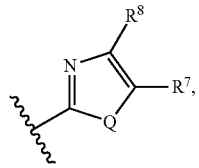

Q is S, $R^7$ is methyl and $R^8$ is hydrogen, one of $R^3$ and $R^4$ is methyl, and the other of $R^3$ and $R^4$ is hydrogen, then at least one of $R^1$, $R^2$, $R^5$ and $R^6$ is not hydrogen.

In certain embodiments, Z is

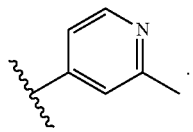 [SMILES: *c1ccnc(C)c1]

In certain embodiments, Z is

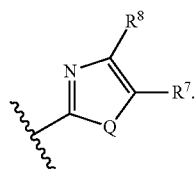

In certain embodiments, Z is

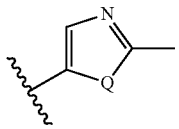

In certain embodiments, Z is

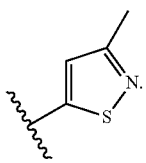 [SMILES: *c1cc(C)ns1]

In certain embodiments, Z is

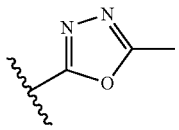

In certain embodiments, Z is

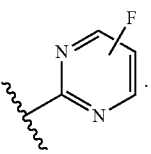

In certain embodiments, $R^1$ is hydrogen. In certain embodiments, $R^1$ is alkyl.

In certain embodiments, $R^2$ is hydrogen. In certain embodiments, $R^2$ is alkyl.

In certain embodiments, $R^3$ is hydrogen. In certain embodiments, $R^3$ is alkyl.

In certain embodiments, $R^4$ is hydrogen. In certain embodiments, $R^4$ is alkyl.

In certain embodiments, $R^5$ is hydrogen. In certain embodiments, $R^5$ is alkyl In certain embodiments, $R^6$ is hydrogen. In certain embodiments, $R^6$ is alkyl In certain embodiments, $R^7$ is hydrogen. In certain embodiments, $R^7$ is alkyl.

In certain embodiments, $R^8$ is hydrogen. In certain embodiments, $R^8$ is alkyl.

In certain embodiments, $R^7$ and $R^8$ together with the atoms to which they are attached form a cycloalkyl ring. In certain embodiments, $R^7$ and $R^8$ together with the atoms to which they are attached form a heterocycloalkyl ring. In certain embodiments, $R^7$ and $R^8$ together with the atoms to which they are attached form an aryl ring. In certain embodiments, $R^7$ and $R^8$ together with the atoms to which they are attached form a heteroaryl ring.

In certain embodiments, a compound of Formula (V) is
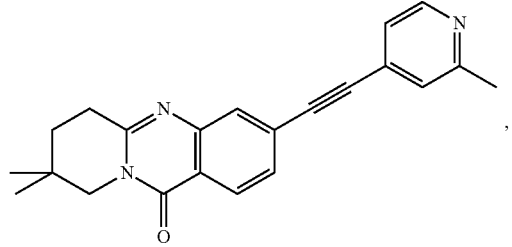
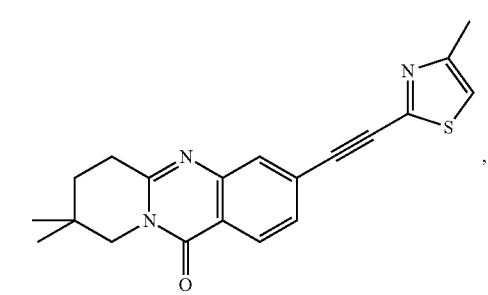
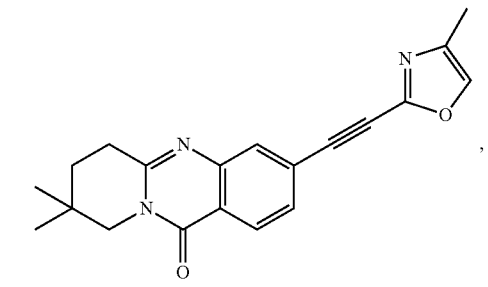
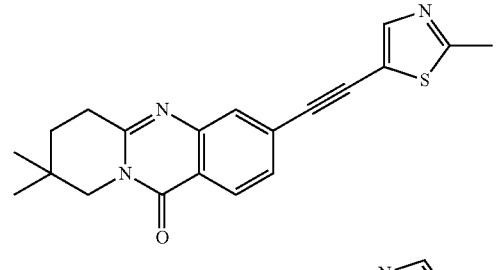
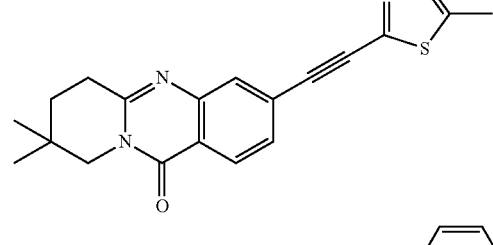
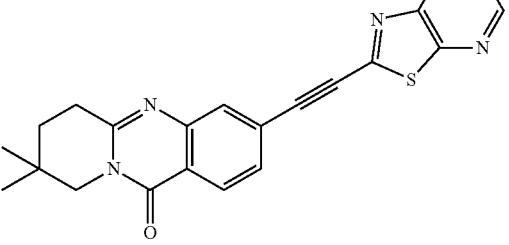
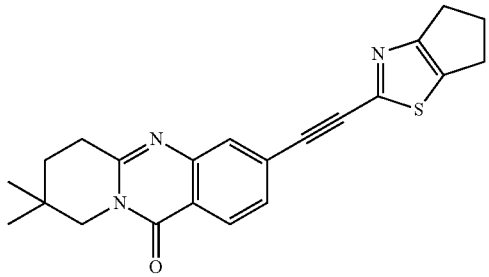
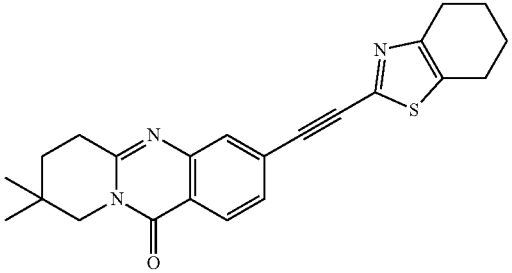
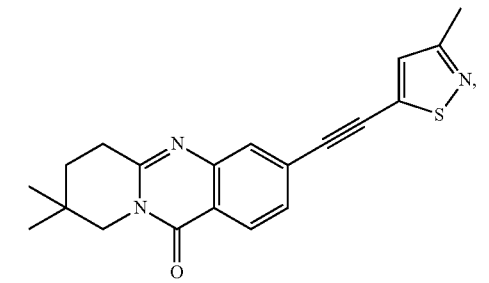
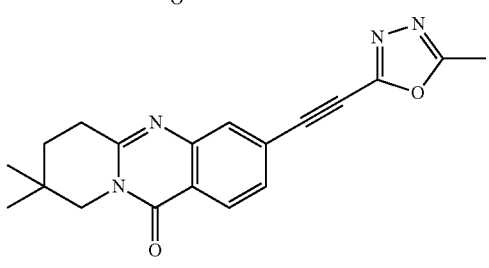
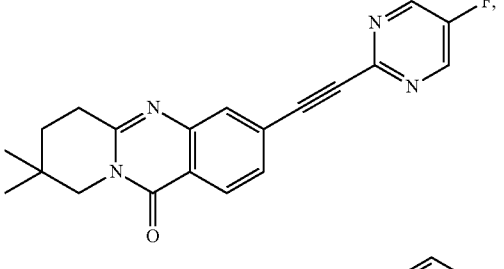
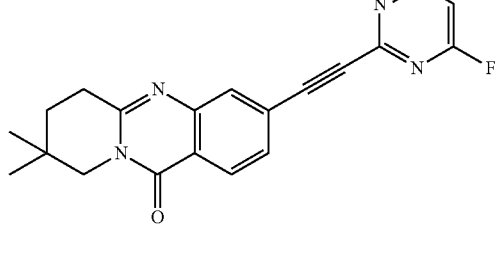
or a pharmaceutically acceptable salt thereof.
In certain embodiments, a compound of formula (VI) or a pharmaceutically acceptable salt thereof is provided:

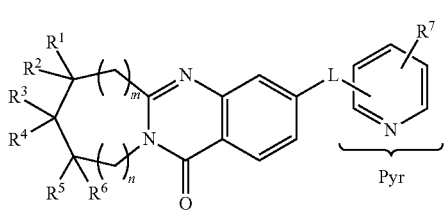

(VI)

wherein
m and n are independently 0 or 1;
L is —R$^8$C=CR$^8$—, —OC(R$^9$)$_2$—, C(O)NR$^{10}$—, or —NR$^{10}$C(O)—;
X is F, Cl, Br, or I;
R$^1$, R$^2$, R$^3$, R$^4$, R$^5$, and R$^6$ are each independently hydrogen, alkyl, or X;
R$^7$ is hydrogen or cyano;
each R$^8$ is hydrogen or X;
R$^9$ and R$^{10}$ are each independently hydrogen or alkyl;
provided that
when m is 0, n is 0, L is —HC=CH—, one of R$^3$ and R$^4$ is methyl, the other of R$^3$ and R$^4$ is hydrogen, R$^1$, R$^2$, R$^5$, and R$^6$ are all hydrogen, and R$^7$ is hydrogen, then Pyr is not 2-pyridyl;
when m is 0, n is 1, L is —HC=CH—, R$^1$, R$^2$, R$^3$, and R$^4$ are all hydrogen, R$^5$ and R$^6$ are both methyl, and R$^7$ is hydrogen or cyano, then Pyr is not 2-pyridyl, preferably Pyr is not

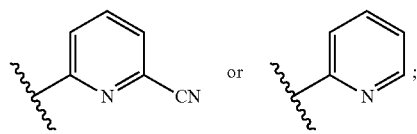 [SMILES: *c1cccc(C#N)n1 ; *c1ccccn1]

when m is 1, n is 0, L is —HC=CH—, R$^1$, R$^2$, R$^5$, and R$^6$ are all hydrogen, R$^3$ and R$^4$ are both methyl, and R$^7$ is hydrogen or cyano, then Pyr is not 2-pyridyl, preferably Pyr is not

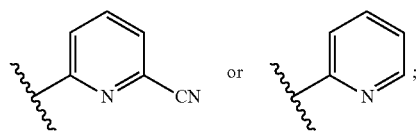 [SMILES: *c1cccc(C#N)n1 ; *c1ccccn1]

when m is 0, n is 1, L is —HC=CH—, R$^1$, R$^2$, R$^5$, and R$^6$ are all hydrogen, R$^3$ and R$^4$ are both methyl, and R$^7$ is hydrogen or cyano, then Pyr is not then Pyr is not 2-pyridyl, preferably Pyr is not

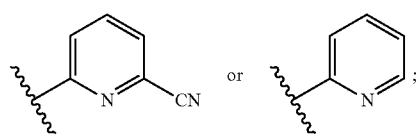 [SMILES: *c1cccc(C#N)n1 ; *c1ccccn1]

when m is 1, n is 0, L is —HC=CH—, R$^3$, R$^4$, R$^5$, and R$^6$ are all hydrogen, R$^1$ and R$^2$ are both methyl, and R$^7$ is hydrogen or cyano, then Pyr is not then Pyr is not 2-pyridyl, preferably Pyr is not

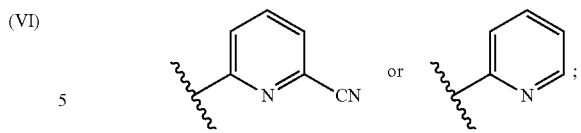

when m is 1, n is 1, L is —HC=CH—, one of R$^3$ and R$^4$ is methyl, the other of R$^3$ and R$^4$ is hydrogen, R$^1$, R$^2$, R$^5$, and R$^6$ are all hydrogen, and R$^7$ is hydrogen or cyano, then Pyr is not then Pyr is not 2-pyridyl, preferably Pyr is not

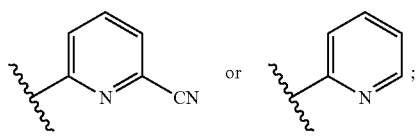 [SMILES: *c1cccc(C#N)n1 ; *c1ccccn1]

and
when m is 1, n is 1, L is —HC=CH—, R$^1$, R$^2$, R$^3$, R$^4$, R$^5$, R$^6$, and R$^7$ are all hydrogen, then Pyr is not 2-pyridyl.

In certain embodiments, m is 0. In certain embodiments, n is 1. In certain embodiments, n is 0. In certain embodiments, n is 1.

In certain embodiments, L is —R$^8$C=CR$^8$—. In certain embodiments, L is —OC(R$^9$)$_2$—. In certain embodiments, L is C(O)NR$^{10}$—. In certain embodiments, L is —NR$^{10}$C(O)—.

In certain embodiments, X is F. In certain embodiments, X is Cl. In certain embodiments, X is Br. In certain embodiments, X is I.

In certain embodiments, R$^1$ is hydrogen. In certain embodiments, R$^1$ is alkyl. In certain embodiments, R$^1$ is X.

In certain embodiments, R$^2$ is hydrogen. In certain embodiments, R$^2$ is alkyl. In certain embodiments, R$^2$ is X.

In certain embodiments, R$^3$ is hydrogen. In certain embodiments, R$^3$ is alkyl. In certain embodiments, R$^3$ is X.

In certain embodiments, R$^4$ is hydrogen. In certain embodiments, R$^4$ is alkyl. In certain embodiments, R$^4$ is X.

In certain embodiments, R$^5$ is hydrogen. In certain embodiments, R$^5$ is alkyl. In certain embodiments, R$^5$ is X.

In certain embodiments, R$^6$ is hydrogen. In certain embodiments, R$^6$ is alkyl. In certain embodiments, R$^6$ is X.

In certain embodiments, R$^7$ is hydrogen. In certain embodiments, R$^7$ is cyano.

In certain embodiments, R$^8$ is hydrogen. In certain embodiments, R$^8$ is X.

In certain embodiments, R$^9$ is hydrogen. In certain embodiments, R$^9$ is alkyl.

In certain embodiments, R$^{10}$ is alkyl. In certain embodiments, R$^{10}$ is hydrogen.

In certain embodiments, a compound of Formula (VI) is

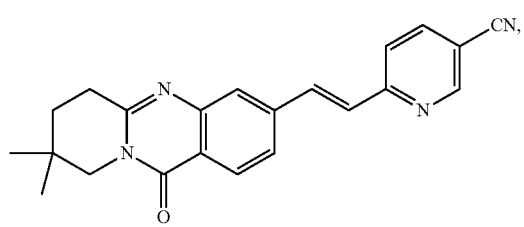

47
-continued
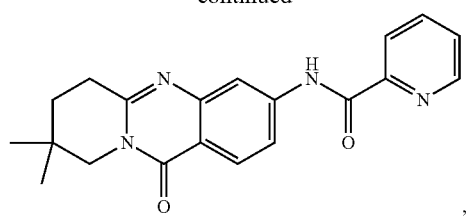
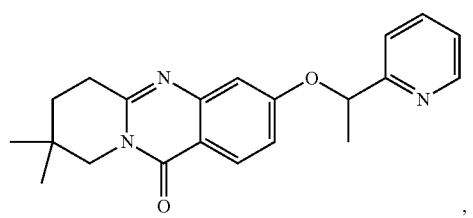
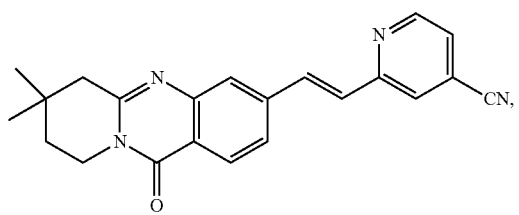
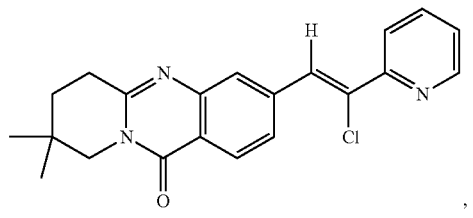
48
-continued
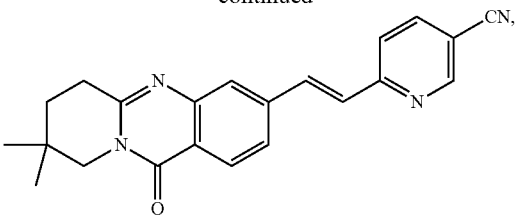
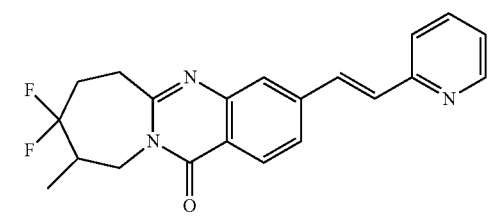
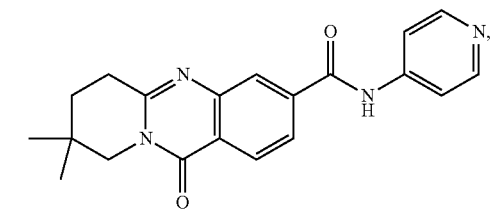
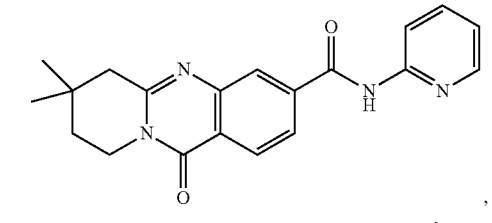

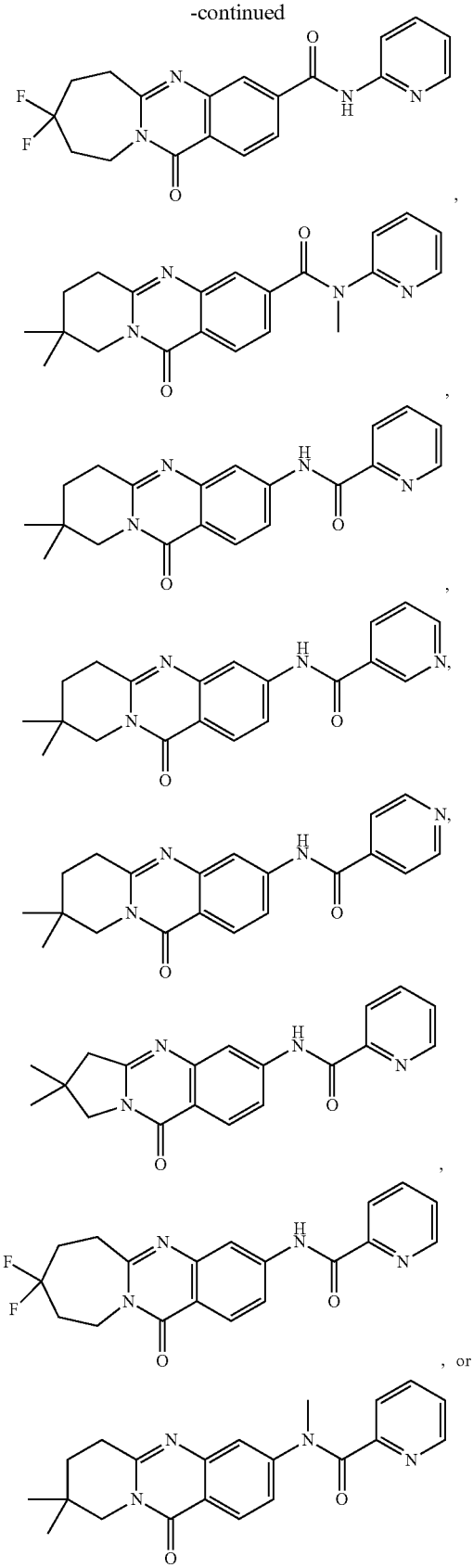
, or a pharmaceutically acceptable salt thereof.
In certain embodiments, a compound of formula (VII) or a pharmaceutically acceptable salt thereof is provided:
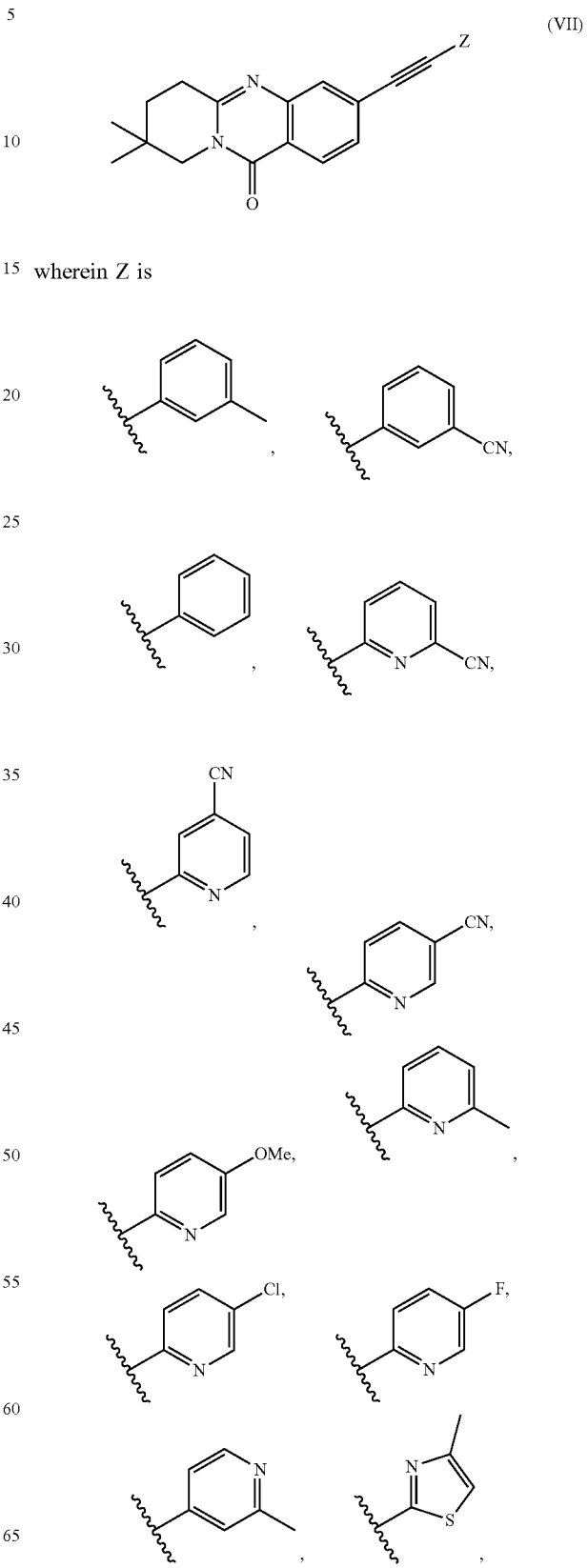
wherein Z is -continued
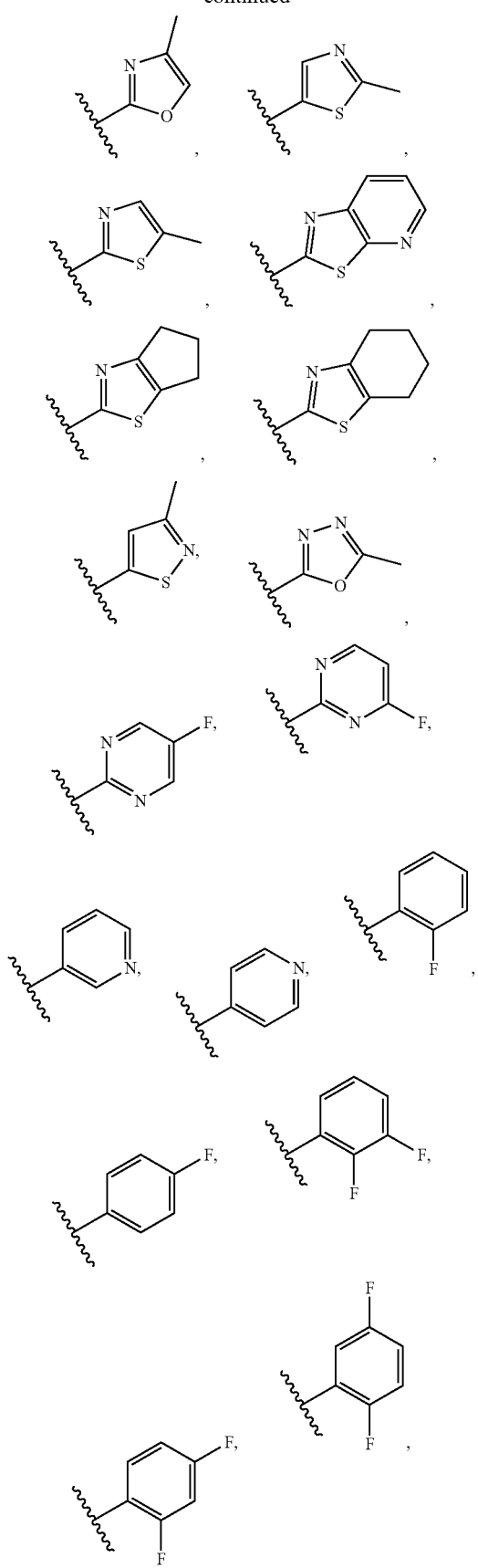
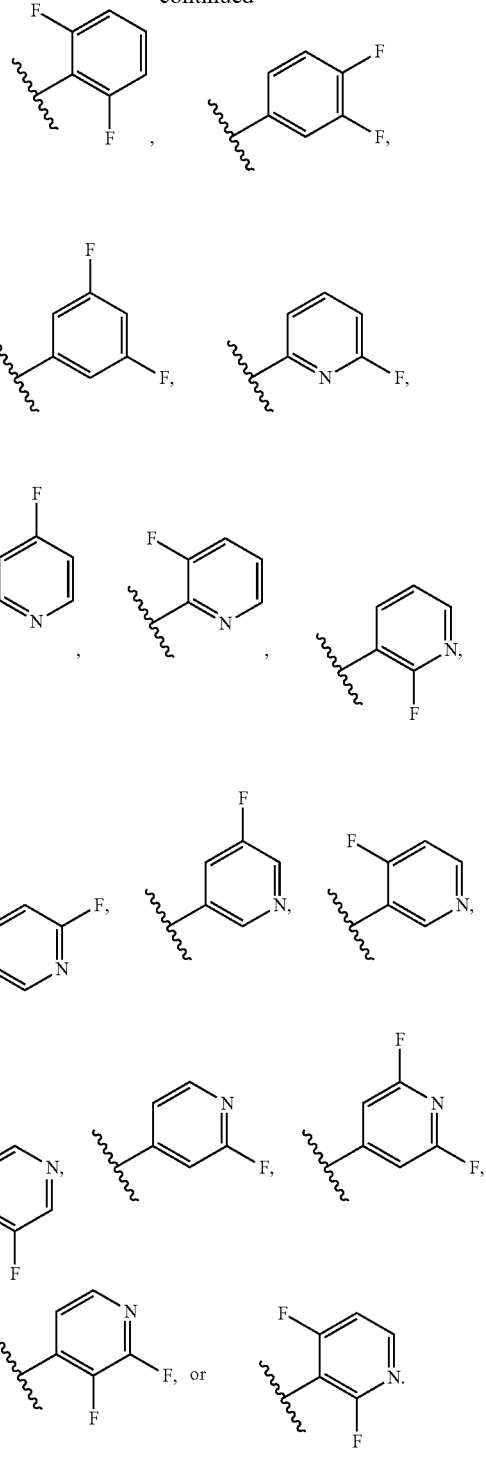
In certain embodiments, Z is
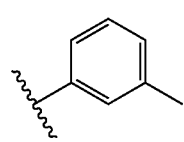

In certain embodiments, Z is

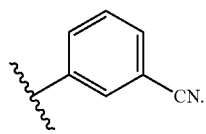 [SMILES: *c1cccc(C#N)c1]

In certain embodiments, Z is

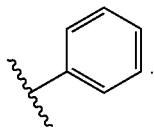 [SMILES: *c1ccccc1]

In certain embodiments, Z is

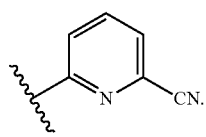 [SMILES: *c1cccc(C#N)n1]

In certain embodiments, Z is

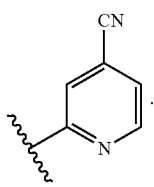 [SMILES: *c1cc(C#N)ccn1]

In certain embodiments, Z is

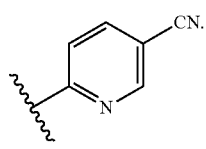 [SMILES: *c1ccc(C#N)cn1]

In certain embodiments, Z is

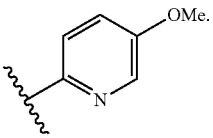 [SMILES: *c1ccc(OC)cn1]

In certain embodiments, Z is

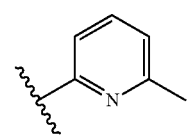

In certain embodiments, Z is

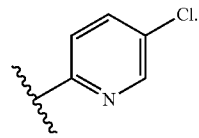 [SMILES: *c1ccc(Cl)cn1]

In certain embodiments, Z is

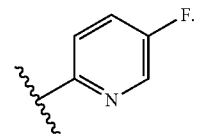 [SMILES: *c1ccc(F)cn1]

In certain embodiments, Z is

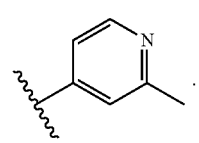 [SMILES: *c1ccnc(C)c1]

In certain embodiments, Z is

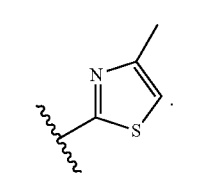

In certain embodiments, Z is

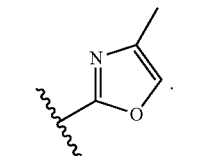

In certain embodiments, Z is

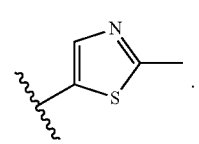 [SMILES: *c1cnc(C)s1]

In certain embodiments, Z is

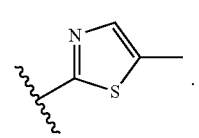 [SMILES: *c1ncc(C)s1]

In certain embodiments, Z is
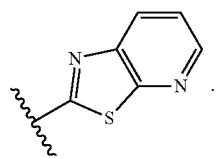 [SMILES: *c1nc2cccnc2s1]
In certain embodiments, Z is
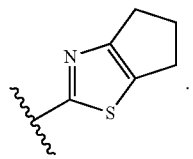 [SMILES: *c1nc2c(s1)CCC2]
In certain embodiments, Z is
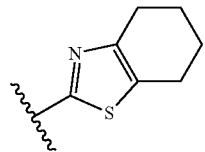
In certain embodiments, Z is
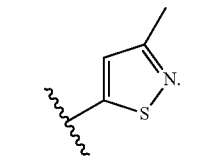 [SMILES: *c1cc(C)ns1]
In certain embodiments, Z is
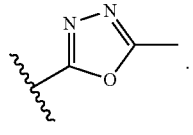 [SMILES: *c1nnc(C)o1]
In certain embodiments, Z is
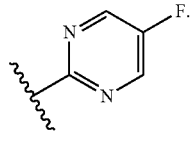 [SMILES: *c1ncc(F)cn1]
In certain embodiments, Z is
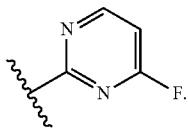 [SMILES: *c1nccc(F)n1]
In certain embodiments, Z is
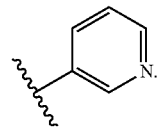
In certain embodiments, Z is
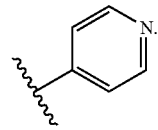
In certain embodiments, Z is
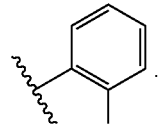
In certain embodiments, Z is
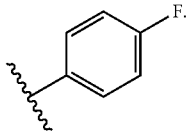 [SMILES: *c1ccc(F)cc1]
In certain embodiments, Z is
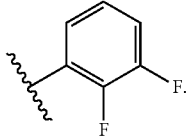 [SMILES: *c1cccc(F)c1F]
In certain embodiments, Z is
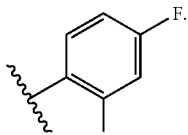

In certain embodiments, Z is
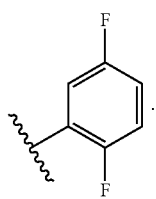 [SMILES: *c1cc(F)ccc1F]
In certain embodiments, Z is
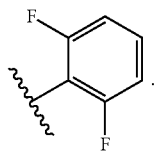 [SMILES: *c1c(F)cccc1F]
In certain embodiments, Z is
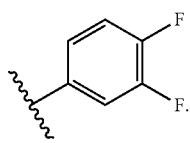 [SMILES: *c1ccc(F)c(F)c1]
In certain embodiments, Z is
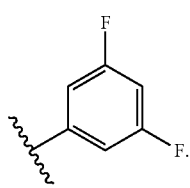 [SMILES: *c1cc(F)cc(F)c1]
In certain embodiments, Z is
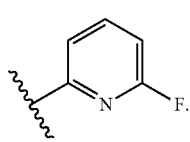 [SMILES: *c1cccc(F)n1]
In certain embodiments, Z is
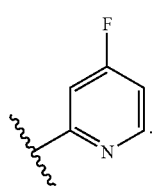 [SMILES: *c1cc(F)ccn1]
In certain embodiments, Z is
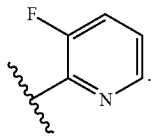
In certain embodiments, Z is
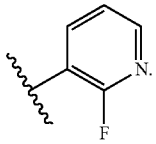
In certain embodiments, Z is
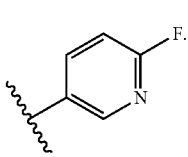 [SMILES: *c1ccc(F)nc1]
In certain embodiments, Z is
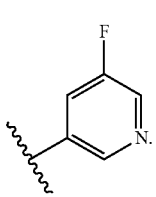 [SMILES: *c1cncc(F)c1]
In certain embodiments, Z is
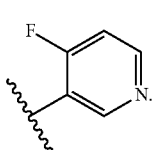
In certain embodiments, Z is
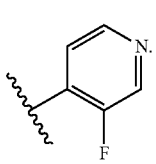 [SMILES: *c1ccncc1F]
In certain embodiments, Z is
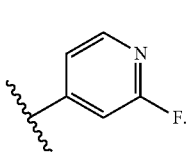 [SMILES: *c1ccnc(F)c1]

In certain embodiments, Z is
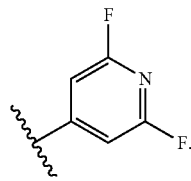 [SMILES: *c1cc(F)nc(F)c1]
In certain embodiments, Z is
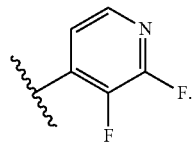 [SMILES: *c1ccnc(F)c1F]
In certain embodiments, Z is
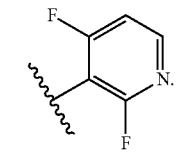 [SMILES: *c1c(F)ccnc1F]
In certain embodiments, a compound of Formula (VII) is
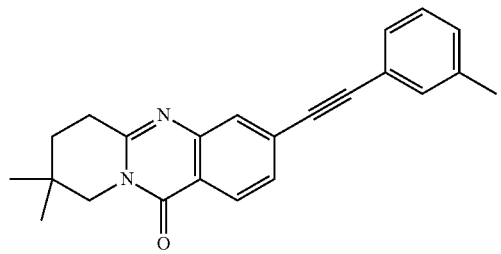
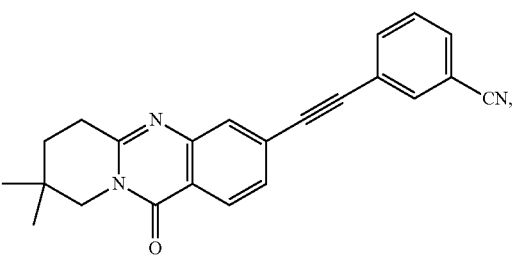
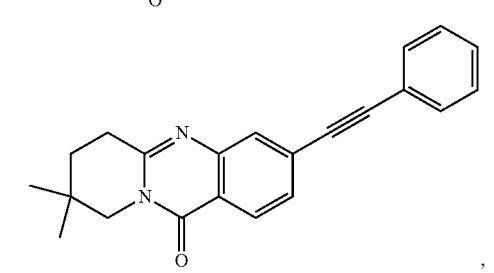
-continued
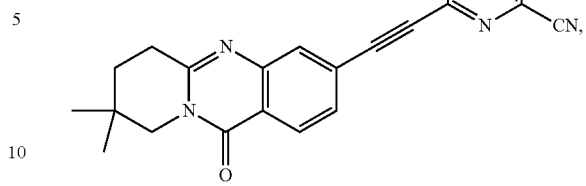
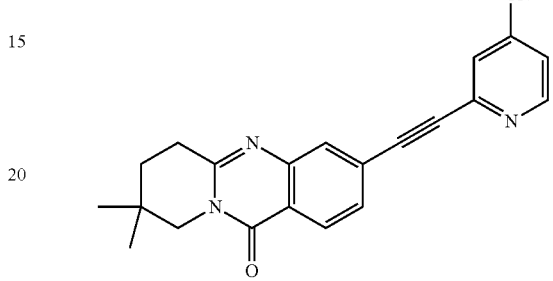
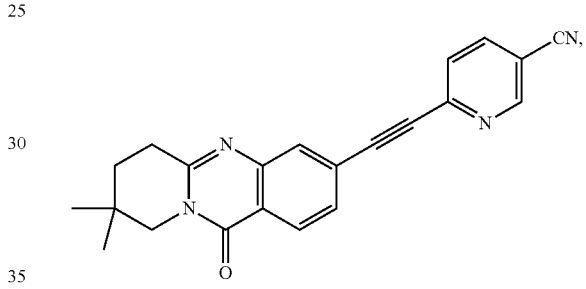
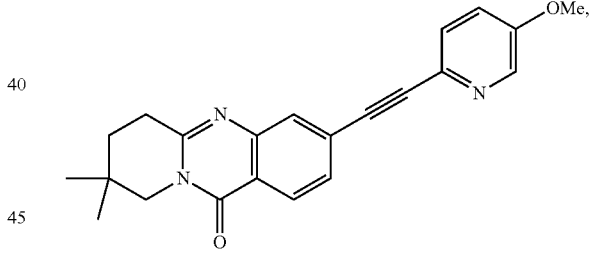
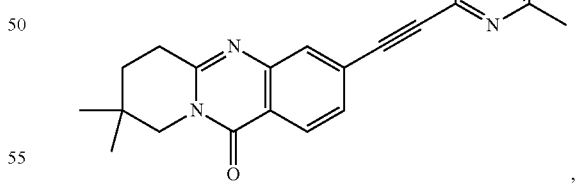
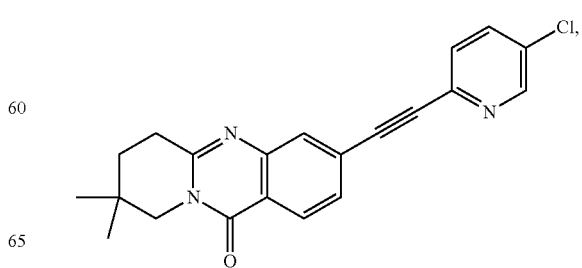

61
-continued
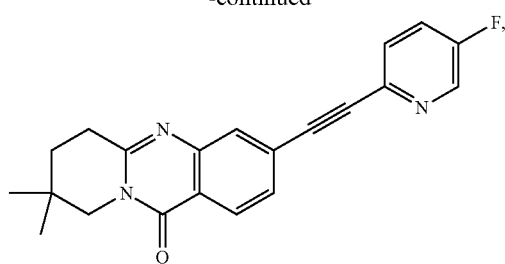,
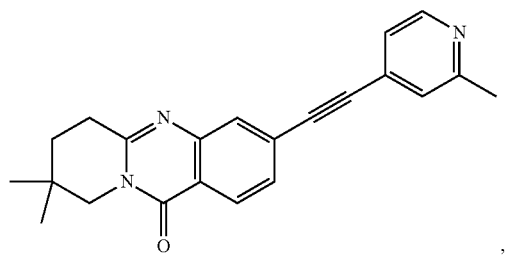,
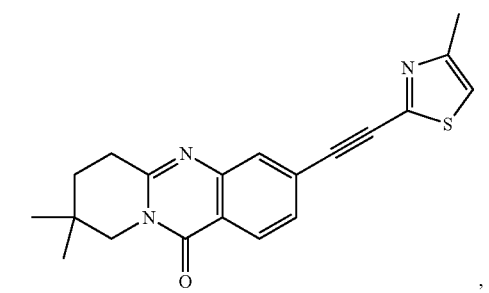,
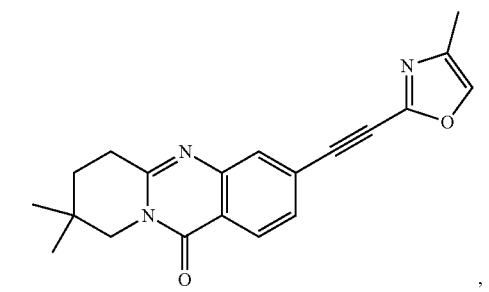,
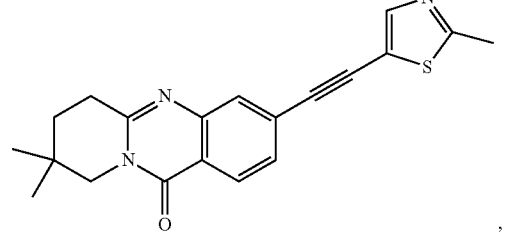,
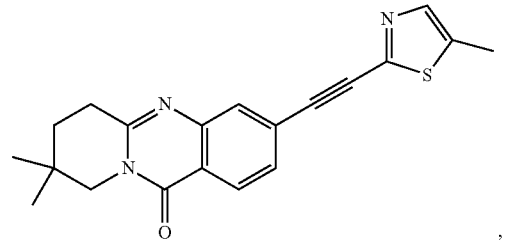,
62
-continued
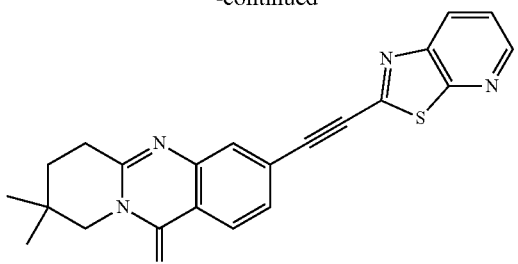,
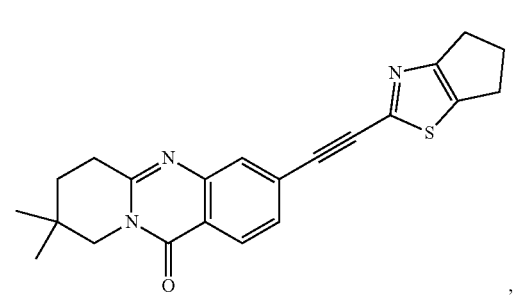,
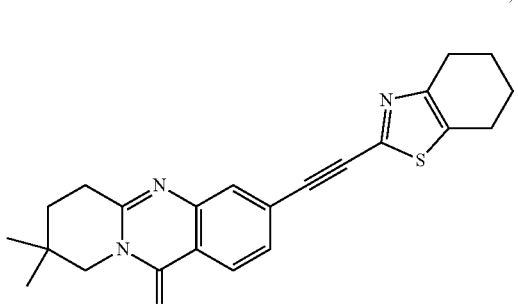,
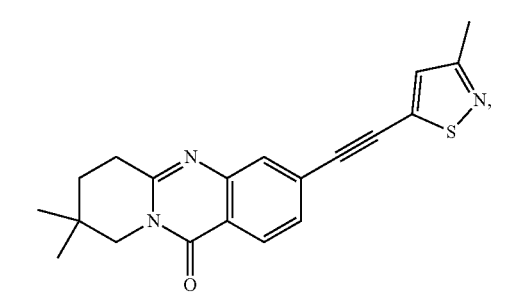,
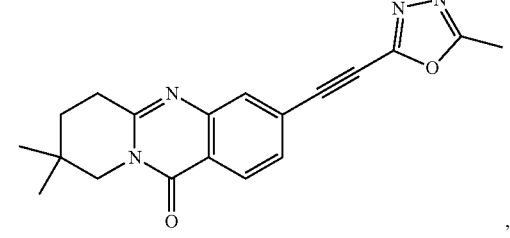,
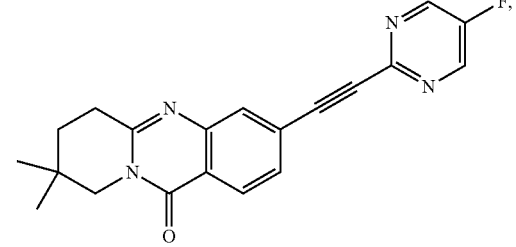,

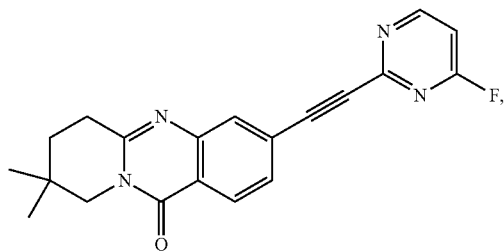
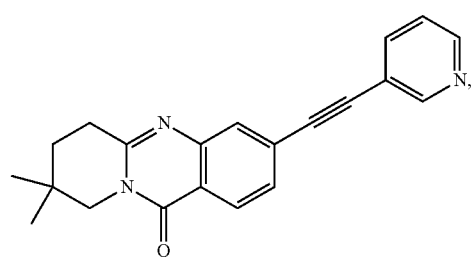
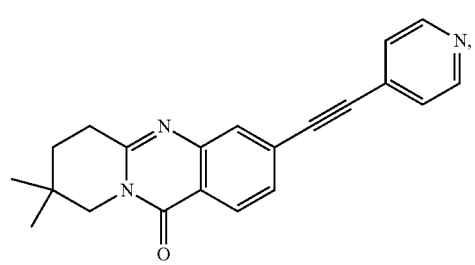
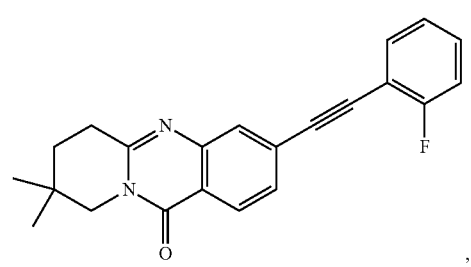
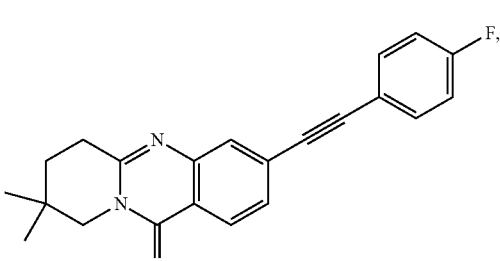
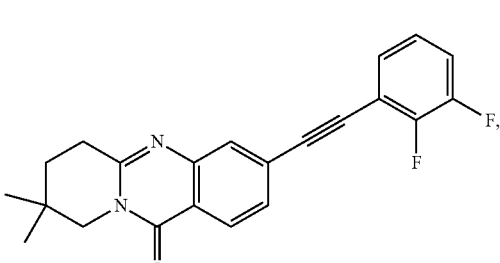
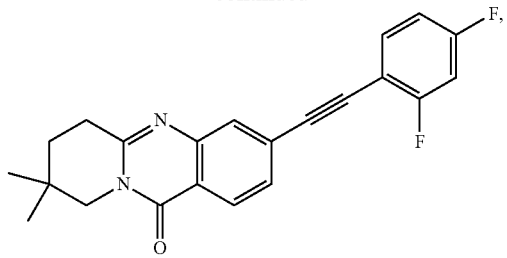
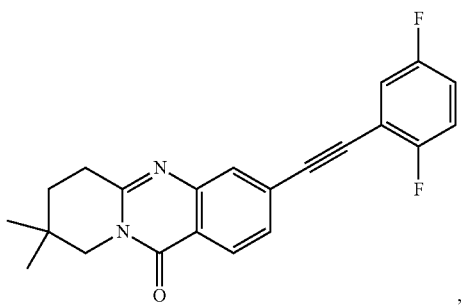
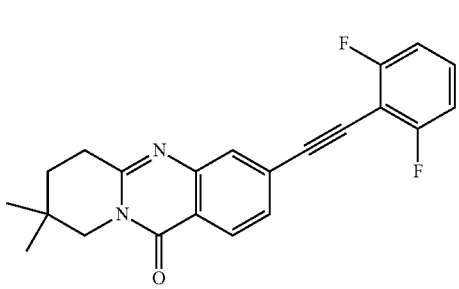
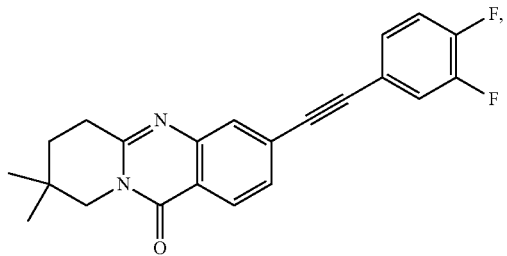
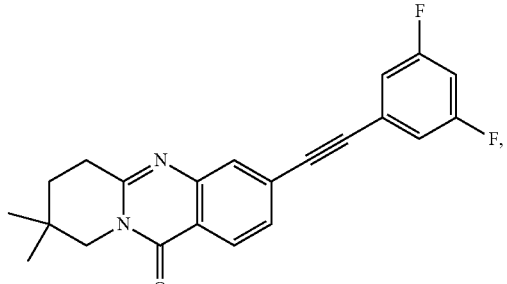
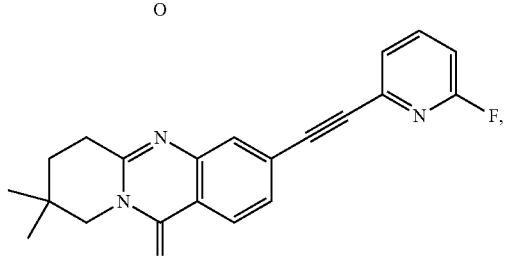

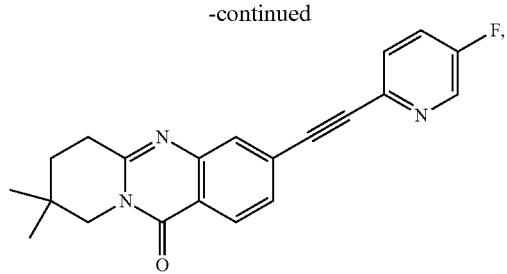
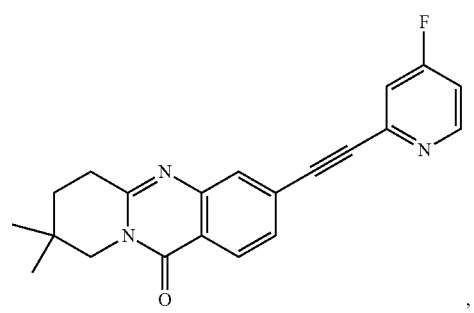
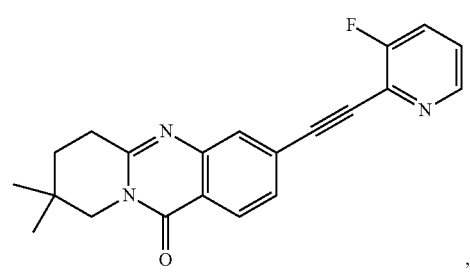
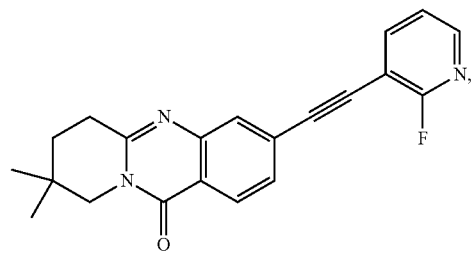
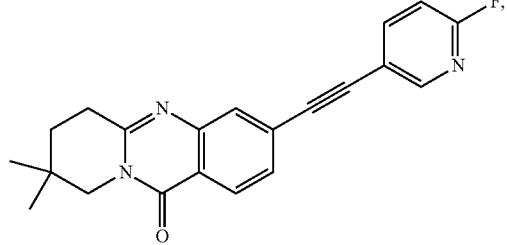
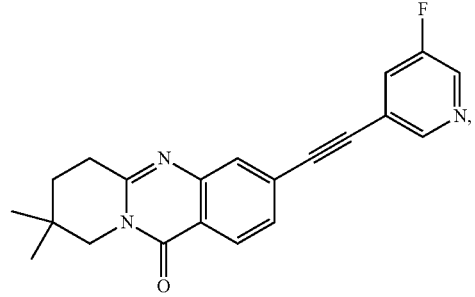
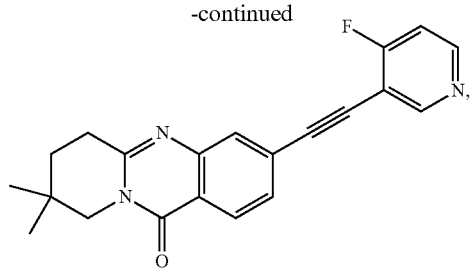
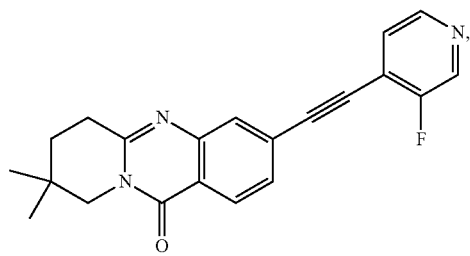
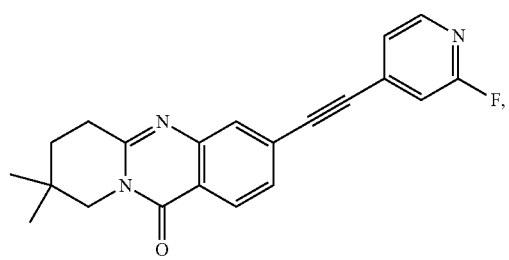
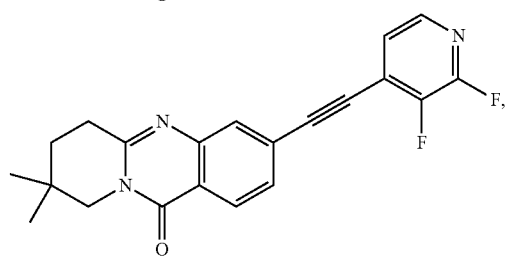
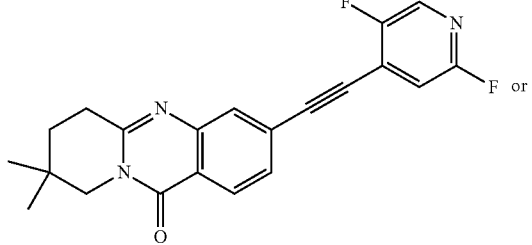
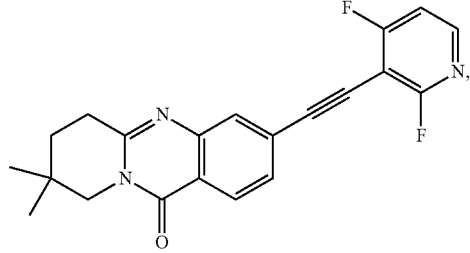
or a pharmaceutically acceptable salt thereof.
In certain embodiments, a compound of formula (VIII) or a pharmaceutically acceptable salt thereof is provided:

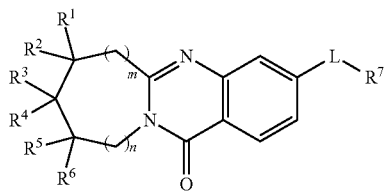

(VIII)

wherein m and n are independently 0 or 1;

R¹, R², R³, R⁴, R⁵, and R⁶ are each independently hydrogen, alkyl, or heteroalkyl; or R¹ and R², R³ and R⁴, or R⁵ and R⁶ together with the atom to which they are bonded form a cycloalkyl or heterocycloalkyl ring;

R⁷ is

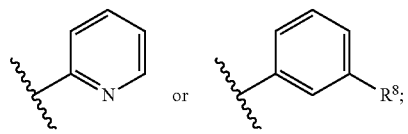

R⁸ is H, F, Cl, Br, or I;

L is O, NH, —CH₂CH(CH₃)—, —CH₂O—, —CH═C(CH₃)—, —C(O)CH₂—, —C(O)CH(CH₃)—, —(CH₂)₃—, —CH₂OCH₂—, —NHC(O)NH—, —C(O)NHNHC(O)—,

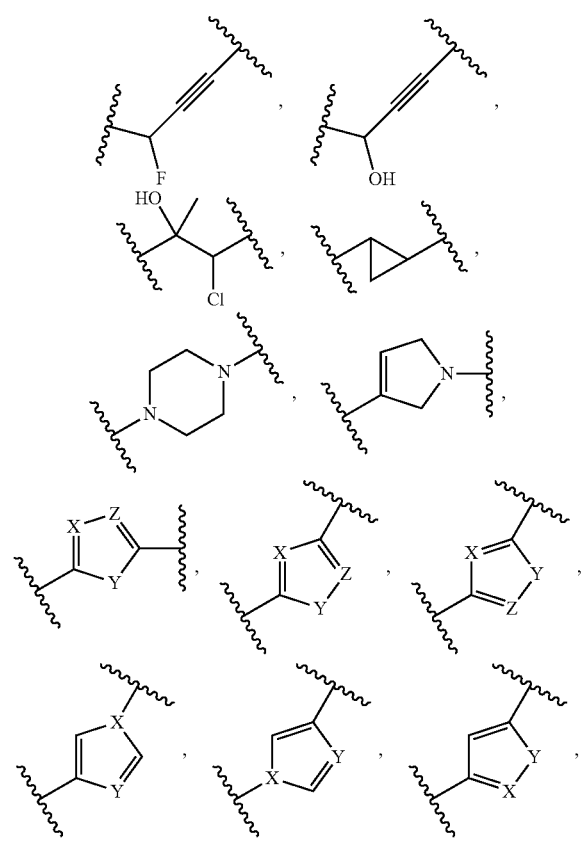

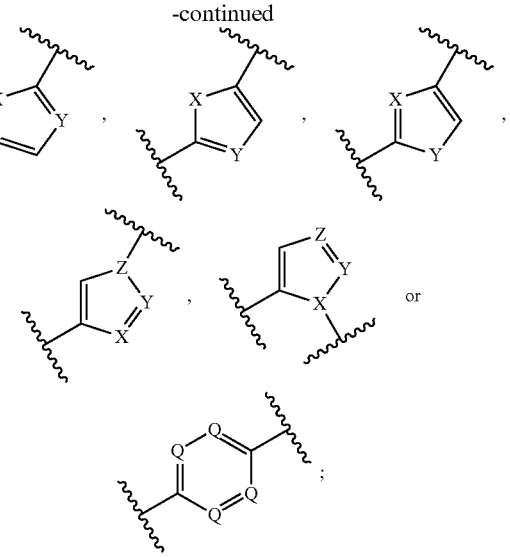

X, Y, and Z are independently O, N, or S;

each Q is independently CH or N;

provided that at least two occurrences of Q are CH; and when m is 1, n is 1, and R¹, R², R³, R⁴, R⁵, R⁶, and R⁸ are all hydrogen, then R⁷ is not

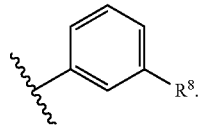

In certain embodiments, m is 0. In certain embodiments, m is 1.

In certain embodiments, n is 0. In certain embodiments, n is 1.

In certain embodiments, R¹ is hydrogen. In certain embodiments, R² is hydrogen.

In certain embodiments, R³ is hydrogen. In certain embodiments, R³ is alkyl (e.g., methyl).

In certain embodiments, R⁴ is hydrogen. In certain embodiments, R⁴ is alkyl (e.g., methyl)

In certain embodiments, R⁵ is hydrogen. In certain embodiments, R⁵ is alkyl (e.g., methyl).

In certain embodiments, R⁶ is hydrogen. In certain embodiments, R⁶ is alkyl (e.g., methyl).

In certain embodiments, L is O, NH, —CH₂CH(CH₃)—, —CH₂O—, —CH═C(CH₃)—, —C(O)CH₂—, —C(O)CH(CH₃)—, —(CH₂)₃—, —CH₂OCH₂—, —NHC(O)NH—, —C(O)NHNHC(O)—,

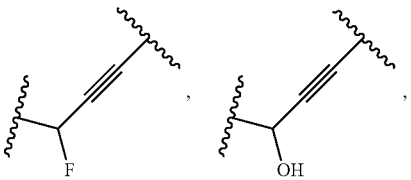

-continued

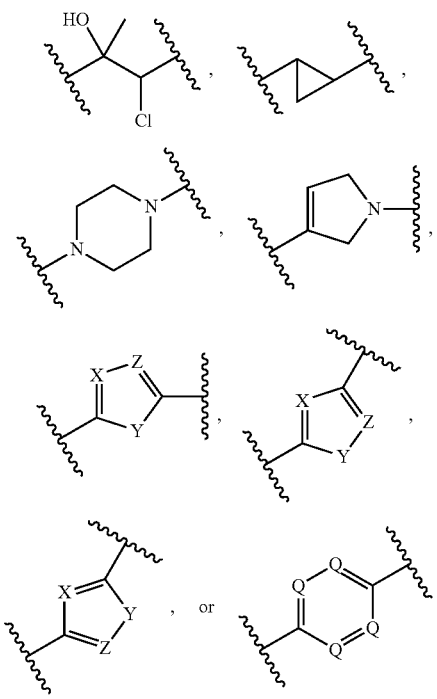

In certain embodiments, L is O. In certain embodiments, L is —CH$_2$O—. In certain embodiments, L is NH. In certain embodiments, L is —CH$_2$CH(CH$_3$)—. In certain embodiments, L is —CH=C(CH$_3$)—. In certain embodiments, L is —C(O)CH$_2$—. In certain embodiments, L is —C(O)CH(CH$_3$)—. In certain embodiments, L is

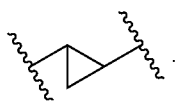

In certain embodiments, L is

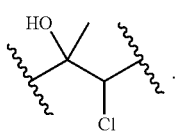

In certain embodiments, L is —(CH$_2$)$_3$—. In certain embodiments, L is —CH$_2$OCH$_2$—. In certain embodiments, L is —NHC(O)NH—. In certain embodiments, L is

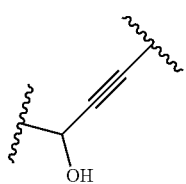

In certain embodiments, L is

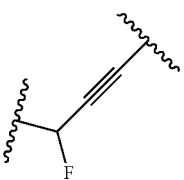

In certain embodiments, L is —C(O)NHNHC(O)—. In certain embodiments, L is

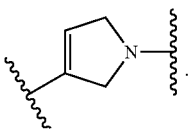

In certain embodiments, L is

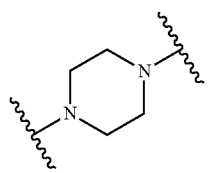

In certain embodiments, L is

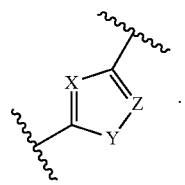

certain embodiments, X is N. In certain embodiments, Y is O. In certain embodiments, Z is N. In certain embodiments, X is N, Y is O and Z is N.

In certain embodiments, L is

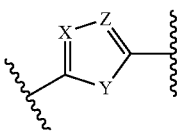

certain embodiments, X is N. In certain embodiments, Y is O. In certain embodiments, Y is S. In certain embodiments, Z is N. In certain embodiments, X is N, Y is O and Z is N. In certain embodiments, X is N, Y is S and Z is N.

In certain embodiments, L is

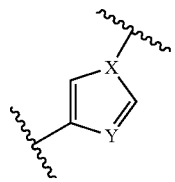

In certain embodiments, X is N. In certain embodiments, Y is N. In certain embodiments, X is N and Y is N.

In certain embodiments, L is

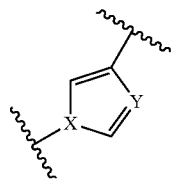

In certain embodiments, X is N. In certain embodiments, Y is N. In certain embodiments, X is N and Y is N.

In certain embodiments, L is

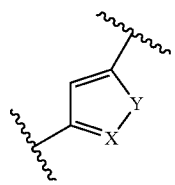

In certain embodiments, X is N. In certain embodiments, Y is O. In certain embodiments, X is N and Y is O.

In certain embodiments, L is

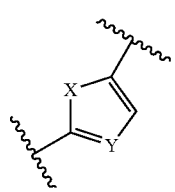

In certain embodiments, X is O. In certain embodiments, X is S. In certain embodiments, Y is N. In certain embodiments, X is O and Y is N. In certain embodiments, X is S and Y is N.

In certain embodiments, L is

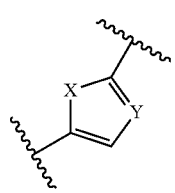

In certain embodiments, X is O. In certain embodiments, X is S. In certain embodiments, Y is N. In certain embodiments, X is O and Y is N. In certain embodiments, X is S and Y is N.

In certain embodiments, L is

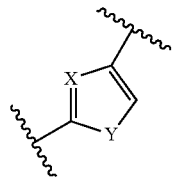

In certain embodiments, X is N. In certain embodiments, Y is S. In certain embodiments, X is N and Y is S.

In certain embodiments, L is

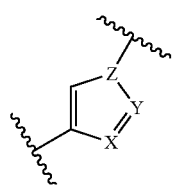

In certain embodiments, X is N. In certain embodiments Y is N. In certain embodiments, Z is N. In certain embodiments, X, Y and Z are N.

In certain embodiments, L is

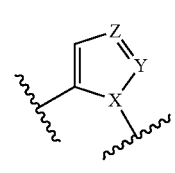

In certain embodiments, X is N. In certain embodiments Y is N. In certain embodiments, Z is N. In certain embodiments, X, Y and Z are N.

In certain embodiments, L is

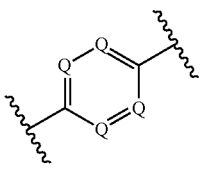

In certain embodiments, each occurrence of Q is CH. In certain embodiments, one occurrence of Q is N and each remaining occurrence of Q is CH. In certain embodiments, two occurrences of Q are N and two occurrences of Q are CH. In certain embodiments, L is In certain embodiments, L is
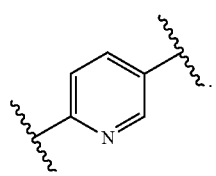 [SMILES: *c1ccc(*)nc1]
In certain embodiments, L is
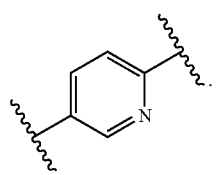 [SMILES: *c1ccc(*)nc1]
In certain embodiments, L is
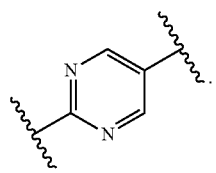 [SMILES: *c1cnc(*)nc1]
In certain embodiments, L is
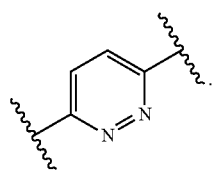 [SMILES: *c1ccc(*)nn1]
In certain embodiments, L is
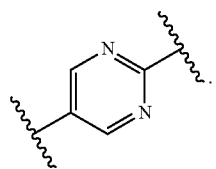 [SMILES: *c1cnc(*)nc1]
In certain embodiments, $R^7$ is
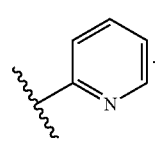 [SMILES: *c1ccccn1]
In certain embodiments, $R^7$ is
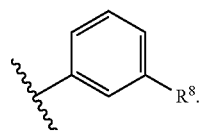
In certain embodiments, $R^8$ is H. In certain embodiments, $R^8$ is F.
In certain embodiments, a compound of Formula (VIII) is
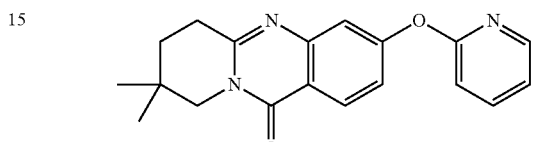
,
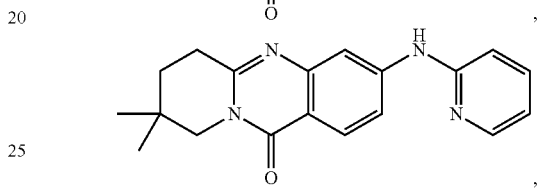
,
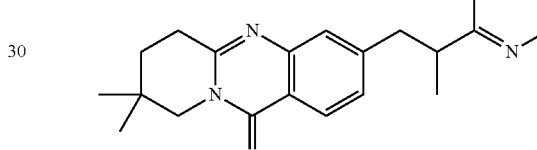
,
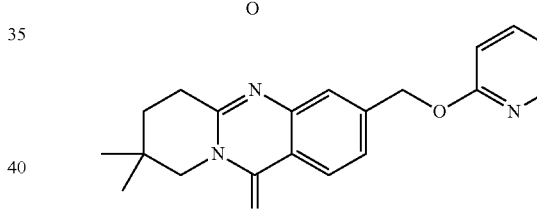
,
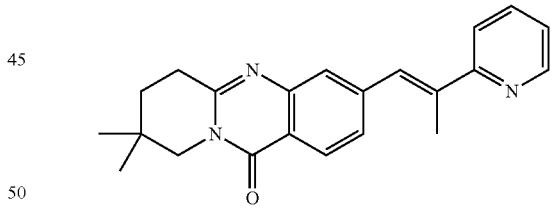
,
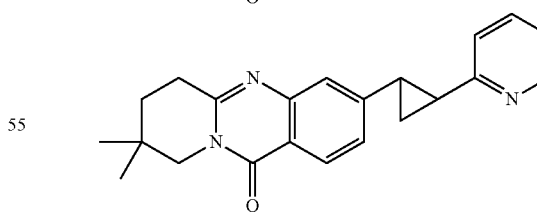
,
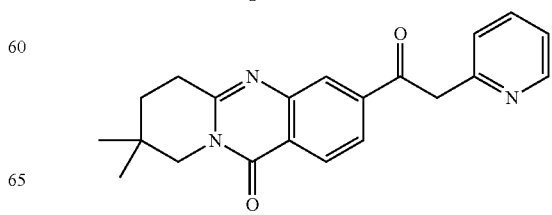
, 75
-continued
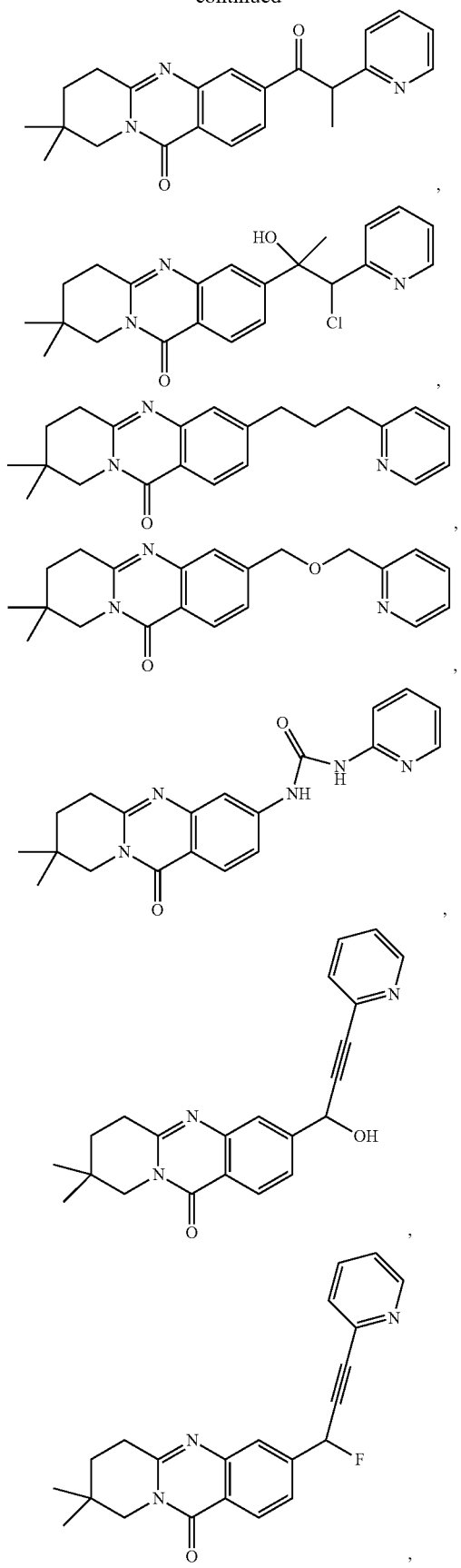
76
-continued
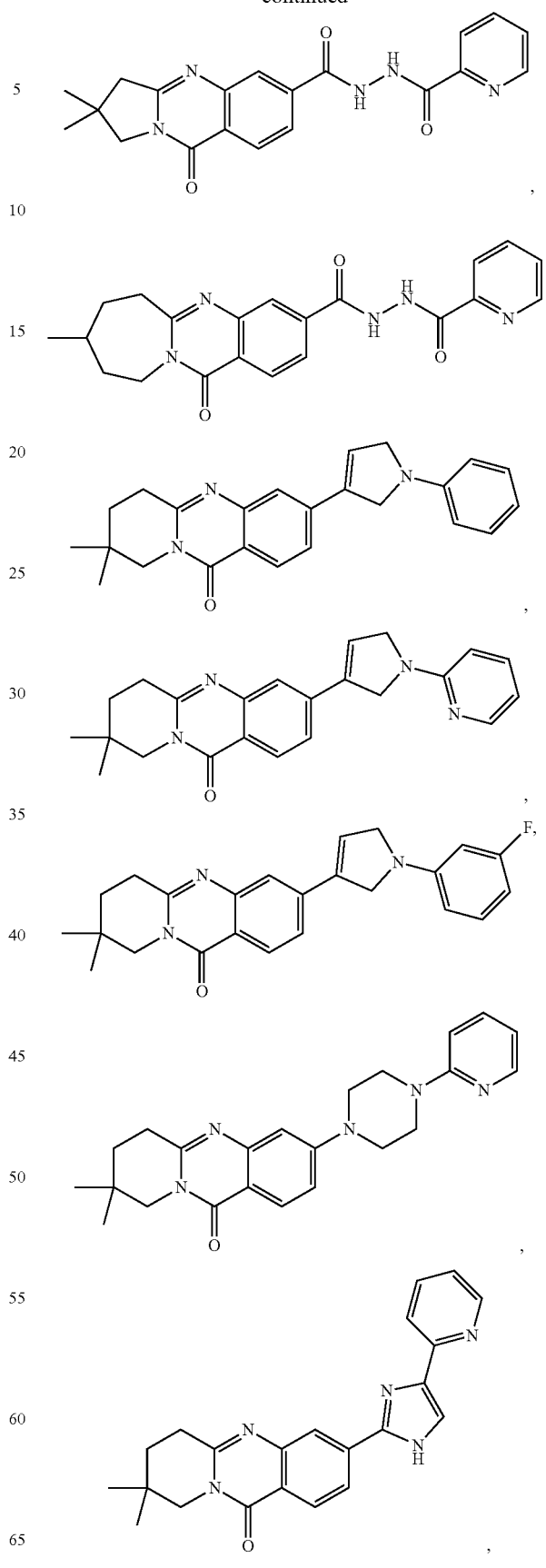

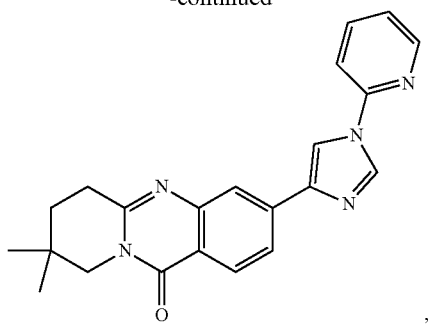,
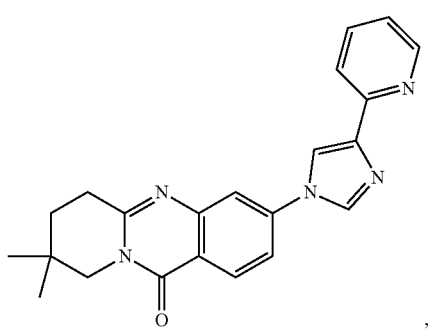,
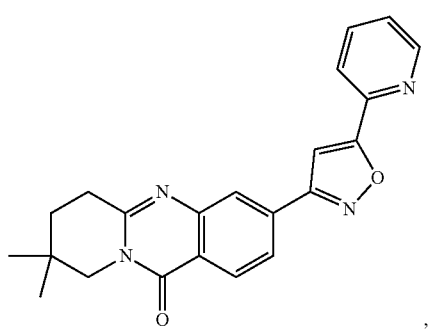,
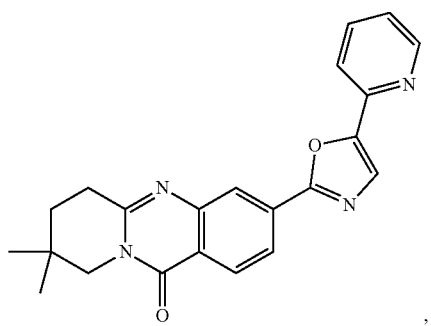,
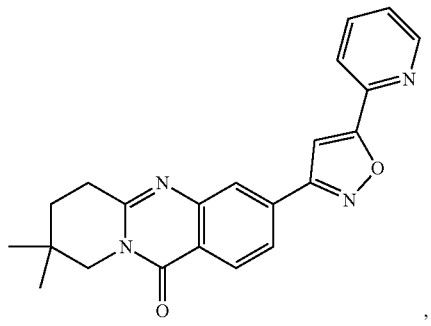,
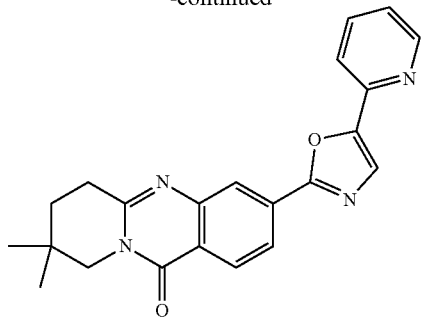,
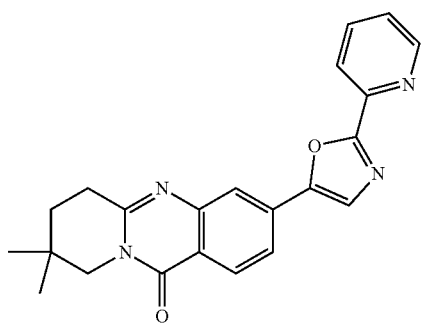,
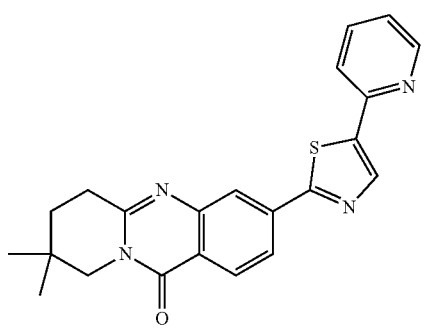,
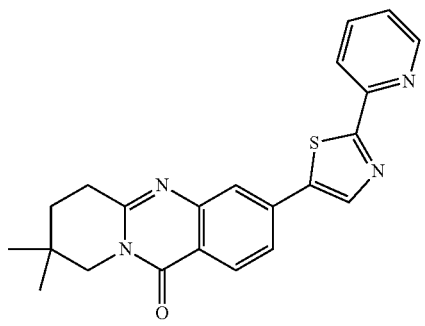,
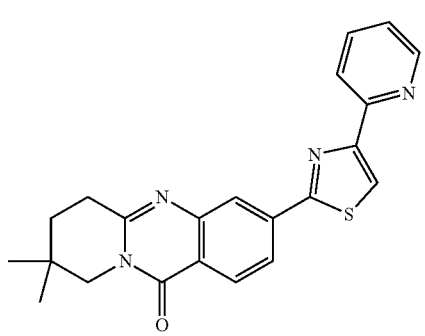,

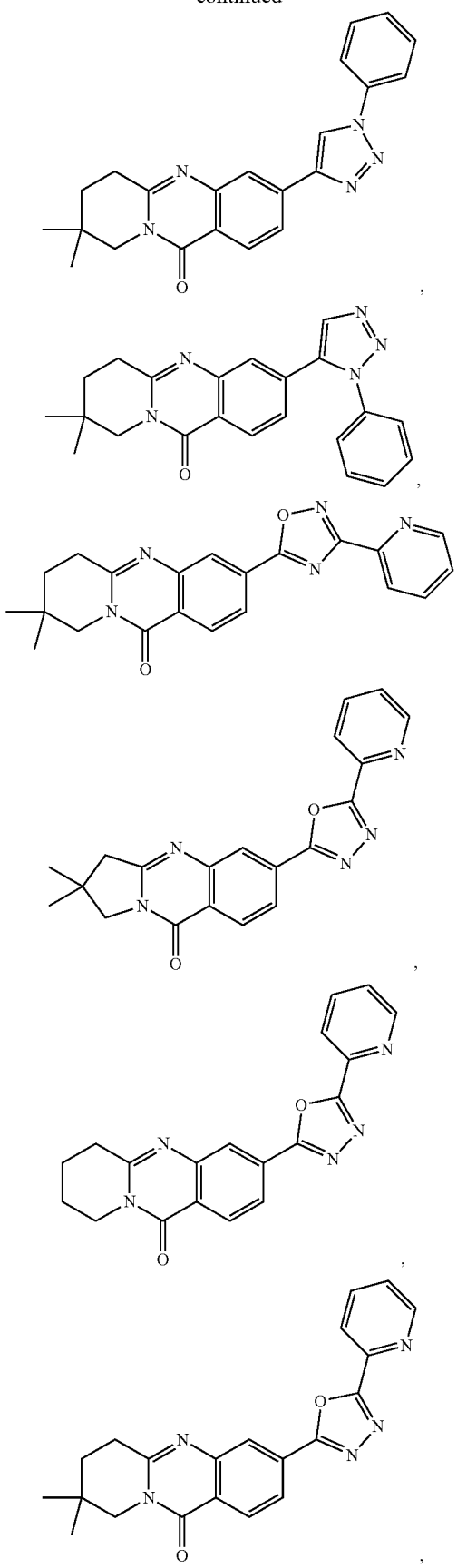
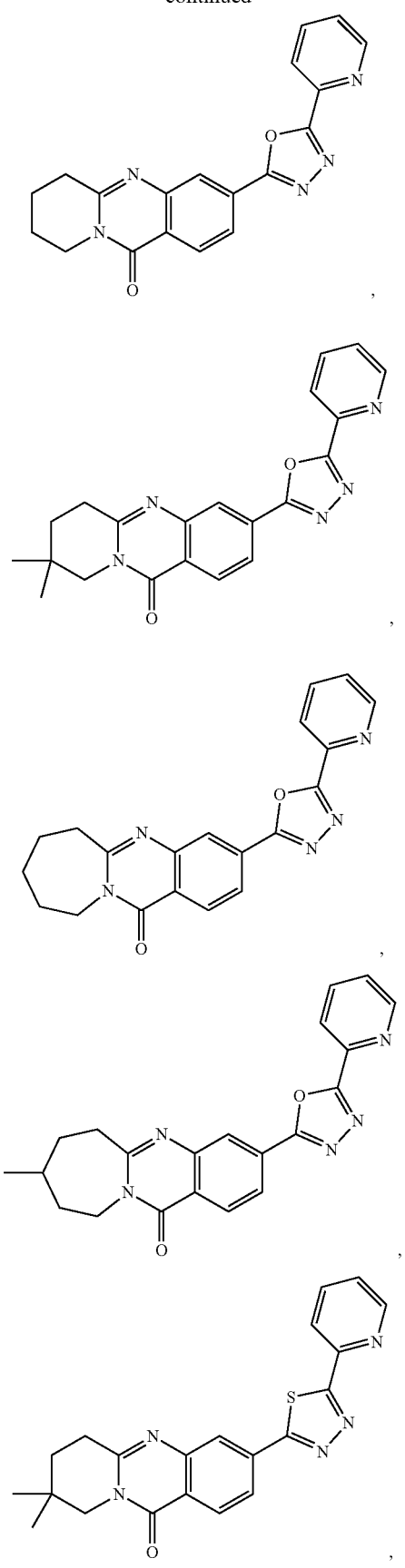

81
-continued
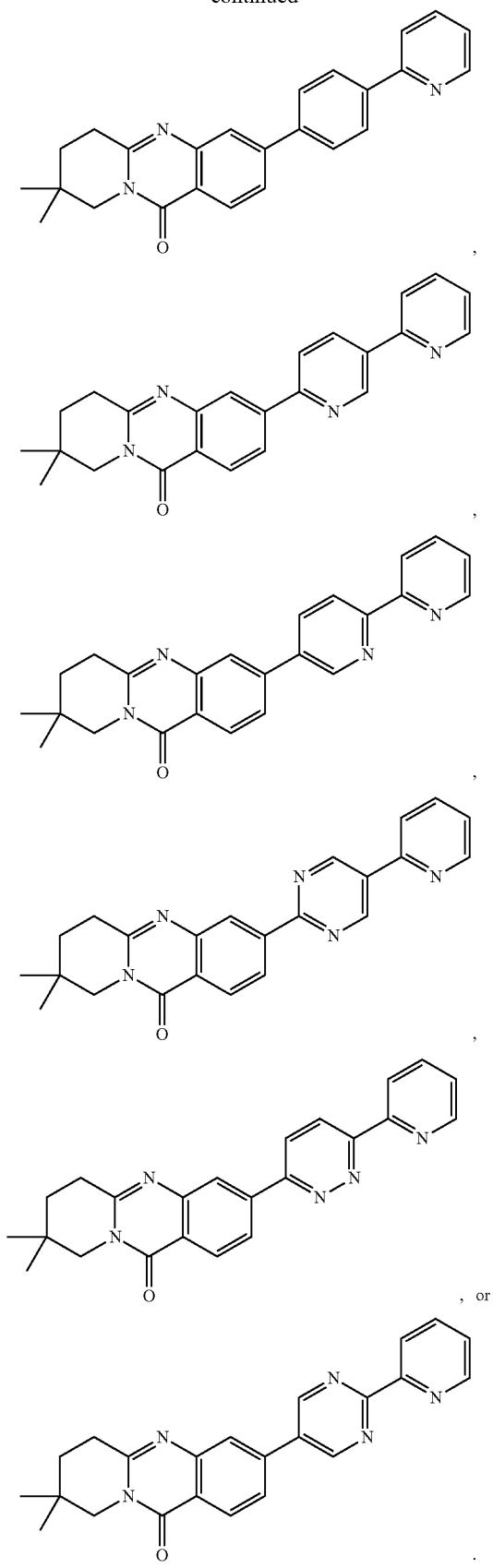
82
In certain embodiments, a compound of the invention is
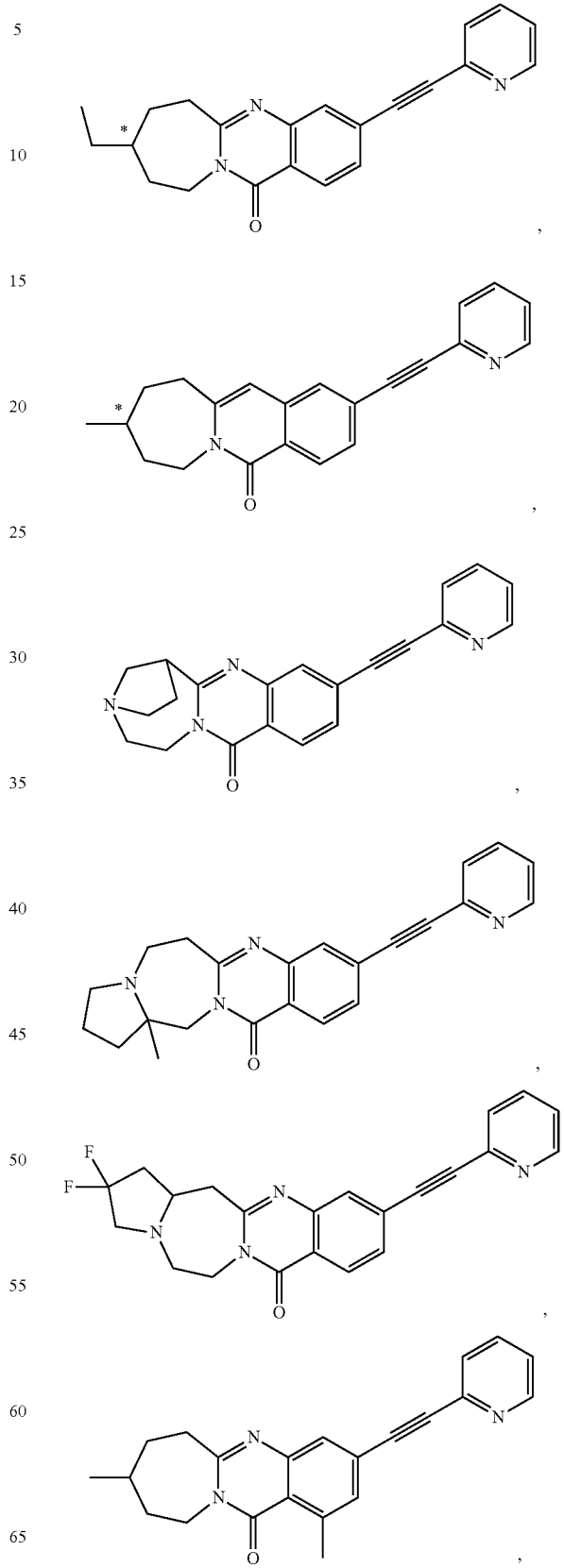

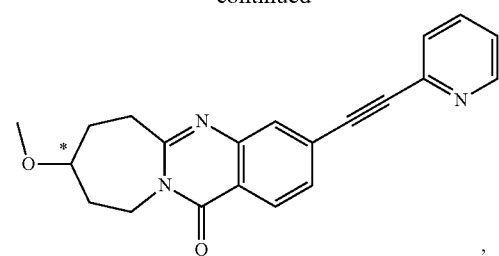,
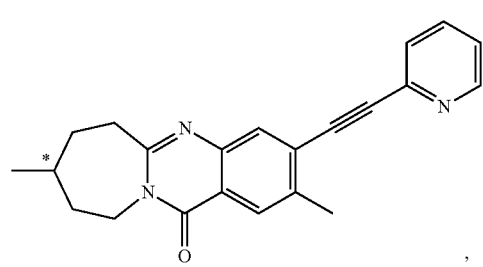,
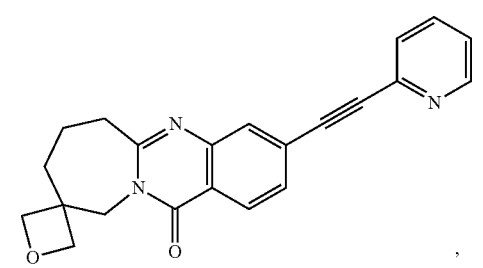,
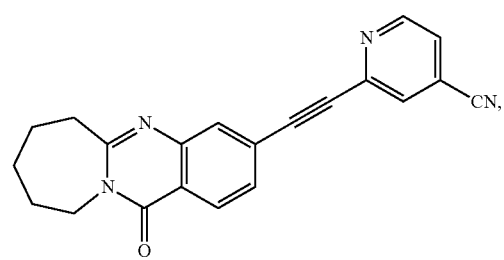,
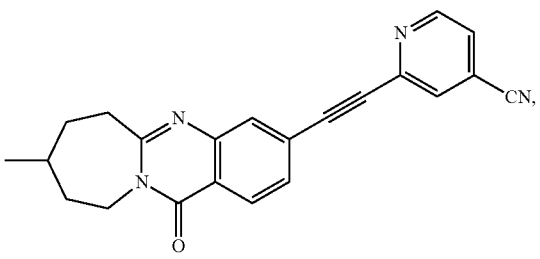,
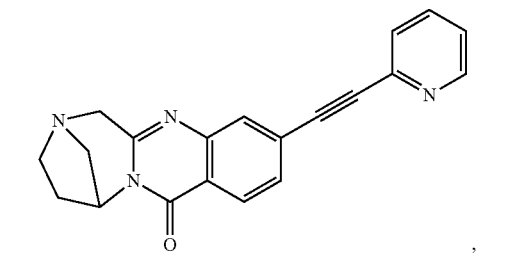,
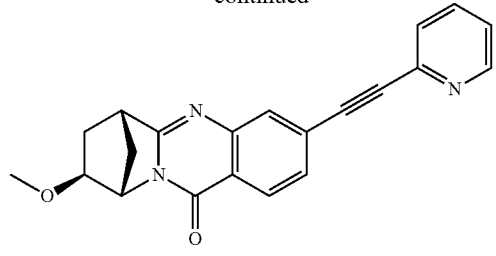,
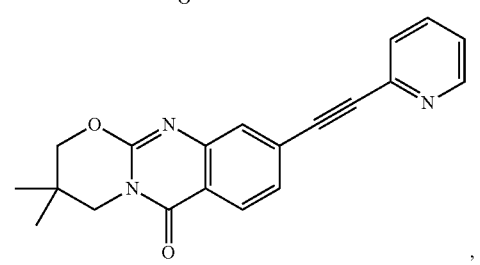,
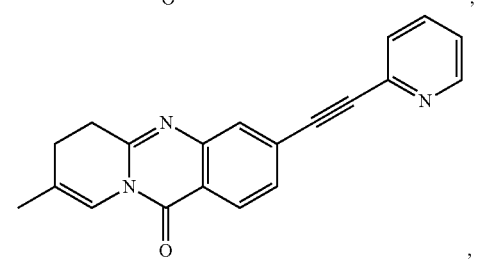,
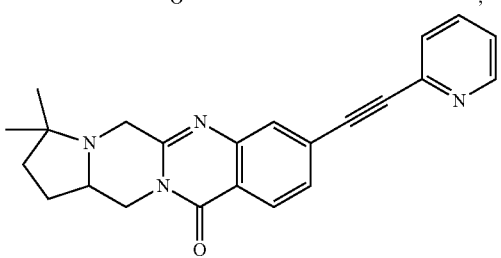,
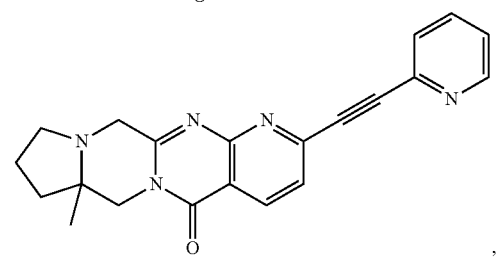,
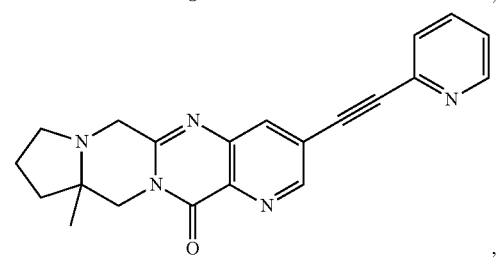,
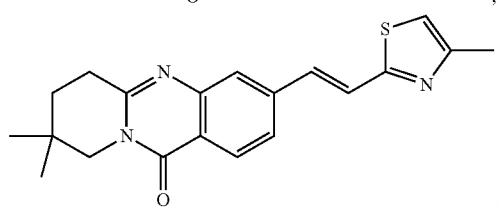, 85
-continued
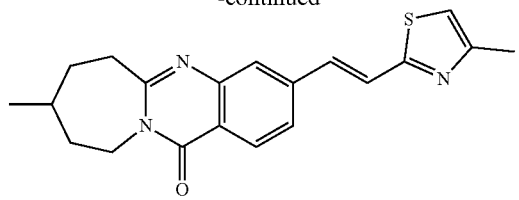
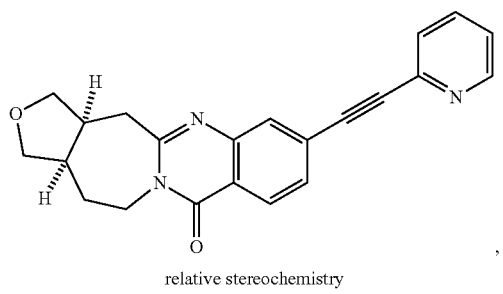
relative stereochemistry
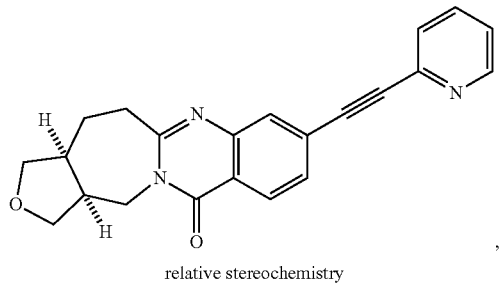
relative stereochemistry
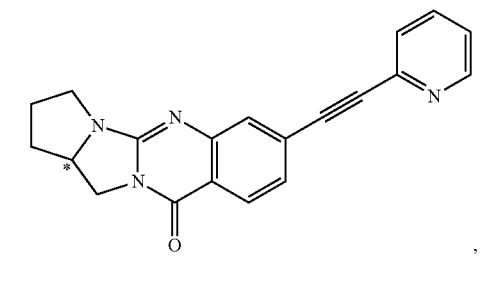
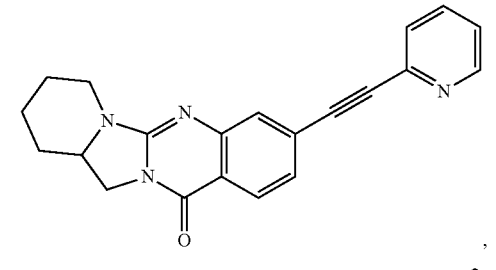
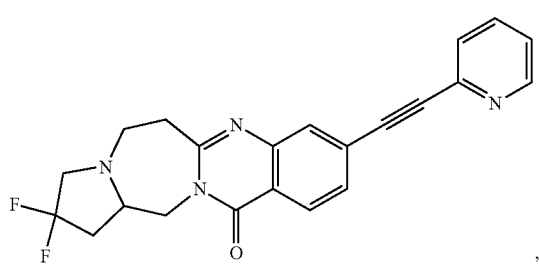
86
-continued
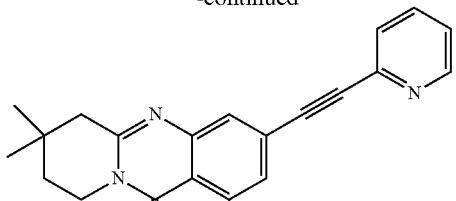
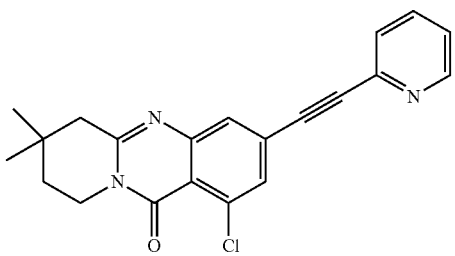
, or
pharmaceutically acceptable salt thereof.
In certain embodiments, a compound of the invention is
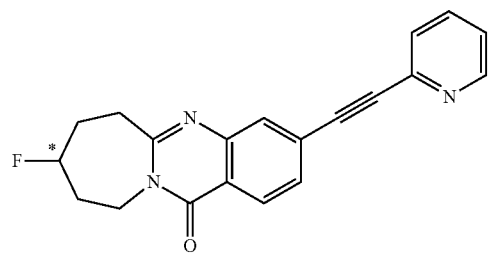
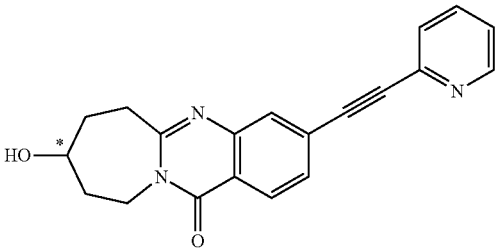
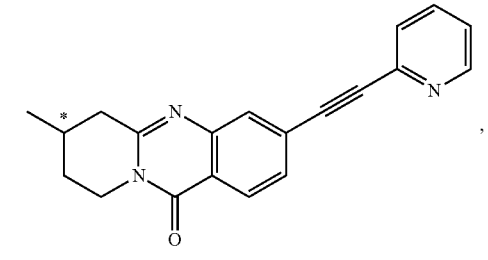
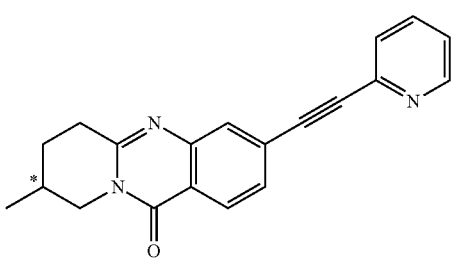

87
-continued
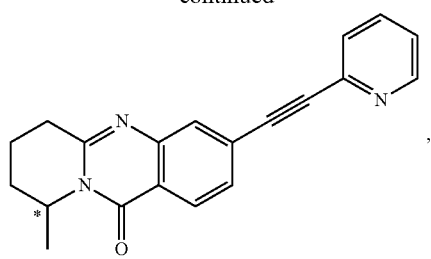
88
-continued
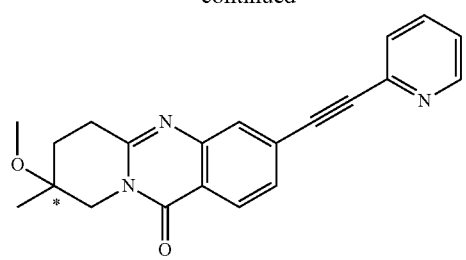
, or

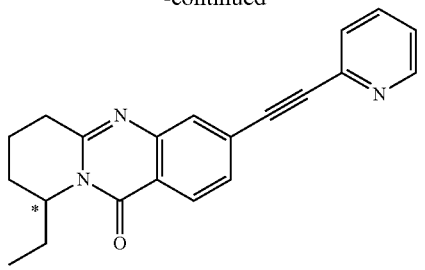

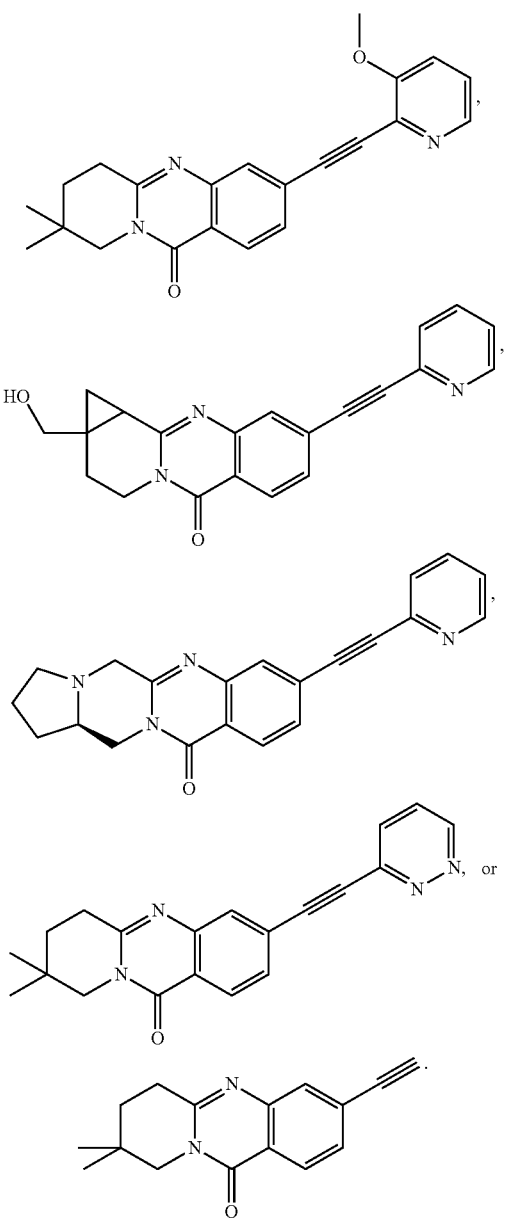

or a pharmaceutically acceptable salt thereof.

In certain embodiments, a compound of the invention is

As used herein, the term "alkyl" includes linear saturated monovalent hydrocarbon radicals that have 1 to 20 ($C_{1-20}$), 1 to 15 ($C_{1-15}$), 1 to 12 ($C_{1-12}$), 1 to 10 ($C_{1-10}$), or 1 to 6 ($C_{1-6}$) carbon atoms, or branched saturated monovalent hydrocarbon radicals having 3 to 20 ($C_{3-20}$), 3 to 15 ($C_{3-15}$), 3 to 12 ($C_{3-12}$), 3 to 10 ($C_{3-10}$), or 3 to 6 ($C_{3-6}$) carbon atoms. As used herein, linear $C_{1-6}$ and branched $C_{3-6}$ alkyl groups are also referred to as "lower alkyl." Examples of alkyl groups include, but are not limited to, methyl, ethyl, propyl (including all isomeric forms, e.g., n-propyl, isopropyl), butyl (including all isomeric forms, e.g., n-butyl, isobutyl, t-butyl), pentyl (including all isomeric forms), and hexyl (including all isomeric forms). For example, $C_{1-6}$ alkyl refers to a linear saturated monovalent hydrocarbon radical of 1 to 6 carbon atoms or a branched saturated monovalent hydrocarbon radical of 3 to 6 carbon atoms. In certain embodiments, the alkyl is optionally substituted as described herein elsewhere. In some embodiments, the alkyl is optionally substituted with one or more halo ("haloalkyl").

As used herein, and unless otherwise specified, the term "alkenyl" refers to a linear or branched monovalent hydrocarbon radical, which contains one or more, in one embodiment, one to five, carbon-carbon double bonds. The alkenyl may be optionally substituted with one or more substituents. The term "alkenyl" encompasses radicals having "cis" and "trans" configurations, or alternatively, "E" and "Z" configurations, as appreciated by those of ordinary skill in the art. As used herein, the term "alkenyl" encompasses both linear and branched alkenyl, unless otherwise specified. For example, $C_{2-6}$ alkenyl refers to a linear unsaturated monovalent hydrocarbon radical of 2 to 6 carbon atoms or a branched unsaturated monovalent hydrocarbon radical of 3 to 6 carbon atoms. In certain embodiments, the alkenyl is a linear monovalent hydrocarbon radical of 2 to 20 ($C_{2-20}$), 2 to 15 ($C_{2-15}$), 2 to 12 ($C_{2-12}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 12 ($C_{3-12}$), 3 to 10 ($C_{3-10}$), or 3 to 6 ($C_{3-6}$) carbon atoms. Examples of alkenyl groups include, but are not limited to, ethenyl, propen-1-yl, propen-2-yl, allyl, butenyl, and 4-methylbutenyl. In certain embodiments, the alkenyl is optionally substituted as described herein elsewhere.

As used herein, and unless otherwise specified, the term "alkoxy" refers to a straight or branched chain, containing the stated number of carbon atoms and an oxygen atom at the terminal position through which the alkoxy group is attached to the molecule. Examples of alkoxy include, but are not limited to, —O—$CH_3$, —O—$CF_3$, —O—$CH_2$—$CH_3$, —O—$CH_2$—$CH_2$—$CH_3$, —O—CH—$(CH_3)_2$, and —O—$CH_2$—$CH_2$—O—$CH_3$. In one embodiment, the alkoxy is optionally substituted as described herein elsewhere.

As used herein, and unless otherwise specified, the term "alkynyl" refers to a linear or branched monovalent hydrocarbon radical, which contains one or more, in one embodiment, one to five, carbon-carbon triple bonds. The alkynyl may be optionally substituted with one or more substituents. The term "alkynyl" also encompasses both linear and branched alkynyl, unless otherwise specified. In certain embodiments, the alkynyl is a linear monovalent hydrocarbon radical of 2 to 20 ($C_{2-20}$), 2 to 15 ($C_{2-15}$), 2 to 12 ($C_{2-12}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 12 ($C_{3-12}$), 3 to 10 ($C_{3-10}$), or 3 to 6 ($C_{3-6}$) carbon atoms. Examples of alkynyl groups include, but are not limited to, ethynyl (—C≡CH) and propargyl (—$CH_2$C≡CH). For example, $C_{2-6}$ alkynyl refers to a linear unsaturated monovalent hydrocarbon radical of 2 to 6 carbon atoms or a branched unsaturated monovalent hydrocarbon radical of 3 to 6 carbon atoms. In certain embodiments, the alkynyl is optionally substituted as described herein elsewhere.

As used herein, and unless otherwise specified, the term "aralkyl" refers to a monovalent alkyl group substituted with aryl. Aralkyl includes, but is not limited to, phenylmethyl (benzyl). In certain embodiments, both the alkyl and aryl portions may be optionally substituted with one or more substituents as described herein elsewhere.

As used herein, and unless otherwise specified, the term "aryl" refers to an optionally substituted monocyclic or multicyclic radical or ring system that contains at least one aromatic hydrocarbon ring. In certain embodiments, the aryl has from 6 to 20, from 6 to 15, or from 6 to 10 ring atoms. Examples of aryl groups include, but are not limited to, phenyl, naphthyl, fluorenyl, azulenyl, anthryl, phenanthryl, pyrenyl, biphenyl, and terphenyl. In certain embodiments, aryl may be bicyclic, tricyclic, or tetracyclic, where one of the rings is aromatic and the other(s) of the rings may be saturated, partially unsaturated, or aromatic, for example, dihydronaphthyl, indenyl, indanyl, or tetrahydronaphthyl (tetralinyl). In certain embodiments, aryl may be a bicyclic, tricyclic, or tetracyclic ring system, where at least one of the rings is aromatic and one or more of the ring(s) is/are saturated or partially unsaturated containing one or more heteroatoms independently selected from O, S, and N. In certain embodiments, the aryl is optionally substituted with one or more substituents as described herein elsewhere.

The terms "bicyclic" and "multicyclic" as used herein include fused, spirocyclic, and bridged bicyclic and multicyclic compounds.

As used herein, and unless otherwise specified, the term "cycloalkyl" refers to a cyclic fully or partially saturated bridged and/or non-bridged hydrocarbon radical or ring system, which may be optionally substituted with one or more substituents. In certain embodiments, the cycloalkyl has from 3 to 20 ($C_{3-20}$), from 3 to 15 ($C_{3-15}$), from 3 to 12 ($C_{3-12}$), from 3 to 10 ($C_{3-10}$), or from 3 to 7 ($C_{3-7}$) carbon atoms. In certain embodiments, cycloalkyl may be a bicyclic, tricyclic, or tetracyclic ring system, where at least one of the rings is a cycloalkyl ring. Examples of cycloalkyl groups include, but are not limited to, cyclopropyl, cyclobutyl, cyclopentyl, cyclohexyl, cycloheptyl, decalinyl, and adamantyl. In certain embodiments, the cycloalkyl is optionally substituted as described herein elsewhere.

The term "haloalkyl" refers to an alkyl as defined above that is substituted by one or more halo groups. In some embodiments, the haloalkyl is monohaloalkyl, dihaloalkyl or polyhaloalkyl, including perhaloalkyl. A monohaloalkyl can have one iodo, bromo, chloro or fluoro within the alkyl group. Dihaloalkyl and polyhaloalkyl groups can have two or more of the same halo atoms or a combination of different halo groups within the alkyl. In some embodiments, the polyhaloalkyl contains up to 12 or 10 or 8 or 6 or 4 or 3 or 2 halo groups. Representative examples of haloalkyl moieties include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloromethyl and dichloropropyl. A perhaloalkyl includes alkyl groups having all hydrogen atoms replaced with halo atoms.

The term "halogen" or "halo" includes fluorine, bromine, chlorine, and iodine.

As used herein, and unless otherwise specified, the term "heteroalkyl" refers to a stable straight or branched chain (saturated or unsaturated), or cyclic hydrocarbon radical, or combinations thereof, consisting of the stated number of carbon atoms and at least one, such as one to three, heteroatoms selected from O, N, Si, and S, and wherein the nitrogen and sulfur atoms are optionally oxidized and the nitrogen heteroatom can optionally be quaternized. In certain embodiments, the heteroatom(s) may be placed at any interior position of the heteroalkyl group. In certain embodiments, the heteroatom(s) may be placed at a terminal position, such as the position at which the alkyl group is attached to the remainder of the molecule. In certain embodiments where an oxygen atom is at the terminal position where the alkyl group is attached to the remainder of the molecule, it is referred to as an "alkoxy" group. Examples of heteroalkyl include, but are not limited to, $-CH_2-CH_2-O-CH_3$, $-CH_2-CH_2-NH-CH_3$, $-CH_2-CH_2-N(CH_3)-CH_3$, $-CH_2-S-CH_2-CH_3$, $-CH_2-CH_2-S(O)-CH_3$, $-CH_2-CH_2-S(O)_2-CH_3$, $-CH=CH-O-CH_3$, $-Si(CH_3)_3$, $-CH_2-CH=N-OCH_3$, and $-CH=CH-N(CH_3)-CH_3$. Up to two heteroatoms can be consecutive, such as, for example, $-CH_2-NH-O-CH_3$ and $-CH_2-O-Si(CH_3)_3$. In certain embodiments, the heteroalkyl is optionally substituted as described herein elsewhere.

The term "heteroaralkyl" as used herein refers to a monovalent alkyl group substituted with heteroaryl. Heteroaralkyl includes, but is not limited to, pyridylmethyl. In certain embodiments, both the alkyl and heteroaryl portions may be optionally substituted with one or more substituents as described herein elsewhere.

As used herein, and unless otherwise specified, the term "heteroaryl" refers to an optionally substituted monocyclic or multicyclic radical or ring system which contains at least one aromatic ring having one or more heteroatoms independently selected from O, S, and N. In certain embodiments, each ring of a heteroaryl group can contain one or two O atoms, one or two S atoms, and/or one to four N atoms, provided that the total number of heteroatoms in each ring is four or less and each ring contains at least one carbon atom. In certain embodiments, each ring of a heteroaryl group can contain one O atom, one S atoms, and/or one to four N atoms, provided that the total number of heteroatoms in each ring is four or less and each ring contains at least one carbon atom. In certain embodiments, the heteroaryl has from 5 to 20, from 5 to 15, or from 5 to 10 ring atoms. In certain embodiments, heteroaryl also refers to bicyclic, tricyclic, or tetracyclic ring systems, where one of the rings is aromatic having one or more heteroatoms independently selected from O, S, and N, and the other(s) of the rings may be saturated, partially unsaturated, or aromatic and may be carbocyclic or contain one or more heteroatoms independently selected from O, S, and N. Examples of monocyclic heteroaryl groups include, but are not limited to, furanyl, imidazolyl, isothiazolyl, isoxazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl, and triazolyl. Examples of bicyclic heteroaryl groups include, but are not limited to, benzofuranyl, benzimidazolyl, benzoisoxazolyl, benzopyranyl, benzothiadiazolyl, benzothiazolyl, benzothienyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quinazolinyl, thiadiazolopyrimidyl, and thienopyridyl. Examples of tricyclic heteroaryl groups include, but are not limited to, acridinyl, benzindolyl, carbazolyl, dibenzofuranyl, perimidinyl, phenanthrolinyl, phenanthridinyl, phenarsazinyl, phenazinyl, phenothiazinyl, phenoxazinyl, and xanthenyl. In certain embodiments, the heteroaryl is optionally substituted with one or more substituents as described herein elsewhere.

The term "heteroatom" includes atoms of any element other than carbon or hydrogen, including, but not limited to, nitrogen, oxygen and sulfur.

As used herein, and unless otherwise specified, the term "heterocycloalkyl" or "heterocyclyl" refers to an optionally substituted monocyclic or multicyclic radical or ring system which contains at least one non-aromatic (saturated or partially saturated) ring having one or more heteroatoms independently selected from O, S, and N. In certain embodiments, the heterocyclyl or heterocycloalkyl group has from 3 to 20, from 3 to 15, from 3 to 10, from 3 to 8, from 4 to 7, or from 5 to 6 ring atoms. In certain embodiments, the heterocyclyl or heterocycloalkyl is a monocyclic, bicyclic, tricyclic, or tetracyclic ring system, and the other(s) of the rings may be saturated, partially unsaturated, or aromatic and may be carbocyclic or contain one or more heteroatoms independently selected from O, S, and N. In certain embodiments, nitrogen or sulfur atoms may be optionally oxidized and the nitrogen atoms may be optionally quaternized. The heterocycloalkyl or heterocyclyl may be attached to the remainder of the molecule at a heteroatom or a carbon atom. Examples include, but are not limited to, azepinyl, benzodioxanyl, benzodioxolyl, benzofuranonyl, benzopyranonyl, benzopyranyl, benzotetrahydrofuranyl, benzotetrahydrothienyl, benzothiopyranyl, benzoxazinyl, β-carbolinyl, chromanyl, chromonyl, cinnolinyl, coumarinyl, decahydroisoquinolinyl, dihydrobenzisothiazinyl, dihydrobenzisoxazinyl, dihydrofuryl, dihydroisoindolyl, dihydropyranyl, dihydropyrazolyl, dihydropyrazinyl, dihydropyridinyl, dihydropyrimidinyl, dihydropyrrolyl, dioxolanyl, 1,4-dithianyl, furanonyl, imidazolidinyl, imidazolinyl, indolinyl, isobenzotetrahydrofuranyl, isobenzotetrahydrothienyl, isochromanyl, isocoumarinyl, isoindolinyl, isothiazolidinyl, isoxazolidinyl, morpholinyl, octahydroindolyl, octahydroisoindolyl, oxazolidinonyl, oxazolidinyl, oxiranyl, piperazinyl, piperidinyl, 4-piperidonyl, pyrazolidinyl, pyrazolinyl, pyrrolidinyl, pyrrolinyl, quinuclidinyl, tetrahydrofuryl, tetrahydroisoquinolinyl, tetrahydropyranyl, tetrahydrothienyl, thiamorpholinyl, thiazolidinyl, tetrahydroquinolinyl, and 1,3,5-trithianyl. In certain embodiments, the heterocyclyl or heterocycloalkyl is optionally substituted with one or more substituents as described herein elsewhere.

As used herein, and unless otherwise specified, the terms "optionally substituted" and "substituted" are intended to mean that a group, including, but not limited to, alkyl, alkenyl, alkynyl, cycloalkyl, heteroalkyl, alkoxy, aryl, aralkyl, heteroaralkyl, heteroaryl, or heterocyclyl, may be substituted with one or more substituents independently selected from, e.g., (a) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl, each optionally substituted with one or more, in one embodiment, one, two, three, or four, substituents $Q^1$; and (b) halo, cyano (—CN), nitro (—NO$_2$), oxo (=O), —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —SR$^a$, —S(O)R$^a$, —S(O)$_2$R$^a$, —S(O)NR$^b$R$^c$, and —S(O)$_2$NR$^b$R$^c$, wherein each R$^a$, R$^b$, R$^c$, and R$^d$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents $Q^1$; or (iii) R$^b$ and R$^c$ together with the N atom to which they are attached form heteroaryl or heterocyclyl, optionally substituted with one or more, in one embodiment, one, two, three, or four, substituents $Q^1$. As used herein, all groups that can be substituted are "optionally substituted," unless otherwise specified.

In one embodiment, each $Q^1$ is independently selected from (a) cyano, halo, oxo, and nitro; and (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl; and (c) —C(O)R$^e$, —C(O)OR$^e$, —C(O)NR$^f$R$^g$, —C(NR$^e$)NR$^f$R$^g$, —OR$^e$, —OC(O)R$^e$, —OC(O)OR$^e$, —OC(O)NR$^f$R$^g$, —OC(=NR$^e$)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, —NR$^e$C(O)OR$^h$, —NR$^e$C(O)NR$^f$R$^g$, —NR$^e$C(=NR$^h$)NR$^f$R$^g$, —NR$^e$S(O)R$^h$, —NR$^e$S(O)$_2$R$^h$, —NR$^e$S(O)NR$^f$R$^g$, —NR$^e$S(O)$_2$NR$^f$R$^g$, —SR$^e$, —S(O)R$^e$, —S(O)$_2$R$^e$, —S(O)NR$^f$R$^g$, and —S(O)$_2$NR$^f$R$^g$; wherein each R$^e$, R$^f$, R$^g$, and R$^h$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) R$^f$ and R$^g$ together with the N atom to which they are attached form heteroaryl or heterocyclyl.

It will be noted that the structure of some of the compounds of this invention include asymmetric carbon atoms. It is to be understood accordingly that the stereoisomers arising from such asymmetry (e.g., all enantiomers and diastereomers) are included within the scope of this invention, unless indicated otherwise. Furthermore, the structures and other compounds and moieties discussed in this application also include any tautomers or geometric isomers (e.g., cis/trans or E/Z) thereof. Accordingly, a compound of the present invention may be in the form of one of the possible isomers, rotamers, atropisomers, tautomers or mixtures thereof, for example, as substantially pure geometric (e.g., cis or trans) isomers, diastereomers, optical isomers (e.g., antipodes), racemates or mixtures thereof.

As used herein, and unless otherwise specified, the term "solvate" refers to a compound provided herein or a salt thereof, which further includes a stoichiometric or non-stoichiometric amount of solvent bound by non-covalent intermolecular forces. Where the solvent is water, the solvate is a hydrate.

As used herein, and unless otherwise specified, the term "stereoisomer" encompasses all enantiomerically/stereomerically pure and enantiomerically/stereomerically enriched compounds provided herein.

As used herein and unless otherwise specified, the term "stereomerically pure" means a composition that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two or more chiral centers is substantially free of other diastereomers. A typical stereomerically pure compound comprises greater than about 80% by weight of one stereoisomer, greater than about 90% by weight of one stereoisomer, greater than about 95% by weight of one stereoisomer, greater than about 97% by weight of one stereoisomer, greater than about 99% by weight, greater than 99.5%, or even greater than 99.9% of one stereoisomer.

In describing an optically active compound, the prefixes R and S are used to denote the absolute configuration of the molecule about its chiral center(s). The (+) and (−) notations are used to denote the optical rotation of the compound, that is, the direction in which a plane of polarized light is rotated by the optically active compound. The (−) prefix indicates that the compound is levorotatory, that is, the compound rotates the plane of polarized light to the left or counter-clockwise. The (+) prefix indicates that the compound is dextrorotatory, that is, the compound rotates the plane of polarized light to the right or clockwise. However, the sign of optical rotation, (+) and (−), is not related to the absolute configuration of the molecule, R and S.

As used herein, and unless otherwise indicated, the terms "treat," "treating" and "treatment" refer to the eradication or amelioration of a disease or disorder, or of one or more symptoms associated with the disease or disorder. In certain embodiments, the terms refer to minimizing the spread or worsening of the disease or disorder resulting from the administration of one or more prophylactic or therapeutic agents to a subject with such a disease or disorder. In some embodiments, the terms refer to the administration of a compound provided herein, with or without other additional active agent(s), after the onset of symptoms of the particular disease (e.g., adjuctive or combination therapy).

As used herein, and unless otherwise specified, a "therapeutically effective amount" of a compound is an amount sufficient to provide a therapeutic benefit in the treatment or management of a disease or disorder, or to delay or minimize one or more symptoms associated with the disease or disorder. A therapeutically effective amount of a compound means an amount of therapeutic agent, alone or in combination with other therapies, which provides a therapeutic benefit in the treatment or management of the disease or disorder. The term "therapeutically effective amount" can encompass an amount that improves overall therapy, reduces or avoids symptoms or causes of disease or disorder, or enhances the therapeutic efficacy of another therapeutic agent.

As used herein, and unless otherwise specified, the term "pharmaceutically acceptable salts" refers to salts prepared from pharmaceutically acceptable non-toxic acids, including inorganic acids and organic acids; or from pharmaceutically acceptable non-toxic bases, including inorganic bases and organic bases. In one embodiment, suitable non-toxic acids include, but are not limited to, acetic, alginic, anthranilic, benzenesulfonic, benzoic, camphorsulfonic, citric, ethenesulfonic, formic, fumaric, furoic, gluconic, glutamic, glucorenic, galacturonic, glycidic, hydrobromic, hydrochloric, isethionic, lactic, maleic, malic, mandelic, methanesulfonic, mucic, nitric, pamoic, pantothenic, phenylacetic, propionic, phosphoric, salicylic, stearic, succinic, sulfanilic, sulfuric, tartaric acid, and p-toluenesulfonic.

Any formula given herein is also intended to include unlabeled forms as well as isotopically labeled forms of the compounds. For example, any hydrogen represented by "H" in the formulae herein is intended to represent all isotopic forms of hydrogen (e.g., $^1$H, $^2$H or D, or $^3$H or T) unless otherwise specified; any carbon represented in any of the formulae disclosed herein are intended to represent all isotopic forms of carbon (e.g., $^{11}$C, $^{13}$C, $^{14}$C) unless otherwise specified; similarly, any nitrogen represented by "N" is intended to represent all isotopic forms of nitrogen (e.g., $^{14}$N, $^{18}$N) unless otherwise specified. Enrichment with heavier isotopes, particularly deuterium (i.e., $^2$H or D) may afford certain therapeutic advantages including, but not limited to, greater metabolic stability, for example increased in vivo half-life or reduced dosage requirements or an improvement in therapeutic index. Other examples of isotopes include, but are not limited to, oxygen, sulfur, phosphorous, fluorine, iodine and chlorine, such as $^{18}$F, $^{15}$O, $^{31}$P, $^{32}$P, $^{35}$S, $^{36}$Cl and $^{125}$I. The invention includes various isotopically labeled compounds as defined herein, for example those into which radioactive isotopes, such as $^3$H, $^{13}$C and $^{14}$C are present. In some embodiments, the atoms in the formulae herein occur in their natural abundance. In some embodiments, one or more hydrogen atom may be enriched in $^2$H; or/and one or more carbon atom may be enriched in $^{11}$C, $^{13}$C or $^{14}$C; or/and one or more nitrogen may be enriched in $^{14}$N.

Isotopically labeled compounds of this invention can generally be prepared by carrying out the procedures disclosed in the schemes or in the examples and preparations described below by substituting a readily available isotopically labeled reagent for a non-isotopically labeled reagent.

It should be noted that if there is a discrepancy between a depicted structure and a chemical name given that structure, the depicted structure is to be accorded more weight.

Neurological Diseases and Disorders

As used herein, and unless otherwise specified, the term "neurological disorder" includes diseases, disorders or conditions of the central or peripheral nervous system of a mammal. The term "neurological disorder" includes, but is not limited to, neurodegenerative diseases, neuropsychiatric diseases, affective disorders, and loss of cognitive function, learning and memory disorders. The term "neurological disorder" also includes conditions associated with the disorder. For instance, a method of treating a neurodegenerative disorder includes methods of treating loss of memory and/or loss of cognition associated with a neurodegenerative disorder. The term "neurological disorder" also includes diseases or conditions that are implicated, at least in part, in monoamine (e.g., norepinephrine) signaling pathways (e.g., cardiovascular disease).

Neurodegenerative Diseases and Disorders

The term "neurodegenerative disease" includes diseases and disorders that are associated with the progressive loss of structure or function of neurons, or death of neurons. Neurodegenerative diseases and disorders include, but are not limited to, Alzheimer's disease (including the associated symptoms of mild, moderate, or severe cognitive impairment); amyotrophic lateral sclerosis (ALS); anoxic and ischemic injuries; ataxia and convulsion (including for the treatment and prevention and prevention of seizures that are caused by schizoaffective disorder or by drugs used to treat schizophrenia); benign forgetfulness; brain edema; cerebellar ataxia including McLeod neuroacanthocytosis syndrome (MLS); closed head injury; coma; contusive injuries (e.g., spinal cord injury and head injury); dementias including multi-infarct dementia and senile dementia; disturbances of consciousness; Down syndrome; drug-induced or medication-induced Parkinsonism (such as neuroleptic-induced acute akathisia, acute dystonia, Parkinsonism, or tardive dyskinesia, neuroleptic malignant syndrome, or medication-induced postural tremor); epilepsy; fragile X syndrome; Gilles de la Tourette's syndrome; head trauma; hearing impairment and loss; Huntington's disease; Lennox syndrome; levodopa-induced dyskinesia; mental retardation; movement disorders including akinesias and akinetic (rigid) syndromes (including basal ganglia calcification, corticobasal degeneration, multiple system atrophy, Parkinsonism-ALS dementia complex, Parkinson's disease, postencephalitic parkinsonism, and progressively supranuclear palsy); muscular spasms and disorders associated with muscular spasticity or weakness including chorea (such as benign hereditary chorea, drug-induced chorea, hemiballism, Huntington's disease, neuroacanthocytosis, Sydenham's chorea, and symptomatic chorea), dyskinesia (including tics such as complex tics, simple tics, and symptomatic tics), myoclonus (including generalized myoclonus and focal cycloclonus), tremor (such as rest tremor, postural tremor, and intention tremor) and dystonia (including axial dystonia, dystonic writer's cramp, hemiplegic dystonia, paroxymal dystonia, and focal dystonia such as blepharospasm, oromandibular dystonia, and spasmodic dysphonia and torticollis); neuronal damage including ocular damage, retinopathy or macular degeneration of the eye; neurotoxic injury which follows cerebral stroke, thromboembolic stroke, hemorrhagic stroke, cerebral ischemia, cerebral vasospasm, hypoglycemia, amnesia, hypoxia, anoxia, perinatal asphyxia and cardiac arrest; Parkinson's disease; seizure; status epilecticus; stroke; tinnitus; tubular sclerosis; and viral infection induced neurodegeneration (e.g., caused by acquired immunodeficiency syndrome (AIDS) and encephalopathies). Neurodegenerative diseases also include, but are not limited to, neurotoxic injury which follows cerebral stroke, thromboembolic stroke, hemorrhagic stroke, cerebral ischemia, cerebral vasospasm, hypoglycemia, amnesia, hypoxia, anoxia, perinatal asphyxia and cardiac arrest. Methods of treating or preventing a neurodegenerative disease also include treating or preventing loss of neuronal function characteristic of neurodegenerative disorder.

Neuropsychiatric Diseases and Disorders

The term "neuropsychiatric disease" includes those neuropsychiatric diseases and disorders set forth in *The Diagnostic and Statistical Manual of Mental Disorders*, Revised, Fourth Ed., (DSM-IV-R), published by the American Psychiatric Association, which is incorporated herein by reference. Such disorders include, but are not limited to, aggression; attention disorders including attention-deficit disorder (ADD), attention-deficit-hyperactivity disorder (ADHD) and conduct disorder; delirium; delusional disorder; persisting dementia; pervasive development disorder including autism, autistic disorder and autism spectrum disorder; psychosis and psychotic disorders (including psychosis associated with affective disorders, brief reactive psychosis, brief psychotic disorder, shared psychotic disorder, and psychotic disorder due to a general medical condition and substance-induced or drug-induced psychotic disorder (e.g., caused by phencyclidine, ketamine and other dissociative anaesthetics, amphetamine, cocaine and other psychostimulants)); schizophrenia (including schizoaffective psychosis and "schizophrenia-spectrum" disorders such as schizoid or schizotypal personality disorders, or illnesses associated with psychosis (such as major depression, manic depressive (bipolar) disorder, Alzheimer's disease and post-traumatic stress syndrome) including both the positive and negative symptoms of schizophrenia and other psychoses); and sensory hyper-excitability.

The terms "attention deficit disorder" (ADD), "attention deficit disorder with hyperactivity (ADDH)," and "attention deficit/hyperactivity disorder" (AD/HD), are used herein in accordance with the accepted meanings as found in the *Diagnostic and Statistical Manual of Mental Disorders*, 4th Ed., American Psychiatric Association (DSM-IV™-R). ADD and ADHD include disorders that are most prevalent in children and are associated with increased motor activity and a decreased attention span that may result in inappropriate actions in learning and social situations.

The term "psychosis" includes mental states in which a subject suffering from psychosis undergoes a loss of contact with reality. Symptoms of psychosis include hallucinations, delusions and impaired sight. In some embodiments, the psychosis may be associated with another neuropsychiatric disorder, for example, schizophrenia, schizophreniform disorder, schizoaffective disorder, brief psychotic disorder, bipolar disorder, clinical depression, psychosocial disorder. In some embodiments, the psychosis is related to general medical conditions, for example, brain tumors, brain damage, an epileptic disorder, dementia, multiple sclerosis, Lyme disease, Alzheimer's disease, Parkinson's disease, electrolyte disorders, hypoglycemia and AIDS. In some embodiments, the psychosis is substance-induced psychosis.

The term "schizophrenia" includes a mental disorders characterized by the disintegration of the process of thinking and emotional responsiveness, and includes symptoms such as auditory hallucinations, paranoid delusions, disorganized speech, disorganized thinking, and extensive withdrawal of the patient's interests from other people. The term "schizophrenia" also includes schizophreniform disorder and schizoaffective disorder. So-called negative symptoms of schizophrenia include affect blunting, anergia, alogia and social withdrawal. Positive symptoms of schizophrenia include delusion and hallucination. Cognitive symptoms of schizophrenia include impairment in obtaining, organizing, and using intellectual knowledge.

Affective Disorders

As used herein, and unless otherwise specified, the term "affective disorder" includes agoraphobia; anxiety and anxiety disorders (including but not limited to acute stress disorder, anxiety due to a general medical condition, dental phobia, generalized anxiety disorder, panic disorder, separation anxiety disorder, social anxiety disorder, social phobia, specific phobia, and substance-induced anxiety disorder); bipolar disorders; depression (including but not limited to dysthymia, major depressive disorder, seasonal affective disorder, seasonal depression, unipolar depression, and postpartum depression); fatigue associated with depression including but limited to chronic fatigue syndrome; mood disorders (including disorders due to a general medical condition and substance-induced mood-disorders); obsessive-compulsive disorder; panic attack; perimenopause, menopause, and male menopause; post-traumatic stress disorder; premenstrual syndrome (PMS) and premenstrual dysphoric disorder (PDD); and sleep disorders including insomnia and narcolepsy.

Cognitive Function, Learning, and Memory Disorders

As used herein, and unless otherwise specified, the terms "cognitive dysfunction," "cognitive function disorder," "learning disorder", and "memory disorder" apply to disorders that may be treated by improving mammalian brain function. The terms include disorders in which subjects exhibit symptoms of memory or learning loss, have impaired ability to learn new information or to recall previously learned information or past efforts. In some embodiments, these disorders cause marked impairment in social or occupational functioning and represent a significant decline from a previous level of functions. In some embodiments, the cognitive dysfunction may be associated with, for example, adult and childhood learning disorders; altruism; amnestic disorders (including Alzheimer's disease-related cognitive decline, normal age-related cognitive decline and persisting amnestic disorder); associative learning; attention; benign forgetfulness; cognitive deficits induced by situational stress (including but not limited to operating machinery for extended time periods or working in emergency or combat situations); cognitive disorders including dementia (associated with acquired immunodeficiency disease, Alzheimer's disease, Creutzfeldt-Jacob disease, HIV infection, Huntington's disease, ischemia, multi-infarct dementia, Parkinson's disease, perinatal hypoxia, Pick's disease, trauma, vascular problems or stroke, other general medical conditions or substance abuse); cooperativity; declarative memory; early consolidation; empathy; episodic memory; executive function; explicit memory; implicit memory; imprinting; language; late consolidation; learning (including electronic, formal, informal, multimedia and rote learning); low IQ; memory deficit; memory loss; mild cognitive impairment (MCI); non-verbal and verbal communicative skills; play; rehearsal; retrieval, semantic memory; sensory integration of environmental cues including temperature, odor, sounds, touch, and taste; social cognition; and speech disorders.

Substance Abuse and Eating Disorders

The term "substance abuse" includes a pattern of behavior in which a subject uses a substance in an abusive manner and is used herein in a manner consistent with its accepted meaning in the art. (See, e.g., DSM-IV™.) Examples of substance abuse include abuse of or addiction to cannabis, cocaine, morphine, opioids, nicotine, or alcohol; substance-abuse related disorders and addictive behaviors (including substance-induced delirium); tolerance, dependence or withdrawal from substances including alcohol, amphetamines, anxiolytics, cannabis, cocaine, hallucinogens, hypnotics, inhalants, nicotine, opioids, phencyclidine, or sedatives.

The term "eating disorder," as used herein, refers to abnormal compulsions to avoid eating or uncontrollable impulses to consume abnormally large amounts of food. Eating disorders include, but are not limited to, anorexia nervosa, binge eating, bulimia nervosa, cachexia, compulsive eating disorder, emesis, and obesity.

Pain

As used herein, and unless otherwise specified, the term "pain" refers to an unpleasant sensory and emotional experience. The term "pain," as used herein, refers to all categories of pain, including pain that is described in terms of stimulus or nerve response, e.g., somatic pain (normal nerve response to a noxious stimulus) and neuropathic pain (abnormal response of a injured or altered sensory pathway, often without clear noxious input); pain that is categorized temporally, e.g., chronic pain and acute pain; pain that is categorized in terms of its severity, e.g., mild, moderate, or severe; and pain that is a symptom or a result of a disease state or syndrome, e.g., inflammatory pain, cancer pain, carpal tunnel syndrome, AIDS pain, arthropathy, migraine, trigeminal neuralgia, cardiac ischaemia, neuropathy arising from chronic alcohol use, and diabetic peripheral neuropathic pain (see, e.g., Harrison's *Principles of Internal Medicine*, pp. 93-98 (Wilson et al., eds., 12th ed. 1991); Williams et al., *J. of Med. Chem.* 42: 1481-1485 (1999), herein each incorporated by reference in their entirety). "Pain" is also meant to include mixed etiology pain, dual mechanism pain, allodynia, causalgia, central pain, hyperesthesia, hyperpathia, dysesthesia, and hyperalgesia. In addition, the term "pain" includes pain resulting from dysfunction of the nervous system: organic pain states that share clinical features of neuropathic pain and possible common pathophysiology mechanisms, but are not initiated by an identifiable lesion in any part of the nervous system.

The term "somatic pain," as used herein, refers to a normal nerve response to a noxious stimulus such as injury or illness, e.g., trauma, burn, infection, inflammation, or disease process such as cancer, and includes both cutaneous pain (e.g., skin, muscle or joint derived) and visceral pain (e.g., organ derived).

The term "neuropathic pain," as used herein, refers to a heterogeneous group of neurological conditions that result from damage to the nervous system. The term also refers to pain resulting from injury to or dysfunctions of peripheral and/or central sensory pathways, and from dysfunctions of the nervous system, where the pain often occurs or persists without an obvious noxious input. This includes pain related to peripheral neuropathies as well as central neuropathic pain. Common types of peripheral neuropathic pain include diabetic neuropathy (also called diabetic peripheral neuropathic pain, or DN, DPN, or DPNP), post-herpetic neuralgia (PHN), and trigeminal neuralgia (TGN). Central neuropathic pain, involving damage to the brain or spinal cord, can occur following stroke, spinal cord injury, and as a result of multiple sclerosis, and is also encompassed by the term. Other types of pain that are meant to be included in the definition of neuropathic pain include, but are not limited to, pain from neuropathic cancer pain, HIV/AIDS induced pain, phantom limb pain, and complex regional pain syndrome.

The term also encompasses the common clinical features of neuropathic pain including, but not limited to, sensory loss, allodynia (non-noxious stimuli produce pain), hyperalgesia and hyperpathia (delayed perception, summation, and painful after sensation). Pain is often a combination of nociceptive and neuropathic types, for example, mechanical spinal pain and radiculopathy or myelopathy.

As used herein, and unless otherwise specified, the term "acute pain" refers to the normal, predicted physiological response to a noxious chemical, thermal or mechanical stimulus typically associated with invasive procedures, trauma and disease. It is generally time-limited, and may be viewed as an appropriate response to a stimulus that threatens and/or produces tissue injury. The term also refers to pain which is marked by short duration or sudden onset.

As used herein, and unless otherwise specified, the term "chronic pain" encompasses the pain occurring in a wide range of disorders, for example, trauma, malignancies and chronic inflammatory diseases such as rheumatoid arthritis. Chronic pain may last more than about six months. In addition, the intensity of chronic pain may be disproportionate to the intensity of the noxious stimulus or underlying process. The term also refers to pain associated with a chronic disorder, or pain that persists beyond resolution of an underlying disorder or healing of an injury, and that is often more intense than the underlying process would predict. It may be subject to frequent recurrence.

As used herein, and unless otherwise specified, the term "inflammatory pain" is pain in response to tissue injury and the resulting inflammatory process. Inflammatory pain is adaptive in that it elicits physiologic responses that promote healing. However, inflammation may also affect neuronal function. Inflammatory mediators, including PGE2 induced by the COX2 enzyme, bradykinins, and other substances, bind to receptors on pain-transmitting neurons and alter their function, increasing their excitability and thus increasing pain sensation. Much chronic pain has an inflammatory component. The term also refers to pain which is produced as a symptom or a result of inflammation or an immune system disorder.

As used herein, and unless otherwise specified, the term "visceral pain" refers to pain which is located in an internal organ.

As used herein, and unless otherwise specified, the term "mixed etiology pain" refers to pain that contains both inflammatory and neuropathic components.

As used herein, and unless otherwise specified, the term "dual mechanism pain" refers to pain that is amplified and maintained by both peripheral and central sensitization.

As used herein, and unless otherwise specified, the term "causalgia" refers to a syndrome of sustained burning, allodynia, and hyperpathia after a traumatic nerve lesion, often combined with vasomotor and sudomotor dysfunction and later trophic changes.

As used herein, and unless otherwise specified, the term "central pain" refers to pain initiated by a primary lesion or dysfunction in the central nervous system.

As used herein, and unless otherwise specified, the term "hyperesthesia" refers to increased sensitivity to stimulation, excluding the special senses.

As used herein, and unless otherwise specified, the term "hyperpathia" refers to a painful syndrome characterized by an abnormally painful reaction to a stimulus, especially a repetitive stimulus, as well as an increased threshold. It may occur with allodynia, hyperesthesia, hyperalgesia, or dysesthesia.

As used herein, and unless otherwise specified, the term "dysesthesia" refers to an unpleasant abnormal sensation, whether spontaneous or evoked. In certain embodiments, dysesthesia include hyperalgesia and allodynia.

As used herein, and unless otherwise specified, the term "hyperalgesia" refers to an increased response to a stimulus that is normally painful. It reflects increased pain on suprathreshold stimulation.

As used herein, and unless otherwise specified, the term "allodynia" refers to pain due to a stimulus that does not normally provoke pain.

As used herein, and unless otherwise specified, the term "Diabetic Peripheral Neuropathic Pain" (DPNP), also called diabetic neuropathy, DN or diabetic peripheral neuropathy), refers to chronic pain caused by neuropathy associated with diabetes mellitus. The classic presentation of DPNP is pain or tingling in the feet that can be described not only as "burning" or "shooting" but also as severe aching pain. Less commonly, patients may describe the pain as itching, tearing, or like a toothache. The pain may be accompanied by allodynia and hyperalgesia and an absence of symptoms, such as numbness.

As used herein, and unless otherwise specified, the term "Post-Herpetic Neuralgia", also called "Postherpetic Neuralgia (PHN)", refers to a painful condition affecting nerve fibers and skin. Without being limited by a particular theory, it is a complication of shingles, a second outbreak of the varicella zoster virus (VZV), which initially causes chickenpox.

As used herein, and unless otherwise specified, the term "neuropathic cancer pain" refers to peripheral neuropathic pain as a result of cancer, and can be caused directly by infiltration or compression of a nerve by a tumor, or indirectly by cancer treatments such as radiation therapy and chemotherapy (chemotherapy-induced neuropathy).

As used herein, and unless otherwise specified, the term "HIV/AIDS peripheral neuropathy" or "HIV/AIDS related neuropathy" refers to peripheral neuropathy caused by HIV/AIDS, such as acute or chronic inflammatory demyelinating neuropathy (AIDP and CIDP, respectively), as well as peripheral neuropathy resulting as a side effect of drugs used to treat HIV/AIDS.

As used herein, and unless otherwise specified, the term "Phantom Limb Pain" refers to pain appearing to come from where an amputated limb used to be. Phantom limb pain can also occur in limbs following paralysis (e.g., following spinal cord injury). "Phantom Limb Pain" is usually chronic in nature.

As used herein, and unless otherwise specified, the term "Trigeminal Neuralgia (TIN)" refers to a disorder of the fifth cranial (trigeminal) nerve that causes episodes of intense, stabbing, electric-shock-like pain in the areas of the face where the branches of the nerve are distributed (lips, eyes, nose, scalp, forehead, upper jaw, and lower jaw). It is also known as the "suicide disease".

As used herein, and unless otherwise specified, the term "Complex Regional Pain Syndrome (CRPS)," formerly known as Reflex Sympathetic Dystrophy (RSD), refers to a chronic pain condition whose key symptom is continuous, intense pain out of proportion to the severity of the injury, which gets worse rather than better over time. The term encompasses type 1 CRPS, which includes conditions caused by tissue injury other than peripheral nerve, and type 2 CRPS, in which the syndrome is provoked by major nerve injury, and is sometimes called causalgia.

As used herein, and unless otherwise specified, the term "fibromyalgia" refers to a chronic condition characterized by diffuse or specific muscle, joint, or bone pain, along with fatigue and a range of other symptoms. Previously, fibromyalgia was known by other names such as fibrositis, chronic muscle pain syndrome, psychogenic rheumatism and tension myalgias.

As used herein, and unless otherwise specified, the term "convulsion" refers to a neurological disorder and is used interchangeably with "seizure," although there are many types of seizure, some of which have subtle or mild symptoms instead of convulsions. Seizures of all types may be caused by disorganized and sudden electrical activity in the brain. In some embodiments, convulsions are a rapid and uncontrollable shaking during which the muscles contract and relax repeatedly.

Pharmaceutical Compositions

In certain embodiments, the present invention provides a pharmaceutical composition comprising a compound as disclosed herein and a pharmaceutically acceptable carrier.

The term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, such like materials and combinations thereof, as would be known to one of ordinary skill in the art (see, for example, *Remington's Pharmaceutical Sciences*, 18th Ed. Mack Printing Company, 1990, pp. 1289-1329). Except insofar as any conventional carrier is incompatible with the active ingredient, its use in the therapeutic or pharmaceutical compositions is contemplated by the invention.

The pharmaceutical composition may be formulated for particular routes of administration such as oral, intravenous, intraperitoneal, parenteral, enteral, sublingual, vaginal, subcutaneous, transdermal, transmucosal, sublabial, buccal, intracerebral, intracerebroventricular, intramuscular, intranasal, intrathecal, inhalation, topical, or rectal administration, etc. In addition, the pharmaceutical compositions of the present invention may be in a solid form including capsules, tablets, pills, granules, powders, thin film, or suppositories, or in a liquid form including solutions, suspensions, gels, creams, or emulsions. The pharmaceutical compositions may be subjected to conventional pharmaceutical operations such as sterilization and/or can contain conventional inert diluents, lubricating agents or buffering agents, as well as adjuvants, such as preservatives, stabilizers, wetting agents, emulsifiers and buffers.

In some embodiments, the pharmaceutical compositions are tablets or gelatin capsules comprising the active ingredient together with a) diluents, (e.g., lactose, dextrose, sucrose, mannitol, sorbitol, cellulose and/or glycine); b)

lubricants, (e.g., silica, talcum, stearic acid, its magnesium or calcium salt and/or polyethyleneglycol); c) binders, (e.g., magnesium aluminum silicate, starch paste, gelatin, tragacanth, methylcellulose, sodium carboxymethylcellulose and/or polyvinylpyrrolidone); d) disintegrants, (e.g., starches, agar, alginic acid or its sodium salt, or effervescent mixtures); or e) absorbents, colorants, flavors and sweeteners; or any combination thereof.

Tablets may be either film coated or enteric coated according to methods known in the art.

Suitable compositions for oral administration include an effective amount of a compound as disclosed herein in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions may contain one or more agents selected from sweetening agents, flavoring agents, coloring agents and preservatives. Tablets generally contain the active ingredient(s) in admixture with nontoxic pharmaceutically acceptable excipients that are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets may be uncoated or coated by known techniques to delay disintegration and absorption in the gastrointestinal tract and thereby provide a sustained action over a longer period. For example, a time delay material such as glyceryl monostearate or glyceryl distearate may be employed. Formulations for oral use may be presented as hard gelatin capsules in which the active ingredient(s) are mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories may be prepared from fatty emulsions or suspensions. Such compositions may be sterilized and/or contain adjuvants, such as preserving, stabilizing, wetting or emulsifying agents, solution promoters, salts for regulating the osmotic pressure and/or buffers. In addition, they may also contain other therapeutic agents. Such compositions may be prepared according to conventional mixing, granulating or coating methods, respectively, and contain about 0.1-75%, or contain about 1-50%, of the active ingredient.

Suitable compositions for transdermal application include an effective amount of a compound as disclosed herein with a carrier. Carriers include absorbable pharmacologically acceptable solvents to assist passage through the skin of the subject. For example, transdermal devices may be in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, (e.g., to the skin and eyes), include aqueous solutions, suspensions, ointments, creams, gels or sprayable formulations, (e.g., for delivery by aerosol and the like). Such topical compositions may contain solubilizers, stabilizers, tonicity enhancing agents, buffers and preservatives.

Topical application may also pertain to an inhalation or to an intranasal application. Such compositions may be delivered in the form of a dry powder (either alone, as a mixture, for example, a dry blend with lactose, or a mixed component particle, for example with phospholipids) from a dry powder inhaler or an aerosol spray presentation from a pressurized container, pump, spray, atomizer or nebuliser, with or without the use of a suitable propellant.

The present invention further provides anhydrous pharmaceutical compositions and dosage forms comprising a compound as disclosed herein as active ingredient(s), since water may facilitate the degradation of certain compounds. Anhydrous pharmaceutical compositions and dosage forms of the invention may be prepared using anhydrous or low moisture containing ingredients and low moisture or low humidity conditions. An anhydrous pharmaceutical composition may be prepared and stored such that its anhydrous nature is maintained. Accordingly, anhydrous compositions are preferably packaged using materials known to prevent exposure to water such that they can be included in suitable formulary kits. Examples of suitable packaging include hermetically sealed foils, plastics, unit dose containers (e.g., vials), blister packs, and strip packs.

The invention further provides pharmaceutical compositions and dosage forms that comprise one or more agents that reduce the rate by which a compound as disclosed herein will decompose. Such agents, referred to herein as "stabilizers," include antioxidants such as ascorbic acid, pH buffers, or salt buffers, etc.

The pharmaceutical composition or combination of the present invention may be present in a unit dosage in an amount of about 0.001 mg-10 g, 0.01-500 mg or about 0.01-250 mg or about 0.01-150 mg or about 0.01-100 mg, or about 0.01-50 mg of active ingredient for a subject of about 50-70 kg. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

A therapeutically effective amount in vivo may range depending on the route of administration, between about 0.0001-500 mg/kg, or between about 0.0001-100 mg/kg, or between about 0.0003-10 mg/kg.

Methods of Treatment, Prevention, and/or Management

Binding to mGluR5 Receptor

In various embodiments, a method of binding a compound as disclosed herein to a metabotropic glutamate receptor, such as mGluR5 is provided. The method comprises contacting mGluR5 with an amount of compound as disclosed herein effective to bind a metabotropic glutamate receptor.

In one embodiment, a method of modulating the activity of mGluR5 via the binding of an mGluR5 ligand to mGluR5 is provided. The method comprises contacting mGluR5 with an amount of a compound as disclosed herein effective to modulate the activity of mGluR5. In one embodiment, the ligand is L-glutamate. In another embodiment, the ligand is a drug molecule or another small molecule known to have binding affinity to mGluR5. In another embodiment, the mGluR5 ligand is a radioactively labeled compound, known to bind to mGluR5. In other embodiments, binding to metabotropic glutamate receptor may be assessed using PET imaging as is known in the art, e.g. utilizing appropriate PET ligands. In some embodiments, the ligand is an allosteric modulator (e.g., a positive or negative allosteric modulator), antagonist, or inverse agonist of mGluR5.

Modulation of mGluR5 Receptor Activity

In various embodiments, a method of modulating (e.g., inhibiting or augmenting) the activity of a metabotropic glutamate receptor, such as mGluR5 is provided. The method comprises contacting the receptor, such as mGluR5, with an amount of a compound as disclosed herein, or a pharmaceutically acceptable salt thereof effective to modulate the activity of a metabotropic glutamate receptor, in vitro or in vivo. In certain embodiments, mGluR5 is contacted with a compound as disclosed herein by administering to a subject a therapeutically effective amount of a compound as disclosed herein, or a pharmaceutically acceptable salt or solvate thereof. In certain embodiments, the subject may be a mammal, such as a human, dog, monkey, baboon, rat, or mouse, preferably a human.

In certain embodiments, a compound as disclosed herein increases or augments the activity of metabotropic glutamate receptor, such as mGluR5. In some embodiments, the activity of mGluR5 is increased or augmented in the presence or absence of an mGluR5 ligand (e.g., glutamate) by about 1%, about 5%, about 10%, about 20%, about 30%, about 40%, about 50%, about 60%, about 70%, about 80%, about 90%, about 95%, about 99% or more, as compared with the activity obtained in the absence of a compound as disclosed herein. In certain such embodiments a compound as disclosed herein will not increase or augment the activity of mGluR5 in the absence of glutamate. In certain embodiments, the increase or augmentation of receptor activity is dose-dependent. Increase of mGluR5 activity may be measured using assays known in the art, for example, by in vitro functional assays as described herein elsewhere. In certain embodiments, the functional assay utilizes an appropriate cell-line expressing the desired metabotropic glutamate receptor, such as mGluR5. In other embodiments, the functional assay utilizes synaptosomes isolated from brain tissue of an appropriate organism. In other embodiments, inhibition of metabotropic glutamate receptor activity may be assessed using receptor binding experiments known in the art, e.g., utilizing appropriate membrane preparations. In certain embodiments, the assay involves treatment of a test subject (e.g., a mouse or a rat) with a compound as disclosed herein as well as a reference compound, followed by isolation of brain tissue and ex vivo analysis of receptor occupancy. In certain embodiments, the mGluR5 modulator is a positive allosteric modulator.

In certain embodiments, methods of increasing or augmenting the activity of a metabotropic glutamate receptor, such as mGluR5 in the presence or absence of glutamate, in a subject (e.g., human) comprising administering to the subject an effective amount of compound as disclosed herein are provided. In some embodiments, the activity of mGluR5 is increased or augmented by about 1%, about 5%, about 10%, about 20%, about 30%, about 40%, about 50%, about 60%, about 70%, about 80%, about 90%, about 95%, about 99% or more, when measured using an assay known in the art compared to the activity obtained in the absence of administration of a compound as disclosed herein.

In certain embodiments, a method of increasing or augmenting the activity of a metabotropic glutamate receptor, such as mGluR5, by a metabotropic glutamate receptor ligand is provided. In one embodiment, the method comprises contacting mGluR5 receptor with a potentiator, an allosteric agonist, or a positive allosteric modulator of the mGluR5 receptor in an amount effective to increase or augment the activity. In another embodiment, a potentiator, an allosteric agonist, or a positive allosteric modulator of the mGluR5 receptor is a compound as disclosed herein.

In certain embodiments, a compound as disclosed herein inhibits or reduces the activity of metabotropic glutamate receptor, such as mGluR5. In some embodiments, the activity of mGluR5 is inhibited or reduced by about 1%, about 5%, about 10%, about 20%, about 30%, about 40%, about 50%, about 60%, about 70%, about 80%, about 90%, about 95%, about 99% or more, as compared with the activity obtained without contacting with the compounds as disclosed herein. In certain embodiments, the inhibition or reduction of receptor activity is dose-dependent. Inhibition of mGluR5 activity may be measured using assays known in the art, for example, the in vitro functional assays as described herein elsewhere. In one embodiment, the functional assay utilizes an appropriate cell-line expressing the desired metabotropic glutamate receptor, such as mGluR5. In other embodiments, the functional assay utilizes synaptosomes isolated from brain tissue of an appropriate organism. In other embodiments, inhibition of metabotropic glutamate receptor activity may be assessed using receptor binding experiments known in the art, e.g. utilizing appropriate membrane preparations. In one embodiment, the assay involves treatment of a test subject (e.g., a mice or a rat) with a compound set forth herein as well as a reference compound, followed by isolation of brain tissue and ex vivo analysis of receptor occupancy. In one embodiment, the mGluR5 modulator is a negative allosteric modulator.

In certain embodiments, methods of inhibiting or reducing the activity of a metabotropic glutamate receptor, such as mGluR5, in a subject (e.g., human) comprising administering to the subject an effective amount of a compound as disclosed herein are provided. In some embodiments, the activity of mGluR5 is inhibited or reduced by about 1%, about 5%, about 10%, about 20%, about 30%, about 40%, about 50%, about 60%, about 70%, about 80%, about 90%, about 95%, about 99% or more, when measured using an assay known in the art and compared to the activity obtained in the absence of administration of a compound as disclosed herein.

In one embodiment, a method of inhibiting or reducing the activity of a metabotropic glutamate receptor, such as mGluR5, by a metabotropic glutamate receptor ligand is provided. In one embodiment, the method comprises contacting mGluR5 receptor with an amount of an antagonist, an inverse agonist, or an allosteric modulator of the mGluR5 receptor effective to inhibit or reduce the activity of the metabotropic glutamate receptor. In another embodiment, an antagonist, an inverse agonist, or an allosteric modulator of the mGluR5 receptor is a compound as disclosed herein.

Treatment, Prevention, and/or Management of mGluR5 Related Disorders and Conditions In certain embodiments, a method of treating, preventing, and/or managing a neurological disorder, such as a neurodegenerative disorder, neuropsychiatric disorder, affective disorder, or a cognitive function, learning or memory disorder, comprising administering to a subject in need thereof an effective amount of a compound as disclosed herein is provided.

In certain embodiments, a method of treating psychosis, schizophrenia, cognitive impairment associated with schizophrenia, or a cognitive disorder (such as Alzheimer's disease), comprising administering to a subject in need thereof an effective amount of a compound as disclosed herein is provided.

In certain embodiments, the compounds as disclosed herein inhibit the activity of mGluR5. In certain embodiments, the compounds as disclosed herein are positive allosteric modulators of mGluR5. In other embodiments, the compounds as disclosed herein are antagonists of mGluR5. In certain embodiments, the compounds as disclosed herein are selective for mGluR5 over other CNS-related targets. In certain embodiments, the compounds as disclosed herein are highly brain penetrable in mammals, such as rodents, and human. In some embodiments, inhibition or potentiation of mGluR5 activity may be assessed by functional assays as described herein elsewhere. In certain embodiments, the efficacious concentration of the compounds set forth herein is less than 10 nM, less than 100 nM, less than 1 µM, less than 10 µM, less than 100 µM, less than 1 µM, or less than 1 mM. In other embodiments, compound's activity may be assessed in various art-recognized animal models.

In some embodiments, a method of treating, preventing, and/or managing a neurodegenerative disease [including but not limited to: Alzheimer's disease (including the accompanying symptoms of mild, moderate, or severe cognitive impairment); amyotropic lateral sclerosis (ALS); anoxic and ischemic injuries; ataxia and convulsion (including for the treatment and prevention of seizures that are caused by schizoaffective disorder or by drugs used to treat schizophrenia); benign forgetfulness; brain edema; cerebellar ataxia including McLeod neuroacanthocytosis syndrome (MLS); closed head injury; coma; contusive injuries (e.g. spinal cord injury and head injury); dementias including multi-infarct dementia and senile dementia; disturbances of consciousness; Down syndrome; drug-induced or medication-induced Parkinsonism (such as neuroleptic-induced acute akathisia, acute dystonia, Parkinsonism, or tardive dyskinesia, neuroleptic malignant syndrome, or medication-induced postural tremor); epilepsy; fragile X syndrome; Gilles de la Tourette's syndrome; head trauma; hearing impairment and loss; Huntington's disease; Lennox syndrome; levodopa-induced dyskinesia; mental retardation; movement disorders including akinesias and akinetic (rigid) syndromes (including basal ganglia calcification, corticobasal degeneration, multiple system atrophy, parkinsonism-ALS dementia complex, Parkinson's disease, postencephalitic parkinsonism, and progressively supranuclear palsy); muscular spasms and disorders associated with muscular spasticity or weakness including chorea (such as benign hereditary chorea, drug-induced chorea, hemiballism, Huntington's disease, neuroacanthocytosis, Sydenham's chorea, and symptomatic chorea), dyskinesia (including tics such as complex tics, simple tics, and symptomatic tics), myoclonus (including generalized myoclonus and focal cyloclonus), tremor (such as rest tremor, postural tremor, and intention tremor), and dystonia (including axial dystonia, dystonic writer's cramp, hemiplegic dystonia, paroxymal dystonia, and focal dystonia such as blepharospasm, oromandibular dystonia, and spasmodic dysphonia and torticollis); neuronal damage including ocular damage, retinopathy or macular degeneration of the eye; neurotoxic injury which follows cerebral stroke, thromboembolic stroke, hemorrhagic stroke, cerebral ischemia, cerebral vasospasm, hypoglycemia, amnesia, hypoxia, anoxia, perinatal asphyxia and cardiac arrest; Parkinson's disease; seizure; status epilecticus; stroke; tinnitus; tubular sclerosis; and viral infection induced neurodegeneration (including but limited to neurodegeneration caused by caused by acquired immunodeficiency syndrome (AIDS) and encephalopathies)], comprising administering to a subject in need thereof an effective amount of a compound as disclosed herein is provided. For example, without being limited by a particular theory, mGluR5 modulators may be effective in treating Parkinson's disease, and efficacious in a variety of animal models for Parkinson's disease. See, e.g., Jaeschke, G., et al., *Expert Opin. Ther. Pat.* 2008, 18, 123; Glatthar R., et al., WO 2006/89700 A1.

In some embodiments, a method of treating, preventing, and/or managing a neuropsychiatric disorder (including but limited to: aggression; attention disorders including attention-deficit disorder (ADD), attention-deficit-hyperactivity disorder (ADHD) and conduct disorder; delirium; delusional disorder; persisting dementia; pervasive development disorder including autism, autistic disorder and autism spectrum disorder; psychosis and psychotic disorders (including psychosis associated with affective disorders, brief reactive psychosis, brief psychotic disorder, shared psychotic disorder, psychotic disorder due to a general medical condition and substance-induced or drug-induced psychotic disorder (e.g., caused by phencyclidine, ketamine and other dissociative anaesthetics, amphetamine, cocaine and other psychostimulants)); schizophrenia (including schizoaffective psychosis and "schizophrenia-spectrum" disorders such as schizoid or schizotypal personality disorders, or illnesses associated with psychosis (such as major depression, manic depressive (bipolar) disorder, Alzheimer's disease and post-traumatic stress syndrome) including both the positive and negative symptoms of schizophrenia and other psychoses); and sensory hyper-excitability), comprising administering to a subject in need thereof an effective amount of a compound as disclosed herein is provided.

In some embodiments, a method of treating, preventing and/or managing disorders of cognition, learning or memory or of improving cognitive function, memory and learning abilities (including but not limited to: adult and childhood learning disorders; altruism; amnestic disorders (including Alzheimer's disease-related cognitive decline, normal age-related cognitive decline and persisting amnestic disorder); associative learning; attention; benign forgetfulness; cognitive deficits induced by situational stress (including but not limited to operating machinery for extended time periods or working in emergency or combat situations); cognitive disorders including dementia (associated with acquired immunodeficiency disease, Alzheimer's disease, Creutzfeldt-Jacob disease, HIV infection, Huntington's disease, ischemia, multi-infarct dementia, Parkinson's disease, perinatal hypoxia, Pick's disease, trauma, vascular problems or stroke, other general medical conditions or substance abuse); cooperativity; declarative memory; early consolidation; empathy; episodic memory; executive function; explicit memory; implicit memory; imprinting; language; late consolidation; learning (including electronic, formal, informal, multimedia and rote learning); low IQ; memory deficit; memory loss; mild cognitive impairment (MCI); non-verbal and verbal communicative skills; play; rehearsal; retrieval, semantic memory; sensory integration of environmental cues including temperature, odor, sounds, touch, and taste; social cognition; and speech disorders), comprising administering to a subject in need thereof an effective amount of a compound as disclosed herein is provided.

In some embodiments, a method of treating, preventing, and/or managing gastrointestinal disorders (including but not limited to acid reflux; dyspepsia; gastroesophageal reflux disorder (GERD); and irritable bowel syndrome), comprising administering to a subject in need thereof an effective amount of a as disclosed herein is provided. For example, without being limited by a particular theory, mGluR5 modulators may be effective in treating gastrointestinal disorders in human. See, e.g., Jaeschke, G., et al., *Expert Opin. Ther. Pat.* 2008, 18, 123; Bolea C., et al., WO 2004/78728 A1.

In some embodiments, a method of treating, preventing, and/or managing all categories of pain (including but not limited to: pain described in terms of stimulus or nerve response; somatic pain (normal nerve response to a noxious stimulus); neuropathic pain (abnormal response of a injured or altered sensory pathway often without clear noxious input, and including chemotherapy-induced neuropathy, diabetic peripheral neuropathic pain, HIV/AIDS peripheral neuropathy, neuropathic cancer pain, and post-herpetic neuralgia); abdominal pain; acute thermal hyperalgesia; allodynia; burns; causalgia; central pain; complex regional pain syndrome (CRPS); dental pain; dual mechanism pain; dysesthesia; ear ache; episiotomy pain; eye pain; fibromyalgia; gynecological pain including dysmeorrhoea; headache (including acute and chronic tension headache and cluster headache); heart pain; hyperalgesia; hyperesthesia; hyperpathia; itching conditions including contact dermatitis, pruritis, and itch due to atopic dermatitis and hemodialysis; labor pain; low back pain; mechanical allodynia; mixed etiology pain; musculo-skeletal pain including that following physical trauma; neck pain; orofacial pain; pain associated with cystitis; pain cause by convulsion; pain resulting from dysfunction of the nervous system (i.e., organic pain states that share clinical features of neuropathic pain and possibly common pathophysiology mechanism, but are not initiated by an identifiable lesion in any part of the nervous system); pain that is a symptom or a result of a disease state or syndrome (such as AIDS pain, ankylosing spondylitis; arthritis pain, cancer pain, cardiac ischaemia, carpal tunnel syndrome, diabetic peripheral neuropathic pain, episcleritis, gout, inflammation, irritable bowel syndrome, migraine, neuropathy arising from chronic alcohol use, repetitive motion injury, pain from autoimmune diseases, pain from respiratory diseases, scar pain, sciatica; scleritis; and trigeminal neuralgia); pain that is categorized in terms of its severity (mild, moderate, or severe pain); pain that is categorized temporally (chronic pain and acute pain); phantom limb pain; post-surgical pain; reflex sympathetic dystrophy; sinus pain; and visceral pain) comprising administering to a subject in need thereof an effective amount of a compound as disclosed herein is provided. See e.g., Jaeschke, G., et al., *Expert Opin. Ther. Pat.* 2008, 18, 123; Cosford, N. D. P., et al., WO 2003/51315 A2.

In some embodiments, a method of treating, preventing, and/or managing migraine, comprising administering to a subject in need thereof an effective amount of a compound as disclosed herein is provided. For example, without being limited by a particular theory, mGluR5 modulators may be effective in the treatment and prevention of migraine in human, and may have comparable efficacy to triptans in treating migraine. See, e.g., Jaeschke, G., et al., *Expert Opin. Ther. Pat.* 2008, 18, 123.

In some embodiments, a method of treating, preventing, and/or managing substance abuse disorder or eating disorder (including but not limited to the abuse of or addiction to cannabis, cocaine, morphine, opioid, nicotine, or alcohol; substance-abuse related disorders and addictive behaviors (including substance-induced delirium); tolerance, dependence or withdrawal from substances including alcohol, amphetamines, anxiolytics, cannabis, cocaine, hallucinogens, hypnotics, inhalants, nicotine, opioids, phencyclidine, or sedatives; anorexia nervosa; binge eating; bulimia nervosa; cachexia; compulsive eating disorder; emesis; and obesity) comprising administering to a subject in need thereof an effective amount of a compound as disclosed herein is provided. See e.g., Jaeschke, G., et al., *Expert Opin. Ther. Pat.* 2008, 18, 123.

In other embodiments, a method of treating, preventing, and/or managing a disorder of the genitourinary tract or a sexual disorder (including but not limited to: lower urinary tract disorder; overactive bladder; urinary incontinence including without limitation involuntary voiding of urine, dribbling or leakage of urine, stress urinary incontinence (SUI), urge incontinence, urinary exertional incontinence, reflex incontinence, passive incontinence, and overflow incontinence; and sexual dysfunction, in men or women, including without limitation sexual dysfunction caused by psychological and/or physiological factors, erectile dysfunction, premature ejaculation, vaginal dryness, lack of sexual excitement, inability to obtain orgasm, and psychosexual dysfunction, including without limitation, inhibited sexual desire, inhibited sexual excitement, inhibited female orgasm, inhibited male orgasm, functional dyspareunia, functional vaginismus, and atypical psychosexual dysfunction), comprising administering to a subject in need thereof an effective amount of a compound as disclosed herein is provided.

In other embodiments, a method of treating, preventing, and/or managing cancer, including but not limited to, oral cancer and glioneuronal cancer, comprising administering to a subject in need thereof an effective amount of a compound as disclosed herein is provided.

In some embodiments, a compound as disclosed herein is active in at least one model, which can be used to measure the activity of the compounds and estimate their efficacy in treating a disorder related to mGluR5. For example, when the model is for depression (e.g., mean immobility), the compounds are active when they inhibit mean immobility of a test subject by about 5%, about 10%, about 20%, about 30%, about 40%, about 50%, about 60%, about 70%, about 80%, about 90%, about 95%, about 99%, or more, when compared to vehicle. In some embodiments, the compound as disclosed herein produce a similar disparity in measured endpoint between treated animals and animals administered vehicle.

Other exemplary diseases and conditions that may be treated, prevented, and/or managed using the methods, compounds as disclosed herein and compositions thereof, include, but are not limited to: metabolic diseases including diabetes and pulmonary/respiratory diseases including asthma, chronic obstructive pulmonary disease (COPD), chronic bronchitis, cystic fibrosis, and emphysema.

In certain embodiments, the compounds as described herein treat, prevent, and/or manage a neurological disorder, without causing addiction to said compounds. Any suitable route of administration can be employed for providing the patient with a therapeutically or prophylactically effective dose of an active ingredient. For example, oral, mucosal (e.g., nasal, sublingual, buccal, rectal, vaginal), parenteral (e.g., intravenous, intramuscular), transdermal, and subcutaneous routes can be employed. Exemplary routes of administration include oral, transdermal, and mucosal. Suitable dosage forms for such routes include, but are not limited to, transdermal patches, ophthalmic solutions, sprays, and aerosols. Transdermal compositions can also take the form of creams, lotions, and/or emulsions, which can be included in an appropriate adhesive for application to the skin or can be included in a transdermal patch of the matrix or reservoir type as are conventional in the art for this purpose. An exemplary transdermal dosage form is a "reservoir type" or "matrix type" patch, which is applied to the skin and worn for a specific period of time to permit the penetration of a desired amount of active ingredient. The patch can be replaced with a fresh patch when necessary to provide constant administration of the active ingredient to the patient.

The amount to be administered to a patient to treat, prevent, and/or manage the disorders described herein will depend upon a variety of factors including the activity of the particular compound employed, or the ester, salt or amide thereof, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount required. For example, the physician or veterinarian could start doses of the compounds employed at levels lower than that required in order to achieve the desired therapeutic effect and gradually increase the dosage until the desired effect is achieved.

In general, a suitable daily dose of a compound set forth herein will be that amount of the compound which is the lowest dose effective to produce a therapeutic or prophylactic effect. Such an effective dose will generally depend upon the factors described above. Generally, oral, intravenous, intracerebroventricular, and subcutaneous doses of the compounds set forth herein for a patient will range from about 0.005 to about 100 mg per kilogram or about 0.05 mg per kilogram to about 5 mg per kilogram of body weight per day. In one embodiment, the oral dose of a compound set forth herein will range from about 1 mg to about 1 g per day or 10 mg to about 300 mg per day. In another embodiment, the oral dose of a compound set forth herein will range from about 20 mg to about 250 mg per day. In another embodiment, the oral dose of a compound set forth herein will range from about 100 mg to about 300 mg per day. In another embodiment, the oral dose of a compound set forth herein will range from about 10 mg to about 100 mg per day. In another embodiment, the oral dose of a compound set forth herein will range from about 25 mg to about 50 mg per day. In another embodiment, the oral dose of a compound set forth herein will range from about 50 mg to about 200 mg per day. Each of the above-recited dosage ranges may be formulated as a single or multiple unit dosage formulations.

In some embodiments, the compounds disclosed herein may be used in combination with one or more second active agents to treat, prevent, and/or manage disorders described herein. In certain embodiments, the second compound is an antipsychotic agent. In certain embodiments, the second active agent is an atypical antipsychotic agent. In certain embodiments, the second active agent is an agent that is useful for the treatment of Alzheimer's disease. In certain embodiments, the second active agent is a cholinesterase inhibitor. In certain embodiments, the second active agent is lurasidone, olanzapine, risperidone, aripiprazole, amisulpride, asenapine, blonanserin, clozapine, clotiapine, iloperidone, mosapramine, paliperidone, quetiapine, remoxipride, sertindole, sulpiride, ziprasidone, zotepine, pimavanserin, loxapine, donepezil, rivastigmine, memantine, galantamine, tacrine, amphetamine, methylphenidate, atomoxetine, modafinil, sertraline, fluoxetine, or L-DOPA.

EXAMPLES

Certain embodiments are illustrated by the following non-limiting examples.

Synthesis of Compounds

In the examples below, unless otherwise indicated, all temperatures are set forth in degrees Celsius and all parts and percentages are by weight. Reagents may be purchased from commercial suppliers, such as Sigma-Aldrich Chemical Company, and may be used without further purification unless otherwise indicated. Reagents may also be prepared following standard literature procedures known to those skilled in the art. Solvents may be purchased from Aldrich in Sure-Seal bottles and used as received. All solvents may be purified using standard methods known to those skilled in the art, unless otherwise indicated.

The reactions set forth below were done generally at ambient temperature, unless otherwise indicated. The reaction flasks were fitted with rubber septa for introduction of substrates and reagents via syringe. Analytical thin layer chromatography (TLC) was performed using glass-backed silica gel pre-coated plates (Merck Art 5719) and eluted with appropriate solvent ratios (v/v). Reactions were assayed by TLC or LCMS, and terminated as judged by the consumption of starting material. Visualization of the TLC plates was done with UV light (254 wavelength) or with an appropriate TLC visualizing solvent, such as basic aqueous $KMnO_4$ solution activated with heat. Flash column chromatography (See, e.g., Still et al., J. Org. Chem., 43: 2923 (1978)) was performed using silica gel 60 (Merck Art 9385) or various HPLC systems.

The compound structures in the examples below were confirmed by one or more of the following methods: proton magnetic resonance spectroscopy, mass spectroscopy, and melting point. Proton magnetic resonance ($^1$H NMR) spectra were determined using an NMR spectrometer operating at 400 MHz field strength. Chemical shifts are reported in the form of delta ($\delta$) values given in parts per million (ppm) relative to an internal standard, such as tetramethylsilane (TMS). Alternatively, $^1$H NMR spectra were referenced to signals from residual protons in deuterated solvents as follows: $CDCl_3$=7.25 ppm; DMSO-$d^6$=2.49 ppm; $C_6D_6$=7.16 ppm; $CD_3OD$=3.30 ppm. Peak multiplicities are designated as follows: s, singlet; d, doublet; dd, doublet of doublets; t, triplet; dt, doublet of triplets; q, quartet; br, broadened; and m, multiplet. Coupling constants are given in Hertz (Hz). Mass spectra (MS) data were obtained using a mass spectrometer with APCI or ESI ionization.

As used herein, and unless otherwise specified, "4 Å MS" means 4 angstrom molecular sieves, "Ac" means acetyl, "AIBN" means 2,2'-azobisisobutyronitrile, "aq" means aqueous, "BINAP" means 2,2'-bis(diphenylphosphino)-1,1'-binaphthyl, "Bn" means benzyl, "BOC" or "Boc" means t-butyloxycarbonyl, "cat." means catalytic, "Cbz" or "Z" means benzyloxycarbonyl, "CDI" means carbonyldiimidazole, "DAST" means (diethylamino)sulfur trifluoride ($Et_2NSF_3$), "DBU" means 1,8-diazabicyclo[5.4.0]undec-7-ene, "DCE" means 1,2-dichloroethane, "DCM" means dichloromethane, "DDQ" means 2,3-dichloro-5,6-dicyano-1,4-benzoquinone, "Dess-Martin reagent" means 1,1,1-tris(acetyloxy)-1,1-dihydro-1,2-benziodoxol-3-(1H)-one (also called DMP), "DIEA" or "DIPEA" means diisopropylethylamine, "DMAP" means 4-dimethylaminopyridine, "DME" means 1,2-dimethoxyethane, "DMF" means dimethylformamide, "DMF-DMA" means N,N-dimethylformamide dimethylacetal, "DMSO" means dimethyl sulfoxide, "dppf" means 1,1'-bis(diphenylphosphino)ferrocene, "EDCI" means N-(3-dimethylaminopropyl)-N'-ethylcarbodiimide hydrochloride, "ee" means enantiomeric excess, "equiv" and "eq" mean equivalent(s), "Et" means ethyl, "EtOAc" means ethyl acetate, "EtOH" means ethanol, "Fmoc" means 9-fluorenylmethoxycarbonyl, "h" or "hr" means hour(s), "HOBt" means hydroxybenzotriazole, "HPLC" means High Pressure Liquid Chromatography", "LAH" means lithium aluminum hydride, "LDA" means lithium diisopropylamide, "M" means molar concentration, "m-CPBA" means 3-chloroperbenzoic acid, "Me" means methyl, "MeCN" means acetonitrile, "MeOH" means methanol, "Ms" means mesyl ($CH_3SO_2$—), "min" means minute(s), "MTBE" means methyl t-butyl ether, "NBS" means N-bromosuccinimide, "NFSI" means N-Fluorobenzenesulfonimide, "NMP" means N-methylpyrrolidone, "PCC" means pyridinium chlorochromate, "PE" means petroleum ether, "PPA" means polyphosphoric acid, "psi" or "PSI" means pounds force per square inch, "RT" or "rt" means room temperature, "Rt" means retention time, "Selectfluor" means 1-(chloromethyl)-4-fluoro-1,4-diazoniabicyclo[2.2.0]octane ditetrafluoroborate, "t" means tert, "TBDMSCl" means tert-butyldimethylsilyl chloride, "t-BuOH" means tert-butanol, "t-BuONa" means sodium tert-butoxide, "TBTU" means 2-(1H-benzotriazole-1-yl)-1,1,3,3-tetramethyluronium tetrafluoroborate, "TEA" means triethylamine, "Tebbe Reagent" means μ-chloro[di(cyclopenta-2,4-dien-1-yl)]dimethyl(μ-methylene)titaniumaluminum, "Tf" means trifluoromethanesulfonyl, "TFA" means trifluoroacetic acid, "THF" means tetrahydrofuran, "TosMIC" means p-toluenesulfonylmethylisocyanide, "TMSI" means iodotrimethylsilane, "o-Tol" means o-tolyl (2-$CH_3C_6H_4$), "m-TOl" means m-tolyl (4-$CH_3C_6H_4$), "Ts" means tosyl (p-$CH_3C_6H_4SO_2$), and "Xantphos" means 4,5-bis(diphenylphosphino)-9,9-dimethylxanthene.

For those compounds containing basic nitrogen center(s), its HCl salt was prepared by treating the freebase with excess HCl etherate solution.

General Synthesis Experimentals

General Example A: Coupling Chemistry

Example A1. General Experimental for Coupling of an Aromatic Bromide or Aromatic Chloride with an Aromatic Alkyne General Scheme:

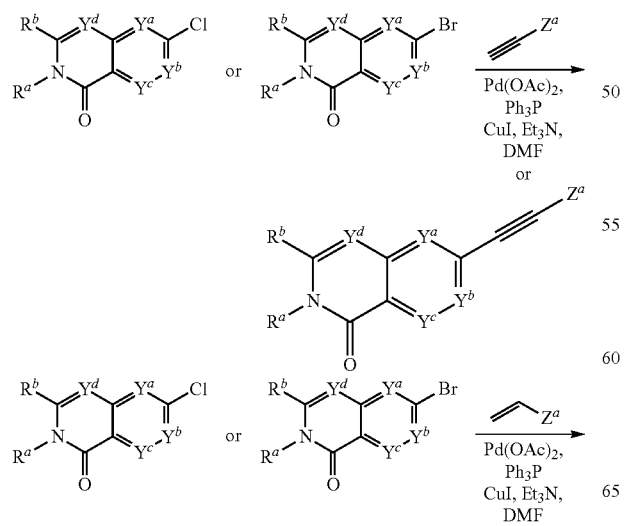

-continued

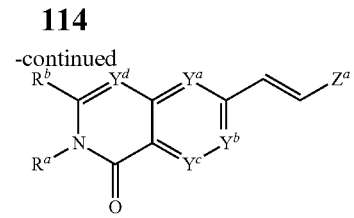

Representative Scheme:

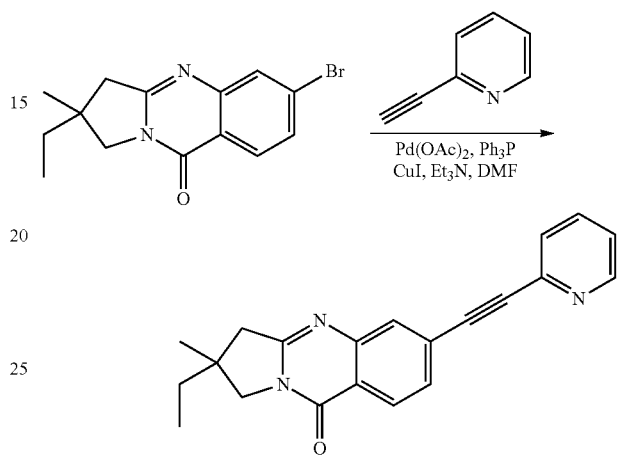

To a solution of 6-bromo-2-ethyl-2-methyl-2,3-dihydropyrrolo[2,1-b]quinazolin-9(1H)-one (1 equiv) in DMF (0.05 M) was charged 2-ethynylpyridine (approx. 2.5 equiv), Pd(OAc)$_2$ (0.2 equiv), PPh$_3$ (0.9 equiv), CuI (0.2 equiv) and Et$_3$N (0.2 equiv). A vacuum was applied and the reaction mixture was back filled with nitrogen three times. The mixture was stirred at approximately 70° C. until the reaction was complete. The reaction was then cooled to room temperature, diluted with H$_2$O, and extracted with ethyl acetate. The combined organic layers were washed with brine and dried over anhydrous sodium sulfate, then concentrated under reduced pressure and purified by column chromatography to give the desired product.

Example A2. General Experimental for Coupling of an Aromatic Bromide or Aromatic Chloride with an Aromatic Alkyne General Scheme:

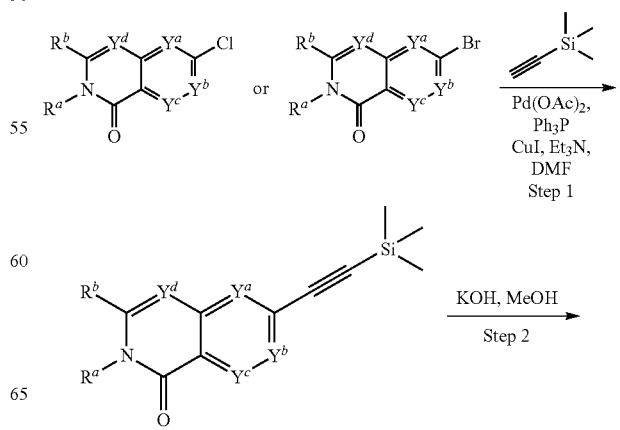

115

-continued

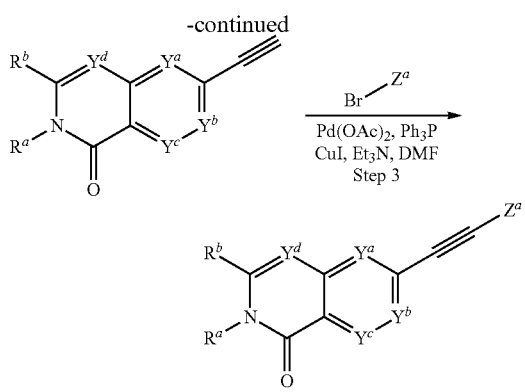

Representative Scheme:

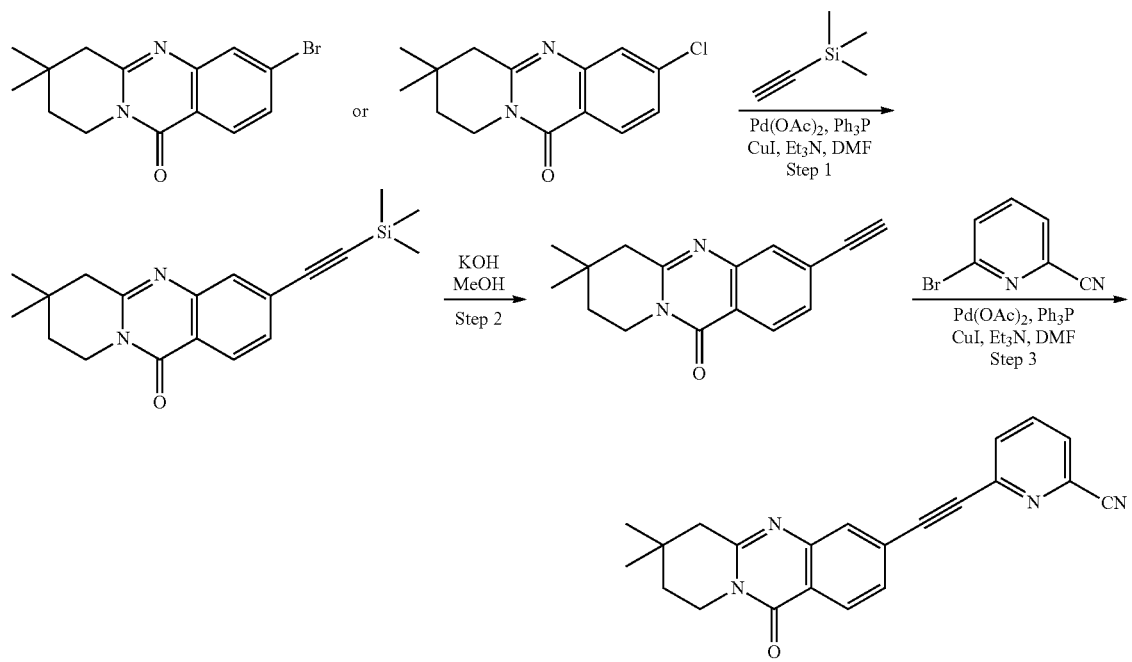

Example A2, Step 1

To a solution of the aromatic bromide (e.g., 3-bromo-7,7-dimethyl-8,9-dihydro-6H-pyrido[2,1-b]quinazolin-11(7H)-one, 1 equiv) in DMF (0.14 M) was charged ethynyltrimethylsilane (2 equiv), Pd(AcO)$_2$ (0.2 equiv), PPh$_3$ (0.8 equiv), CuI (0.2 equiv) and Et$_3$N (0.2 equiv). The mixture was stirred in a sealed tube at approximately 80° C. until the reaction was complete (approximately 3.5 h). The reaction was then cooled to room temperature, diluted with H$_2$O, and extracted with ethyl acetate. The combined organic layers were washed with brine and dried over anhydrous sodium sulfate, then concentrated under reduced pressure to obtain the desired trimethylsilylalkyne-containing desired product (e.g., 7,7-dimethyl-3-((trimethylsilyl)ethynyl)-8,9-dihydro-6H-pyrido[2,1-b]quinazolin-11(7H)-one). The crude product was directly used for the next step without purification.

116

Example A2, Step 2

A solution of the trimethylsilylalkyne-containing starting material (e.g., 7,7-dimethyl-3-((trimethylsilyl)ethynyl)-8,9-dihydro-6H-pyrido[2,1-b]quinazolin-11(7H)-one, 1 equiv) and 1 N KOH aqueous in methanol was stirred at room temperature until the reaction was complete (approximately 0.5 h). The reaction mixture was quenched with water and extracted with ethyl acetate. The combined organic layers were washed with brine and dried over anhydrous sodium sulfate, then concentrated under reduced pressure. The desired deprotected alkyne (e.g., 3-ethynyl-7,7-dimethyl-8,9-dihydro-6H-pyrido[2,1-b]quinazolin-11(7H)-one) was obtained by silica gel chromatography purification.

Example A3. General Experimental for the Suzuki Coupling of Aryl Bromides or Chlorides with Boronic Acids General Scheme:

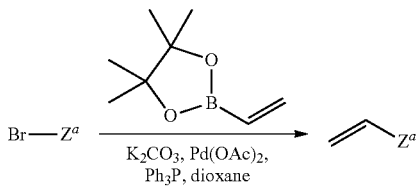

Representative Scheme:

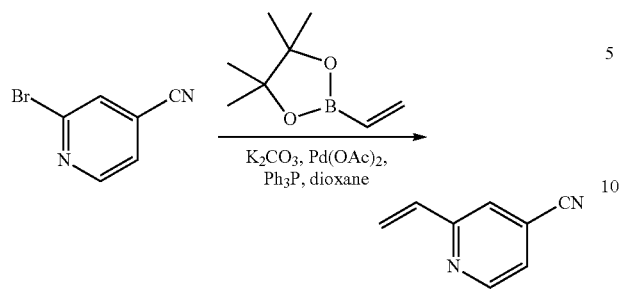

A solution of the aryl bromide or aryl chloride (e.g., 6-bromonicotinonitrile, 1 equiv), 4,4,5,5-tetramethyl-2-vinyl-1,3,2-dioxaborolane (2 equiv), $K_2CO_3$ (2 equiv), $Pd(AcO)_2$ (0.4 equiv) and $Ph_3P$ (0.8 equiv) in 1,4-dioxane was stirred under $N_2$ at 85° C. until the reaction was complete (approximately 4 h). After cooling to room temperature, the mixture was quenched with water (50 mL) and extracted with ethyl acetate (3×50 mL). The combined organic layers were dried over $Na_2SO_4$ and concentrated under reduced pressure. The crude vinyl-containing product (e.g., 2-vinylisonicotinonitrile) was purified by silica gel chromatography.

Example A4. General Experimental for the Suzuki Coupling of Aryl Bromides or Chlorides with Aryl Bromides, Chlorides or Iodines General Scheme:

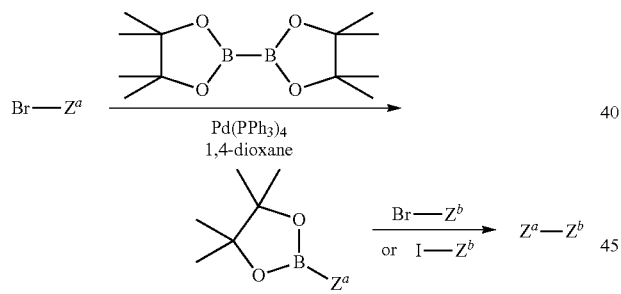

Representative Scheme:

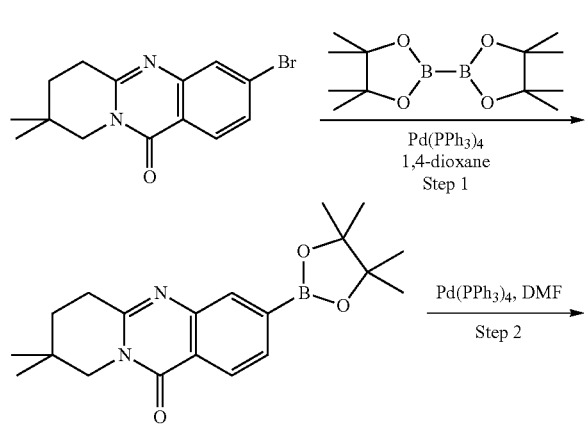

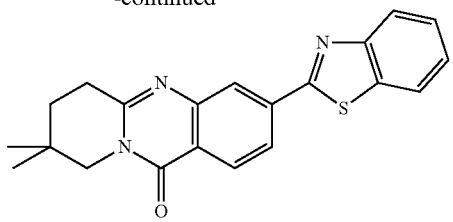

Example A4, Step 1

A solution of aryl bromide (e.g., 3-bromo-8,8-dimethyl-8,9-dihydro-6H-pyrido[2,1-b]quinazolin-11(7H)-one, 1 equiv), bis(pinacolato)diboron (1.2 equiv), $CH_3COOK$ (2 equiv) and tetrakis(triphenylphosphine)palladium (0.05 equiv) in 1,4-dioxane was stirred under $N_2$ at 90° C. for 6 h. After cooling to room temperature, the reaction mixture was poured into $H_2O$ and extracted with EtOAc. The combined organic layers were washed with brine, then dried over $Na_2SO_4$. After filtration and concentration, the crude product was purified by column chromatography (EtOAc:n-hexane=1:5) to give the desired boric ester (e.g., 8,8-dimethyl-3-(4,4,5,5-tetramethyl-1,3,2-dioxaborolan-2-yl)-8,9-dihydro-6H-pyrido[2,1-b]quinazolin-11(7H)-one).

Example A4, Step 2

A solution of the boric ester (e.g., 8,8-dimethyl-3-(4,4,5,5-tetramethyl-1,3,2-dioxaborolan-2-yl)-8,9-dihydro-6H-pyrido[2,1-b]quinazolin-11(7H)-one, 1 equiv), aryl bromide (e.g., 2-bromobenzo[d]thiazole, 1.5 equiv), $Cs_2CO_3$ (2 equiv), tetrakis(triphenylphosphine)palladium (0.1 equiv) in DMF was warmed to 160° C. by microwave reaction for 10 min. After cooling to room temperature, the reaction mixture was diluted $H_2O$ and extracted with EtOAc. The combined organic layers were washed with brine, dried over $Na_2SO_4$. After filtration and concentration, the residue was purified by preparative chromatography to give the C—C coupling product (e.g., 3-(benzo[d]thiazol-2-yl)-8,8-dimethyl-8,9-dihydro-6H-pyrido[2,1-b]quinazolin-11(7H)-one).

Example A5. General Experimental for the Still Coupling of Aryl Bromides or Aryl Chlorides with Tin General Scheme:

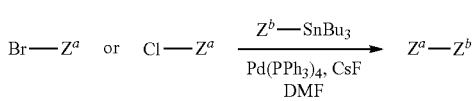

Representative Scheme:

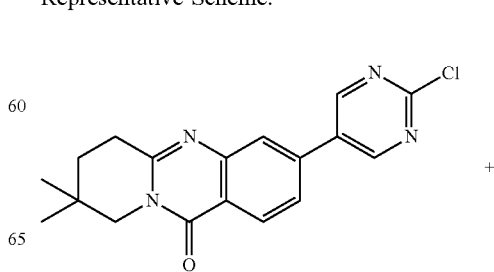

-continued

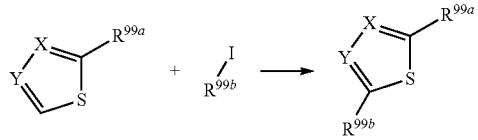

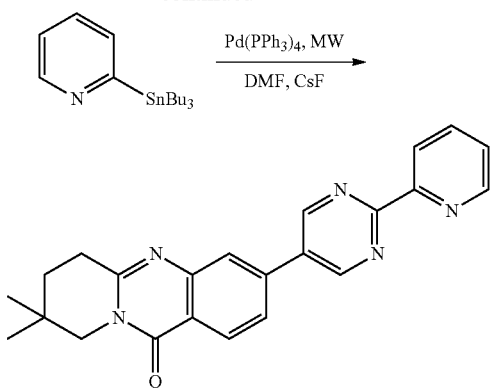

A solution of aryl bromide or aryl chloride (e.g., [2,1-b]quinazolin-11(7H)-one, 1 equiv), 2-(tributylstannyl)pyridine (1.5 equiv), tetrakis(triphenylphosphine)palladium (0.1 equiv) and CsF (2.2 equiv) in DMF was warmed to 90° C. for 20 min by microwave reactor. The reaction mixture was poured into H$_2$O and extracted with EtOAc. The combined organic layers were washed with brine and dried over Na$_2$SO$_4$. After filtration and concentration, the residue was washed with ethyl ether to give the desired C—C coupling product (e.g., 8,8-dimethyl-3-(2-(pyridin-2-yl)pyrimidin-5-yl)-8,9-dihydro-6H-pyrido[2,1-b]quinazolin-11(7H)-one).

Example A6. General Experimental for the Negishi Cross-Coupling

General Scheme:

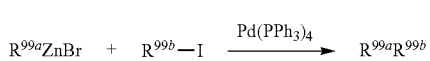

Representative Scheme:

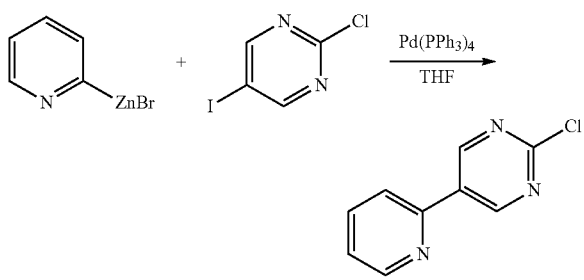

To a solution of tetrakis(triphenylphosphine)palladium (0.05 equiv) in THF was added the organozinc reagent (e.g., pyridin-2-ylzinc bromide, 2 equiv) at 15° C. under N$_2$. Then, a solution of aryl iodine (e.g., 2-chloro-5-iodopyrimidine, 1 equiv) in THF was added. The reaction mixture was stirred at room temperature for 3 h. The mixture was poured into H$_2$O and extracted with EtOAc. The combined organic layers were washed with brine, dried over Na$_2$SO$_4$. After filtration and concentration, the crude product was purified by silica-gel column to give the C—C coupling product (e.g., 2-chloro-5-(pyridin-2-yl)pyrimidine).

Example A7. General Experimental for the Coupling of Thiazole-H with Aryl Iodine General Scheme:

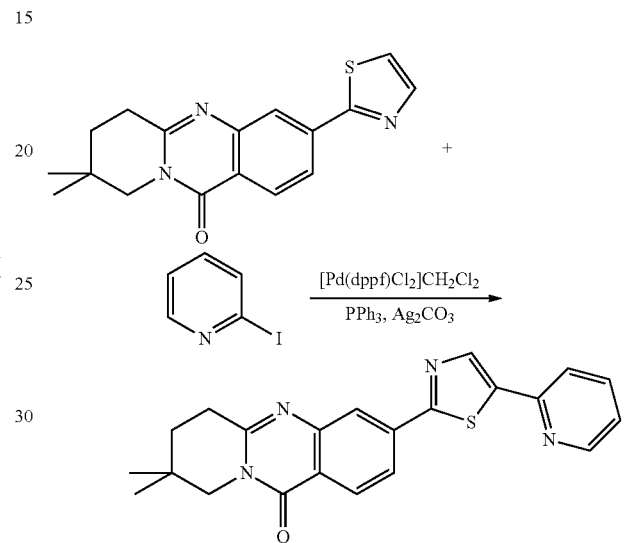

Representative Scheme:

A solution of thiazole (e.g., 8,8-dimethyl-3-(thiazol-2-yl)-8,9-dihydro-6H-pyrido[2,1-b]quinazolin-11(7H)-one, 1 equiv), aryl iodine (e.g., 2-iodopyridine, 1.3 equiv), Pd(dppf)Cl$_2$.CH$_2$Cl$_2$ (0.15 equiv), Ag$_2$CO$_3$ (2 equiv) and PPh$_3$ (1 equiv) in H$_2$O was stirred at 60° C. under N$_2$ overnight. Then, CH$_2$Cl$_2$ was added to dilute the mixture. After filtration, the reaction mixture was extracted with CH$_2$Cl$_2$. The combined organic layers were washed with brine, dried over Na$_2$SO$_4$. After filtration and concentration, the crude product was purified by preparative chromatography to give the desired product.

Example A8. General Experimental for the Coupling of Bis(Pinacolato)Diboron with Triflate General Scheme:

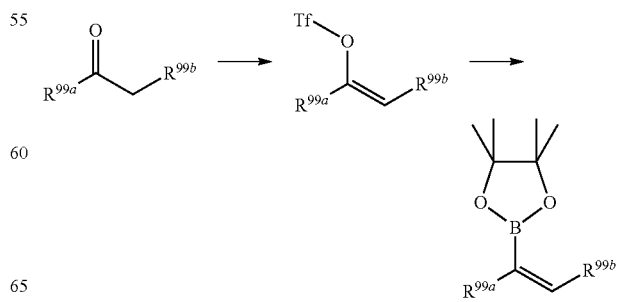

Representative Scheme:

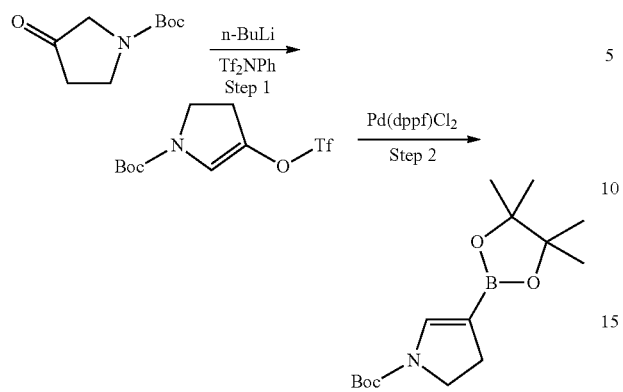

Example A8, Step 1

To a solution of diisopropylamine (1.2 equiv) in dry THF was added n-BuLi (1.2 equiv) slowly at 0° C. under nitrogen. After 30 min, the mixture was cooled to −78° C., and then the ketone (e.g., tert-butyl 3-oxopyrrolidine-1-carboxylate, 1 equiv) in THF was added dropwise. The mixture was stirred for 30 min. Tf$_2$NPh (1.1 equiv) in THF was added dropwise to the reaction mixture and stirred at 0° C. overnight. The mixture was concentrated and purified column chromatography through a plug of alumina (ethyl acetate:heptane=1:9) to give the triflate (e.g., tert-butyl 4-(trifluoromethylsulfonyloxy)-2,3-dihydro-1H-pyrrole-1-carboxylate).

Example A8, Step 2

To a stirred solution of the triflate (e.g., tert-butyl 4-(trifluoromethylsulfonyloxy)-2,3-dihydro-1H-pyrrole-1-carboxylate, 1 equiv), Pd(dppf)Cl$_2$ (0.02 equiv), bis(pinacolato)diboron (1 equiv) and potassium carbonate (2 equiv) in 1,4-dioxane was heated at 80° C. overnight. After cooling to room temperature, the mixture was diluted with water and extracted with ethyl acetate. The combined organic phase was washed with brine, dried over anhydrous Na$_2$SO$_4$ and concentrated under reduced pressure. The residue was purified by column chromatography on silica gel to give the boric ester (e.g., tert-butyl 4-(4,4,5,5-tetramethyl-1,3,2-dioxaborolan-2-yl)-2,3-dihydro-1H-pyrrole-1-carboxylate).

General Example B: Condensation Chemistry

Example B1. General Experimental for the Condensation of a Lactam with an Aromatic Amino Acid General Scheme:

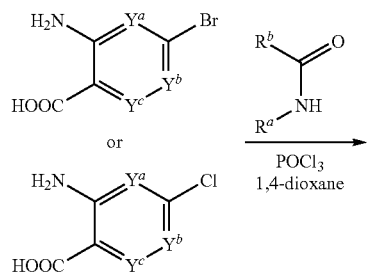

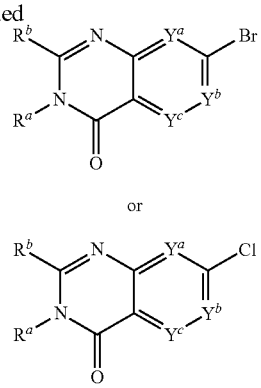

or

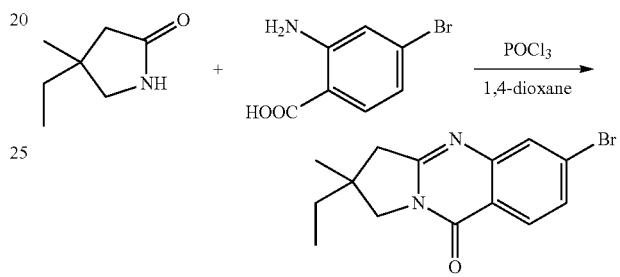

To a solution of an aromatic amino acid (e.g., 2-amino-4-bromobenzoic acid, 1.1 equiv) and a lactam (e.g., 4-ethyl-4-methylpyrrolidin-2-one, 1 equiv) in toluene (0.15 M) was charged POCl$_3$ (1.2 equiv) and the mixture was stirred at 80° C. until the reaction was complete (approximately 5 h), then the reaction was cooled to room temperature, and an Na$_2$CO$_3$ aqueous solution was added. The water layer was extracted with ethyl acetate and the combined organic layers were dried over Na$_2$SO$_4$, filtered, and evaporated to give the desired product (e.g., 6-bromo-2-ethyl-2-methyl-2,3-dihydropyrrolo[2,1-b]quinazolin-9(1H)-one), which was used directly for the next step.

Example B2. General Experimental for the Condensation of an Imidate with a Bromoisochroman-1,3-Dione or a Chloroisochroman-1,3-Dione General Scheme:

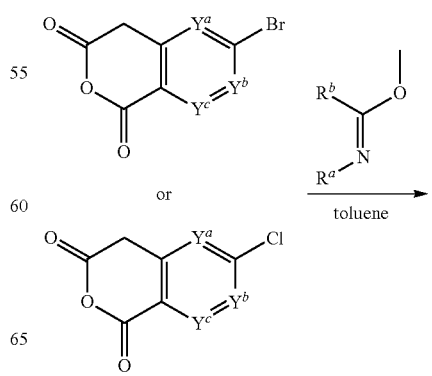

-continued

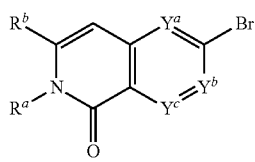

or

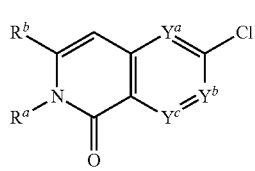

Representative Scheme:

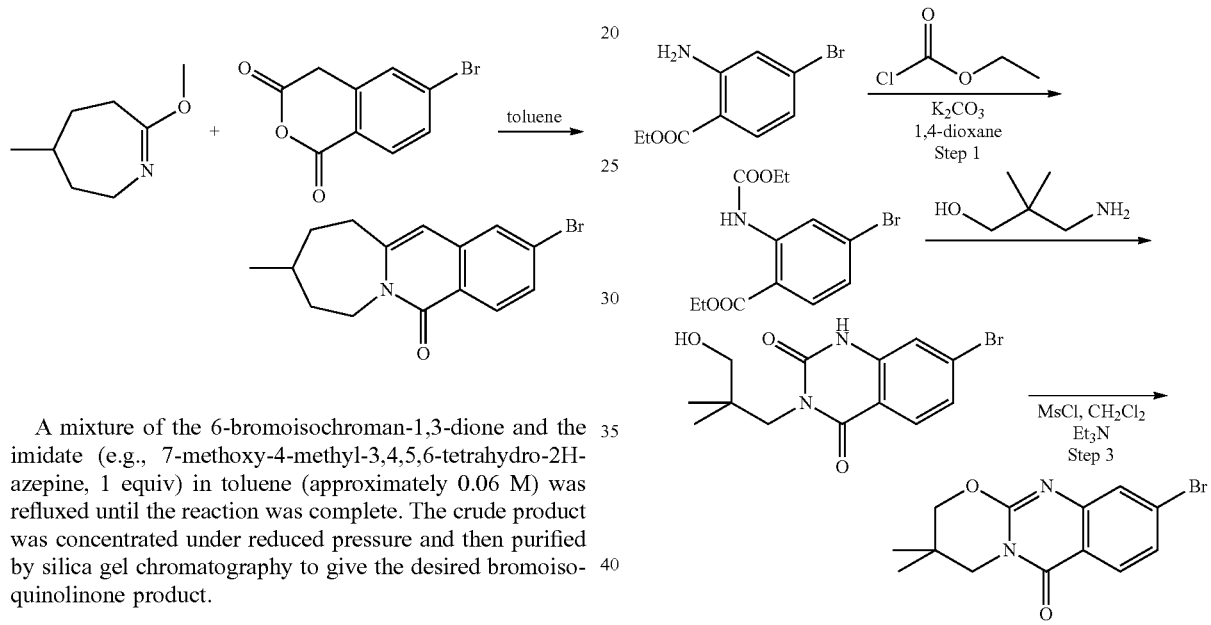

A mixture of the 6-bromoisochroman-1,3-dione and the imidate (e.g., 7-methoxy-4-methyl-3,4,5,6-tetrahydro-2H-azepine, 1 equiv) in toluene (approximately 0.06 M) was refluxed until the reaction was complete. The crude product was concentrated under reduced pressure and then purified by silica gel chromatography to give the desired bromoisoquinolinone product.

Example B3. General Experimental for the Synthesis of Precursors, Condensation to Quinazoline-2,4(1H,3H)-Diones, and Further Ring Cyclization General Scheme:

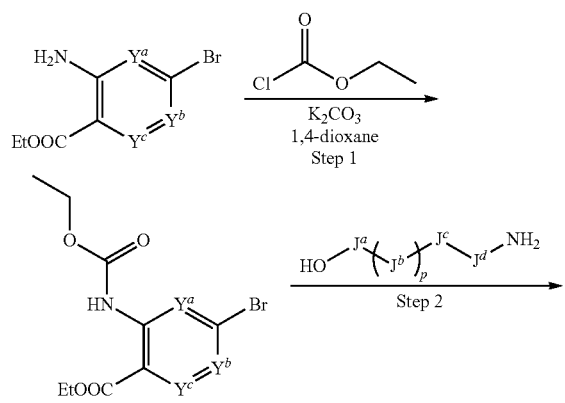

-continued

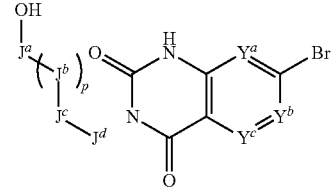

Representative Scheme:

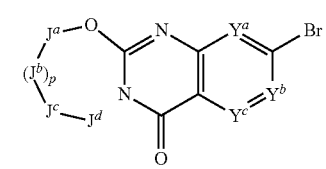

Example B3, Step 1

The solution of the amino-ester starting material (e.g., ethyl 2-amino-4-bromobenzoate, 1 equiv), ethyl chloroformate (2 equiv), K$_2$CO$_3$ (2 equiv) in 1,4-dioxane (0.24 M) was stirred at approximately 70° C. until the reaction was complete. The reaction was diluted with H$_2$O (200 mL) and extracted with EtOAc. The organic layers were washed with brine, dried over NaSO$_4$ and concentrated to give the desired carbonate product (e.g. ethyl 4-bromo-2-(ethoxycarbonylamino)benzoate).

Example B3, Step 2

A mixture of the carbonate starting material (e.g., ethyl 4-bromo-2-(ethoxycarbonylamino)benzoate, 1 equiv) and neat amino alcohol (e.g., 3-amino-2,2-dimethylpropan-1-ol, 20 equiv) was stirred at approximately 120° C. overnight. The reaction mixture was concentrated and the residue was purified by column chromatography to give the desired alcohol-containing product (e.g., 7-bromo-3-(3-hydroxy-2,2-dimethylpropyl)quinazoline-2,4(1H,3H)-dione).

Example B3, Step 3

To a solution of the alcohol-containing starting material (e.g., 7-bromo-3-(3-hydroxy-2,2-dimethylpropyl)quinazoline-2,4(1H,3H)-dione, 1 equiv) in $CH_2Cl_2$ (0.03 M) was added methanesulfonyl chloride (2 equiv) and $Et_3N$ (2.5 equiv). The mixture was stirred at room temperature overnight or until complete. The reaction mixture was concentrated and the residue was purified by column chromatography to give the desired product (e.g., 9-bromo-3,3-dimethyl-3,4-dihydro-[1,3]oxazino[2,3-b]quinazolin-6(2H)-one).

Example B4. General Experimental for the Synthesis of Precursors, Condensation to Bromoisochroman-1,3-Diones General Scheme:

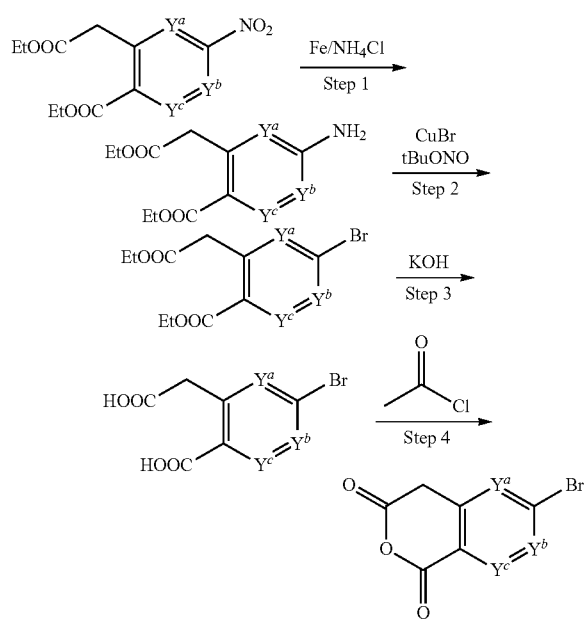

Representative Scheme:

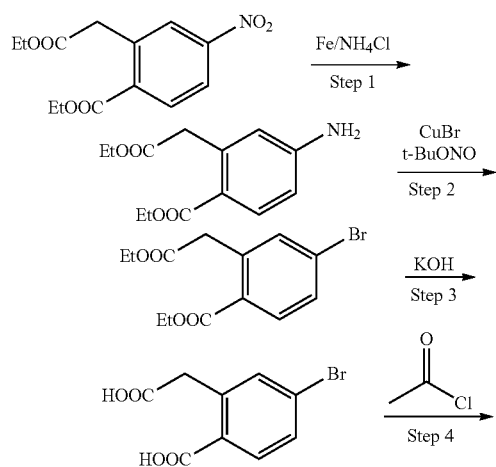

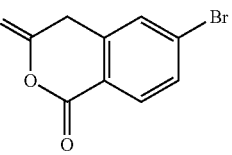

Example B4, Step 1

To a stirred mixture of iron powder (10 g, 178.6 mmol) and ammonium chloride (2.4 g, 44.8 mmol) in $H_2O$ (200 mL) was added diethyl 4-nitrophthalate (8 g, 28.4 mmol) at 55° C. After stirring at the same temperature for 3 hours, the reaction mixture was basified to pH to 9 with aqueous solution of sodium hydroxide and extracted with ethyl acetate (2×200 mL). The combined organic layers were washed with brine (200 mL), dried over $Na_2SO_4$ and concentrated under reduced pressure. The crude product (diethyl 4-aminophthalate) was used for the next step without further purification. MS (ESI+): m/z 238 (MH+).

Example B4, Step 2

To a solution of diethyl 4-aminophthalate (7.0 g, 27.9 mmol) in 250 mL acetonitrile below 0° C. was added cuprous bromide (9.2 g, 55.8 mmol) and then t-butyl nitrite. The mixture was warmed to room temperature and stirred overnight. The reaction mixture was then concentrated to 100 mL and diluted with water (300 mL). The resulting mixture was adjusted to pH around 5~6 and extracted with ethyl acetate (3×300 mL). The combined organic layers were washed with brine and dried over $Na_2SO_4$. After filtration and concentration, the residue was purified by silica gel chromatography to give 5.0 g of diethyl 4-bromophthalate. MS (ESI+): m/z 301, 303 (MH+).

Example B4, Step 3

To a solution of diethyl 4-bromophthalate (5.0 g, 15.9 mmol) in acetonitrile (180 mL) was added an aqueous solution (60 mL) of potassium hydroxide (3.6 g, 63.7 mmol). The mixture was stirred at 60° C. overnight and then concentrated to 100 mL. The residue was diluted with 150 mL of water, adjusted pH to 2 and extracted with ethyl acetate (3×300 mL). The combined organic layers were washed with brine, dried over $Na_2SO_4$ and concentrated under reduced pressure to give 4-bromo-2-carboxymethyl-benzoic acid (4.5 g).

Example B4, Step 4

A solution of 4-bromo-2-carboxymethyl-benzoic acid (500 mg, 1.94 mmol) in 4 mL acetone was treated with acetyl chloride (912 mg, 11.6 mmol) and the solution was stirred at room temperature for 17 h. The reaction mixture was concentrated and then azeotroped with toluene to yield the crude desired product and it was used for the next step without further purification.

Example B5. General Experimental for the Condensation of a Lactam with an Aromatic Amino Acid General Scheme:

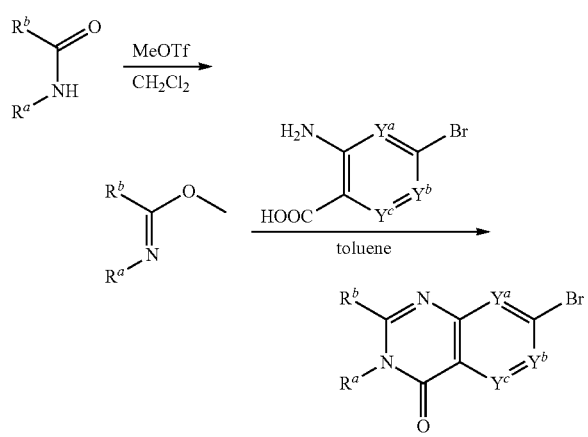

Representative Scheme:

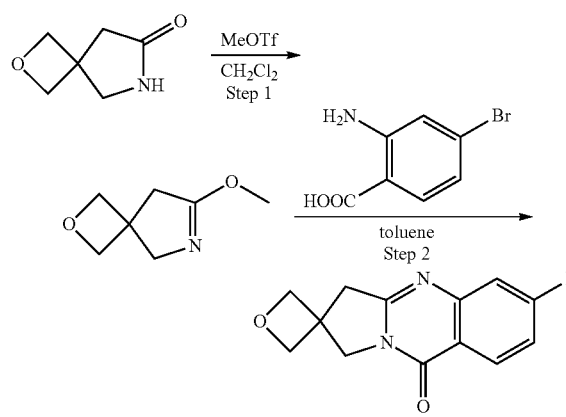

Example B5, Step 1

A solution of the lactam (e.g., 2-oxa-6-azaspiro[3.4]octan-7-one, 1 equiv) and methyl trifluoromethanesulfonate (2 equiv) in CH$_2$Cl$_2$ (0.03 M) was stirred at room temperature until the reaction was complete (approximately 5 h). The reaction mixture was then quenched with saturated sodium carbonate and extracted with CH$_2$Cl$_2$. The combined organic layers were washed with brine, dried over Na$_2$SO$_4$ and concentrated to give the desired product (e.g., 7-methoxy-2-oxa-6-azaspiro[3.4]oct-6-ene).

Example B5, Step 2

A solution of the starting material (e.g., 7-methoxy-2-oxa-6-azaspiro[3.4]oct-6-ene, 1 equiv) and 3-amino-5-bromopicolinic acid (1.5 equiv) in toluene (0.02 M) was refluxed under nitrogen atmosphere until the reaction was complete. After concentration, the residue was purified by silica gel chromatography to give the desired product (e.g., 6'-bromo-1'H-spiro[oxetane-3,2'-pyrrolo[2,1-b]quinazolin]-9'(3'H)-one).

General Example C: Synthesis of Lactam and Isoxazolidin-3-One Starting Materials

Example C1. General Experimental for the Synthesis of Lactam Starting Materials General Scheme:

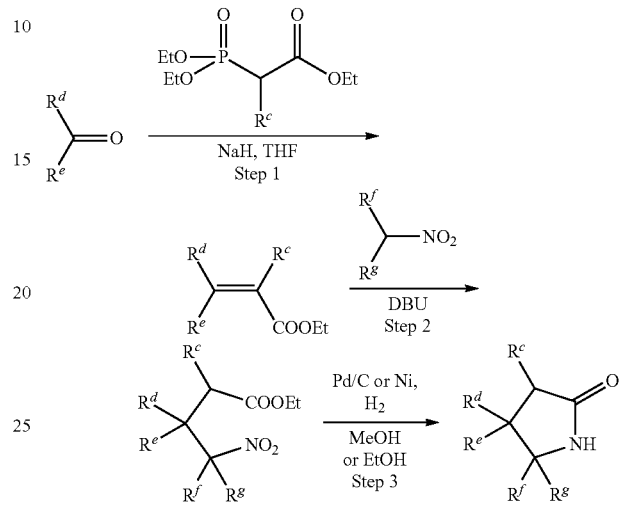

Representative Scheme:

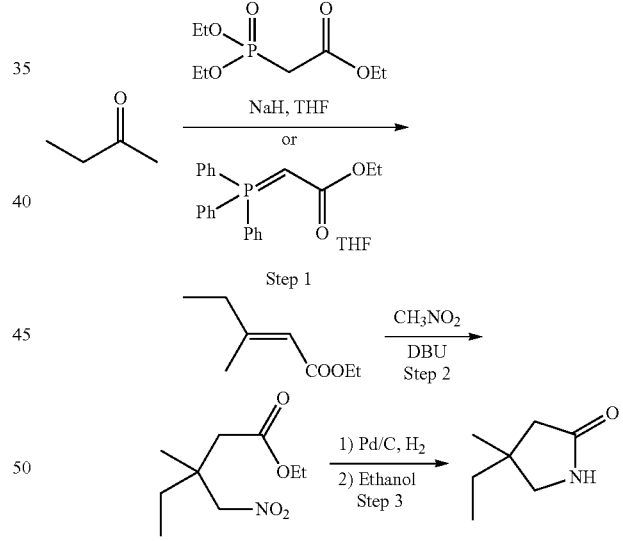

Example C1, Step 1, Version 1

To a 1 M suspension of 60% NaH (approximately 1.25 equiv) in anhydrous THF was added triethyl phosphonoacetate (approximately 1.25 equiv) at approximately 0° C. under nitrogen atmosphere. The mixture was stirred at room temperature for 1 h, then the ketone (e.g., butan-2-one, 1 equiv) was added and the mixture was refluxed until the reaction was complete (approximately 1 h). The mixture was poured in water and extracted with Et$_2$O. The organic layers were washed with brine and dried. The solvent was evaporated to give the desired product α,β-unsaturated ester (e.g., ethyl 3-methylpent-2-enoate).

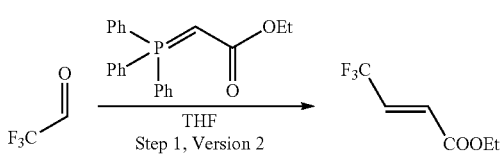

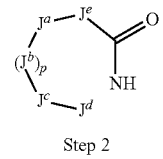

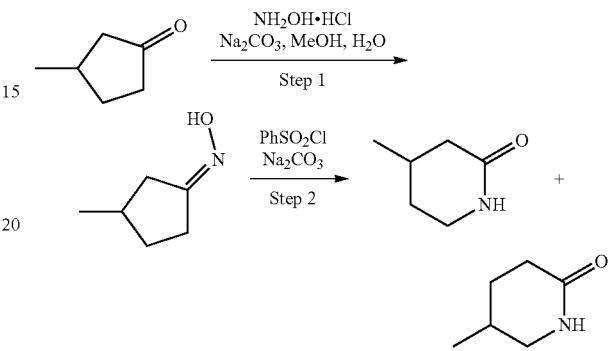

Step 2

Example C1, Step 1 Version 2

To the 0.4 M solution of carboethoxymethylidene triphenyl phosphorane (approximately 1.2 equiv) in dry THF was added the ketone starting material (e.g., trifluoroacetaldehyde hydrate, 1 equiv). The reaction was stirred at room temperature until the reaction was complete. The solvent was evaporated, and ethyl ether was added. The mixture was filtered and the residue was washed with ethyl ether. The filtrate was dried over $Na_2SO_4$ and concentrated under reduced pressure. The desired product α,β-unsaturated ester (e.g., ethyl 4,4,4-trifluorobut-2-enoate) used for the next reaction without further purification.

Example C1, Step 2

To a mixture of α,β-unsaturated ester (e.g., ethyl 3-methyl-pent-2-enoate, 1 equiv) and the nitroalkane (e.g., $MeNO_2$, approximately 5.2 equiv) was slowly added DBU (approximately 1 equiv) at approximately 0° C. under nitrogen atmosphere, then the mixture was stirred at 25° C. until the reaction was complete (approximately 3 h). The reaction was quenched with 6 M HCl, and extracted with $Et_2O$. The organic layers were washed with brine and dried over $Na_2SO_4$. After concentration, the residue was purified by silica gel chromatography to give the desired nitro-containing product (e.g., ethyl 3-methyl-3-(nitromethyl)pentanoate).

Example C1, Step 3

The solution of the nitro-containing starting material (e.g., ethyl 3-methyl-3-(nitromethyl)pentanoate, 1 equiv), 10% Pd/C (approximately 14.5 mg/mmol nitro-containing starting material) in methanol (approximately 0.14 M) was stirred under a hydrogen atmosphere until the hydrogenation of the nitro group was complete. The mixture was filtered and the solvent was evaporated under reduced pressure. The residue was dissolved in ethanol and refluxed until the cyclization was complete (approximately 2 h). The solvent was concentrated to give the desired lactam product (e.g., 4-ethyl-4-methylpyrrolidin-2-one).

Example C2. General Experimental for the Synthesis of Lactam Starting Materials General Scheme:

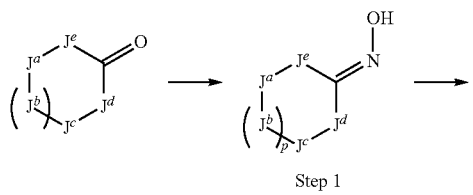

Step 1

Representative Scheme:

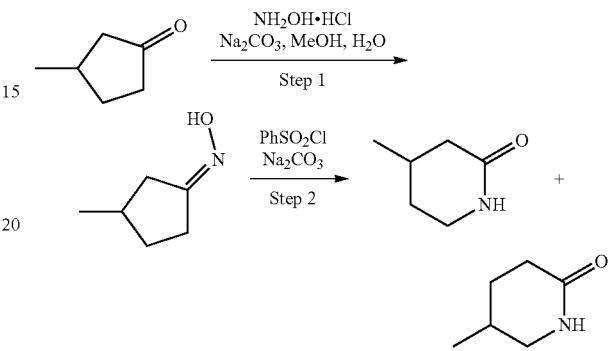

Example C2, Step 1

A solution of the ketone starting material (e.g., 3-methylcyclopentanone, 1 equiv), hydroxylamine hydrochloride (2.0 equiv) and $Na_2CO_3$ (3 equiv) in MeOH/water (1.7:1, 0.6 M) was stirred at room temperature until the reaction was complete (approximately 5 h). The solvent was then removed from the reaction mixture under reduced pressure. The residue was partitioned between ethyl acetate and water, and the organic layer was washed with brine and dried over anhydrous sodium sulfate. Concentration under reduced pressure provided the crude product (e.g., 3-methylcyclopentanone oxime) that was used without purification in the next step.

Example C2, Step 2

To a solution of the oxime starting material (e.g., 3-methylcyclopentanone oxime, 1 equiv) and $Na_2CO_3$ (4 equiv) in acetone (0.18 M) and water (0.18 M) was added phenylsulfonyl chloride (2 equiv) dropwise at 0° C. The reaction mixture was stirred overnight, quenched with water, and extracted with $CH_2Cl_2$. The combined organic layers were dried over $Na_2SO_4$ and concentrated under reduced pressure to give the desired lactam product (e.g. 4-methylpiperidin-2-one and 5-methylpiperidin-2-one).

Example C3. General Experimental for the Synthesis of Isoxazolidin-3-One Starting Materials General Scheme:

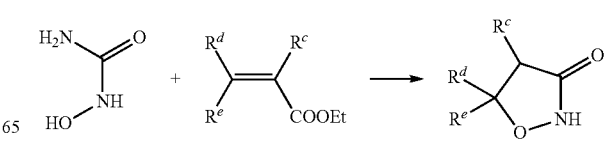

Representative Scheme:

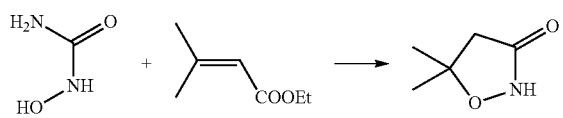

Sodium (0.45 g, 19.57 mmol) was dissolved in methanol (30 mL) at room temperature, and then hydroxy urea (1 equiv) was added slowly. α,β-Unsaturated ester (e.g., 3-methyl-but-2-enoic acid ethyl ester, 1 equiv) was added dropwise. The reaction mixture was stirred at room temperature until the reaction was complete (approximately 18 hours). The solid was removed by filtration and the filtrate was concentrated. The residue was dissolved in water and stirred for approximately 15 minutes, and then aqueous hydrochloric acid (2 M) was added dropwise to acidify the mixture. The aqueous solution was extracted with $CH_2Cl_2$. The organic layers were washed with brine, dried over magnesium sulfate and concentrated to give the desired isoxazolidin-3-one (e.g., 5,5-dimethyl-isoxazolidin-3-one).

Example C4. General Experimental for the Synthesis of Lactam Starting Materials

General Scheme:

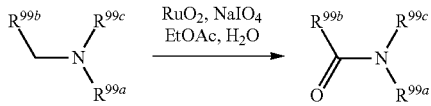

Representative Scheme:

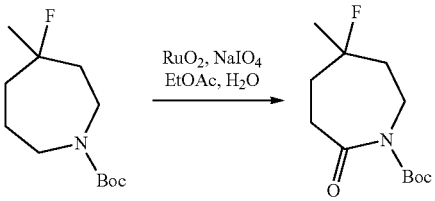 [SMILES: CC1(F)CCCN(C(=O)OC(C)(C)C)CC1 ; CC1(F)CCC(=O)N(C(=O)OC(C)(C)C)CC1]

To a solution of the amine starting material (e.g. tert-butyl 4-fluoro-4-methylazepane-1-carboxylate, 1 equiv) in ethyl acetate (0.07 M) and water (0.1 M) was added $RuO_2$ (0.4 equiv) and $NaIO_4$ (5 equiv). The mixture was stirred at room temperature for 1 hour, then the solution was heated at 70° C. until the reaction was complete (approximately 3 h). The reaction was then cooled to room temperature, and the mixture was diluted with water and extracted with ethyl acetate. The combined organic phase was washed with $Na_2CO_3$ solution, dried over anhydrous $Na_2SO_4$ and concentrated under reduce pressure. The crude was purified by silica gel chromatography to give the desired amide-containing product (e.g., tert-butyl 5-fluoro-5-methyl-2-oxoazepane-1-carboxylate).

Example C5. General Experimental for the Synthesis of Lactam Starting Materials

General Scheme:

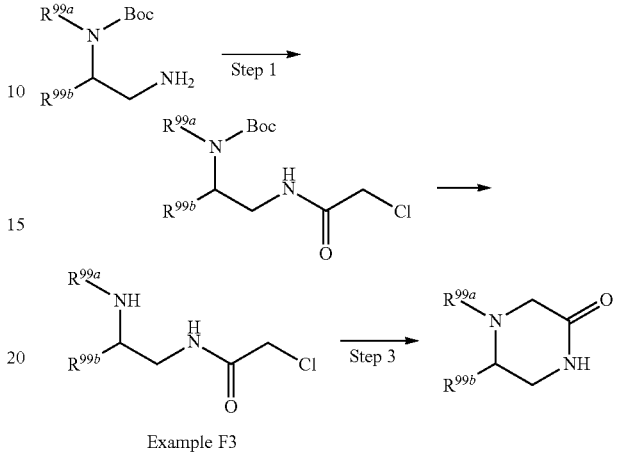

Example F3

Representative Scheme:

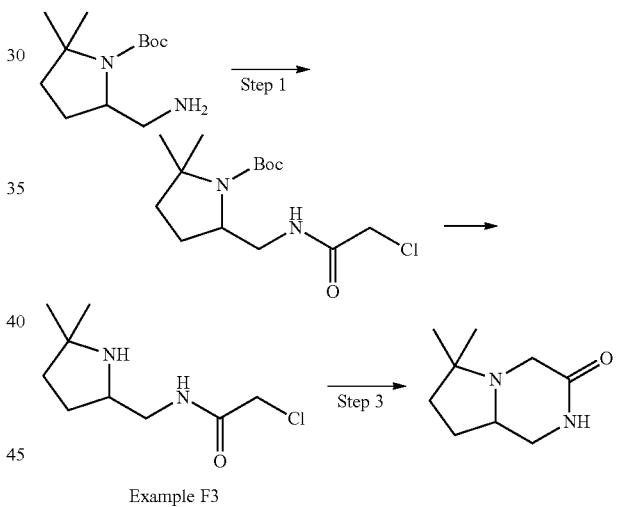

Example F3

Example C5, Step 1

A solution of the amine (e.g., tert-butyl 5-(aminomethyl)-2,2-dimethylpyrrolidine-1-carboxylate, 4 g), 2-chloroacetyl chloride (4 mL, excess amount) and $iPr_2NEt$ (5 mL) in $CH_2Cl_2$ was stirred at room temperature until the reaction was complete (approximately 2 h). The reaction was concentrated under reduced pressure, and the desired amide-containing product was purified by column chromatography.

Example C5, Step 3

A solution of the starting material (e.g., 2-chloro-N-((5,5-dimethylpyrrolidin-2-yl)methyl)acetamide (crude, synthesized according to Example F3) $K_2CO_3$ (3.0 g, 21.6 mmol, based on 9.9 mmol of starting material used in the previous step) and catalytic amount of NaI in $CH_3CN$ was stirred at 80° C. until the reaction was complete (approximately 3 h).

Then the suspension was quenched with water and extracted with $CH_2Cl_2$. The organic layer was concentrated to give the desired lactam product (e.g., 6,6-dimethylhexahydropyrrolo[1,2-a]pyrazin-3(4H)-one, 1.5 g).

Example C6: General Experimental for the Synthesis of Lactam Starting Materials General Scheme:

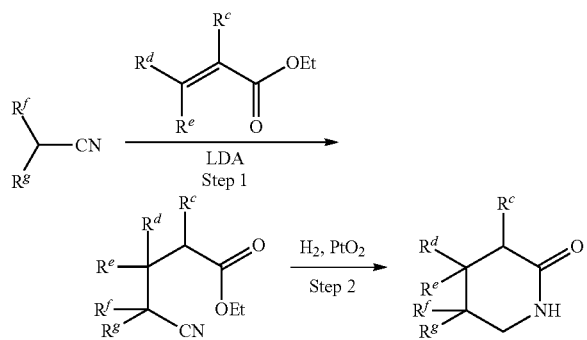

Representative Scheme

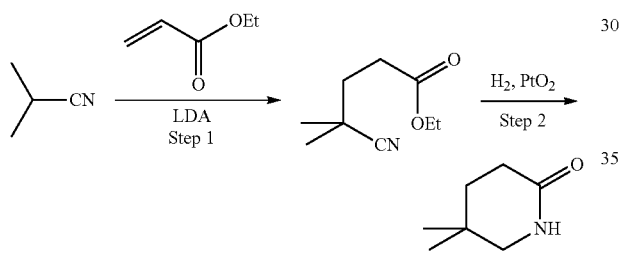

Example C6, Step 1

To a solution of diisopropyl amine (54 mmol) in anhydrous THF (70 mL) was added 2.5 N n-BuLi in hexanes (21 mL, 52 mmol) at approximately −35° C. The solution was stirred at 0° C. for 30 min., and was then cooled to −78° C. Iosbutyronitrile (58 mmol) was slowly introduced, and the reaction mixture was stirred at −78° C. for additional 2 h. The solution of ethyl acrylate (2.9 g, 29 mmol) in anhydrous THF (15 mL) was added slowly, and the reaction was stirred at −78° C. until the reaction was complete (approximately 50 min). The reaction mixture was then poured into $NH_4Cl$ (sat.) aqueous solution (and diluted with MTBE. The organic layer was washed with water and brine and concentrated. The resulting was purified by silica gel column chromatography tp provide the cyano-ester product (e.g. ethyl 4-cyano-4-methylpentanoate).

Example C6, Step 2

The mixture of the cyano-ester starting material (e.g., ethyl 4-cyano-4-methylpentanoate, 30 mmol) and $PtO_2$ (65 mg) in AcOH (10 mL) was purged with $N_2$ three times, then subjected to hydrogen gas to at 80 to 120 Psi until hydrogen uptake stopped. The catalyst was filtered and rinsed with EtOAc. The filtrate was slowly added into 6N NaOH (aq), then diluted with EtOAc. The aqueous layer was extracted with additional EtOAc. The combined organic layer was washed with brine and concentrated to give the desired lactam product (e.g. 5,5-dimethylpiperidin-2-one, 84% yield).

General Example D: Synthesis of Substituted 2-Amino-4-Bromobenzoic Acids and 2-Amino-4-Chlorobenzoic Acids

Example D1. General Experimental for the Synthesis of Substituted 2-Amino-4-Bromobenzoic Acids and 2-Amino-4-Chlorobenzoic Acids General Scheme:

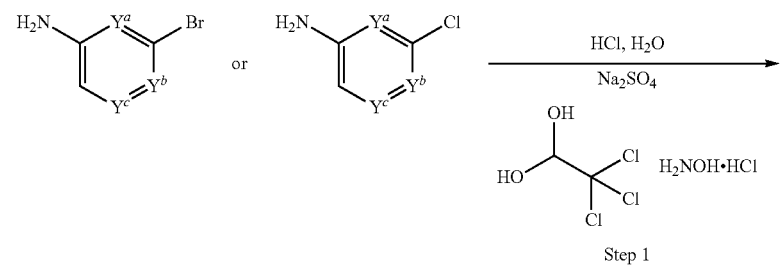

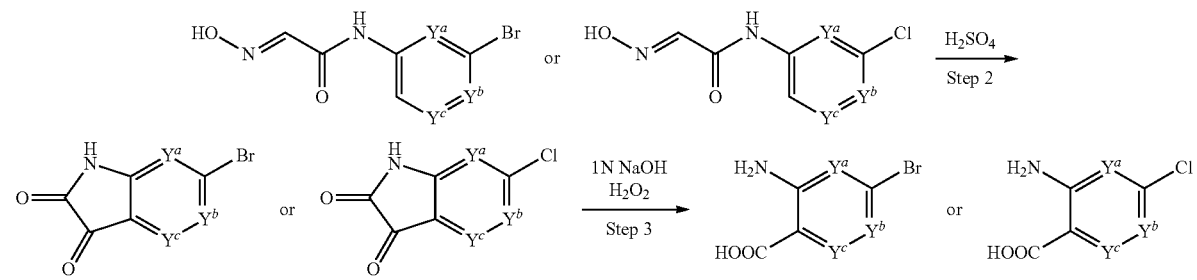

Representative Scheme:

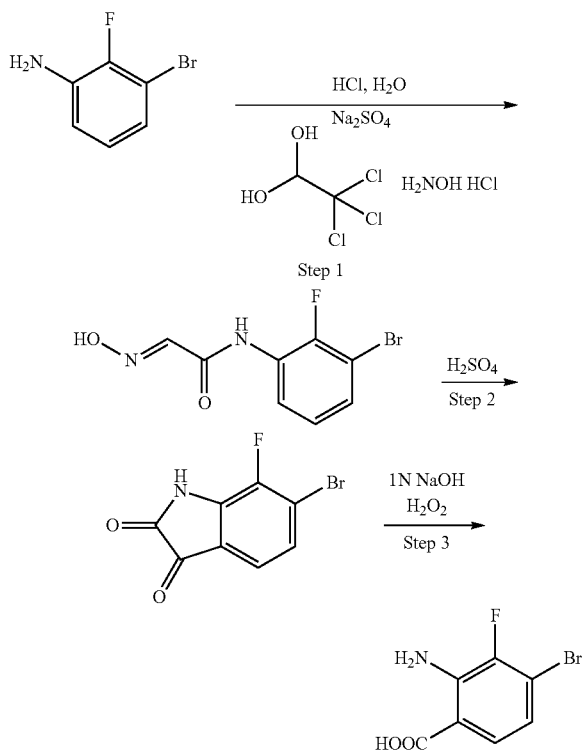

Example D1, Step 1

A mixture of the 2-amino-4-bromobenzoic acid (e.g., 3-bromo-2-fluoroaniline, 1 equiv) in conc. HCl (approximately 0.45 mL/mmol benzoic acid) and water (approximately 0.09 mL) was heated until it became a clear solution. Subsequently, 2,2,2-trichloroethane-1,1-diol (1.1 equiv) and $Na_2SO_4$ (7.7 equiv) were pre-warmed to 50° C. and added to the mixture. The mixture was then stirred, and a solution of hydroxylamine hydrochloride (3 equiv) in water was added dropwise. The resulting mixture was refluxed until complete (approximately 1 hour). After cooling to room temperature, the insoluble solid was filtered and washed with excess water, then evaporated to obtain the desired, crude hydroxyimino acetamide (e.g., (E)-N-(3-bromo-2-fluorophenyl)-2-(hydroxyimino)acetamide), which was used in the next step.

Example D1, Step 2

The hydroxyimino acetamide starting material (e.g., (E)-N-(3-bromo-2-fluorophenyl)-2-(hydroxyimino)acetamide, 1 equiv) was slowly added to a solution of conc. $H_2SO_4$ (3.9 mL/mmol starting material) in an ice bath. The reaction mixture was maintained below 50° C. during addition. After addition was complete, the solution was heated to 90° C. until the reaction was complete (approximately 1 hour). After cooling to room temperature, the mixture was poured into ice water and stirred vigorously for 1 hour. The 6-bromoindoline-2,3-dione (e.g., 6-bromo-7-fluoroindoline-2,3-dione) product was filtered and washed with water, evaporated to obtained crude that was used directly in the next step.

Example D1, Step 3

To a solution of the 6-bromoindoline-2,3-dione (e.g., 6-bromo-7-fluoroindoline-2,3-dione, 1 equiv) in 1 N NaOH (0.14 M) was added $H_2O_2$ (1.8 M) dropwise and the resulting mixture was stirred at room temperature until the reaction was complete (approximately 2 hours). The mixture was filtered and the filtrate was acidified to pH 2 with hydrochloric acid. The precipitate that formed was filtered, washed with water, and concentrated to provide the 2-amino-4-bromobenzoic acid (e.g., 2-amino-4-bromo-3-fluorobenzoic acid).

General Example E: Fluorination Chemistry

Example E1. General Experimental for the Conversion of an Alcohol to Group to a Fluoro Group General Scheme:

Representative Scheme:

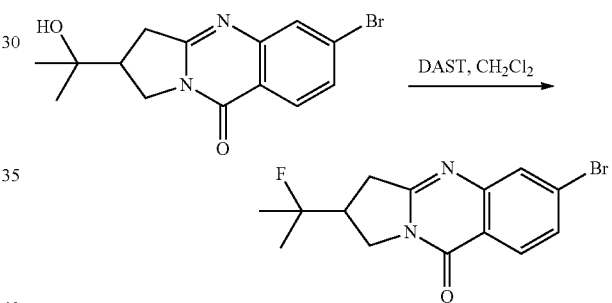

To a stirred solution of the alcohol (e.g., 6-bromo-2-(2-hydroxypropan-2-yl)-2,3-dihydropyrrolo[2,1-b]quinazolin-9(1H)-one, 1 equiv) in $CH_2Cl_2$ was added excess DAST under $N_2$ at room temperature. The mixture was stirred until it was complete (approximately 3 hours). The reaction mixture was quenched with water and extracted with ethyl acetate. The combined organic layers were dried over $Na_2SO_4$ and concentrated under reduced pressure. The crude was purified by silica gel chromatography to obtain the desired fluoro-containing product (e.g., 6-bromo-2-(2-fluoropropan-2-yl)-2,3-dihydropyrrolo[2,1-b]quinazolin-9(1H)-one).

Example E2. General Experimental for the Conversion of a Keto Group to a Difluoro Group General Scheme:

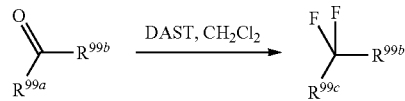

Representative Scheme:

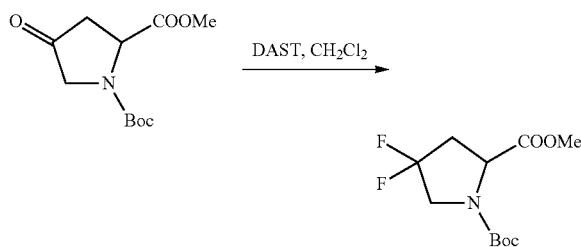

To a solution of ketone starting material (e.g., 1-tert-butyl 2-methyl 4-oxopyrrolidine-1,2-dicarboxylate, 0.75 g) in $CH_2Cl_2$ (0.03 M) was added DAST (approximately 57 equiv) dropwise under $N_2$ atmosphere. The resulting mixture was stirred at room temperature overnight or until the reaction was complete. The reaction mixture was washed with $H_2O$ and extracted with $CH_2Cl_2$. The combined organic layers were dried over $Na_2SO_4$, then concentrated under reduced pressure to give the desired difluoro-substituted product (e.g., 1-tert-butyl 2-methyl 4,4-difluoropyrrolidine-1,2-dicarboxylate.

Example E3. General Experimental for the Synthesis of Substituted 2-Amino-4-Bromobenzoic Acids General Scheme:

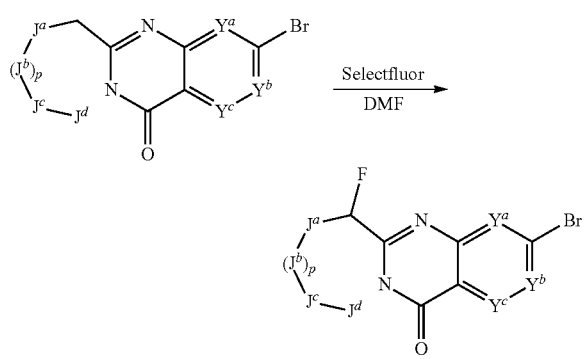

Representative Scheme:

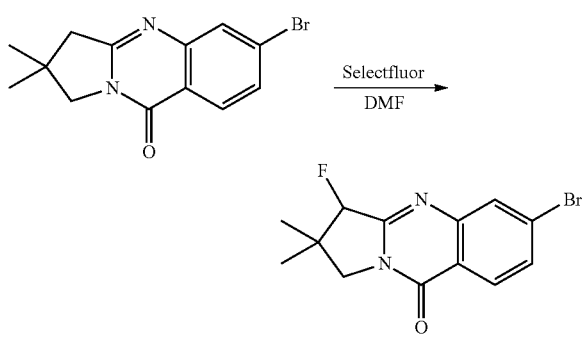

The solution of the starting material (e.g., 6-bromo-2,2-dimethyl-2,3-dihydropyrrolo[2,1-b]quinazolin-9(1H)-one, 1 equiv) and Selectfluor (approximately 1.5 equiv) in DMF (approximately 0.07 M) was stirred at approximately 90° C. until the reaction was complete (approximately 3 h). The reaction was then cooled to room temperature, diluted with $H_2O$, and extracted with EtOAc. The organic layers were washed with brine and dried over $Na_2SO_4$. After the crude was concentrated under reduced pressure, and the residue was purified by column chromatography to give the desired fluoro-substituted product (e.g., 6-bromo-3-fluoro-2,2-dimethyl-2,3-dihydropyrrolo[2,1-b]quinazolin-9(1H)-one).

Example E4. General Experimental for Fluorination α- to a Ketone Carbonyl

General Scheme:

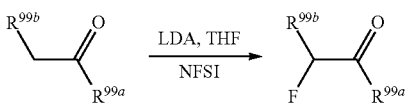

Representative Scheme:

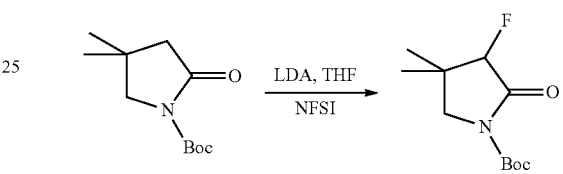

To a solution of the ketone (e.g., tert-butyl 4,4-dimethyl-2-oxopyrrolidine-1-carboxylate, 1 equiv) 1.9 mmol) in THF (0.2 M) was added fresh LDA (1.3 equiv, 0.5 M in LDA) at −60° C. After 1 h, N-Fluorobenzenesulfonimide (1.3 equiv) in THF (0.4 M in NFSI) was added slowly, then the temperature was raised to 0° C. The reaction mixture was stirred until the reaction was complete (approximately 0.5 h). The reaction was quenched with saturated $NH_4Cl$, and the residue was extracted with ethyl acetate. The organic layer was washed with brine, dried over $Na_2SO_4$ and concentrated to get the crude fluorinated product (e.g., 3-fluoro-4,4-dimethylpyrrolidin-2-one) that was used directly in the next step.

General Example F: Protection/Deprotection Chemistry

Example F1. General Experimental for Fmoc Protection of an Alcohol

General Scheme:

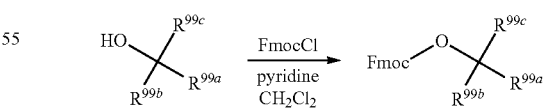

Representative Scheme:

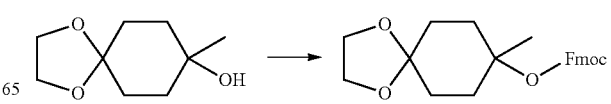

To a stirred solution of the alcohol starting material (e.g., 8-methyl-1,4-dioxaspiro[4.5]decan-8-ol, 1 equiv) and excess pyridine in $CH_2Cl_2$ (0.1 M) was added (9H-fluoren-9-yl)methyl carbonochloridate (2 equiv). The mixture was stirred at room temperature until the reaction was complete (approximately 2 h). The reaction mixture was then quenched with hydrochloride (1 M) and extracted with ethyl acetate. The organic phase was dried over anhydrous $Na_2SO_4$ and concentrated under reduced pressure to give the desired Fmoc-protected alcohol (e.g., (9H-fluoren-9-yl) methyl 8-methyl-1,4-dioxaspiro[4.5]decan-8-yl carbonate).

Example F2. General Experimental for Ketal Deprotection

General Scheme:

Representative Scheme:

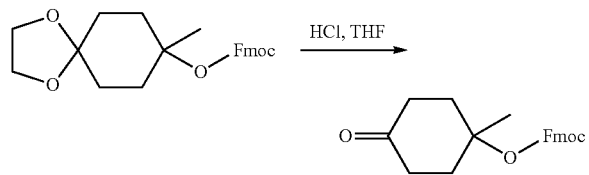

A solution of the starting ketal (e.g., (9H-fluoren-9-yl) methyl 8-methyl-1,4-dioxaspiro[4.5]decan-8-yl carbonate, 1 equiv) and hydrochloric acid (4 M) in THF (0.02 M) was refluxed for 3 h. After cooling to room temperature, the mixture was extracted with ethyl acetate. The organic phase was dried over anhydrous $Na_2SO_4$, and concentrated under reduced pressure to provide the desired ketone product (e.g., (9H-fluoren-9-yl)methyl (1-methyl-4-oxocyclohexyl) carbonate).

Example F3. General Experimental for N-Boc Deprotection

General Scheme:

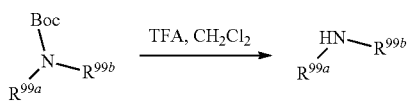

Representative Scheme:

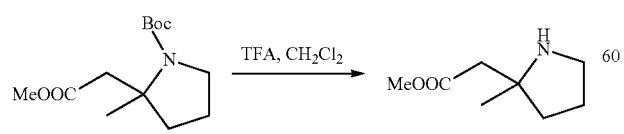

A mixture of the Boc-protected amine starting material (e.g., 2-(2-methoxy-2-oxoethyl)-2-methylpyrrolidine-1-carboxylate, 1 equiv), TFA (1.2 M) and $CH_2Cl_2$ (0.44 M) was stirred at room temperature until the reaction was complete (approximately 4 h). After the solution was concentrated, the residue was redissolved in $CH_2Cl_2$ and treated with $Et_3N$ at 0° C. until pH>7. Then the solution and $Et_3N$ were evaporated to give the crude product (e.g., methyl 2-(2-methylpyrrolidin-2-yl)acetate) which was used for the next step without further purification.

Example F4. General Experimental for Fmoc Deprotection

General Scheme:

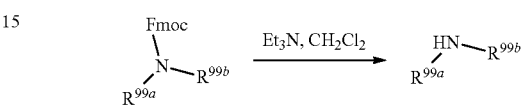

Representative Scheme:

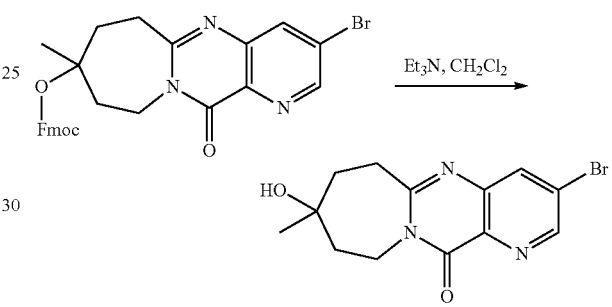

A solution of the Fmoc-containing starting material (e.g., (9H-fluoren-9-yl)methyl (3-bromo-8-methyl-12-oxo-6,7,8,9,10,12-hexahydropyrido[3',2':4,5]pyrimido[1,2-a]azepin-8-yl) carbonate, 1 equiv) and $Et_3N$ (0.07 M) in $CH_2Cl_2$ (0.02 M) was stirred at room temperature overnight or until the reaction was complete. The mixture was concentrated under reduced pressure and purified by silica gel chromatography to give the desired deprotected amine (e.g., 3-bromo-8-hydroxy-8-methyl-7,8,9,10-tetrahydropyrido[3',2':4,5]pyrimido[1,2-a]azepin-12(6H)-one).

Example F5. General Experimental for Boc Protection

General Scheme:

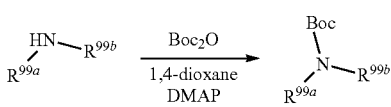

Representative Scheme:

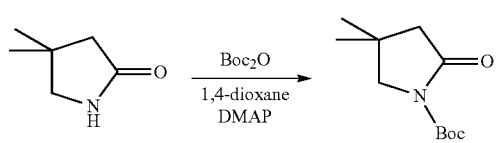

To a solution of the amine or amide-containing starting material (e.g., 4,4-dimethylpyrrolidin-2-one, 1 equiv, 8.9 mmol) in 1,4-dioxane (0.4 M) was added 4-dimethylaminopyridine (1.2 equiv) and (Boc)₂O (1.2 equiv). The reaction mixture was stirred for 45° C. until the reaction was complete (approximately 2 h). Then the mixture was diluted with H₂O and extracted with ethyl acetate. The organic layers were washed with 3 M HCl, brine, dried over Na₂SO₄ and concentrated to give the desired Boc-protected product (e.g., tert-butyl 4,4-dimethyl-2-oxopyrrolidine-1-carboxylate).

Example F6. General Experimental for Boc Protection

General Scheme:

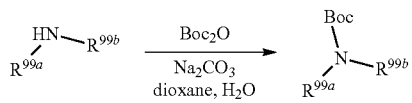

Representative Scheme:

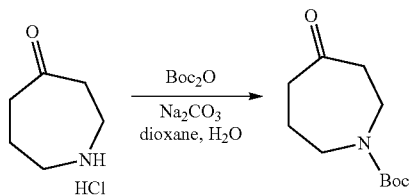 [SMILES: "Boc2O" ; O=C1CCCNCC1 ; "Na2CO3dioxane, H2O" ; CC(C)(C)OC(=O)N1CCCC(=O)CC1 ; Cl]

A solution of the amine (e.g., azepan-4-one HCl salt, 1 equiv), Na₂CO₃ (2 equiv) and (Boc)₂O (1.1 equiv) in 1,4-dioxane (0.7 M) and H₂O (3.3 M) was stirred at room temperature until the reaction was complete. The mixture was diluted with water and extracted with ethyl acetate. The organic phase was dried over anhydrous Na₂SO₄ and concentrated under reduce pressure to give the desired Boc-protected product (e.g., tert-butyl 4-oxoazepane-1-carboxylate).

Example F7. General Experimental for Cbz Deprotection

General Scheme:
Representative Scheme:

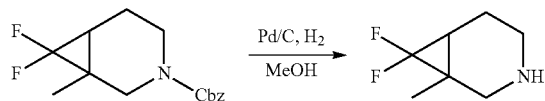

A mixture of the Cbz protected amine (e.g., benzyl 7,7-difluoro-1-methyl-3-azabicyclo[4.1.0]heptane-3-carboxylate) and 10% Pd/C (catalytic amount) in MeOH was stirred at room temperature under hydrogen atmosphere overnight. The mixture was filtered and the filtrate was evaporated under reduced pressure to give the amine (e.g., 7,7-difluoro-1-methyl-3-azabicyclo[4.1.0]heptane).

General Example G: Various Functional Group Interconversions

Example G1. General Experimental for the Esterification of a Carboxylic Acid

General Scheme:

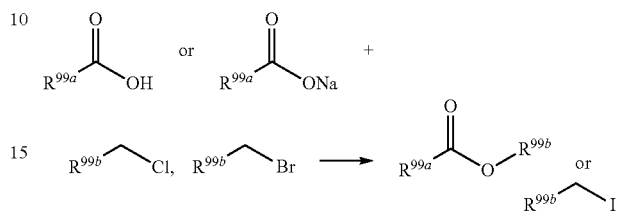

Representative Scheme A:

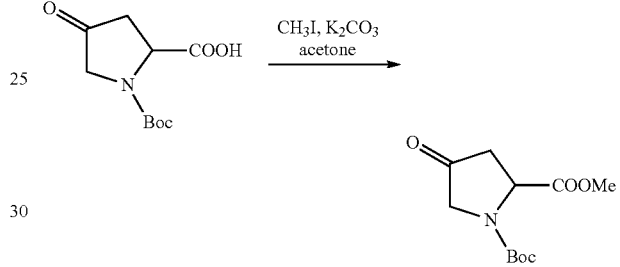

A solution of carboxylic acid starting material (e.g., 1-(tert-butoxycarbonyl)-4-oxopyrrolidine-2-carboxylic acid, 1 equiv), CH₃I (2.5 equiv) and K₂CO₃ (2.0 equiv) in acetone (0.23 M) was refluxed until the reaction was complete (approximately 2 h). After cooling to room temperature, the reaction mixture was filtered and acetone was distilled off under reduced pressure. Then ethyl acetate was added into the residue and the organic phase was washed with brine, dried over anhydrous sodium sulfate and concentrated under reduced pressure to give the desired ester product (e.g., 1-tert-butyl 2-methyl 4-oxopyrrolidine-1,2-dicarboxylate).

Representative Scheme B:

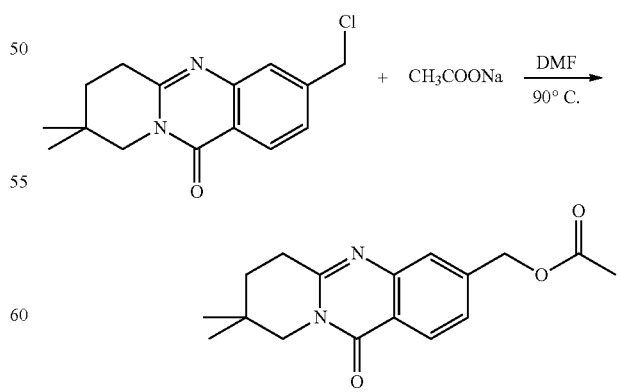

To a solution of a benzyl chloride or a benzyl bromide (e.g., 3-(chloromethyl)-8,8-dimethyl-8,9-dihydro-6H-pyrido[2,1-b]quinazolin-11(7H)-one, 1 equiv), sodium acetate (10 equiv) in DMF was stirred at 90° C. for 3 h. After the reaction was cooled to room temperature, the reaction mixture was diluted with water and extracted with ethyl acetate. The combined organic layers were washed with water, dried over anhydrous Na₂SO₄ and concentrated under reduced pressure to give the ester (e.g., (8,8-dimethyl-11-oxo-7,8,9,11-tetrahydro-6H-pyrido[2,1-b]quinazolin-3-yl) methyl acetate).

Example G2. General Experimental for the Hydrolysis of an Ester to a Carboxylic Acid General Scheme:

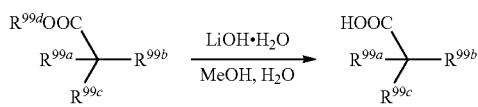

Representative Scheme:

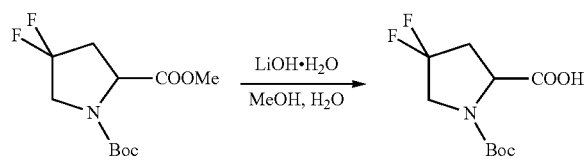

To a solution of the ester (e.g., 1-tert-butyl 2-methyl 4,4-difluoropyrrolidine-1,2-dicarboxylate, 1 equiv) in MeOH (0.22 M) and H₂O (0.65 M) was added LiOH.H₂O (4.0 equiv) at room temperature. The resulting mixture was stirred until the reaction was complete (approximately 2.5 h). The MeOH was evaporated and the residue mixture was extracted with diethyl ether (3×100 mL). The combined aqueous layers were acidified to pH ~3 with hydrochloric acid (1 M) and extracted with ethyl acetate. The combined organic layers were dried over anhydrous sodium sulfate, concentrated under reduced pressure to give the desired carboxylic acid-containing compound (e.g., 1-(tert-butoxycarbonyl)-4,4-difluoropyrrolidine-2-carboxylic acid).

Example G3. General Experimental for the Conversion of a Methyl Ester to a Primary Amide General Scheme:

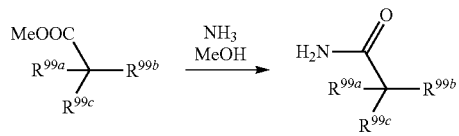

Representative Scheme:

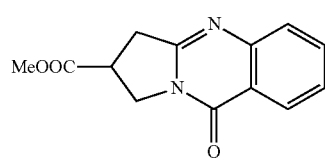

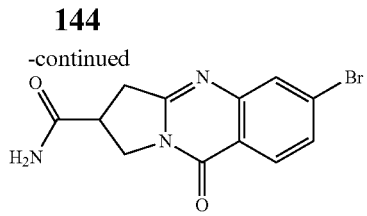

To a sealed tube was added the methyl ester starting material (e.g., methyl 6-bromo-9-oxo-1,2,3,9-tetrahydropyrrolo[2,1-b]quinazoline-2-carboxylate, 1 equiv) and excess NH₃/MeOH solution. The mixture was stirred at approximately 80° C. until the reaction was complete (approximately 5 h). After cooling to room temperature, the mixture was concentrated under reduced pressure to give the desired amide product (e.g., 6-bromo-9-oxo-1,2,3,9-tetrahydropyrrolo[2,1-b]quinazoline-2-carboxamide).

Example G4. General Experimental for the Conversion of an Amide to a Nitrile

General Scheme:

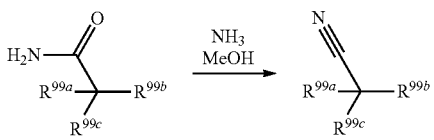

Representative Scheme:

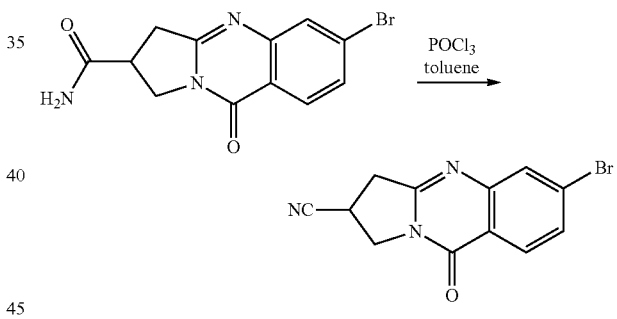

A solution of the amide starting material (e.g., 6-bromo-9-oxo-1,2,3,9-tetrahydropyrrolo[2,1-b]quinazoline-2-carboxamide, 1 equiv) and excess POCl₃ in toluene was refluxed until the reaction was complete (approximately 2 h). After cooling to room temperature, the mixture was poured into water and extracted with ethyl acetate. The combined organic phase was dried over Na₂SO₄ and concentrated under reduced pressure to give the desired carbonitrile product (e.g., 6-bromo-9-oxo-1,2,3,9-tetrahydropyrrolo[2,1-b]quinazoline-2-carbonitrile).

Example G5. General Experimental for Two Step Carbon Homologation

General Scheme:

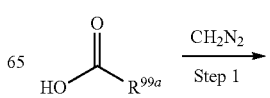

Representative Scheme:

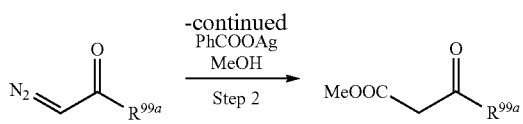

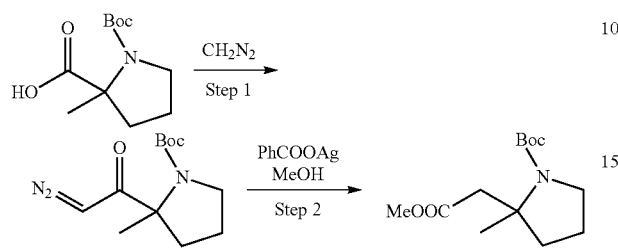

Example G5, Step 1

Under N$_2$ atmosphere, the carboxylic acid (e.g., 1-(tert-butoxycarbonyl)-2-methylpyrrolidine-2-carboxylic acid, 1 equiv) was dissolved in dry THF (0.3 M) and cooled to −30° C., then Et$_3$N (1.1 equiv) was added. To the solution was added isobutyl carbonochloridate (1.1 equiv) dropwise. After stirring for 3 hours, CH$_2$N$_2$ (prepared from 6.4 equiv of N,4-dimethyl-N-nitrosobenzenesulfonamide and 24 equiv KOH) in ether (1.8 M in KOH) was added and the resulting mixture was stirred at 0° C. overnight or until the reaction was complete. The reaction mixture was quenched with several drops of acetic acid. After evaporation of the solvent, the residue was dissolved in ethyl acetate. The organic layers were washed with aqueous NaHCO$_3$. Then the combined organic layers were dried over Na$_2$SO$_4$ and concentrated under reduced pressure to give the crude product (e.g., tert-butyl 2-(2-diazoacetyl)-2-methylpyrrolidine-1-carboxylate) which was purification by column chromatography.

Example G5, Step 2

PhCOOAg in Et$_3$N (0.3 M in PhCOOAg) was added dropwise to the solution of the diazo starting material (e.g., tert-butyl 2-(2-diazoacetyl)-2-methylpyrrolidine-1-carboxylate, 1 equiv) in MeOH (0.26 M) at −35° C. under nitrogen atmosphere. Then the mixture reaction was stirred until the reaction was complete, and the temperature was allowed to warm to room temperature slowly. The solution was evaporated and the residue was dissolved in ethyl acetate. After filtration through Celite, the filtrate was concentrated to give the crude product (e.g., tert-butyl 2-(2-methoxy-2-oxo-ethyl)-2-methylpyrrolidine-1-carboxylate) which was purified by column chromatography.

Example G6. General Experimental for Grignard Addition to an Ester

General Scheme:

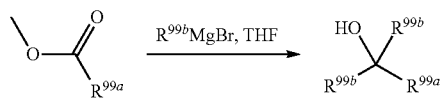

Representative Scheme:

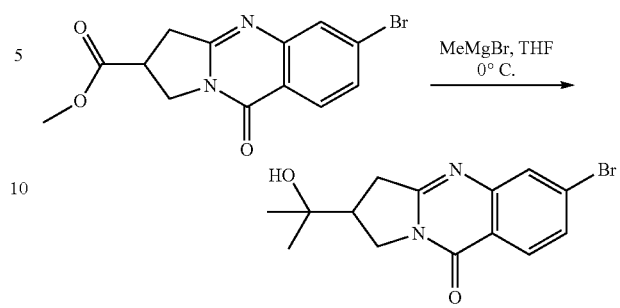

To a solution of the ester starting material (e.g., methyl 6-bromo-9-oxo-1,2,3,9-tetrahydropyrrolo[2,1-b]quinazoline-2-carboxylate, 1 equiv) (obtained from 2-amino-4-bromobenzoic acid and methyl 5-oxopyrrolidine-3-carboxylate according to Example B1) in dry THF was added the Grignard reagent (e.g., CH$_3$MgBr, 2 equiv) at approximately 0° C. and the resulting mixture was stirred until the reaction was complete (approximately 4 hours). The mixture was quenched with NH$_4$Cl aqueous and extracted with ethyl acetate, dried over Na$_2$SO$_4$ and concentrated under reduced pressure to give the desired product (e.g., 6-bromo-2-(2-hydroxypropan-2-yl)-2,3-dihydropyrrolo[2,1-b]quinazolin-9(1H)-one).

Example G7. General Experimental for Reduction of a Ketone

General Scheme:

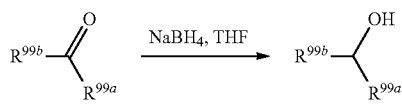

Representative Scheme:

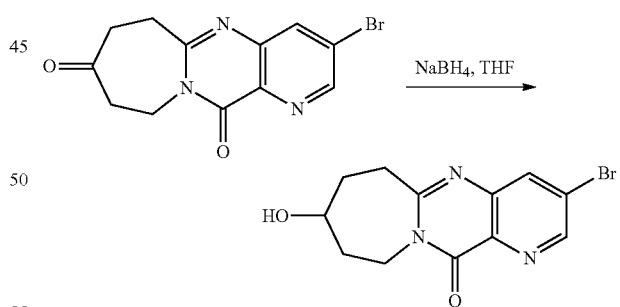

A solution of the ketone starting material (e.g., 3-bromo-6,7,9,10-tetrahydropyrido[3',2':4,5]pyrimido[1,2-a]azepine-8,12-dione, 1 equiv), and NaBH$_4$ (2 equiv) in THF (0.07 M) was stirred at room temperature until the reaction was complete (approximately 0.5 h). The reaction mixture was quenched with water and extracted with ethyl acetate. The combined organic layers were dried over Na$_2$SO$_4$. After filtration and concentration, the residue was purified by silica gel chromatography to give the desired alcohol product (e.g., 3-bromo-8-hydroxy-7,8,9,10-tetrahydropyrido[3',2':4,5]pyrimido[1,2-a]azepin-12(6H)-one).

Example G8. General Experimental for Grignard Addition to a Ketone

General Scheme:

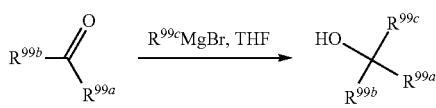

Representative Scheme:

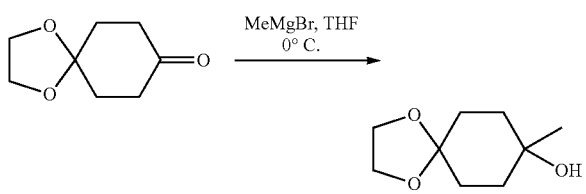

To a solution of the ketone starting material (e.g., 1,4-dioxaspiro[4.5]decan-8-one, 1 equiv) in dry THF was added CH₃MgBr (1.1 equiv) at 0° C. until the reaction was complete (approximately 4 h). The mixture was quenched with NH₄Cl aqueous and extracted with ethyl acetate, dried over Na₂SO₄ and concentrated under reduced pressure to give the desired alcohol product (e.g., 8-methyl-1,4-dioxaspiro[4.5]decan-8-ol).

Example G9. General Experimental for Alkylation α- to a Ketone

General Scheme:

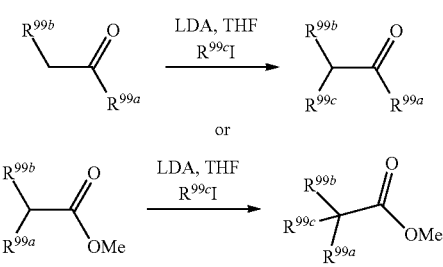

Representative Scheme:

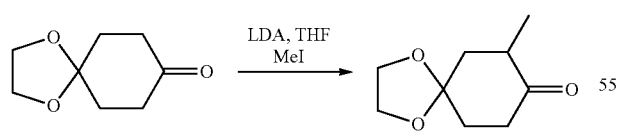

A solution of the ketone or ester starting material (e.g., 1,4-cyclohexanedione monoethylene acetal, 1 equiv), in dry THF (0.64 M) was added dropwise to lithium diisopropylamide (1 equiv) and stirred for 2 hours at 0° C. under N₂ atmosphere. A solution of the alkyl halide (e.g., CH₃I, 1.2 equiv) in dry THF (0.8 M in CH₃I) was added dropwise to the reaction mixture at −78° C. and stirred overnight at room temperature. The reaction mixture was quenched with NH₄Cl solution and extracted with ethyl acetate. The combined organic layers were dried over Na₂SO₄. After filtration and concentration, the residue was purified by silica gel chromatography to give the desired alkylated product (e.g., 7-methyl-1,4-dioxaspiro[4.5]decan-8-one).

Example G10. General Experimental for the Addition of an Amine to Methyl Acrylate General Scheme:

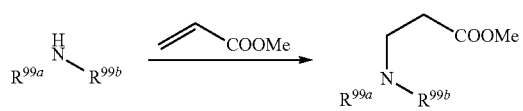

Representative Scheme:

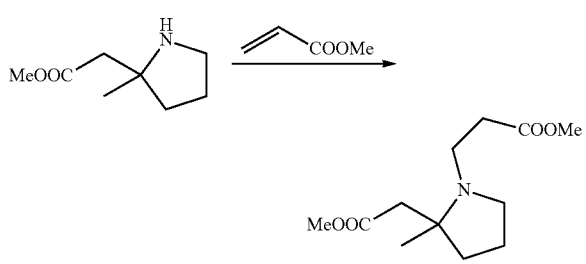

The amine (e.g., methyl 2-(2-methylpyrrolidin-2-yl)acetate was dissolved in methyl acrylate and refluxed until the reaction was complete. Then the solution was evaporated and the residue was purified by column chromatography to the desired product (e.g., methyl 3-(2-(2-methoxy-2-oxoethyl)-2-methylpyrrolidin-1-yl)propanoate).

Example G11. General Experimental for the Dieckmann Condensation of a Diester General Scheme:

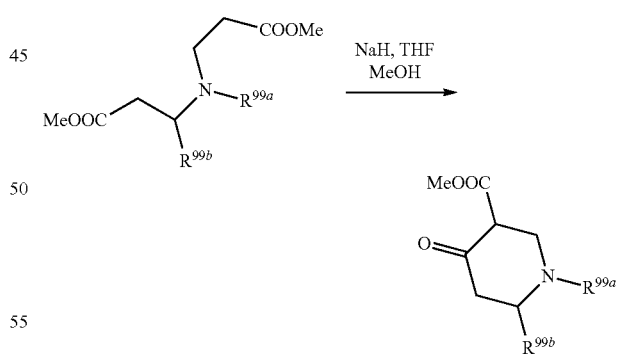

Representative Scheme:

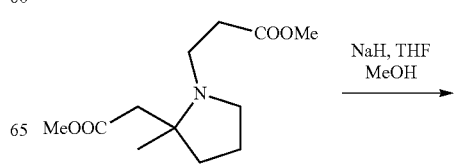

-continued

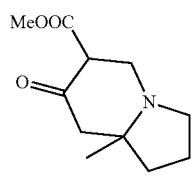

To a solution of diester starting material (e.g., methyl 3-(2-(2-methoxy-2-oxoethyl)-2-methylpyrrolidin-1-yl)-propanoate, 1 equiv) in dry THF (0.16 M) and drops of MeOH was added NaH (5.0 equiv, 60% in oil) at room temperature. MeOH was added to quench the reaction after the reaction was stirred overnight. Then the solution was concentrated to give the α-keto ester desired product (e.g., methyl 8a-methyl-7-oxooctahydroindolizine-6-carboxylate), which was used for the next step without further purification.

Example G12. General Experimental for Decarboxylation of an Ester

General Scheme:

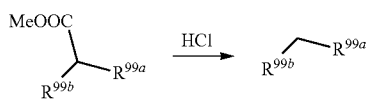

Representative Scheme:

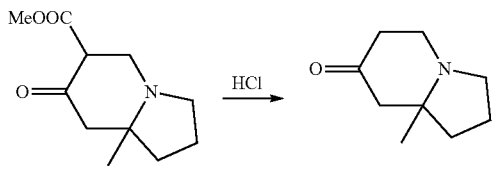

The ester starting material (e.g., methyl 8-methyl-7-oxooctahydroindolizine-6-carboxylate) was dissolved in 4M HCl and refluxed until the reaction was complete (approximately 3 h). After the mixture was cooled to room temperature, K$_2$CO$_3$ was added carefully until the pH=10. Then the solution was extracted with CH$_2$Cl$_2$ (6×50 mL). The organic layers were combined, dried over Na$_2$SO$_4$, filtered and concentrated to give the desired decarboxylated product (e.g., 8a-methylhexahydroindolizin-7(1H)-one).

Example G13. General Experimental for Alkylation of an Alcohol

General Scheme:

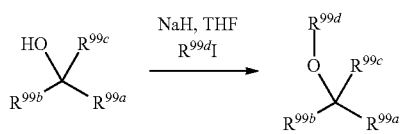

Representative Scheme:

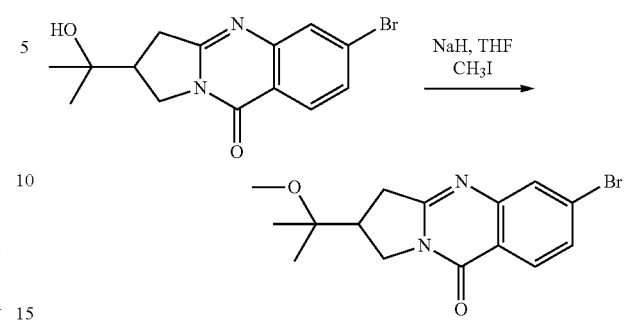

A solution of alcohol starting material (e.g., 6-bromo-2-(2-hydroxypropan-2-yl)-2,3-dihydropyrrolo[2,1-b]quinazolin-9(1H)-one, 1 equiv) and sodium hydride (approximately 3 equiv) in THF (approximately 0.03 M) was refluxed for approximately 0.5 h. The reaction was then cooled to room temperature, and an alkyl halide (e.g., iodomethane, approximately 2 equiv) was added to the mixture. The mixture was heated at reflux until the reaction was complete (approximately 2 h). The reaction was then cooled to room temperature, quenched with water, and extracted with ethyl acetate. The organic phase was dried over anhydrous Na$_2$SO$_4$, concentrated under reduced pressure to give the desired ether product (e.g., 6-bromo-2-(2-methoxypropan-2-yl)-2,3-dihydropyrrolo[2,1-b]quinazolin-9(1H)-one).

Example G14. Experimental for Elimination of an Alcohol

Representative Scheme:

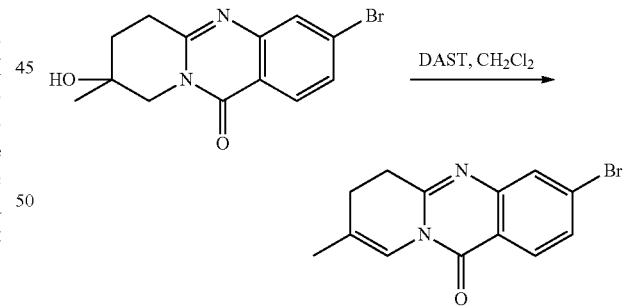

To a solution of 3-bromo-8-hydroxy-8-methyl-8,9-dihydro-6H-pyrido[2,1-b]quinazolin-11(7H)-one) in CH$_2$Cl$_2$ was added excess DAST under N$_2$ at room temperature. The mixture was stirred at the room temperature until the reaction was complete (approximately 3 h). The reaction mixture was quenched with water and extracted with ethyl acetate. The combined organic layers were dried over Na$_2$SO$_4$ and concentrated under reduced pressure. The crude product was purified by silica gel chromatography to obtain the desired alkene-containing product (e.g., 3-bromo-8-methyl-6H-pyrido[2,1-b]quinazolin-11(7H)-one).

Example G15. General Experimental for Oxidation of an Alcohol to an Aldehyde or a Ketone General Scheme:

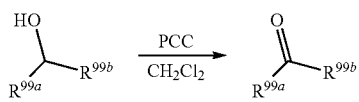

Representative Scheme:

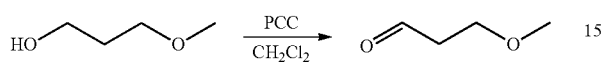

Pyridinium chlorochromate (1 equiv) was suspended in CH$_2$Cl$_2$ (0.002 M) at room temperature and alcohol (e.g., 3-methoxypropanol, 1 equiv) was rapidly added. When the reaction was complete (approximately 2 h), the reaction was diluted with diethyl ether, the solvent was decanted and the solid was washed twice with diethyl ether. The organic solvent was washed with water, brine, and dried over Na$_2$SO$_4$. The organic layer was concentrated under reduced pressure to give the crude product (e.g., 3-methoxypropanal), which was used in the next step.

Example G16. General Experimental for Oxidation of an Alcohol to an Aldehyde or a Ketone General Scheme:

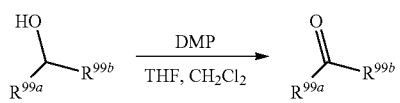

Representative Scheme:

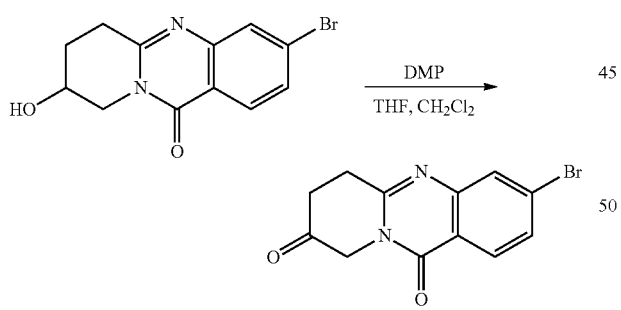

To a solution of alcohol (e.g., 3-bromo-8-hydroxy-8,9-dihydro-6H-pyrido[2,1-b]quinazolin-11(7H)-one, 1 equiv) in THF (0.11 M) and CH$_2$Cl$_2$ (0.17 M) at 0° C. was added Dess-Martin reagent (DMP) (2 equiv). The resulting mixture was stirred at room temperature until the reaction was complete (approximately 3 h). 60 mL of aqueous Na$_2$S$_2$O$_3$ was then added, and the mixture was extracted with ethyl acetate and dried over Na$_2$SO$_4$. After filtration and concentration, the desired ketone product (e.g., 3-bromo-6H-pyrido[2,1-b]quinazoline-8,11 (7H,9H)-dione) was obtained, which was directly used for the next step without further purification.

Example G17. General Experimental for Reduction of an Ester to an Aldehyde

General Scheme:

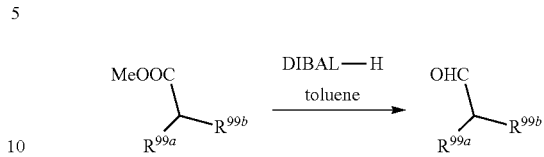

Representative Scheme:

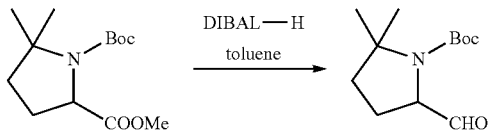

To a solution of the ester starting material (e.g., 1-tert-butyl 2-methyl 5,5-dimethylpyrrolidine-1,2-dicarboxylate, 1 equiv) (4.8 g, 18.7 mmol) in toluene at −78° C. was added DIBAL-H (37.4 mmol, 1.7 mol/L) dropwise, maintaining the temperature below −65° C. The reaction was stirred at −78° C. until the reaction was complete (approximately 2 h) and then quenched with methanol (10 mL). The mixture was then diluted with ethyl acetate, saturated NH$_4$Cl was added, and the mixture was stirred vigorously for 20 min at room temperature. The two phases were then separated and the aqueous layer was extracted with CH$_2$Cl$_2$. The combined organics were then washed with brine, dried over Na$_2$SO$_4$, concentrated under reduced pressure and purified by column chromatography to give the desired aldehyde-containing (e.g., tert-butyl 5-formyl-2,2-dimethylpyrrolidine-1l-carboxylate, 5 g) product.

Example G18. General Experimental for Reductive Amination of an Aldehyde

General Scheme:

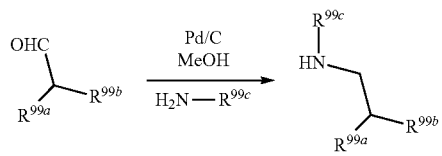

Representative Scheme:

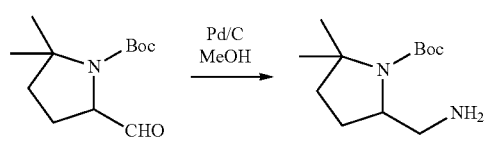 [SMILES: CC(C)(C)OC(=O)N1C(C=O)CCC1(C)C ; CC(C)(C)OC(=O)N1C(CN)CCC1(C)C]

To a saturated ammonia MeOH solution, the starting amine (e.g., tert-butyl 5-formyl-2,2-dimethylpyrrolidine-1-carboxylate, 22 mmol) and 10% Pd/C (2 g) was added and stirred under hydrogen atmosphere at room temperature until the reaction was complete. The catalyst was removed by filtration, then the filtrate was concentrated under reduced pressure to give the crude desired amine-containing product (e.g., tert-butyl 5-(aminomethyl)-2,2-dimethylpyrrolidine-1-carboxylate), which was used for the next step without further purification.

Example G19. General Experimental for O-Demethylation

General Scheme:

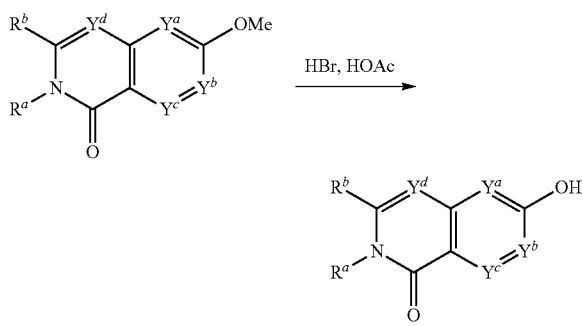

Representative Scheme:

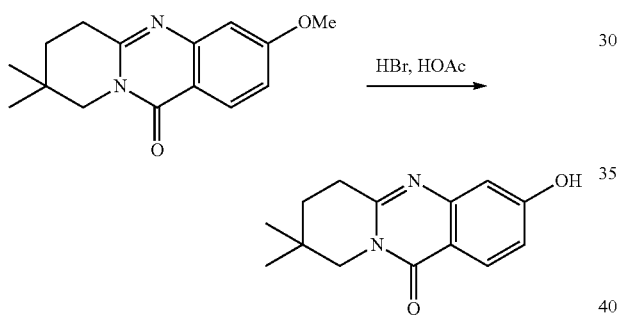

A solution of the methyl ester (e.g., 3-methoxy-8,8-dimethyl-8,9-dihydro-6H-pyrido[2,1-b]quinazolin-11(7H)-one, 1 equiv) in hydrobromic acid (0.06 M) and acetic acid (0.12 M) was stirred at reflux until the reaction was complete. The mixture was diluted with water and extracted with ethyl acetate. The organic phase was dried over anhydrous Na$_2$SO$_4$ and concentrated under reduced pressure. The crude was purified by silica gel chromatography to give the desired alcohol product (e.g., 3-hydroxy-8,8-dimethyl-8,9-dihydro-6H-pyrido[2,1-b]quinazolin-11(7H)-one).

Example G20. General Experimental for Conversion of an Alcohol to the Corresponding Mesylate General Scheme:

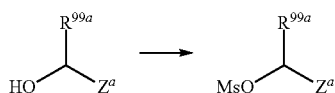

Representative Scheme:

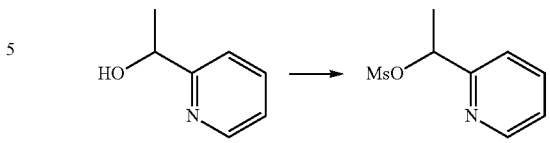

To a stirred solution of the alcohol starting material (e.g., 1-(pyridin-2-yl)ethanol, 4.1 mmol) and Et$_3$N (1.1 mL) in CH$_2$Cl$_2$ was added MsCl (0.5 mL) under N$_2$ in ice bath. The mixture was stirred at the same temperature until the reaction was complete (approximately 0.5 h). The reaction mixture was quenched with water and extracted with ethyl acetate. The combined organic layers were dried over Na$_2$SO$_4$ and concentrated under reduced pressure to yield the crude mesylate product (e.g., 1-(pyridin-2-yl)ethyl methanesulfonate, 1.1 g).

Example G21. General Experimental for the Alkylation of an Aromatic or Heteroaromatic Alcohol General Scheme:

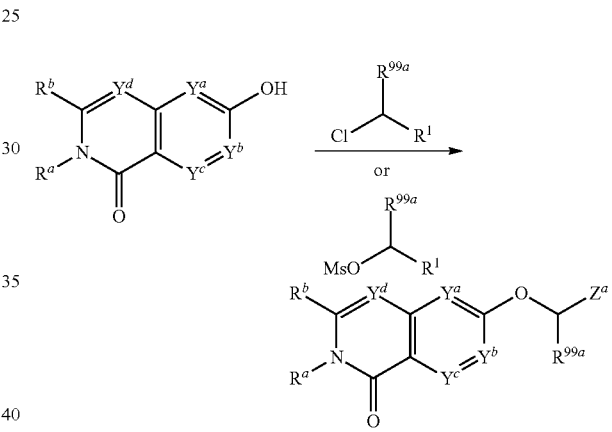

Representative Scheme A:

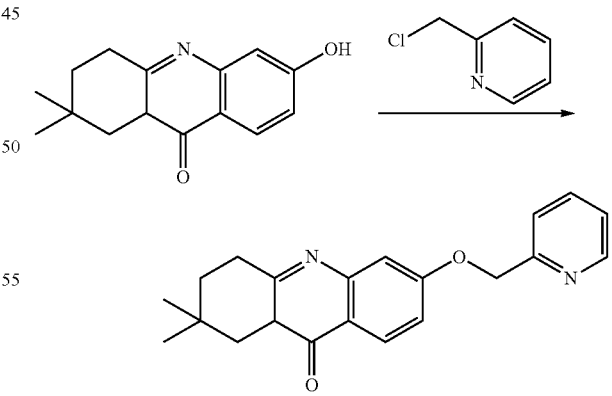

A solution of the starting alcohol (e.g., 3-hydroxy-8,8-dimethyl-8,9-dihydro-6H-pyrido[2,1-b]quinazolin-11(7H)-one, 0.41 mmol), K$_2$CO$_3$ (3 equiv) and the alkyl halide (e.g., 2-(chloromethyl)pyridine, 1.1 equiv) in DMF (0.05 M in alkyl halide) was stirred at 120° C. until the reaction was complete (approximately 2 h). The mixture was diluted with water and extracted with ethyl acetate. The organic layer was dried over anhydrous Na$_2$SO$_4$ and concentrated under reduced pressure. The crude mixture was purified by silica gel chromatography to give the desired ether product (e.g., 8,8-dimethyl-3-(pyridin-2-ylmethoxy)-8,9-dihydro-6H-pyrido[2,1-b]quinazolin-11(7H)-one, 80 mg).
Representative Scheme B:

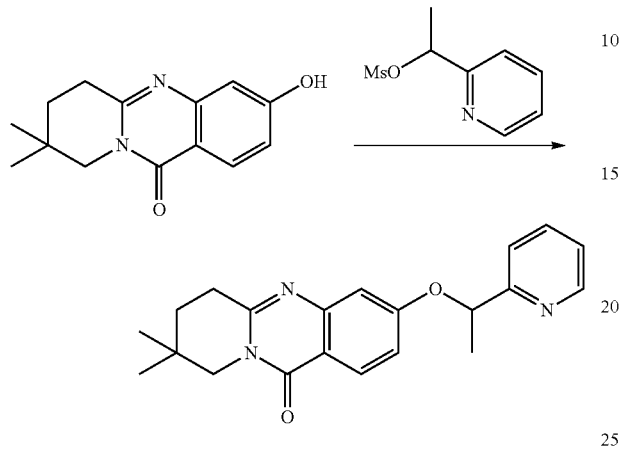

A solution of the alcohol (e.g., 3-hydroxy-8,8-dimethyl-8,9-dihydro-6H-pyrido[2,1-b]quinazolin-11(7H)-one, 0.41 mmol), K$_2$CO$_3$ (2 equiv) and the mesylate starting material (e.g., 1-(pyridin-2-yl)ethyl methanesulfonate, 2.4 equiv) in DMF (0.07 M in mesylate) was stirred at 120° C. until the reaction was complete (approximately 2 h). The mixture was diluted with water and extracted with ethyl acetate. The organic layer was dried over anhydrous Na$_2$SO$_4$ and concentrated under reduced pressure. The crude mixture was purified by silica gel chromatography to give the desired ether product (e.g., 8,8-dimethyl-3-(1-(pyridin-2-yl)ethoxy)-8,9-dihydro-6H-pyrido[2,1-b]quinazolin-11(7H)-one, 80 mg).
Representative Scheme C:

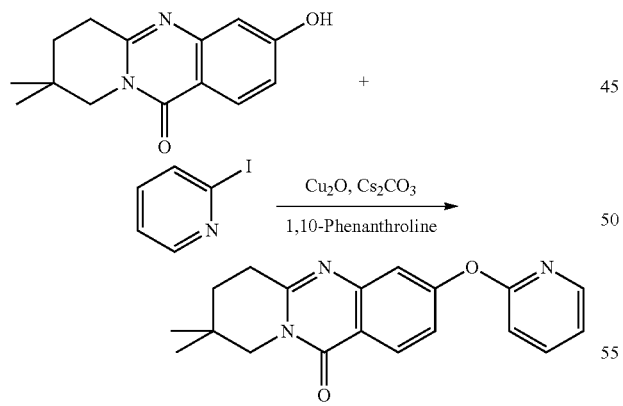

A solution of the alcohol (e.g., 3-hydroxy-8,8-dimethyl-8,9-dihydro-6H-pyrido[2,1-b]quinazolin-11(7H)-one, 1 equiv), the aryl halide (e.g., 2-iodopyridine, 1.5 equiv), 1,10-phenanthroline (0.15 equiv), Cs$_2$CO$_3$ (1.5 equiv) and CuI (0.15 equiv) in DMSO was stirred in a sealed tube at 90° C. for 3.5 hours. The reaction was cooled to room temperature, then the reaction mixture was diluted with H$_2$O and extracted with EtOAc. The combined organic layers were washed with brine and dried over anhydrous sodium sulfate. After concentration under reduced pressure, the residue was purified by silica gel chromatography (EtOAc:n-hexane=1:3) to give the desired ether product (e.g., 8,8-dimethyl-3-(pyridin-2-yloxy)-8,9-dihydro-6H-pyrido[2,1-b]quinazolin-11(7H)-one).
Representative Scheme D:

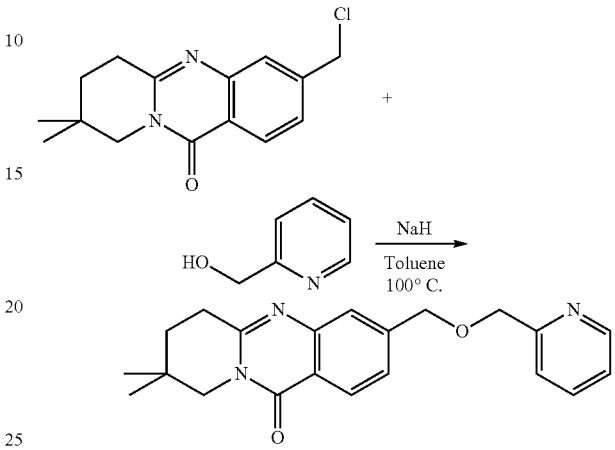

To a solution of alcohol (e.g., pyridin-2-ylmethanol, 2 equiv) in toluene at 100° C. was added 60% NaH in mineral oil (4 equiv). The resulting solution was stirred for 1 h. To the mixture was added the benzyl chloride (e.g., 3-(chloromethyl)-8,8-dimethyl-8,9-dihydro-6H-pyrido[2,1-b]quinazolin-11(7H)-one, 1 equiv) and kept at 100° C. for 2 h. After cooling to room temperature, the mixture was diluted with water and extracted with ethyl acetate. The combined organic layers were concentrated and purified by column chromatography on silica gel to give 6.5 mg of the desired ether product (e.g., 8,8-dimethyl-3-((pyridin-2-ylmethoxy)methyl)-8,9-dihydro-6H-pyrido[2,1-b]quinazolin-11(7H)-one).
Representative Scheme E:

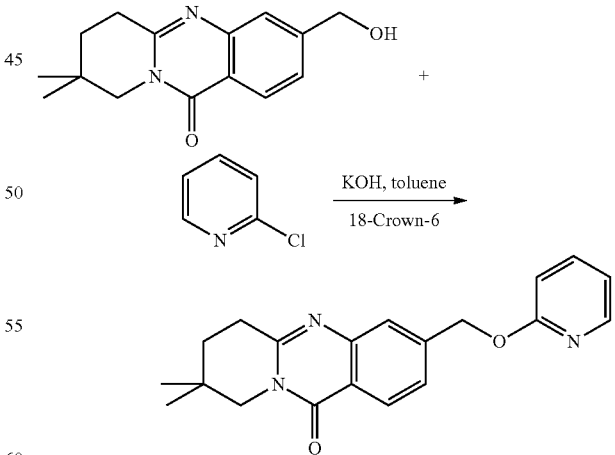

A solution of alcohol (e.g., 3-(hydroxymethyl)-8,8-dimethyl-8,9-dihydro-6H-pyrido[2,1-b]quinazolin-11(7H)-one, 1 equiv), aryl bromide or aryl chloride (e.g., 2-chloropyridine, 1.6 equiv), KOH (3.3 equiv) and 18-crown-6 (0.01 equiv) in toluene was heated at reflux for 2 h. The reaction mixture was then cooled to room temperature and partitioned between ethyl acetate and water. The organic layers were washed with brine, dried over Na$_2$SO$_4$, filtered, concentrated under vacuum and purified by silica column chromatography to give the desired ether product (e.g., 8,8-dimethyl-3-((pyridin-2-yloxy)methyl)-8,9-dihydro-6H-pyrido[2,1-b]quinazolin-11 (7H)-one).

Example G22. General Experimental for the Olefination of a Ketone

General Scheme:

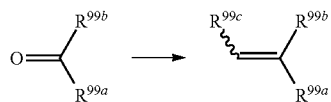

Representative Scheme:

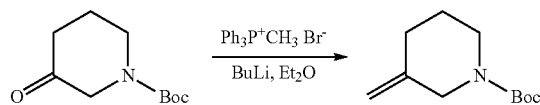

Wittig olefination of tert-butyl 3-oxopiperidine-1-carboxylate to tert-butyl 3-methylenepiperidine-1-carboxylate can be achieved by the procedures described by Beak, Peter; Lee, Burnell. et al. in *Journal of Organic Chemistry* 1989, 54(2), 458-64.

Example G23. General Experimental for the Cyclopropanation of an Olefin

General Scheme:

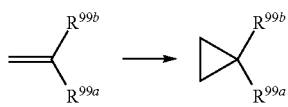

Representative Scheme A:

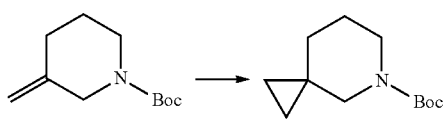

Cyclopropanation of the olefin can be effected by various modifications of Simmons-Smith reaction as described by O. Irie et al. in *Bioorg. Med. Chem. Lett.* 2008, 18, 4642-46460 or by A. B. Charette, A. Beauchemin et al. in *Journal of Organometallic Chemistry*, 2001, 617-618 702-708.

Representative Scheme B:

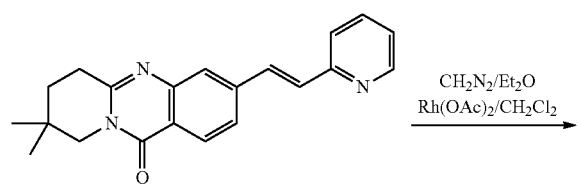

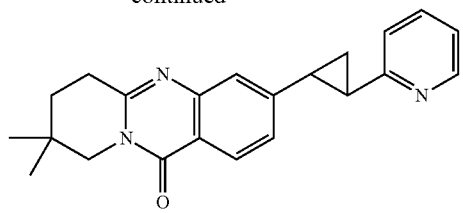

To a solution of KOH (119 equiv) in H$_2$O and ethanol heated to 65° C. was added N-methyl-N-nitroso-p-toluene-sul-fonamide (3 equiv) in ether. The diazomethane ether solution was distillated and collected at −78° C. Then, a solution of vinyl-containing material (e.g., 8,8-dimethyl-3-(2-(pyridin-2-yl)vinyl)-8,9-dihydro-6H-pyrido[2,1-b]-quinazolin-11(7H)-one, 1 equiv) and Rh(OAc)$_2$ (0.1 equiv) in CH$_2$Cl$_2$ was added to the ethereal diazomethane solution and stirred overnight at room temperature. The mixture was quenched with 10% acetic acid in ethyl acetate, diluted with H$_2$O and extracted with EtOAc. The combined organic layers were washed with brine, dried over Na$_2$SO$_4$. After filtration and concentration, the residue was purified by column chromatography (EtOAc:n-hexane=1:3) to give the cyclopropanated product (e.g., 8,8-dimethyl-3-(2-(pyridin-2-yl)cyclopropyl)-8,9-dihydro-6H-pyrido[2,1-b]quinazolin-11(7H)-one).

Example G24. General Experimental for the Cyclopropanation of an Olefin

General Scheme:

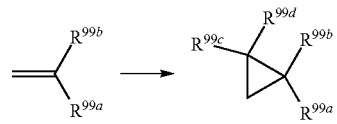

Representative Scheme:

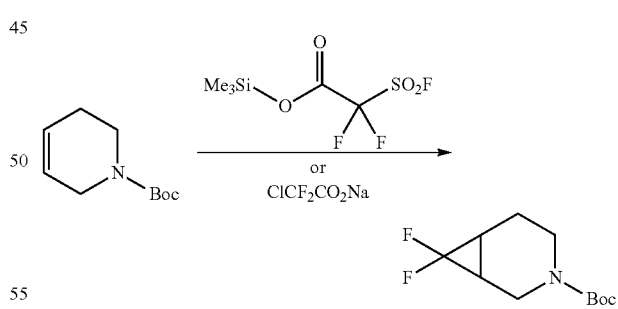

Difluorocyclopropanation from tert-butyl 5,6-dihydro-pyridine-1(2H)-carboxylate to tert-butyl 7,7-difluoro-3-azabicyclo[4.1.0]heptane-3-carboxylate can be achieved by the procedures described by Stanislaw F. Wnuk et al. (Journal of Fluorine Chemistry, 130 (2009), 321-328) using an "acid free" trimethylsilyl 2-fluorosulfonyl-2,2-difluoroacetate (TFDA) in anhydrous benzene containing catalytic amount of dried NaF at under heating, or by the chemistry with sodium chlorodifluoroacetate in diglyme under heating (WO 2005/079798, p 37) or by the chemistry described by Chun Cai et al. in *Chemistry Letters*, Vol. 34, No. 10, 2005, using sodium trifluoroacetate with and AIBN in DMF at 150-180° C.

Example G25. General Experimental for Reduction of Alcohols to Alkanes

General Scheme:

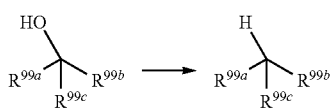

Representative Scheme:

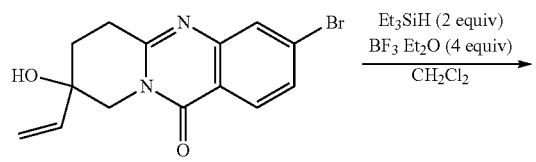

Reductive cleavage of tertial allylic alcohol to the corresponding alkane can be effected by the procedure described in WO 2008/124922, example 16, compound 79, page 118.

Example G26. General Experimental for Carbonyl Chloride Formation from Acid

General Scheme:

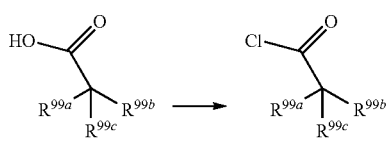

Representative Scheme:

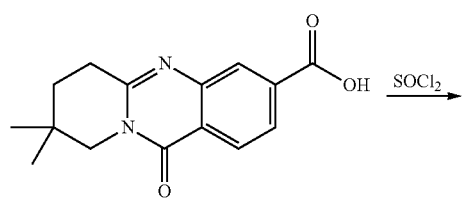

A solution of the carboxylic acid (e.g., 8,8-dimethyl-11-oxo-7,8,9,11-tetrahydro-6H-pyrido[2,1-b]quinazoline-3-carboxylic acid, 0.54 mmol) in $SOCl_2$ (8 mL) was stirred at reflux until the reaction was complete (approximately 5 h). The excess $SOCl_2$ was then removed under reduced pressure. The crude carbonyl chloride product (e.g., 8,8-dimethyl-1-oxo-7,8,9,11-tetrahydro-6H-pyrido[2,1-b]quinazoline-3-carbonyl chloride) was used without further purification for the next step.

Example G27. General Experimental for Amide Formation from Carbonyl Chloride

General Scheme:

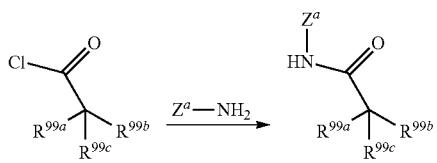

Representative Scheme:

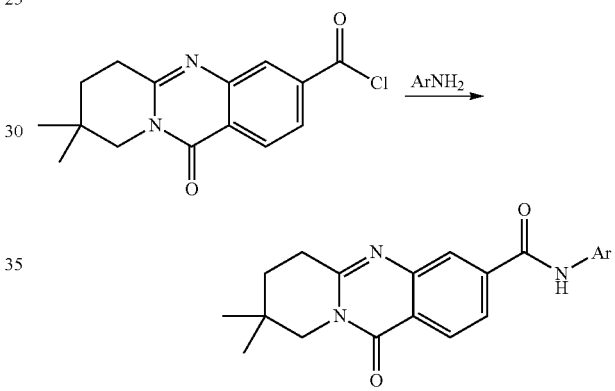

The crude carbonyl chloride (e.g., 8,8-dimethyl-11-oxo-7,8,9,11-tetrahydro-6H-pyrido[2,1-b]quinazoline-3-carbonyl chloride) from Example G26 was dissolved in anhydrous THF and added to a solution of the aromatic amine (0.81 mmol) in $CHCl_3$ (10 mL). The reaction was stirred at room temperature until the reaction was complete (approximately 0.5 h), and then poured into water. The mixture was extracted with ethyl acetate, and the organic layer was washed with brine, dried over anhydrous sodium sulfate. After filtration and concentration, the crude product was purified by silica gel chromatography purification to provide the desired amide product.

Example G28. General Experimental for Amide Formation by Direct Coupling of Carboxylic Acid and Amine General Scheme:

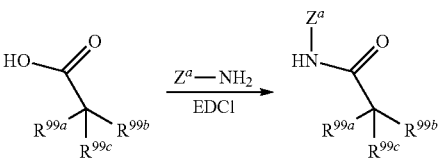

Representative Scheme:

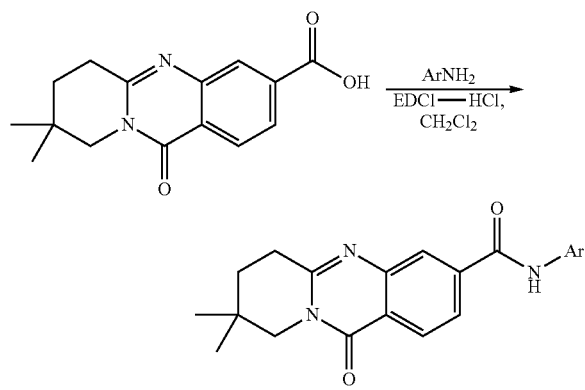

To a solution of the carboxylic acid (e.g., 8,8-dimethyl-11-oxo-7,8,9,11-tetrahydro-6H-pyrido[2,1-b]quinazoline-3-carboxylic acid, 0.22 mmol) and EDCI-HCl (0.42 mmol) in CH$_2$Cl$_2$ (10 mL) was added the aromatic amine (0.22 mmol). The mixture was stirred at room temperature until the reaction was complete (approximately 10 min) and then poured into 2 N HCl. The mixture was extracted with CH$_2$Cl$_2$ (30 mL) and the organic layer was washed with aqueous NaHCO$_3$, brine, dried over anhydrous sodium sulfate. After filtration and concentration, the crude amide product was purified by preparative HPLC.

Example G29. General Experimental for ArNO$_2$ Reduction to ArNH$_2$

General Scheme:

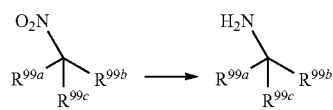

Representative Scheme:

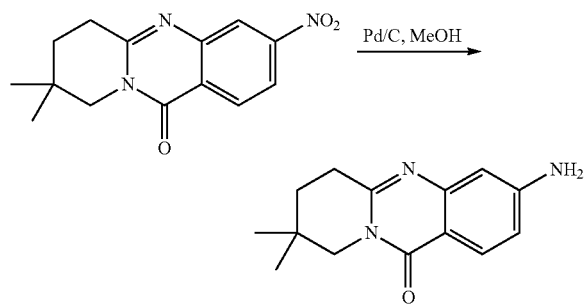

The nitro-containing starting material (e.g., 8,8-dimethyl-3-nitro-8,9-dihydro-6H-pyrido[2,1-b]quinazolin-11(7H)-one, 0.25 mmol) was dissolved in MeOH (5 mL). To the solution was added a catalytic amount of Pd/C. The reaction mixture was vacuumed and then back filled with hydrogen gas three times. The solution was stirred under H$_2$ (1 atm) for 1 h. The reaction mixture was filtered and washed with methanol. The filtration was concentrated to give the desired amine product (e.g., 3-amino-8,8-dimethyl-8,9-dihydro-6H-pyrido[2,1-b]quinazolin-11 (7H)-one).

Example G30: General Experimental for 1,4-Addition to α,β-Unsaturated Ketones

General Scheme:

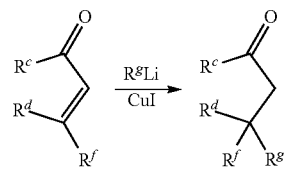

General Scheme:

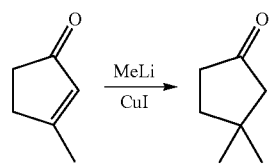

To a stirred slurry of CuI (0.33 mol, 1.2 equiv) in anhydrous ether (1.5 L) at −5 to 0° C. was added dropwise an ethereal solution of methyllithium (500 mL of 1.31 mol/L, 0.655 mol, 2.4 equiv) over 1.5 h. After additional one hour of stirring, a solution of 3-methylcyclopent-2-enone (26 g, 0.27 mol, 1.0 eq) in 150 mL of anhydrous ether was added dropwise at −5 to 0° C. over 0.5 h. After stirring at −5 to 0° C. for 30 min, the reaction mixture was quenched with aq. NH$_4$Cl solution. The mixture was then adjusted pH to 8 with aqueous ammonia and extracted with CH$_2$Cl$_2$. The combined organic layers were washed with brine twice and dried over Na$_2$SO$_4$. The solvents were removed to ⅕ of the original volume at 15° C. under reduced pressure. The crude product was directly used for the next step.

Example G31. General Experimental for Reduction of a Ester

General Scheme:

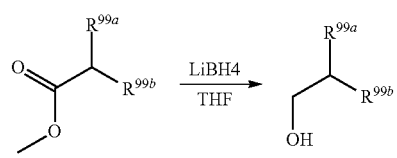

Representative Scheme:

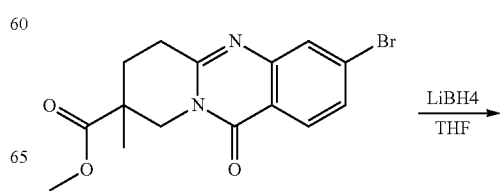

-continued

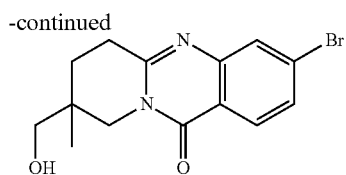

To a solution of the ester (e.g., methyl 3-bromo-8-methyl-11-oxo-7,8,9,11-tetrahydro-6H-pyrido[2,1-b]quinazoline-8-carboxylate, 1 equiv) in THF was added LiBH₄ (5 equiv). The reaction was stirred at room temperature for 3 h, then the reaction mixture was diluted with water and extracted with ethyl acetate. The combined organic layers were washed with NaHCO₃ solution, dried over anhydrous Na₂SO₄ and concentrated under reduced pressure. The residue was purified by column chromatography on silica gel to give the desired alcohol (e.g., 3-bromo-8-(hydroxymethyl)-8-methyl-8,9-dihydro-6H-pyrido[2,1-b]quinazolin-11(7H)-one).

Example G32. General Experimental for Amination

General Scheme:

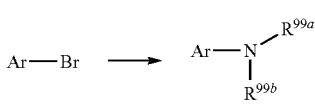

Representative Scheme A:

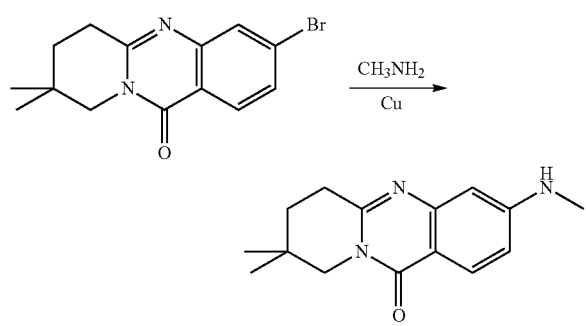

A solution of aryl bromide (e.g., 3-bromo-8,8-dimethyl-8,9-dihydro-6H-pyrido[2,1-b]quinazolin-11(7H)-one, 1 equiv), copper powder (1.6 equiv) in excess 33% methylamine ethanol solution and H₂O was stirred in a sealed tube at 80° C. overnight. The reaction was cooled to room temperature, then the mixture was diluted with water and extracted with ethyl acetate. The organic layers were washed with brine and dried over Na₂SO₄. After concentration, the residue was purified by silica gel chromatography to give the amine product (e.g., 8,8-dimethyl-3-(methylamino)-8,9-dihydro-6H-pyrido[2,1-b]quinazolin-11(7H)-one).

Representative Scheme B:

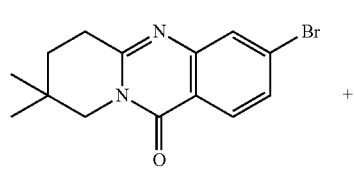

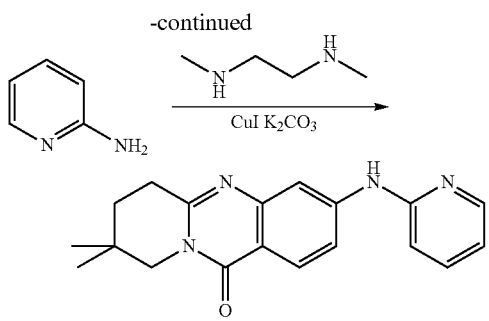

A solution of aryl bromide (e.g., 3-bromo-8,8-dimethyl-8,9-dihydro-6H-pyrido[2,1-b]quinazolin-11(7H)-one, 1 equiv), aromatic amine (e.g., pyridin-2-amine, 1.1 equiv), K₂CO₃ (2.3 equiv), CuI (0.2 equiv) and N, N-dimethylethane-1,2-diamine (0.5 equiv) in 1,4-dioxane was stirred at 105° C. under N₂ overnight. The reaction was cooled to room temperature, then the reaction mixture was diluted with H₂O and extracted with EtOAc. The combined organic layers were washed with brine, dried over Na₂SO₄. After filtration and concentration, the crude product was purified by silica column chromatography to give the desired product.

Representative Scheme C:

A solution of aryl bromide (e.g., 2-bromopyridine, 1.5 equiv), imidazole (e.g., 4-bromo-1H-imidazole, 1 equiv), L-Proline (0.2 equiv), CuI (0.1 equiv), K₂CO₃ (2 equiv) in DMSO was stirred at 110° C. under N₂ overnight. The reaction was cooled to room temperature, then the reaction mixture was diluted with H₂O and extracted with EtOAc. The combined organic layers were washed with brine, dried over Na₂SO₄. After filtration and concentration, the crude product was purified column chromatography (EtOAc:n-hexane=1:3) to give the C—N coupling product (e.g., 2-(4-bromo-1H-imidazol-1-yl)pyridine).

Representative Scheme D:

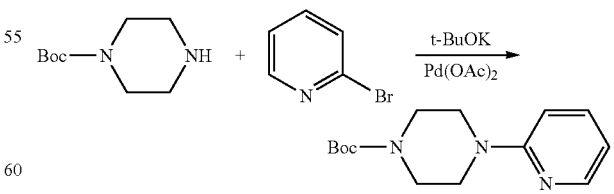

To a stirred solution of the starting amine (e.g., tert-butyl piperazine-1-carboxylate, 1 equiv), Pd(OAc)₂ (0.005 equiv), racemic-2,2'-Bis(diphenylphosphino)-1,1'-binaphthyl (0.01 equiv), potassium tert-butoxide (1.5 equiv) and 2-bromopyridine (1.2 equiv) in toluene was heated at 90° C. for 1.5 h. The mixture was diluted with water and extracted with ethyl acetate. The organic phase was washed with brine, dried over anhydrous Na$_2$SO$_4$ and concentrated under reduced pressure to give the C—N coupling product (e.g., tert-butyl 4-(pyridin-2-yl)piperazine-1-carboxylate).

Example G33. General Experimental for Hydrogenation of Olefin or Alkyne

General Scheme:

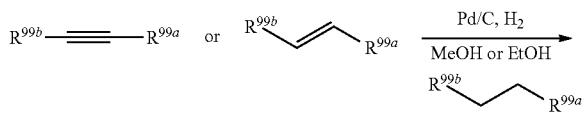

Representative Scheme:

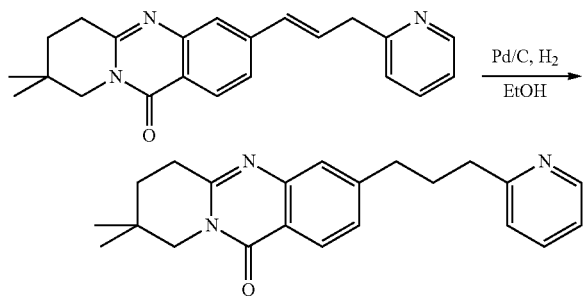

A solution of alkyne or olefin (e.g., (E)-8,8-dimethyl-3-(3-(pyridin-2-yl)prop-1-enyl)-8,9-dihydro-6H-pyrido[2,1-b]quinazolin-11(7H)-one and Pd/C (catalytic amount) in EtOH was stirred under H$_2$ atmosphere at 1 atm for 2 h. The reaction mixture was filtered and concentrated under reduced pressure. The crude product was purified by column chromatography on silica gel to give the alkyl product (e.g., 8,8-dimethyl-3-(3-(pyridin-2-yl)propyl)-6,7,8,9-tetrahydropyrido[2,1-b]quinazolin-11-one).

Example G34. General Experimental for Oxidation of Alkyne to Ketone

General Scheme:

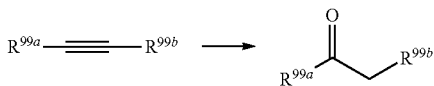

Representative Scheme:

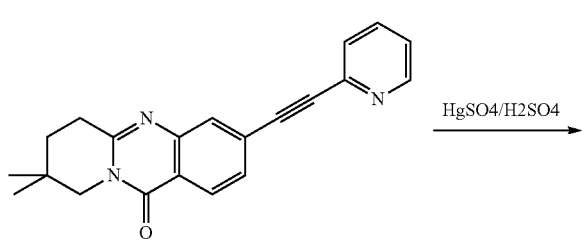

-continued

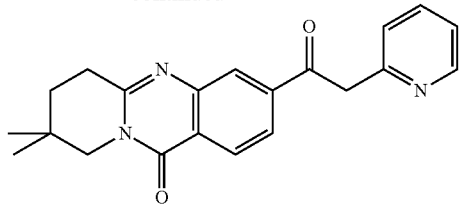

To a solution of the alkyne (e.g., 8,8-dimethyl-3-(pyridin-2-ylethynyl)-8,9-dihydro-6H-pyrido[2,1-b]quinazolin-11(7H)-one (1 equiv) in 98% H$_2$SO$_4$ (100 equiv) was added HgSO$_4$ (0.55 equiv). The mixture was stirred at room temperature for 5 h and then quenched with saturated sodium carbonate aqueous solution. After filtration, the mixture was extracted with EtOAc. The combined organic layers were washed with brine, dried over Na$_2$SO$_4$. After filtration and concentration, the crude product was purified by column chromatography (EtOAc:n-hexane=1:3) to give the desired ketone (e.g., 8,8-dimethyl-3-(2-(pyridin-2-yl)acetyl)-6,7,8,9-tetrahydropyrido[2,1-b]quinazolin-11-one).

Example G35. General Experimental for Hydroxylamination of Nitriles

General Scheme:

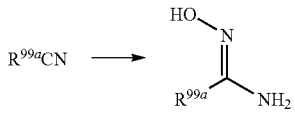

Representative Scheme:

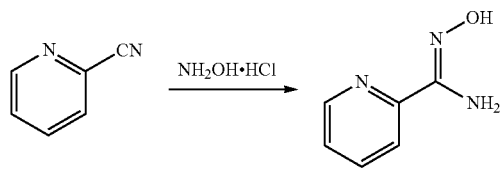

To a solution of aromatic nitrile (e.g., picolinonitrile, 1 equiv) and NH$_2$OH.HCl (1.2 equiv) in H$_2$O was added NaHCO$_3$ (2.4 equiv) in three portions. The reaction was stirred at room temperature overnight, then the mixture was diluted with H$_2$O and extracted with ethyl acetate. The combined organic layers were washed with brine and dried over Na$_2$SO$_4$. After filtration, the solvent was removed to give the desired product (e.g., (Z)—N'-hydroxypicolinamidine).

Example G36. General Experimental for the Synthesis of Azide from Aromatic Chloride or Aromatic Bromide General Scheme:

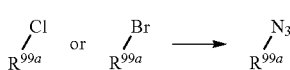

Representative Scheme:

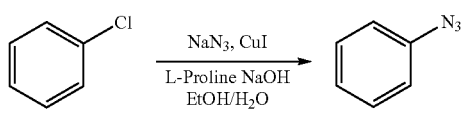

A solution of aryl bromide or aryl chloride (e.g., chlorobenzene, 1 equiv), CuI (0.1 equip), L-Proline (0.3 equiv), NaN$_3$ (2 equiv) and NaOH (1 equiv) in ethanol/water (7:3 ratio) was heated at reflux overnight. The reaction was cooled to room temperature, then the mixture was extracted with Et$_2$O. The combined organic layers were washed with brine, dried over Na$_2$SO$_4$. After filtration, the filtrate was concentrated to ⅕ volume and directly used for the next step.

Example G37. General Experimental for the Synthesis of Tin

General Scheme:

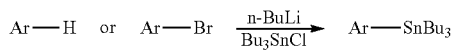

Representative Scheme:

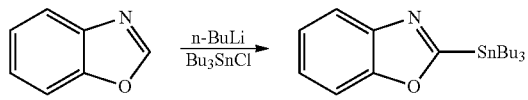

To a solution of the aryl bromide or aryl-H (e.g., benzo[d]oxazole, 1 equiv) in anhydrous Et$_2$O was added n-BuLi (1.06 equiv) slowly at −65° C. The reaction was then stirred at the same temperature for 30 min. Then, chlorotributylstannane tributyltin chloride (1 equiv) was added and the mixture was allowed to warm to room temperature and stirred for 1.5 h. After filtration through celite, the filtrate was evaporated. The crude product (e.g., 2-(tributylstannyl)benzo[d]oxazole) was directly used for the next step without further purification.

Example G38. General Experimental for the Reaction of Aldehyde with Alkyne

General Scheme:

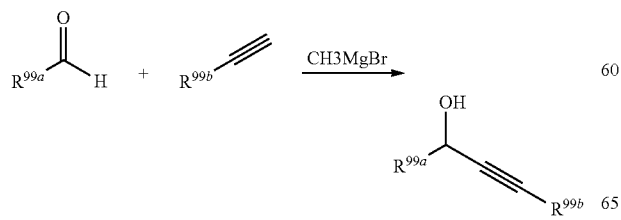

Representative Scheme:

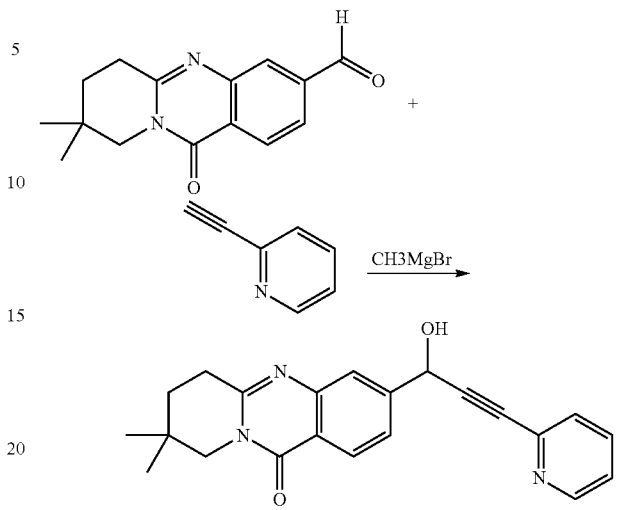

To a solution of alkyne (e.g., 2-ethynylpyridine, 3 equip) in THF at rt was added CH$_3$MgBr (3 equiv) dropwise over 5 min. The resulting solution was stirred for additional 15 min. To the mixture was added the aldehyde (e.g., 8,8-dimethyl-11-oxo-7,8,9,11-tetrahydro-6H-pyrido[2,1-b]quinazoline-3-carbaldehyde, 1 equiv) in THF over 10 min and stirred at rt for 1 h. The reaction mixture was diluted with water and extracted with ethyl acetate. The combined organic layers were concentrated and purified by column chromatography on silica gel to give the desired product (e.g., 3-(1-hydroxy-3-(pyridin-2-yl)prop-2-ynyl)-8,8-dimethyl-6,7,8,9-tetrahydropyrido[2,1-b]quinazolin-11-one).

General Example H: Other Synthetic Schemes

Example H1 Synthesis of (1S,4R,6S)-6-methoxy-2-azabicyclo[2.2.1]heptan-3-one

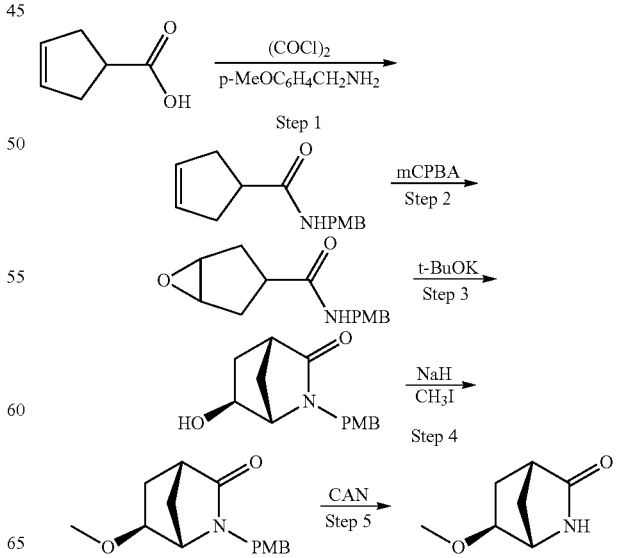

Example H1, Step 1

To a solution of cyclopent-3-enecarboxylic acid (5.0 g, 44.6 mmol) in CH$_2$Cl$_2$ (50 mL) at 0° C. under argon atmosphere were added oxalyl chloride (4.3 mL, 49.1 mmol) and DMF (5 drops). After stirring at ambient temperature for 3 h, CH$_2$Cl$_2$ (50 mL), pyridine (70 mL), p-methoxybenzylamine (7.6 mL, 58.0 mmol), and 4-dimethylaminopyridine (545 mg, 4.46 mmol) were added to the reaction mixture at 0° C. The reaction mixture was stirred at ambient temperature for 12 h. The reaction was quenched with water at 0° C. and extracted by EtOAc. The combined organic extracts were washed with water, 1. M aq HCl, brine, dried over Na$_2$SO$_4$, filtered through Celite, and evaporated to give the desired product for the next step. MS (ESI+): m/z 232 (M+H$^+$).

Example H1, Step 2

To a solution of the crude N-(4-methoxybenzyl)cyclopent-3-enecarboxamide from the last step in CH$_2$Cl$_2$ (50 mL) was added m-chloroperbenzoic acid (69 wt %, 13.4 g, 53.5 mmol). After stirring at ambient temperature for 4 h, the CH$_2$Cl$_2$ was evaporated. The residue was suspended in water and extracted with EtOAc (200 mL×3). The combined organic extracts were washed with 1 M aq NaOH (100 mL), water (100 mL), brined, dried over Na$_2$SO$_4$, filtered through Celite, and evaporated to give the desired product (N-(4-methoxybenzyl)-6-oxabicyclo[3.1.0]hexane-3-carboxamide). MS (ESI+): m/z 248 (M+H$^+$).

Example H1, Step 3

To a solution of the crude N-(4-methoxybenzyl)-6-oxabicyclo[3.1.0]hexane-3-carboxamide from the last step in t-BuOH (200 mL) was quickly added t-BuOK (10.0 g, 89.2 mmol). After stirring at 80° C. for 4 h, the reaction was quenched by aq NH$_4$Cl and water, and extracted by EtOAc. The combined organic extracts were washed with brine, dried over Na$_2$SO$_4$, filtered through Celite, and evaporated. The product ((1S,4R,6S)-6-hydroxy-2-(4-methoxybenzyl)-2-azabicyclo[2.2.1]heptan-3-one) was purified by silica gel chromatography (EtOAc/hexane=1:1) (4.7 g). MS (ESI+): m/z 248 (M+H$^+$).

Example H1, Step 4

To a solution of the (1S,4R,6S)-6-hydroxy-2-(4-methoxybenzyl)-2-azabicyclo[2.2.1]-heptan-3-one (500 mg, 2.02 mmol) in anhydrous THF (20 mL) was added NaH (60 wt %, 4.04 mmol) at room temperature. The mixture was stirred at 40° C. for 30 min. After cooling to room temperature, CH$_3$I (0.41 mL, 8.08 mmol) was added. The reaction mixture was stirred for 1 h at ambient temperature and quenched with water (50 mL), extracted by EtOAc. The combined organic extracts were washed with brine, dried over Na$_2$SO$_4$, and evaporated to give (1S,4R,6S)-6-methoxy-2-(4-methoxybenzyl)-2-azabicyclo[2.2.1]heptan-3-one. MS (ESI+): m/z 262 (M+H$^+$).

Example H1, Step 5

A solution of ammonium cerium(IV) (3.3 g, 6.06 mmol) in water (10 mL) was added to (1S,4R,6S)-6-methoxy-2-(4-methoxybenzyl)-2-azabicyclo[2.2.1]heptan-3-one (527 mg, 2.02 mmol) in CH$_3$CN (40 mL). The reaction mixture was stirred at ambient temperature for 2 h and extracted by EtOAc (60 mL). The organic extract was washed with water and brine, dried over Na$_2$SO$_4$, and evaporated to give the crude (1S,4R,6S)-6-methoxy-2-azabicyclo[2.2.1]heptan-3-one. MS (ESI+): m/z 142 (M+H$^+$).

Example H2 Synthesis of (3aS,7aR)-hexahydroisobenzofuran-5(1H)-one

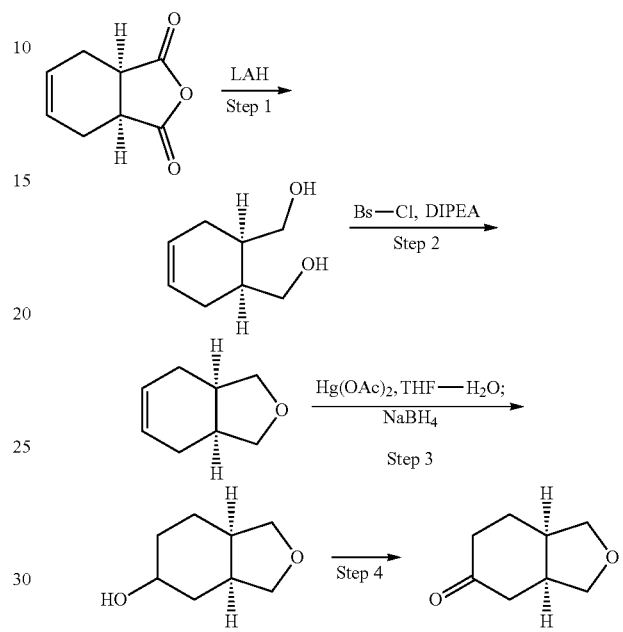

Example H2, Step 1

To a solution of lithium aluminum hydride (14 g, 396 mmol) in anhydrous THF (200 mL) was added (3aR,7aS)-3a,4,7,7a-tetrahydroisobenzofuran-1,3-dione (15 g, 99 mmol) at 0° C. under nitrogen atmosphere. The reaction mixture was stirred at room temperature overnight. After cooling with ice-water, the mixture was quenched with water (300 mL) and extracted with ethyl acetate (3×400 mL). The combined organic layers were washed with brine, dried over Na$_2$SO$_4$ and concentrated under reduced pressure to give the crude product (12 g). The crude product was used for the next step without further purification. MS (ESI+): m/z 143 (M+H$^+$).

Example H2, Step 2

A solution of (1R,2S)-cyclohex-4-ene-1,2-diyldimethanol (12 g, 8.5 mmol), benzene sulfonyl chloride (16 g, 9.3 mmol) and N,N-diisopropylethylamine (21.8 g, 17 mmol) in 1,4-dioxane (200 mL) was refluxed overnight. After cooling to room temperature, the mixture was diluted with water (500 mL) and extracted with ethyl acetate (3×400 mL). The combined organic layers were washed with brine, dried over Na$_2$SO$_4$. After concentration under reduced pressure, the crude product was purified by silica gel chromatography to give the desired product (7.0 g). MS (ESI+): m/z 125 (M+H$^+$).

Example H2, Step 3

To a solution of mercuric acetate (10.2 g, 32 mmol) in THF (20 mL) and H$_2$O (20 mL) was added 3aR,7aS)-1,3, 3a,4,7,7a-hexahydroisobenzofuran (2 g, 32 mmol) in THF (10 mL) at 0° C. The reaction mixture was stirred at room temperature overnight. The resulting mixture was cooled to 0° C., then 29 mL of 3 N sodium hydroxide aqueous solution was added to the mixture followed by 29 mL of 0.5 M sodium borohydride in 3N sodium hydroxide aqueous solution. The mercury was allowed to settle, and the supernatant liquid was decanted and extracted with ether (3×100 mL). The combined organic layers were washed with brine, dried over $Na_2SO_4$ and concentrated to give the crude product (2.1 g). MS (ESI+): m/z 143 (M+H$^+$).

Example H2, Step 4

A solution of (3aS,7aR)-octahydroisobenzofuran-5-ol (2.1 g, 14.8 mmol), Dess-Matin periodinane (13 g, 44.4 mmol) in DCM (50 mL) was stirred at room temperature for 2 h. The reaction mixture was then quenched with $Na_2CO_3$ aqueous solution (50 mL) and extracted with $CH_2Cl_2$ (2×100 mL). The combined organic layers were washed with brine, dried over $Na_2SO_4$ and concentrated under reduced pressure to give the crude product (2.0 g).

Example H3. Synthesis of (3aS,7aR)-hexahydroisobenzofuran-5(1H)-one

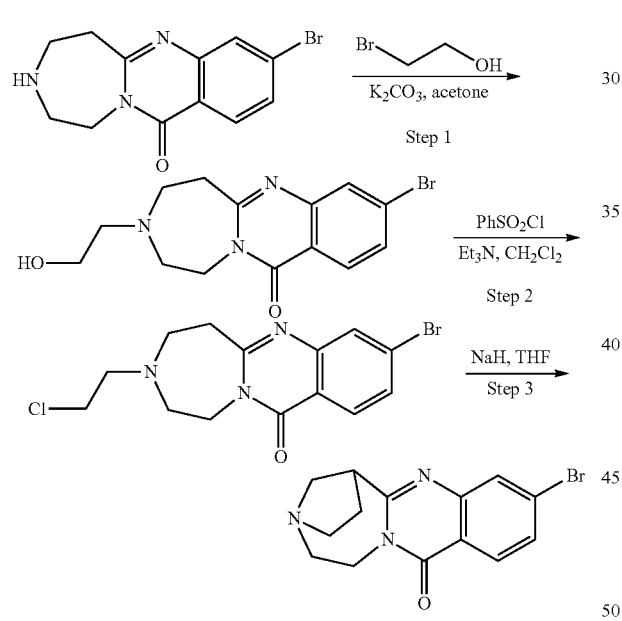

Example H3, Step 1

To a solution of 8-bromo-2,3,4,5-tetrahydro-[1,4]diazepino[7,1-b]quinazolin-11 (1H)-one (0.8 g, 2.7 mmol) and $K_2CO_3$ in acetone (60 mL) was added excess 2-bromoethanol. The mixture was stirred at room temperature for 6 h. The mixture was diluted with water and extracted with $CH_2Cl_2$ (3×60 mL). The combined organic layers were dried over $Na_2SO_4$, filtered, and evaporated to give 0.7 g of the desired product. MS (ESI): m/z 338, 340 (M+H$^+$).

Example H3, Step 2

To a solution of 8-bromo-3-(2-hydroxyethyl)-2,3,4,5-tetrahydro-[1,4]diazepino[7,1-b]quinazolin-11(1H)-one (0.7 g, 2.1 mmol) and $Et_3N$ in $CH_2Cl_2$ (60 mL) was added benzenesulfonyl chloride. The mixture was stirred at room temperature for 2 h. The mixture was diluted with water and extracted with ethyl acetate (3×60 mL). The combined organic layers were dried over $Na_2SO_4$, filtered, and evaporated to give 230 mg of the desired product. MS (ESI+): m/z 356, 358 (M+H$^+$).

Example H3, Step 3

A solution of 8-bromo-3-(2-chloroethyl)-2,3,4,5-tetrahydro-[1,4]diazepino[7,1-b]quinazolin-11(1H)-one (0.2 g, 0.5 mmol) and NaI in THF (10 mL) was stirred at room temperature overnight. The mixture was diluted with water and extracted with ethyl acetate (3×20 mL). The combined organic layers were dried over $Na_2SO_4$, filtered, and evaporated to give 260 mg of the crude. MS (ESI+): m/z 320, 322 (M+H$^+$).

Example H4. Synthesis of (5,5-bis(fluoromethyl)piperidin-2-one

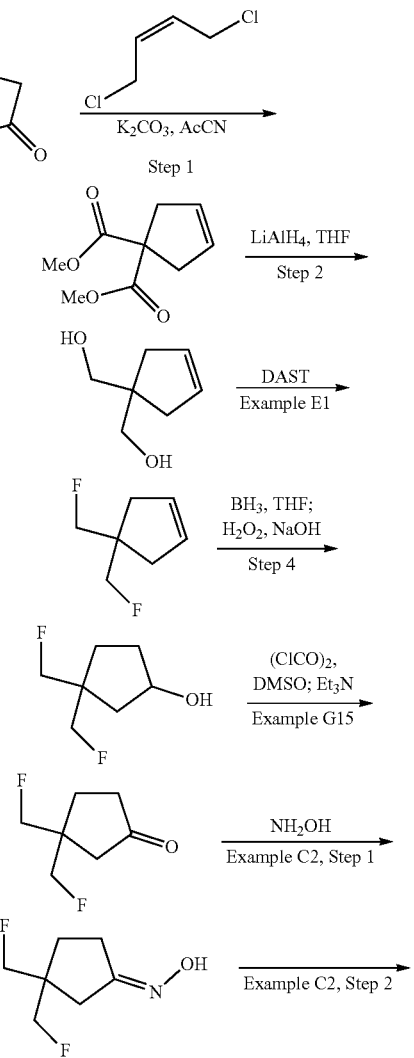

173
-continued

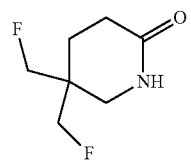

5,5-Bis(fluoromethyl)piperidin-2-one may be synthesized by the chemistry depicted in the above scheme. Bisalkylation of dimethyl malonate with (Z)-1,4-dichlorobut-2-ene under basic conditions provides dimethyl cyclopent-3-ene-1,1-dicarboxylate, which can be transformed into 4,4-bis (fluoromethyl)cyclopent-1-ene by LiAlH$_4$ reduction and DAST-mediated fluorination (Example E1). Hydroboration of the olefin functionality followed by Swern oxidation provides the ketone. Treatment of ketone with NH$_2$OH provides the oxime intermediate, and Beckmann rearrangement (Example C2) delivers (5,5-bis(fluoromethyl)piperidin-2-one.

Example H5. Synthesis of 1-methylbicyclo[3.1.0]hexan-3-one

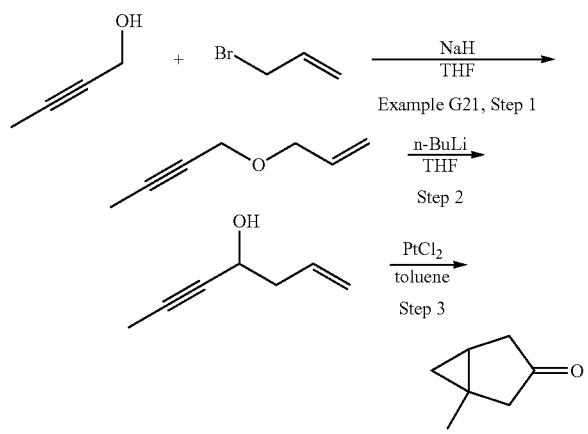

Example H5, Step 2

To a solution of 1-(allyloxy)but-2-yne (11.9 g, 0.11 mol) in anhydrous THF (300 mL) at −65° C. was added n-BuLi (70 mL, 0.175 mol, 2.5 M) slowly under N$_2$ and the reaction was stirred for 3 h. The reaction was quenched with H$_2$O (80 mL) at −65° C., then the mixture was extracted with Et$_2$O (3×150 mL). The combined organic layers were washed with brine, dried over Na$_2$SO$_4$. After filtration and concentration, the crude product was purified by silica column chromatography [Et$_2$O:Petroleum ether (30° C.~60° C.)=1:6] to give the desired product.

Example H5, Step 3

A solution of hept-1-en-5-yn-4-ol (3.8 g, 34.5 mmol) and PtCl$_2$ (0.5 g, 1.88 mmol) in toluene (150 mL) was stirred at 65° C. for 7 h. After filtration, the filtrate was directly used for next step without further purification.

174

Example H6. Synthesis of Oxadiazole

General Scheme:

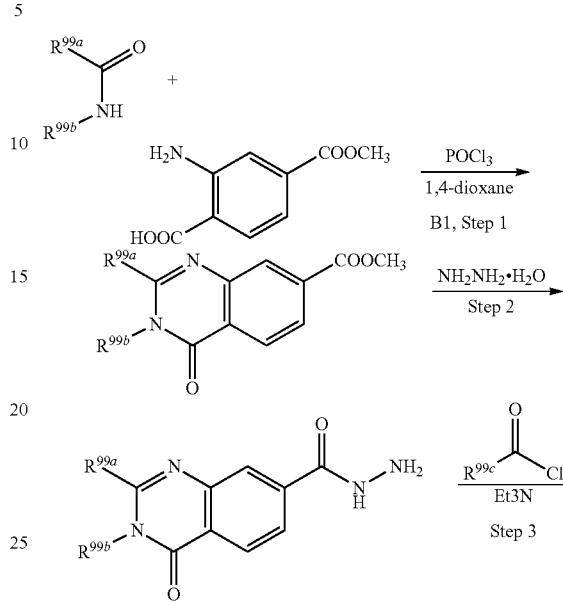

Representative Scheme:

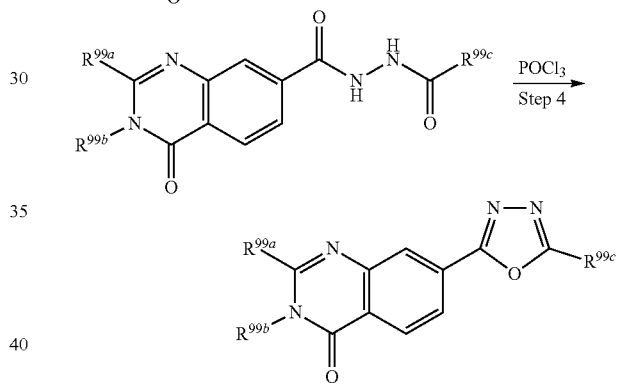

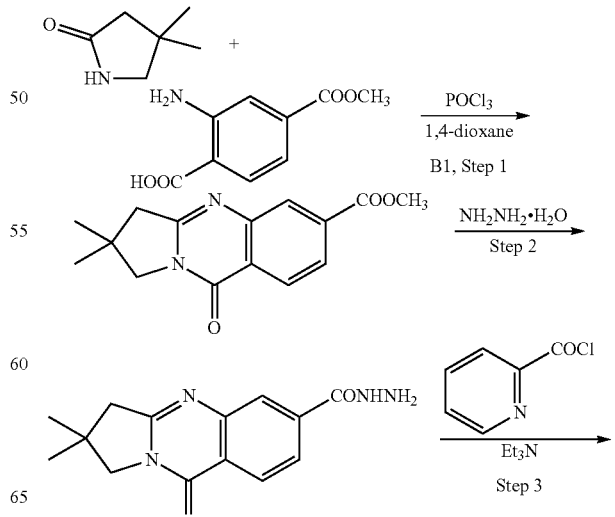

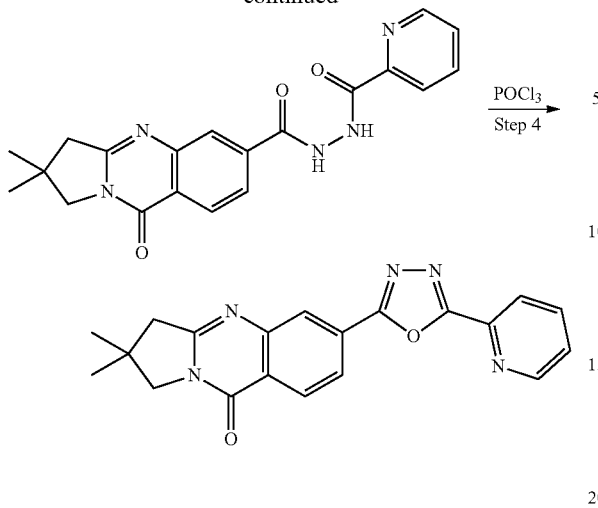

Example H6, Step 2

To a solution of an aromatic acid ester (e.g., methyl 2,2-dimethyl-9-oxo-1,2,3,9-tetrahydropyrrolo[2,1-b]quinazoline-6-carboxylate) prepared from Example B1 in ethanol was added excess 80% hydrazine hydrate. The reaction mixture was heated at reflux for 2 h. The reaction was cooled to room temperature, then the slurry was filtered. The filtrate was washed with ethanol twice and was used directly in next step.

Example H6, Step 3

A solution of aromatic acid (e.g., picolinic acid) in excess $SOCl_2$ was heated at reflux for 3 h. Then excess $SOCl_2$ was removed. The residue was dissolved in $CH_2Cl_2$ and added to a solution of a carbohydrazide (e.g., 2,2-dimethyl-9-oxo-1,2,3,9-tetrahydropyrrolo[2,1-b]quinazoline-6-carbohydrazide, 1.84 mmol) in $CH_2Cl_2$. Then $Et_3N$ (4 equiv) was added. The reaction mixture was stirred at room temperature for 15 min, poured into $H_2O$ and extracted with $CH_2Cl_2$. The combined organic layers were washed with brine, dried over $Na_2SO_4$. After filtration and concentration, the crude residue was purified by preparative chromatography to give the desired carbohydrazide (e.g., 2,2-dimethyl-9-oxo-N'-picolinoyl-1,2,3,9-tetrahydropyrrolo[2,1-b]quinazoline-6-carbohydrazide).

Example H6, Step 4

A solution of carbohydrazide (e.g., 2,2-dimethyl-9-oxo-N'-picolinoyl-1,2,3,9-tetrahydropyrrolo[2,1-b]quinazoline-6-carbohydrazide) in excess $POCl_3$ was heated at reflux for 6 h. Then excess $POCl_3$ was then removed. The residue was quenched with saturated sodium carbonate solution and extracted with EtOAc. The combined organic layers were washed with brine, dried over $Na_2SO_4$. After filtration and concentration, the crude residue was purified by preparative chromatography to give the desired oxadiazole (e.g., 2,2-dimethyl-6-(5-(pyridin-2-yl)-1,3,4-oxadiazol-2-yl)-2,3-dihydropyrrolo[2,1-b]quinazolin-9(1H)-one).

Example H7. Synthesis of Thiadiazole

General Scheme:

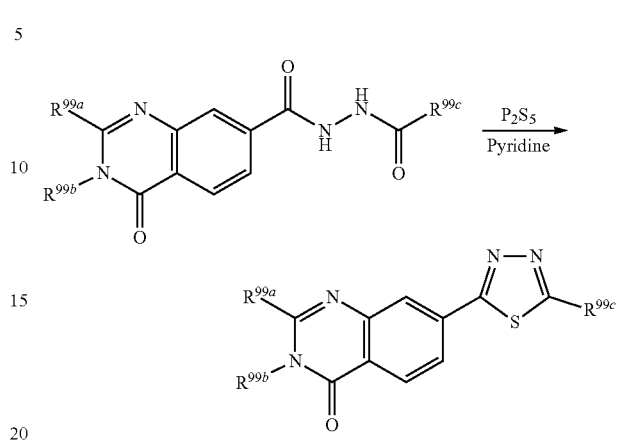

Representative Scheme:

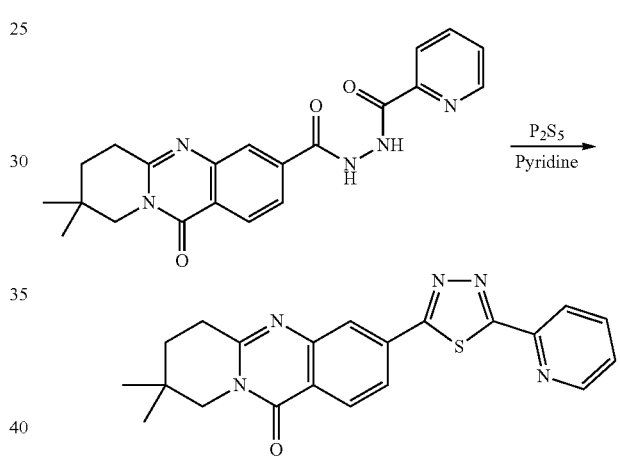

A mixture of carbohydrazide (e.g., 8,8-dimethyl-11-oxo-N'-picolinoyl-7,8,9,11-tetrahydro-6H-pyrido[2,1-b]quinazoline-3-carbohydrazide, 1 equiv) and $P_2S_5$ (8 equiv) in pyridine (0.1 M) was stirred at 70° C. for 6 h. The reaction was cooled to room temperature, then the mixture was poured into $H_2O$ and extracted with EtOAc. The combined organic layers were washed with brine, dried over $Na_2SO_4$. After filtration and concentration, the crude residue was purified by preparative chromatography to give the desired thiadiazole (e.g., 8,8-dimethyl-3-(5-(pyridin-2-yl)-1,3,4-thiadiazol-2-yl)-6,7,8,9-tetrahydropyrido[2,1-b]quinazolin-11-one).

Example H8. Synthesis of Oxadiazole

General Scheme:

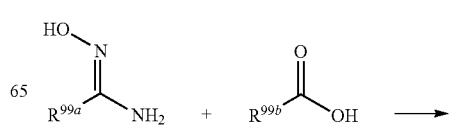

Representative Scheme:

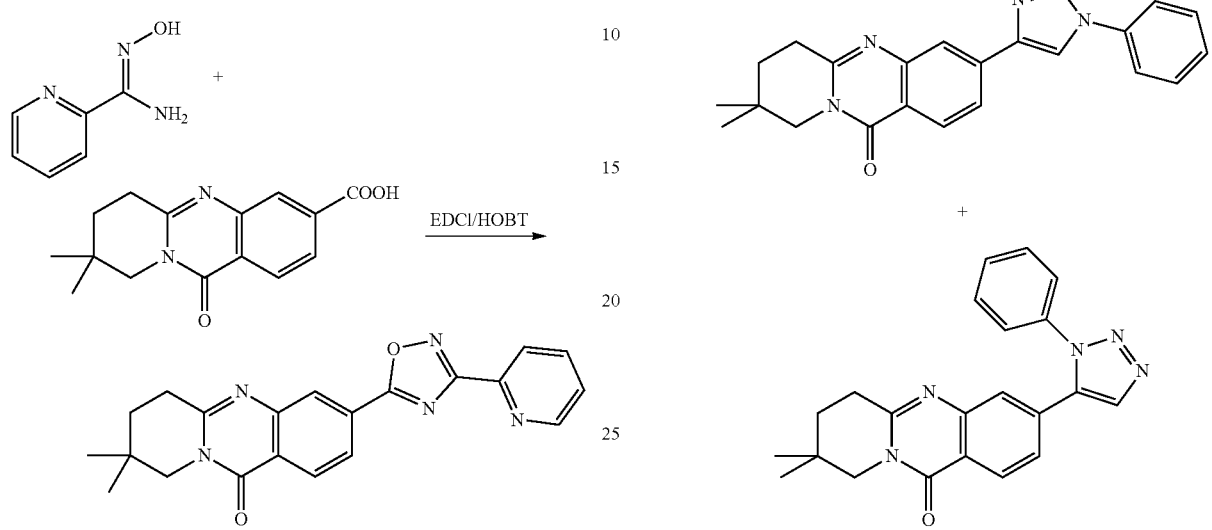

A solution of an acid (e.g., 8,8-dimethyl-11-oxo-7,8,9,11-tetrahydro-6H-pyrido[2,1-b]quinazoline-3-carboxylic acid, 1 equiv), N'-hydroxypicolinimidamide (1.5 equiv), EDCI (1.5 equiv) and HOBt (1.5 equiv) in DMF was stirred at 80° C. overnight. The reaction was cooled to room temperature, then the reaction mixture was diluted with H₂O and extracted with EtOAc. The combined organic layers were washed with brine and dried over Na₂SO₄. After filtration and concentration, the crude residue was purified by preparative chromatography to give the desired oxadiazole-containing product (e.g., 8,8-dimethyl-3-(3-(pyridin-2-yl)-1,2,4-oxadiazol-5-yl)-6,7,8,9-tetrahydropyrido[2,1-b]quinazolin-11-one).

A solution of the aromatic alkyne (e.g., 3-ethynyl-8,8-dimethyl-8,9-dihydro-6H-pyrido[2,1-b]quinazolin-11(7H)-one, 0.6 mmol), sodium L-ascorbate (3 equiv), saturated CuSO₄ aqueous solution (0.24 M) and the azide (e.g., azidobenzene in Et₂O solution, 3 equiv) in CH₃CN was stirred at room temperature for 4 days. The reaction was then diluted with H₂O, and the mixture was extracted with ethyl acetate. The combined organic layers were washed with brine, dried over Na₂SO₄. After filtration and concentration, the crude residue was purified by silica column chromatography to give the triazole (e.g., 8,8-dimethyl-3-(1-phenyl-1H-1,2,3-triazol-4-yl)-6,7,8,9-tetrahydropyrido[2,1-b]quinazolin-11-one).

Example H9. Synthesis of 1,2,3-Triazole

General Scheme:

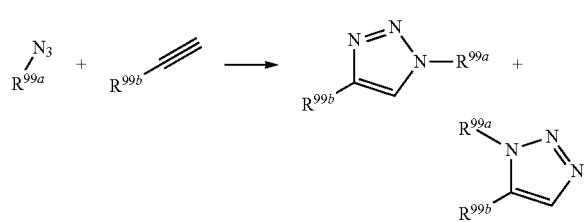

Representative Scheme:

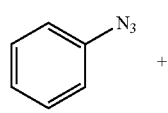

Example H10. Synthesis of 2-bromo-4-(pyridin-2-yl)thiazole

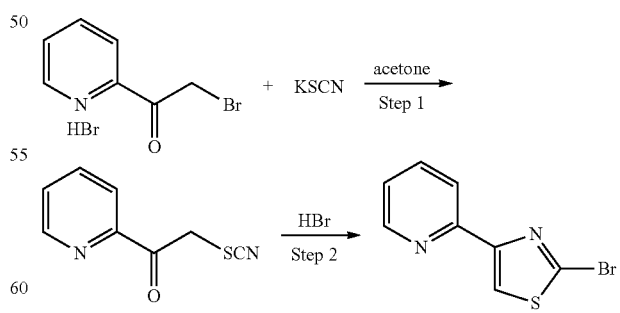

Example H10, Step 1

A solution of 2-bromo-1-(pyridin-2-yl)ethanone hydrobromide (1.0 g, 3.56 mmol) and KSCN (410 mg, 4.27 mmol)

in acetone (50 mL) was stirred at reflux overnight. The solvent was then removed, and the residue was directly used for the next step.

Example H10, Step 2

To a solution of 1-(pyridin-2-yl)-2-thiocyanatoethanone hydrobromide prepared from step 1 in acetic acid (20 mL) was added 33% HBr in acetic acid (5 mL). The mixture was stirred at 50° C. for 5 h. After adjusting to pH=9 with saturated Na$_2$CO$_3$ aqueous solution, the mixture was extracted with ethyl ether (3×200 mL). The combined organic layers were washed with brine and dried over Na$_2$SO$_4$. After filtration and concentration, the crude product was purified by silica column chromatography to give the desired product.

Example H11. Synthesis of 5-bromo-2-(pyridin-2-yl)oxazole

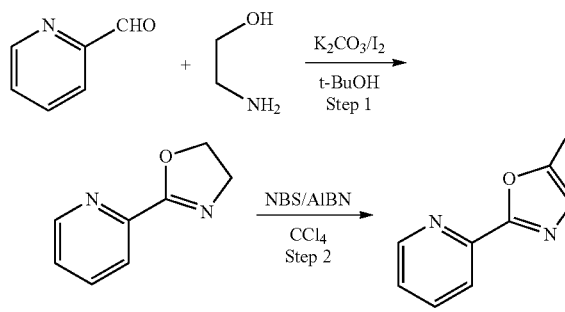

Example H11, Step 1

To a solution of picolinaldehyde (5.0 g, 46.7 mmol) and 2-aminoethanol (3.42 g, 56.1 mmol) in t-BuOH (400 mL) was added K$_2$CO$_3$ (19.3 g, 140.1 mmol) and iodine (11.8 g, 93.4 mmol). The reaction mixture was heated at reflux overnight. After quenching with saturated Na$_2$SO$_3$ aqueous solution, the mixture was extracted with ethyl ether (8×100 mL). The combined organic layers were washed with brine, dried over Na$_2$SO$_4$. After filtration and concentration, the crude product was purified by silica column chromatography to give the desired product (800 mg).

Example H11, Step 2

To a solution of 2-(pyridin-2-yl)-4,5-dihydrooxazole (710 mg, 4.8 mmol) in CCl$_4$ (50 mL) was added NBS (2.56 g, 1.4.4 mmol) and AIBN (40 mg, 0.24 mmol). The reaction mixture was stirred at 70° C. overnight. After filtration and concentration, the crude product was purified by silica column chromatography to give the desired product (116 mg).

Example H12. Synthesis of 5-(pyridin-2-yl)oxazole

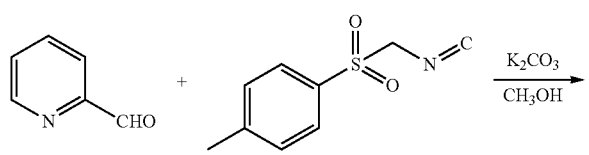

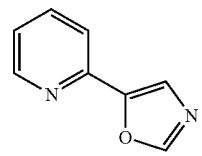

A mixture of picolinaldehyde (2.3 g, 42.6 mmol), TosMIC (4.4 g, 45.2 mmol) and K$_2$CO$_3$ (3.4 g, 48.8 mmol) in methanol (70 mL) was reflux for 2 h. The reaction was cooled to room temperature, then the mixture was concentrated and purified by silica gel column chromatography to give the desired product (3.05 g).

Example H13. Synthesis of Imidazole Ring

Representative Scheme A:

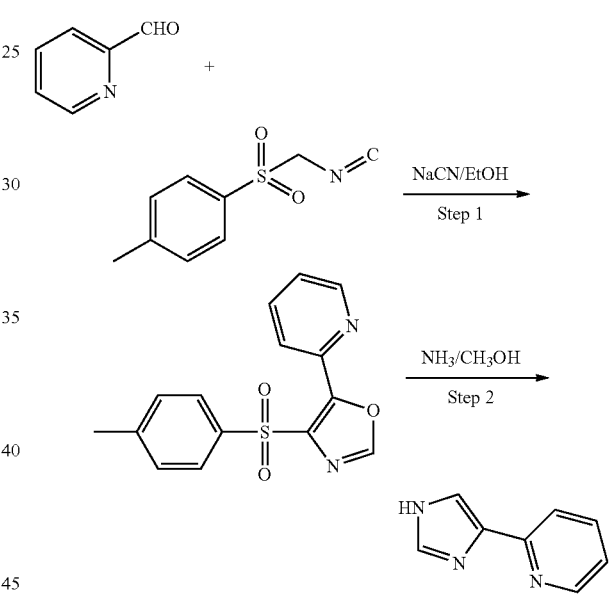

Example H13-A, Step 1

To a mixture of the aromatic aldehyde (e.g., picolinaldehyde 1.0 g, 93 mmol) and TosMIC (1.83 g, 93 mmol) in ethanol (20 mL) was added NaCN (20 mg). The reaction mixture immediately became clear and then solid separated out. The reaction was stirred for another 40 min, then the mixture was filtered to give a pale yellow solid (2.2 g), which was directly used for the next step.

Example H13-A, Step 2

A mixture 5-(pyridin-2-yl)-4-tosyloxazole (2.2 g, 7.3 mmol) and NH$_3$/CH$_3$OH (15 mL) was stirred at 80° C. for 2 days in a sealed tube. After the solvent was removed, the residue was purified by silica column chromatography (DCM:CH$_3$OH=2:1) to give the desired product (400 mg).

Representative Scheme B:

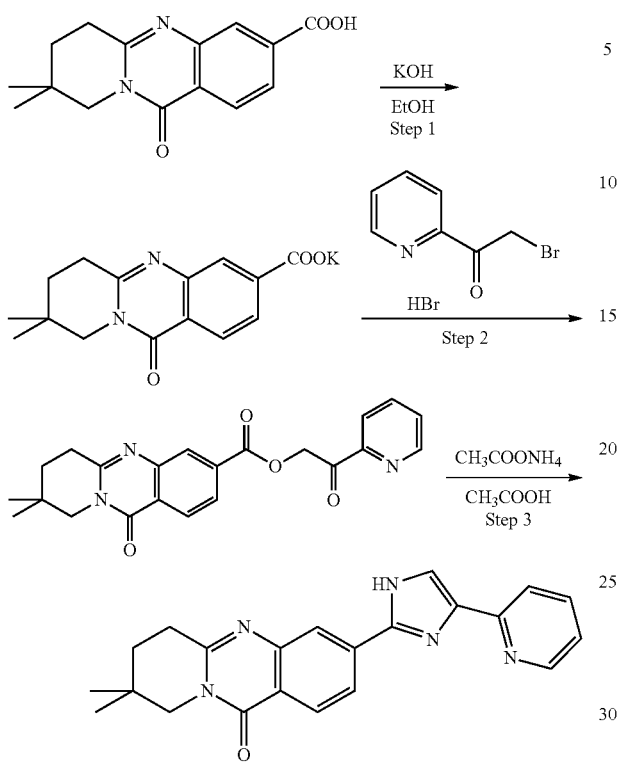

Example H13-B, Step 1 and 2

A solution of a starting acid (e.g., 8,8-dimethyl-11-oxo-7,8,9,11-tetrahydro-6H-pyrido[2,1-b]quinazoline-3-carboxylic acid, 1 equiv) and KOH (1.1 equiv) in ethanol was stirred at room temperature overnight. The solvent was removed to give a buff solid. Then the solid and HBr salt of 2-bromo-1-(pyridin-2-yl)ethanone (1 equiv) were dissolved in DMF and stirred at room temperature overnight. The reaction mixture was poured into H₂O and extracted with EtOAc. The combined organic layers were washed with brine, dried over Na₂SO₄. After filtration and concentration, the crude ester intermediate (e.g., 2-oxo-2-(pyridin-2-yl) ethyl 8,8-dimethyl-11-oxo-7,8,9,11-tetrahydro-6H-pyrido [2,1-b]quinazoline-3-carboxylate) was used directly for next step.

Example H13-B, Step 3

A solution of the crude ester intermediate (e.g., 2-oxo-2-(pyridin-2-yl)ethyl 8,8-dimethyl-11-oxo-7,8,9,11-tetrahydro-6H-pyrido[2,1-b]quinazoline-3-carboxylate (1 equip) and CH₃COONH₄ (9 equiv) in acetic acid (0.1 M) was stirred at 80° C. overnight. After adjusting to pH=8 with saturated Na₂CO₃, the mixture was extracted with EtOAc. The combined organic layers were washed with brine, dried over Na₂SO₄. After filtration and concentration, the crude product (e.g., 8,8-dimethyl-3-(4-(pyridin-2-yl)-1H-imidazol-2-yl)-6,7,8,9-tetrahydropyrido[2,1-b]quinazolin-11-one) was purified by preparative chromatography.

Example H14. Synthesis of 2-oxa-6-azaspiro[3.6]decan-7-one

Representative Scheme:

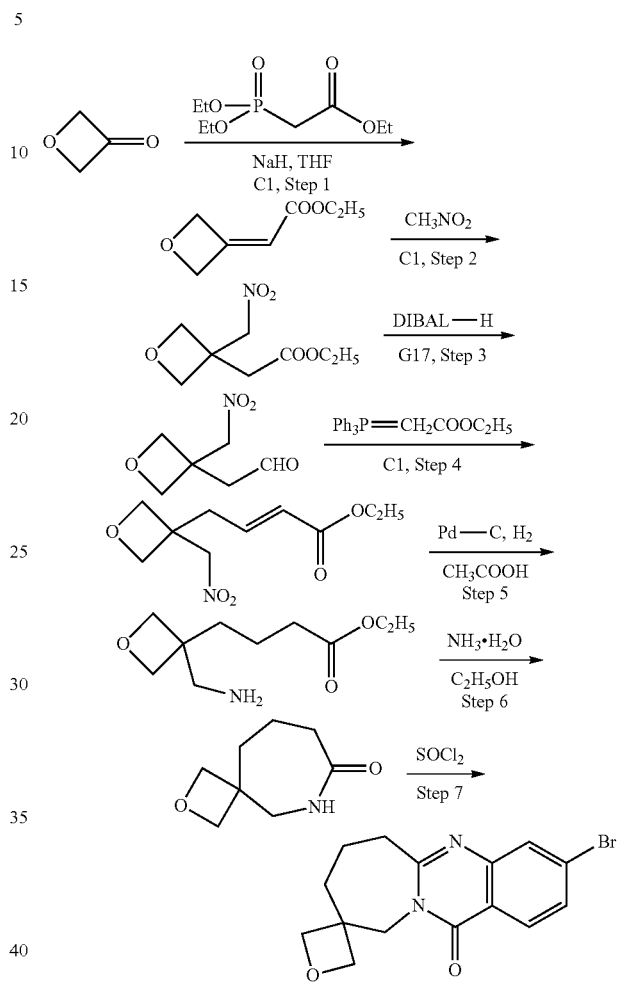

Example H14, Step 5

A solution of ethyl 4-(3-(nitromethyl)oxetan-3-yl)but-2-enoate (600 mg, 2.6 mmol) and 10% Pd—C (100 mg) in CH₃COOH (15 mL) was stirred at room temperature for 4 h under H₂ atmosphere. After filtration, the filtrate was adjusted pH to 8-9 and extracted with CH₂Cl₂ (4×100 mL). The organic layers were washed with brine (200 mL) and dried over Na₂SO₄. After concentrated, the residue was purified by silica gel chromatography to give the desired product as a yellow oil (400 mg).

Example H14, Step 6

To a solution of ethyl 4-(3-(aminomethyl)oxetan-3-yl) butanoate (400 mg, 2.6 mmol) in ethanol (10 mL) was added aqueous NH₃ (4 mL). The mixture was stirred in sealed tube at 85° C. for 2 days. The reaction mixture was concentrated under reduced pressure to give crude product for the next step without further purification.

Example H14, Step 7

To a solution of 2-amino-4-bromobenzoic acid (200 mg, 0.93 mmol) in benzene (15 mL) was added SOCl₂ (3 mL).

The reaction mixture was heated at reflux for 2 h and then concentrated under reduced pressure. Then additional benzene (10 mL) was added and concentrated to dryness. Then benzene (15 mL) and 2-oxa-6-azaspiro[3.6]decan-7-one (100 mg, 0.65) were added to the residue and heated at reflux for 3 h. The reaction was cooled to room temperature, then the solution was washed with saturated aqueous $Na_2CO_3$ and brine. After concentration, the residue was purified by silica gel chromatography to give the desired product (70 mg).

Example H15. Synthesis of hexahydroimidazo[1,5-a]pyridin-3(5H)-one

Representative Scheme:

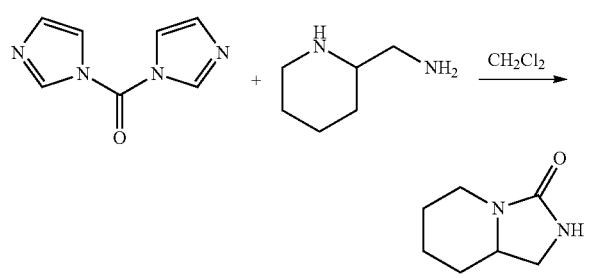

A solution of CDI (830 mg, 5.1 mmol) and piperidin-2-ylmethanamine (520 mg, 4.6 mmol) in DCM (20 mL) was stirred at room temperature overnight. After the solvent was removed, the residue was directly used for the next step without further purification.

Example H16. Synthesis of Isoxazole

General Scheme:

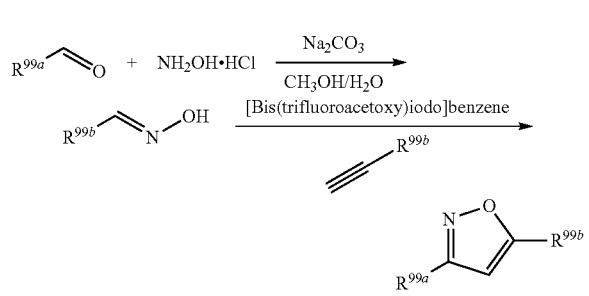

Representative Scheme:

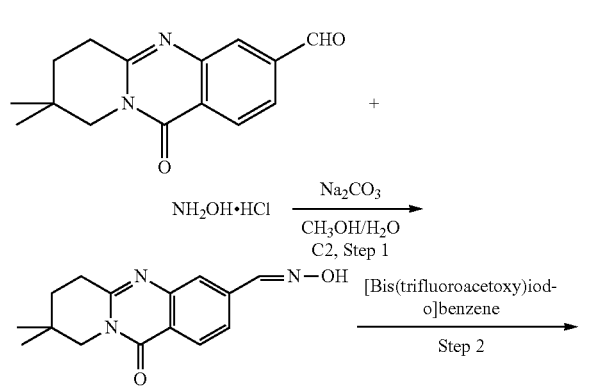

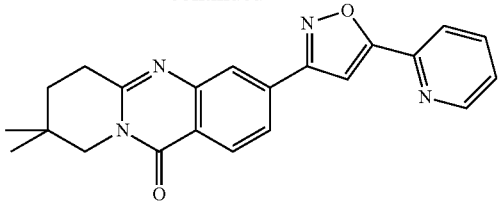

Example H16, Step 2

A solution of an oxime (e.g., 8,8-dimethyl-11-oxo-7,8,9,11-tetrahydro-6H-pyrido[2,1-b]quinazoline-3-carbaldehyde oxime, 1 equiv) prepared from step 1 in $CH_3OH$ and $H_2O$ was added to aromatic alkyne (e.g., 2-ethynylpyridine, 1 equiv) and [bis(trifluoroacetoxy)iodo]benzene (1.2 equiv). The reaction mixture was stirred at room temperature for 4 h. After diluting with $H_2O$, the mixture was extracted with ethyl acetate. The combined organic layers were washed with brine, dried over $Na_2SO_4$. After filtration and concentration, the crude isoxazole (e.g., 8,8-dimethyl-3-(5-(pyridin-2-yl)isoxazol-3-yl)-6,7,8,9-tetrahydropyrido[2,1-b]quinazolin-11-one) was purified by preparative chromatography.

Example H17. Synthesis of Urea

General Scheme:

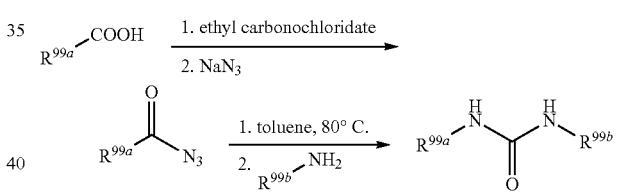

Representative Scheme:

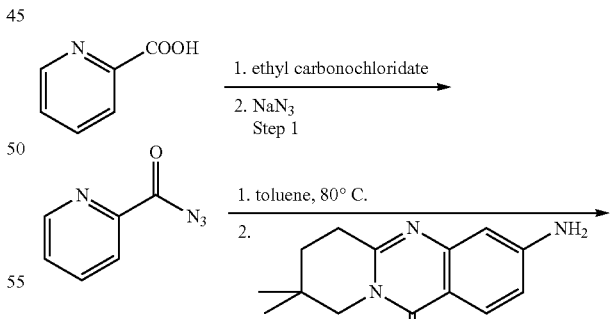

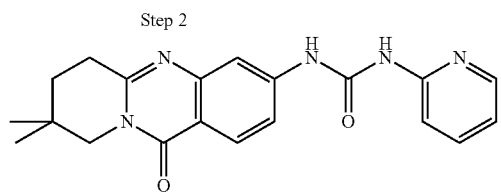

Example H17, Step 1

To a solution of aromatic acid (e.g., picolinic acid, 8.1 mmol) in acetone and water was added triethylamine (1.5 equiv). The mixture was cooled to 0° C. in a ice-bath. Ethylchloroformate (1.5 equiv) was then added and the resulting mixture was stirred at 0° C. for 1.5 h. To the mixture was added sodium azide (1.6 equiv), and the mixture was stirred for another 1.5 h. After the mixture was concentrated, the residue was diluted with dichloromethane and washed with water. The organic layer was dried over $Na_2SO_4$. After concentrating, the residue was purified by silica column chromatography to give the desired carboxyl azide (e.g. azido(pyridin-2-yl)methanone).

Example H17, Step 2

A solution of carboxyl azide (e.g., picolinoyl azide, 2 equiv) in toluene (0.7 M) was stirred at 80° C. for 2 h. Then aromatic amine (e.g., 3-amino-8,8-dimethyl-8,9-dihydro-6H-pyrido[2,1-b]quinazolin-11(7H)-one, 1 equiv) was added. The mixture was stirred at 100° C. overnight and then heated at reflux for 3 h. After the solvent was evaporated, the residue was purified by preparative chromatography to give the desired urea (e.g., 1-(8,8-dimethyl-11-oxo-7,8,9,11-tetrahydro-6H-pyrido[2,1-b]quinazolin-3-yl)-3-(pyridin-2-yl)urea).

Example H18. Synthesis of 1a-(hydroxymethyl)-8-bromo-1,2,3,10b-tetrahydrocyclopropa[3,4]pyrido[2,1-b]quinazolin-5(1aH)-one Representative Scheme:

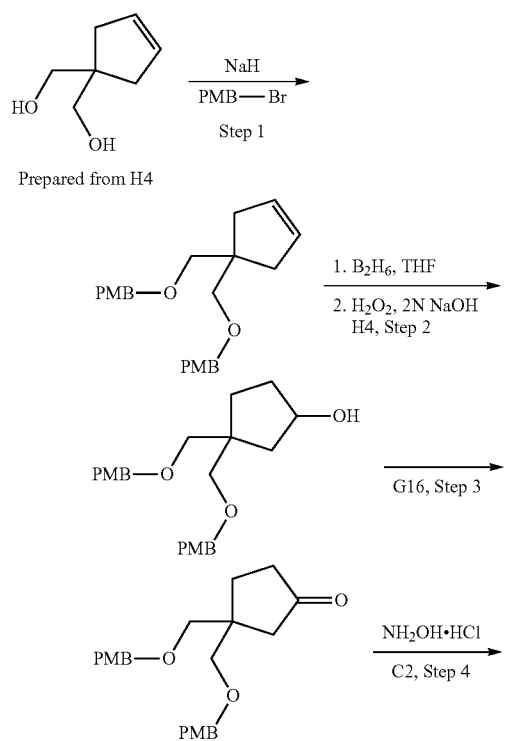

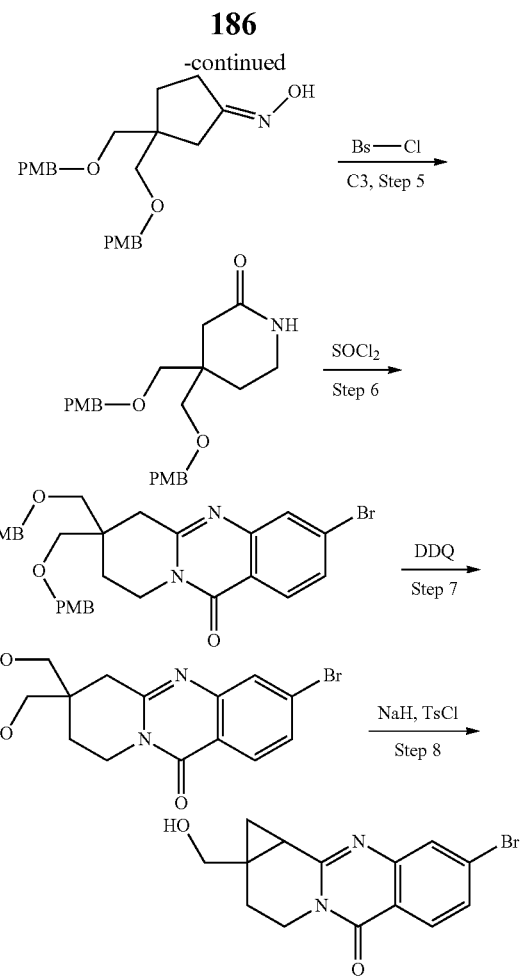

Example H18, Step 1

To a solution of cyclopent-3-ene-1,1-diyldimethanol (6.0 g, 46.8 mmol) in dry THF (120 mL) was added NaH (7.5 g, 187.2 mmol) at 0° C. under nitrogen atmosphere. After 1.5 h, 1-(bromomethyl)-4-methoxybenzene (20.5 mL, 140 mmol) was added and the reaction mixture was stirred overnight at rt. The reaction mixture was quenched by aq $NH_4Cl$ and extracted with ethyl acetate. The organic layers were washed with brine, dried over $Na_2SO_4$, filtrated and concentrated to give the crude product (30 g) which was used for the nest step without purification.

Example H18, Step 6

A solution of 2-amino-4-bromobenzoic acid (4.32 g, 20.0 mmol), $SOCl_2$ (7.2 mL, 100 mmol) in toluene (300 mL) were stirred for 4 h at 80° C. under nitrogen atmosphere. After the solvent and excess $SOCl_2$ were evaporated under reduced pressure, toluene (200 mL) and 4,4-bis((4-methoxybenzyloxy)methyl)piperidin-2-one (2.0 g, 5.0 mmol) were added and stirred for 4 h at 70° C. under nitrogen atmosphere. Then the mixture was concentrated and redissolved in ethyl acetate, washed with aq $Na_2CO_3$, dried over $Na_2SO_4$, filtrated and concentrated to give the crude product which was used for the next step without further purification.

Example H18, Step 7

To a solution of 3-bromo-7,7-bis((4-methoxybenzyloxy)methyl)-8,9-dihydro-6H-pyrido[2,1-b]quinazolin-11(7H)- one (~5.0 mmol) in DCM (100 mL) and H$_2$O (12 mL) was added DDQ (4.54 g, 20.0 mmol) and the mixture was stirred for 1 h. The reaction mixture was poured into 2N NaOH, and the organic layer was separated. The aqueous phase was extracted with DCM. The organic layers were combined and washed with brine, dried over Na$_2$SO$_4$, filtered and concentrated to give the crude product which was purified by column chromatography and 0.6 g of the desired product was obtained.

Example H18, Step 8

NaH (84 mg, 2.08 mmol) was added to the solution of 3-bromo-7,7-bis(hydroxymethyl)-8,9-dihydro-6H-pyrido[2,1-b]quinazolin-11(7H)-one (270 mg, 0.796 mmol) in dry THF (50 mL) at 0° C. under nitrogen atmosphere. After 1 h, the solution of TsCl (106 mg, 0.557 mmol) in dry THF was added dropwise and stirred overnight at room temperature. The reaction mixture was quenched with aq NH$_4$Cl and extracted with DCM. The organic layers were combined and dried over Na$_2$SO$_4$, filtered and concentrated to give the crude product. After purification with column chromatography, 60 mg of the desired product was obtained. MS (ESI+): 321, 323 (M+H$^+$).

Example H19. Synthesis of (R)-hexahydropyrrolo[1,2-a]pyrazin-3(4H)-one

Representative Scheme:

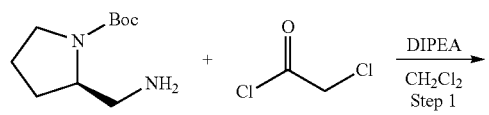

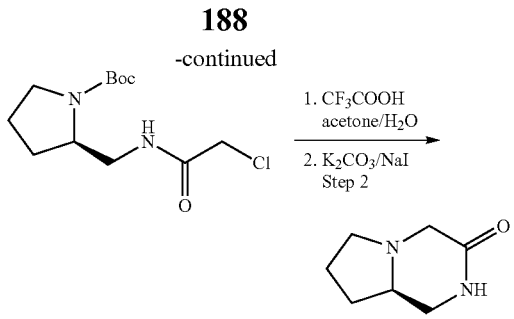

Example H19, Step 1

To a solution of (R)-tert-butyl 2-(aminomethyl)pyrrolidine-1-carboxylate (5.0 g, 25 mmol) and DIPEA (1.6 g, 12.4 mmol) in CH$_2$Cl$_2$ (30 mL) was added 2-chloroacetyl chloride (3.0 g, 26.5 mmol) in CH$_2$Cl$_2$ (10 mL) at 0° C. The mixture was stirred at room temperature overnight. Then the reaction mixture was poured into H$_2$O (30 mL) and extracted with CH$_2$Cl$_2$ (3×50 mL). The combined organic layers were washed with brine, dried over Na$_2$SO$_4$. After filtration and concentration, the crude product was purified by column chromatography (EtOAc:n-hexane=1:1) to give the desired product (5.6 g).

Example H19, Step 2

To a solution of (R)-tert-butyl 2-((2-chloroacetamido)methyl)pyrrolidine-1-carboxylate (5.6 g, 20.2 mmol) in H$_2$O (20 mL) and acetone (20 mL) was added trifluoroacetic acid (10 mL). The reaction mixture was stirred at room temperature overnight and adjusted pH to 7 with 10% NaOH. To the aqueous solution was added K$_2$CO$_3$ (2.0 g) and a catalytic amount of KI. The mixture was heated at reflux for 3 h. The reaction was cooled to room temperature, then the mixture was extracted with CH$_2$Cl$_2$ (3×50 mL). The combined organic layers were washed with brine, dried over Na$_2$SO$_4$ and concentrated under reduced pressure to give the crude product (1.7 g), which was directly used for the next step without further purification.

mGluR5 PAM EC$_{50}$ values: +++++<10 nM; ++++ is between 10 and 30 nM; +++ is between 30 and 100 nM; ++ is between 100 and 300 nM; + is between 300 and 1,000 nM. Fold shift at 10 μM: +++>3; ++ is between 2.0 and 2.9; + is between 1.5 and 1.9. Fold shift at 1 μM: +++>3; ++ is between 2.0 and 2.9; + is between 1.5 and 1.9.

| Compound | Synthesis Method & Data |
|---|---|
| Example I.1<br>2-(methoxymethyl)-6-(pyridin-2-ylethynyl)-2,3-dihydropyrrolo[2,1-b]quinazolin-9(1H)-one | See PCT/US2010/061147. |

| Compound | Synthesis Method & Data |
|---|---|
| Example 1.2<br>2-(2-hydroxypropan-2-yl)-6-(pyridin-2-ylethynyl)-2,3-dihydropyrrolo[2,1-b]quinazolin-9(1H)-one | Synthesized from methyl 5-oxopyrrolidine-3-carboxylate, 2-amino-4-bromobenzoic acid, and 2-ethynylpyridine according to General Experimentals B1, G6 and A1. MS (ESI+): m/z 346 (M + H⁺); ¹H NMR (300 MHz, CD₃OD) δ 8.89-8.79 (brs, 1H), 8.55-8.50 (t, J = 7.82 Hz, 1H), 8.41-8.38 (d, J = 8.28 Hz, 1H), 8.24-8.21 (d, J = 7.83 Hz, 1H), 8.01-7.97 (m, 2H), 7.93-7.90 (d, J = 8.25 Hz, 1H), 4.46-4.39 (dd, J = 12.00, 8.70 Hz, 1H), 4.23-4.16 (dd, J = 12.00, 8.40 Hz, 1H), 3.56-3.36 (m, 2H), 2.92-2.86 (t, J = 8.70 Hz, 1H), 1.32 (s, 6H). |
| Example 1.3<br>2-(2-fluoropropan-2-yl)-6-(pyridin-2-ylethynyl)-2,3-dihydropyrrolo[2,1-b]quinazolin-9(1H)-one | Synthesized from methyl 5-oxopyrrolidine-3-carboxylate, 2-amino-4-bromobenzoic acid, and 2-ethynylpyridine according to General Experimentals B1, G5, E1, and A1. MS (ESI+): m/z 348 (M + H⁺); ¹H NMR (300 MHz, CD₃OD) δ 8.89-8.88 (d, J = 5.37 Hz, 1H), 8.60-8.55 (t, J = 7.96 Hz, 1H), 8.40-8.37 (d, J = 8.28 Hz, 1H), 8.27-8.25 (d, J = 7.95 Hz, 1H), 8.05-8.03 (m, 1H), 8.01 (s, 1H), 7.90-7.87 (d, J = 8.19 Hz, 1H), 4.53-4.47 (dd, J = 12.00, 9.00 Hz, 1H), 4.19-4.12 (dd, J = 12.30, 8.70 Hz, 1H), 3.46-3.43 (m, 2H), 3.12-3.01 (m, 1H), 1.53-1.46 (d, J = 21.19 Hz, 6H). |
| Example 1.4<br>2-(2-methoxypropan-2-yl)-6-(pyridin-2-ylethynyl)-2,3-dihydropyrrolo[2,1-b]quinazolin-9(1H)-one | Synthesized from methyl 5-oxopyrrolidine-3-carboxylate, 2-amino-4-bromobenzoic acid, and 2-ethynylpyridine according to General Experimentals B1, G6, G13, and A1. MS (ESI+): m/z 360 (M + H⁺); ¹H NMR (300 MHz, CD₃OD) δ 8.87-8.85 (d, J = 5.67 Hz, 1H), 8.52-8.47 (t, J = 7.94 Hz, 1H), 8.39-8.37 (d, J = 8.28 Hz, 1H), 8.21-8.18 (d, J = 8.25 Hz, 1H), 7.97-7.94 (m, 2H), 7.91-7.88 (d, J = 8.37 Hz, 1H), 4.42-4.35 (m, 1H), 4.25-4.18 (m, 1H), 3.56-3.48 (m, 2H), 3.39 (s, 3H), 3.01-2.92 (m, 1H), 1.30 (s, 6H). mGluR5 PAM EC₅₀: ++++. Fold shift at 1 µM: +++. |
| Example 1.5<br>2-(2-methoxyethyl)-6-(pyridin-2-ylethynyl)-2,3-dihydropyrrolo[2,1-b]quinazolin-9(1H)-one | Synthesized from 3-methoxypropan-1-ol, 2-amino-4-bromobenzoic acid, and 2-ethynylpyridine according to General Experimentals G15, C1, B1, and A1. MS (ESI+): m/z 346 (M + H⁺); ¹H NMR (300 MHz, MeOD): δ 8.67 (d, J = 4.4 Hz, 1H), 8.27 (d, J = 8.2 Hz, 1H), 7.87 (s, 1H), 7.76-7.71 (m, 1H), 7.65-7.58 (m, 2H), 7.33-7.30 (m, 1H), 4.45-4.39 (m, 1H), 3.85-3.78 (m, 1H), 3.53-3.49 (t, J = 5.9 Hz, 2H), 3.35 (s, 3H), 3.32-3.27 (m, 1H), 2.97-2.88 (m, 1H), 2.83-2.73 (m, 1H), 1.90-1.84 (m, 2H). mGluR5 PAM EC₅₀: ++. |

-continued

| Compound | Synthesis Method & Data |
|---|---|
| Example 1.6<br>6'-(pyridin-2-ylethynyl)-1'H-spiro[oxetane-3,2'-pyrrolo[2,1-b]quinazolin]-9'(3'H)-one | Synthesized from oxetan-3-one, 2-amino-4-bromobenzoic acid, and 2-ethynylpyridine according to General Experimentals C1, B1, and A1. MS (ESI+): m/z 330 (M + H$^+$); $^1$H NMR (300 MHz, CD$_3$OD) δ 8.60 (d, J = 5.1 Hz, 1H), 8.25 (d, J = 8.4 Hz, 1H), 7.96-7.90 (m, 1H), 7.85 (s, 1H), 7.75-7.68 (m, 2H), 7.50-7.46 (s, 1H), 4.80 (s, 4H), 4.50 (s, 2H), 3.60 (s, 2H). mGluR5 PAM EC$_{50}$: +++. |
| Example 1.7<br>6'-(pyridin-2-ylethynyl)-1'H-spiro[cyclobutane-1,2'-pyrrolo[2,1-b]quinazolin]-9'(3'H)-one | Synthesized from cyclobutanone, 2-amino-4-bromobenzoic acid, and 2-ethynylpyridine according to General Experimentals C1, B1, and A1. MS (ESI+): m/z 328 (M + H$^+$); $^1$H NMR (300 MHz, CD$_3$OD) δ 8.97 (d, J = 5.7 Hz, 1H), 8.72-8.66 (m, 1H), 8.45 (d, J = 8.3 Hz, 1H), 8.36 (d, J = 8.0 Hz, 1H), 8.16-8.11 (m, 2H), 8.04-8.00 (dd, J = 8.3, 1.4 Hz, 1H), 4.41 (s, 2H), 3.70 (s, 2H), 2.35-2.30 (m, 4H), 2.11-2.01 (m, 2H). mGluR5 PAM EC$_{50}$: ++++. Fold shift at 1 µM: +++. |
| Example 1.8<br>6-(pyridin-2-ylethynyl)-2-(trifluoromethyl)-2,3-dihydropyrrolo[2,1-b]quinazolin-9(1H)-one | Synthesized from 4-(trifluoromethyl)pyrrolidin-2-one, 2-amino-4-bromobenzoic acid and 2-ethynylpyridine according to General Experimentals C1, B1 and A1. MS (ESI+): m/z 356 (M + H$^+$); $^1$H NMR (300 MHz, CD$_3$OD): δ 8.94 (d, J = 5.4 Hz, 1H), 8.72-8.66 (m, 1H), 8.39-8.34 (m, 2H), 8.15-8.10 (m, 1H), 8.05 (s, 1H), 7.90-7.87 (dd, J = 8.2, 1.2 Hz, 1H), 4.58-4.51 (m, 1H), 4.41-4.35 (m, 1H), 3.77-3.66 (m, 2H), 3.55-3.47 (m, 1H). |
| Example 1.9<br>2-(fluoromethyl)-6-(pyridin-2-ylethynyl)-2,3-dihydropyrrolo[2,1-b]quinazolin-9(1H)-one | Synthesized from 2-fluoroacetaldehyde, 2-amino-4-bromobenzoic acid, and 2-ethynylpyridine according to General Experimentals C1, B1 and A1. MS (ESI+): m/z 320 (M + H$^+$); $^1$H NMR (300 MHz, CD$_3$OD): δ 8.93 (d, J = 5.1 Hz, 1H), 8.69-8.63 (m, 1H), 8.44-8.41 (d, J = 8.3 Hz, 1H), 8.33 (d, J = 8.0 Hz, 1H), 8.13-8.07 (m ,2H), 7.98-7.95 (dd, J = 8.3, 1.3 Hz, 1H), 4.74-4.56 (dd, J = 48.0, 5.1 Hz, 2H), 4.54-4.47 (m, 1H), 4.25-4.19 (m, 1H), 3.75-3.66 (m, 1H), 3.47-3.33 (m, 2H). |

| Compound | Synthesis Method & Data |
|---|---|
| Example 1.10<br>2-ethyl-2-methyl-6-(pyridin-2-ylethynyl)-2,3-dihydropyrrolo[2,1-b]quinazolin-9(1H)-one | Synthesized from butan-2-one, 2-amino-4-bromobenzoic acid, and 2-ethynylpyridine according to General Experimentals C1, B1 and A1. MS (ESI+): m/z 330 (M + H$^+$); $^1$H NMR (300 MHz, CD$_3$OD): δ 8.96 (d, J = 5.8 Hz, 1H), 8.72-8.67 (m, 1H), 8.45 (d, J = 8.3 Hz, 1H), 8.37 (d, J = 8.0 Hz, 1H), 8.16-8.12 (m, 2H), 8.04-8.01 (d, J = 8.3 Hz, 1H), 4.13 (s, 2H), 3.37 (s, 2H), 1.79-1.71 (q, J = 7.5 Hz, 2H), 1.34 (s, 3H), 1.07-1.02 (t, J = 7.5 Hz. 3H). mGluR5 PAM EC$_{50}$: ++++. Fold shift at 1 μM: +++. |
| Example 1.11<br>3-fluoro-2,2-dimethyl-6-(pyridin-2-ylethynyl)-2,3-dihydropyrrolo[2,1-b]quinazolin-9(1H)-one | Synthesized from 4,4-dimethylpyrrolidin-2-one, 2-amino-4-bromobenzoic acid, and 2-ethynylpyridine according to General Experimentals B1, E3, and A1. MS (ESI+): m/z 334 (M + H$^+$); $^1$H NMR (300 MHz, CD$_3$OD): δ 8.93 (d, J = 5.8 Hz, 1H), 8.71-8.66 (m, 1H), 8.40-8.34 (m, 2H), 8.13-8.09 (m, 2H), 7.88 (d, J = 7.0 Hz, 1H), 5.49 (d, J = 53.1 Hz, 1H), 4.08-4.04 (m, 1H), 3.95-3.91 (m, 1H), 1.43-1.27 (m, 6H). |
| Example 1.12<br>9-oxo-6-(pyridin-2-ylethynyl)-1,2,3,9-tetrahydropyrrolo[2,1-b]quinazoline-2-carbonitrile | Synthesized from methyl 5-oxopyrrolidine-3-carboxylate, 2-amino-4-bromobenzoic acid, and 2-ethynylpyridine according to General Experimentals B1, G3, G4, and A1. MS (ESI+): m/z 313 (M + H$^+$); $^1$H NMR (300 MHz, DMSO-d$_6$) δ 8.68-8.67 (d, J = 4.32 Hz, 1H), 8.19-8.17 (d, J = 8.16 Hz, 1H), 7.98-7.93 (t, J = 7.41 Hz, 1H), 7.86 (s, 1H), 7.80-7.77 (d, J = 7.65 Hz, 1H), 7.71-7.68 (dd, J = 8.15, 1.31 Hz, 1H), 7.53-7.50 (t, J = 5.25 Hz, 1H), 4.51-4.45 (m, 1H), 4.27-4.21 (m, 1H), 3.96-3.91 (t, J = 7.80 Hz, 1H), 3.60-3.46 (m, 2H). |
| Example 1.13<br>2-methyl-8-(pyridin-2-ylethynyl)-2,3-dihydropyrrolo[1,2-b]isoquinolin-5(1H)-one | Synthesized from ethyl 4-bromo-2-(2-ethoxy-2-oxoethyl)benzoate, 4-methylpyrrolidin-2-one and 2-ethynylpyridine according to General Experimentals B4, B2, and A1. MS (ESI+): m/z 301 (M + H$^+$); $^1$H NMR (300 MHz, CD$_3$OD) δ 8.92 (d, J = 6.0 Hz, 1H), 8.69-8.66 (m, 1H), 8.38-8.30 (m, 2H), 8.14-8.09 (m, 1H), 8.02 (s, 1H), 7.74-7.70 (dd, J = 8.4, 1.2 Hz, 1H), 6.70 (s, 1H), 4.39-4.32 (m, 1H), 3.78-3.71 (m, 1H), 3.36-3.32 (m, 1H), 3.30-2.71 (m, 2H), 1.21 (d, J = 8.7 Hz, 3H). |

-continued

| Compound | Synthesis Method & Data |
|---|---|
| Example 1.15<br>2,2-dimethyl-6-(pyridin-2-ylethynyl)-2H-isoxazolo[3,2-b]quinazolin-9(3H)-one | Synthesized from ethyl 3-methylbut-2-enoate, 2-amino-4-bromobenzoic acid, and 2-ethynylpyridine according to General Experimentals C3, B1, and A1. MS (ESI+): m/z 318 (M + H$^+$); $^1$H NMR (300 MHz, CD$_3$OD): δ 8.94-8.92 (d, J = 5.91 Hz, 1H), 8.73-8.67 (td, J = 7.97 Hz, 1.50 Hz, 1H), 8.38-8.34 (m, 2H), 8.15-8.09 (m, 2H), 7.86-7.83 (d, J = 6.37 Hz, 1H), 3.54 (s, 2H), 1.64 (s, 6H). mGluR5 PAM EC$_{50}$: +++. Fold shift at 1 μM: +. |
| Example 1.16<br>5-fluoro-2,2-dimethyl-6-(pyriidn-2-ylethynyl)-2,3-dihydropyrrolo[2,1-b]quinazolin-9(1H)-one | Synthesized from 3,3-dimethylcyclopentanone; 3-bromo-2-fluoroaniline, and 2-ethynylpyridine according to General Experimentals D1, B1, and A1. MS (ESI+): m/z 334 (M + H$^+$); $^1$H NMR (300 MHz, CD$_3$OD) δ 8.95-8.93 (d, J = 5.88 Hz, 1H), 8.72-8.66 (td, J = 7.99, 1.49 Hz, 1H), 8.37-8.35 (d, J = 8.01 Hz, 1H), 8.17-8.11 (m, 2H), 7.86-7.81 (m, 1H), 4.02 (s, 2H), 3.16 (s, 2H), 1.33 (s, 6H). mGluR5 PAM EC$_{50}$: +++++. |
| Example 1.17<br>3-(pyridin-2-ylethynyl)-7-(trifluoromethyl)-7,8-dihydropyrido[3,2-d]pyrrolo[1,2-a]pyrimidin-10(6H)-one | Synthesized from 4-(trifluoromethyl)pyrrolidin-2-one, 3-amino-5-bromopicolinic acid, and 2-ethynylpyridine according to General Experimentals C1, B1, and A1. MS (ESI+): m/z 357 (M + H$^+$); $^1$H NMR (300 MHz, CD$_3$OD): δ 9.04 (d, J = 1.7 Hz, 1H), 8.98 (d, J = 5.9 Hz, 1H), 8.75-8.69 (m, 1H), 8.46 (d, J = 1.8 Hz, 1H), 8.40 (d, J = 8.0 Hz, 1H), 8.18-8.13 (m, 1H), 4.60-4.52 (m, 1H), 4.42-4.36 (m, 1H), 3.77-3.59 (m, 2H), 3.67-3.38 (m, 1H). mGluR5 PAM EC$_{50}$: ++. |
| Example 1.18<br>7-(2-methoxyethyl)-3-(pyridin-2-ylethynyl)-7,8-dihydropyrido[3,2-d]pyrrolo[1,2-a]pyrimidin-10(6H)-one | Synthesized from 3-methoxypropan-1-ol, 3-amino-5-bromopicolinic acid, and 2-ethynylpyridine according to General Experimentals G15, C1, B1, and A1. MS (ESI+): m/z 347 (M + H$^+$); $^1$H NMR (300 MHz, CD$_3$OD): 8.98 (d, J = 1.8 Hz, 1H), δ 8.70 (d, J = 4.8 Hz, 1H), 8.16 (d, J = 1.8 Hz, 1H), 7.80-7.84 (m, 1H), 7.65-7.63 (m, 1H), 7.37-7.33 (m, 1H), 4.56-4.49 (m, 1H), 3.94-3.85 (m, 1H), 3.53-3.49 (t, J = 5.9 Hz, 2H), 3.37 (s, 3H), 3.32-3.29 (m, 1H), 3.01-2.92 (m, 1H), 2.88-2.78 (m, 1H), 1.92-1.88 (m, 2H). mGluR5 PAM EC$_{50}$: +. |

| Compound | Synthesis Method & Data |
|---|---|
| Example 1.19<br>7-ethyl-7-methyl-3-(pyridin-2-ylethynyl)-7,8-dihydropyrido[3,2-d]pyrrolo[1,2-a]pyrimidin-10(6H)-one | Synthesized from butan-2-one, 3-amino-5-bromopicolinic acid, and 2-ethynylpyridine according to General Experimentals C1, B1, and A1. MS (ESI+): m/z 331 (M + H$^+$); $^1$H NMR (300 MHz, CD$_3$OD): δ 9.01 (s, 1H), 8.94 (d, J = 5.8 Hz, 1H), 8.65 (m, 1H), 8.41 (s, 1H), 8.34 (d, J = 7.9 Hz, 1H), 8.12-8.07 (m, 1H), 4.03 (s, 2H), 3.20-2.99 (m, 2H), 1.73-1.66 (q, J = 7.5 Hz, 2H), 1.27 (s, 3H), 1.04-0.99 (t, J = 7.5 Hz, 3H). mGluR5 PAM EC$_{50}$: +++. Fold shift at 1 μM: ++. |
| Example 1.20<br>6-fluoro-7,7-dimethyl-3-(pyridin-2-ylethynyl)-7,8-dihydropyrido[3,2-d]pyrrolo[1,2-a]pyrimidin-10(6H)-one | Synthesized from 3,3-dimethylcyclopentanone, 3-amino-5-bromopicolinic acid, and 2-ethynylpyridine according to General Experimentals B1, E3, and A1. MS (ESI+): m/z 335 (M + H$^+$); $^1$H NMR (300 MHz, CD$_3$OD): δ 9.05 (s, 1H), 8.95 (d, 1H), 8.70-8.67 (m, 1H), 8.64 (s, 1H), 8.54-8.37 (m, 1H), 8.14-8.09 (m, 1H), 5.49 (d, J = 52.5 Hz, 1H), 4.13-3.95 (m, 2H), 1.35 (s, 6H). mGluR5 PAM EC$_{50}$: ++. |
| Example 1.22<br>3-(pyridin-2-ylethynyl)-9,10,10a,11-tetrahydro-7H-pyrido[1′2′:3,4]imidazo[2,1-b]quinazolin-13(8H)-one | Synthesized from (R)-pyrrolidin-2-ylmethanamine, 2-amino-4-bromobenzoic acid and 2-ethynylpyridine according to General Experimentals H15, B1, and A1. MS (ESI+): m/z 329 (M + H$^+$); 1H NMR (300 MHz, CD$_3$OD): δ 8.88 (d, J = 5.1 Hz, 1H), 8.55-8.51 (t, J = 4.8 Hz, 1H), 8.28 (d, J = 8.1 Hz, 1H), 8.23 (d, J = 8.1 Hz, 1H), 8.03-8.01 (m, 1H), 7.99 (s, 1H), 7.81-7.77 (dd, J = 8.1, 1.5 Hz, 1H), 4.55-4.46 (m, 2H), 4.22-4.19 (m, 1H), 3.77-3.73 (m, 2H), 2.36-2.29 (m, 3H), 1.82-1.78 (m, 1H). mGluR5 PAM EC$_{50}$: +++. Fold shift at 1 μM: +++. |
| Example 1.22<br>3-(pyridin-2-ylethynyl)-9,10,10a,11-tetrahydro-7H-pyrido[1′,2′:3,4]imidazo[2,1-b]quinazolin-13(8H)-one | Synthesized from (S)-pyrrolidin-2-ylmethanamine, 2-amino-4-bromobenzoic acid and 2-ethynylpyridine according to General Experimentals H15, B1, and A1. MS (ESI+): m/z 329 (M + H$^+$). mGluR5 PAM EC$_{50}$: ++. |

| Compound | Synthesis Method & Data |
|---|---|
| 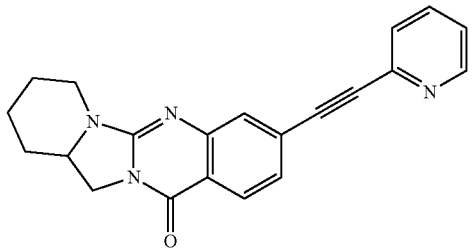<br>Example 1.23<br>3-(pyridin-2-ylethynyl)-<br>9,10,10a,11-tetrahydro-7H-<br>pyrido[1′,2′:3,4]imidazo[2,1-<br>b]quinazolin-13(8H)-one | Synthesized from piperidin-2-ylmethanamine, 2-amino-4-bromobenzoic acid and 2-ethynylpyridine according to General Experimentals H15, B1, and A1. MS (ESI): 343 (MH$^+$); $^1$H NMR (300 MHz, CDCl$_3$) δ 8.92-8.91 (d, J = 4.8 Hz, 1H), 8.65-8.59 (m, 1H), 8.31-8.26 (m, 2H), 8.10-8.05 (m, 1H), 7.94 (s, 1H), 7.80-7.76 (dd, J = 1.5 Hz, 8.4 Hz, 1H), 4.56-4.53 (m, 1H), 4.40-4.20 (m, 2H), 3.95-3.89 (m, 1H), 3.55-3.40 (m, 1H), 2.20-2.10 (m, 1H), 2.10-1.90 (m, 2H), 1.80-1.70 (m, 3H). mGluR5 PAM EC$_{50}$: +++. |
| 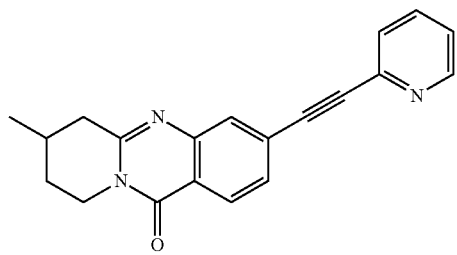<br>Example 2.1<br>7-methyl-3-(pyridin-2-ylethynyl)-8,9-dihydro-6H-pyrido[2,1-b]quinazolin-11(7H)-one | See PCT/US2010/061147. |
| 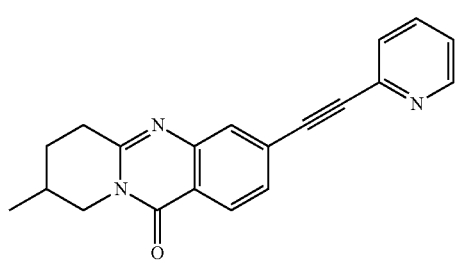<br>Example 2.2<br>8-methyl-3-(pyridin-2-ylethynyl)-8,9-dihydro-6H-pyrido[2,1-b]quinazolin-11(7H)-one | See PCT/US2010/061147. |

| Compound | Synthesis Method & Data |
|---|---|
| Example 2.3<br>9-methyl-3-(pyridin-2-ylethynyl)-8,9-dihydro-6H-pyrido[2,1-b]quinazolin-11(7H)-one | See PCT/US2010/061147. |
| Example 2.4<br>3-methyl-9-(pyridin-2-ylethynyl)-3,4-dihydro-[1,4]oxazino[3,4-b]quinazolin-6(1H)-one | See PCT/US2010/061147. |
| Example 2.5<br>2,3-dimethyl-9-(pyridin-2-ylethynyl)-3,4-dihydro-1H-pyrazino[2,1-b]quinazolin-6(2H)-one | See PCT/US2010/061147. |
| Example 2.6<br>8-methoxy-3-(pyridin-2-ylethynyl)-8,9-dihydro-6H-pyrido[2,1-b]quinazolin-11(7H)-one | See PCT/US2010/061147. |

| Compound | Synthesis Method & Data |
|---|---|
| 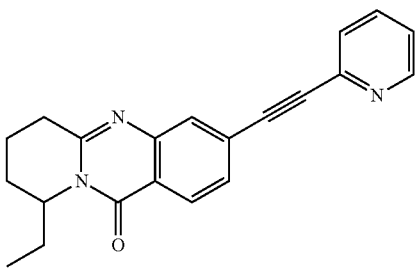<br>Example 2.7<br>9-ethyl-3-(pyridin-2-ylethynyl)-<br>8,9-dihydro-6H-pyrido[2,1-<br>b]quinazolin-11(7H)-one | See PCT/US2010/061147. |
| 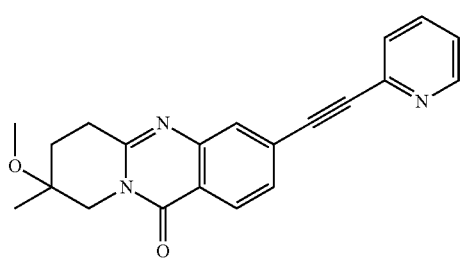<br>Eaxmple 2.8<br>8-methoxy-8-methyl-3-(pyridin-<br>2-ylethynyl)-8,9-dihydro-6H-<br>pyrido[2,1-b]quinazolin-11(7H)-<br>one | See PCT/US2010/061147. |
| 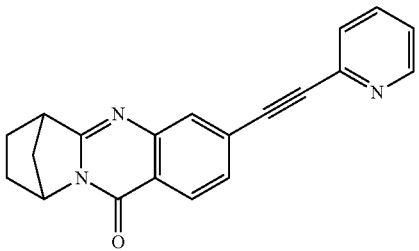<br>Example 2.9<br>3-(pyridin-2-ylethynyl)-8,9-<br>dihydro-6H-6,9-<br>methanopyrido[2,1-b]quinazolin-<br>11(7H)-one | See PCT/US2010/061147. |
| 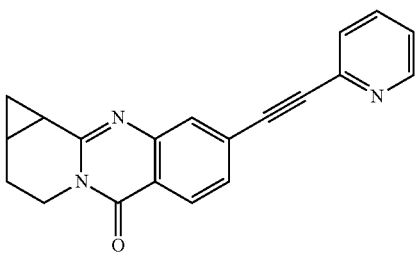<br>Example 2.10<br>8-(pyridin-2-ylethynyl)-<br>1,2,3,10b-<br>tetrahydrocyclopropan[3,4]pyrido<br>[2,1-b]quinazolin-5(1aH)-one | See PCT/US2010/061147. |

| Compound | Synthesis Method & Data |
|---|---|
| 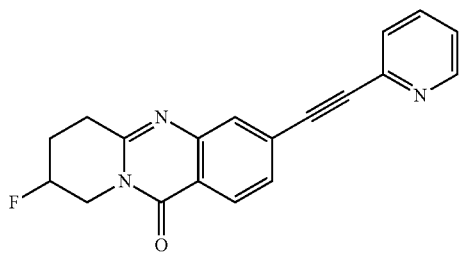<br>Example 2.11<br>8-fluoro-3-(pyridin-2-ylethynyl)-8,9-dihydro-6H-pyrido[2,1-b]quinazolin-11(7H)-one | See PCT/US2010/061147. |
| 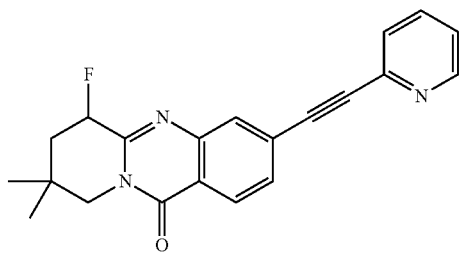<br>Example 2.12<br>6-fluoro-8,8-dimethyl-3-(pyridin-2-ylethynyl)-8,9-dihydro-6H-pyrido[2,1-b]quinazolin-11(7H)-one | See PCT/US2010/061147. |
| 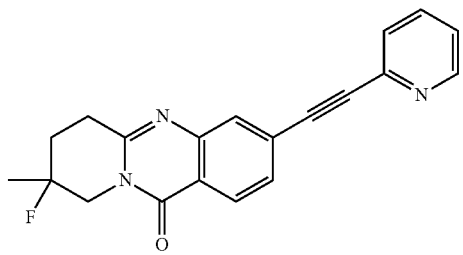<br>Example 2.13<br>8-fluoro-8-methyl-3-(pyridin-2-ylethynyl)-8,9-dihydro-6H-pyrido[2,1-b]quinazolin-11(7H)-one | Synthesized from 5-hydroxypiperidin-2-one, 2-amino-4-bromobenzoic acid, and 2-ethynylpyridine according to General Experimentals F1, B1, F4, G16, G8, E1 and A1. MS (ESI+): m/z 334 (M + H$^+$); $^1$H NMR (300 MHz, CD$_3$OD) δ 8.93-8.92 (d, J = 5.67 Hz, 1H), 8.64-8.59 (t, J = 7.95 Hz, 1H), 8.46-8.44 (d, J = 8.28 Hz, 1H), 8.32-8.29 (d, J = 8.07 Hz, 1H), 8.09-8.00 (m, 3H), 4.70-4.69 (t, J = 15.09 Hz, 1H), 3.98-3.81 (q, 1H), 3.49-3.40 (m, 2H), 2.46-2.37 (m, 1H), 2.31-2.13 (m, 1H), 1.73-1.67 (d, J = 20.96 Hz, 3H). |
| 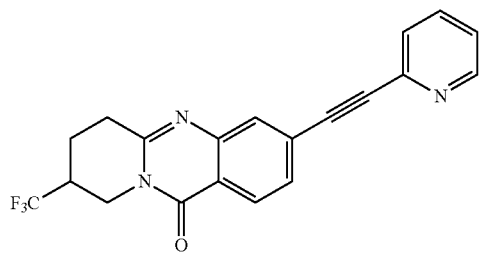<br>Example 2.14<br>3-(pyridin-2-ylethynyl)-8-(trifluoromethyl)-8,9-dihydro-6H-pyrido[2,1-b]quinazolin-11(7H)-one | Synthesized from 5-(trifluoromethyl)piperidin-2-one, 2-amino-4-bromobenzoic acid, and 2-ethynylpyridine according to General Experimentals B1 and A1. MS (ESI): 370 (M + H+); $^1$H NMR (300 MHz, CD$_3$OD) δ 8.92-8.90 (d, J = 5.6 Hz, 1H), 8.61-8.56 (td, J = 8.0, 1.5 Hz, 1H), 8.45-8.43 (d, J = 8.3 Hz, 1H), 8.29-8.27 (d, J = 8.0 Hz, 1H), 8.07-8.02 (m, 2H), 7.99-7.96 (dd, J = 8.3, 1.3 Hz, 1H), 4.62-4.55 (dd, J = 14.2, 5.7 Hz, 1H), 4.09-4.01 (m, 1H), 3.40-3.36 (m, 2H), 3.21-3.09 (m, 1H), 2.45-2.39 (m, 1H), 2.14-2.04 (m, 1H). |

| Compound | Synthesis Method & Data |
|---|---|
| 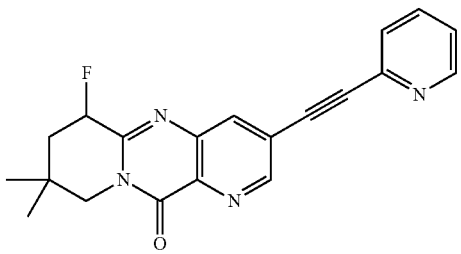

Example 2.15
6-fluoro-8,8-dimethyl-3-(pyridin-2-ylethynyl)-8,9-dihydro-6H-dipyrido[1,2-a:3′,2′-d]pyrimidin-11(7H)-one | Synthesized from 3-methylcyclopentenone, 3-amino-5-bromopicolinic acid, and 2-ethynylpyridine according to General Experimentals G30, C2, B1, E3 and A1. MS (ESI+): m/z 349 (M + H$^+$); $^1$H NMR (300 MHz, CD$_3$OD) δ 9.08 (s, 1H), 8.98-8.96 (d, J = 5.82 Hz, 1H), 8.72-8.67 (td, J = 7.98, 1.86 Hz, 1H), 8.54 (s, 1H), 8.40-8.37 (d, J = 7.92 Hz, 1H), 8.20-8.12 (t, J = 7.05 Hz, 1H), 5.75-5.56 (dt, J = 48.00, 5.72 Hz, 1H), 4.10-3.95 (q, 2H), 2.29-2.14 (m, 2H), 1.20 (s, 3H), 1.16 (s, 3H). |
| 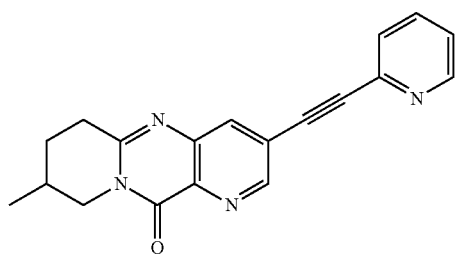

Example 2.16
8-methyl-3-(pyridin-2-ylethynyl)-8,9-dihydro-6H-dipyrido[1,2-a:3′,2′-d]pyrimidin-11(7H)-one and

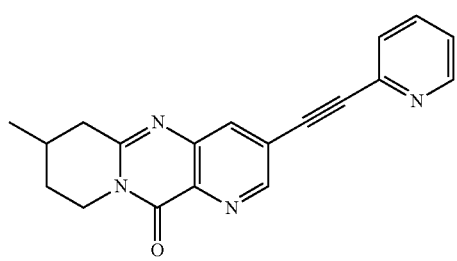

Example 2.17
7-methyl-3-(pyridin-2-ylethynyl)-8,9-dihydro-6H-dipyrido[1,2-a:3′,2′-d]pyrimidin-11(7H)-one | Synthesized from 3-methylcyclopentanone, 3-amino-5-bromopicolinic acid, and 2-ethynylpyridine according to General Experimentals C2, B1, and A1. MS (ESI+): m/z 317 (M + H$^+$). |

| Compound | Synthesis Method & Data |
|---|---|
| Example 2.18<br>8-hydroxy-3-(pyridin-2-ylethynyl)-8-vinyl-8,9-dihydro-6H-pyrido[2,1-b]quinazolin-11(7H)-one | Synthesized from 5-hydroxypiperidin-2-one, 2-amino-4-bromobenzoic acid, and 2-ethynylpyridine according to General Experimentals F1, B1, F4, G16, G8, and A1. MS (ESI+): m/z 344 (M + H$^+$). mGluR5 PAM EC$_{50}$: +. |
| Example 2.19<br>11-oxo-3-(pyridin-2-ylethynyl)-7,8,9,11-tetrahydro-6H-pyrido[2,1-b]quinazoline-8-carboxamide | Synthesized from methyl 6-oxopiperidine-3-carboxylate, 2-amino-4-bromobenzoic acid, and 2-ethynylpyridine according to General Experimentals B1, G3, and A1. MS (ESI+): m/z 345 (M + H$^+$); $^1$H NMR (300 MHz, CD$_3$OD) δ 8.61-8.59 (d, J = 4.71 Hz, 1H), 8.25-8.22 (d, J = 8.28 Hz, 1H), 7.95-7.90 (td, J = 7.80, 1.50 Hz, 1H), 7.82 (s, 1H), 7.75-7.72 (d, J = 7.83 Hz, 1H), 7.68-7.65 (d, J = 8.13 Hz, 1H), 7.50-7.46 (m, 1H), 4.41-4.34 (m, 1H), 4.17-4.10 (m, 1H), 3.18-2.98 (m, 3H), 2.28-2.11 (m, 2H). |
| Example 2.20<br>(6R,8S,9S)-8-methoxy-3-(pyridin-2-ylethynyl)-8,9-dihydro-6H-6,9-methanopyrido[2,1-b]quinazolin-11(7H)-one | Synthesized from cyclopent-3-enecarboxylic acid, 2-amino-4-bromobenzoic acid, and 2-ethynylpyridine according to General Experimentals H1, B1, and A1. MS (ESI+): m/z 344 (M + H$^+$); $^1$H NMR (300 MHz, CD$_3$OD) δ 8.95-8.93 (d, J = 6.0 Hz, 1H), 8.71-8.65 (m, 1H), 8.39-8.33 (m, 2H), 8.14-8.11 (m, 1H), 8.04 (s, 1H), 7.93-7.89 (dd, J = 8.1, 1.5 Hz, 1H), 5.27 (s, 1H), 3.84-3.81 (m, 1H), 3.64-3.63 (m, 1H), 3.51 (s, 3H), 2.31-2.15 (m, 3H), 2.06-2.03 (m, 1H). |

| Compound | Synthesis Method & Data |
| --- | --- |
| Example 2.21<br>3-(pyridin-2-ylethynyl)-7-(trifluoromethyl)-8,9-dihydro-6H-dipyrido[1,2-a:3',2'-d]pyrimidin-11(7H)-one | Synthesized from 4-(trifluoromethyl)piperidine, 3-amino-5-bromopicolinic acid, and 2-ethynylpyridine according to General Experimentals F6, C4, F3, B1, and A1. MS (ESI+): m/z 371 (M + H$^+$). mGluR5 PAM EC$_{50}$: +++. |
| Example 2.22<br>7-ethyl-3-(pyridin-2-ylethynyl)-8,9-dihydro-6H-dipyrido[1,2-a:3',2'-d]pyrimidin-11(7H)-one<br><br>and<br><br>Example 2.23<br>8-ethyl-3-(pyridin-2-ylethynyl)-8,9-dihydro-6H-dipyrido[1,2-a:3',2'-d]pyrimidin-11(7H)-one | The mixture of Example 2.22 and Example 2.23 were synthesized from 3-ethylcyclopentanone, 3-amino-5-bromopicolinic acid, and 2-ethynylpyridine according to General Experimentals C2, B1, and A1. MS (ESI+): m/z 331 (M + H$^+$). mGluR5 PAM EC$_{50}$: ++. |
| Example 2.24a<br>6-((7,7-dimethyl-11-oxo-7,8,9,11-tetrahydro-6H-pyrido[2,1-b]quinazolin-3-yl)ethynyl)picolinonitrile | Synthesized from 3-methylcyclopentenone, 2-amino-4-bromobenzoic acid, and 6-bromopicolinonitrile according to General Experimentals G30, C2, B1, and A2. MS (ESI+): m/z 355 (M + H$^+$); $^1$H NMR (300 MHz, CD$_3$OD) δ 8.41-8.38 (d, J = 8.28 Hz, 1H), 8.14-8.09 (t, J = 7.86 Hz, 1H), 8.00-7.89 (m, 4H), 4.21-4.17 (t, J = 6.43 Hz, 2H), 3.07 (s, 2H), 2.01-1.97 (t, J = 6.48 Hz, 2H), 1.22 (s, 6H). mGluR5 PAM EC$_{50}$: +++++. |

| Compound | Synthesis Method & Data |
|---|---|
| 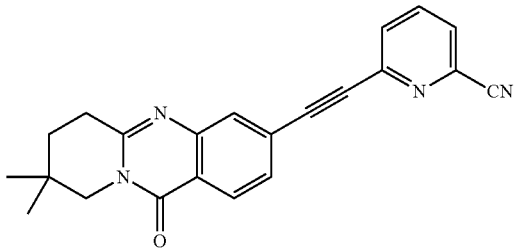

Example 2.24b
6-((8,8-dimethyl-11-oxo-7,8,9,11-tetrahydro-6H-pyrido[2,1-b]quinazolin-3-yl)ethynyl)picolinonitrile | Synthesized from 3-methylcyclopentenone, 2-amino-4-bromobenzoic acid, and 6-bromopicolinonitrile according to General Experimentals G30, C2, B1, and A2. MS (ESI+): m/z 348 (M + H$^+$); $^1$H NMR (300 MHz, CD$_3$OD) δ 8.41-8.38 (d, J = 8.22 Hz, 1H), 8.14-8.09 (t, J = 7.83 Hz, 1H), 8.00-7.91 (m, 4H), 3.88 (s, 2H), 3.37-3.33 (m, 2H), 1.90-1.86 (t, J = 6.68 Hz, 2H), 1.19 (s, 6H). mGluR5 PAM EC$_{50}$: ++++. |
| 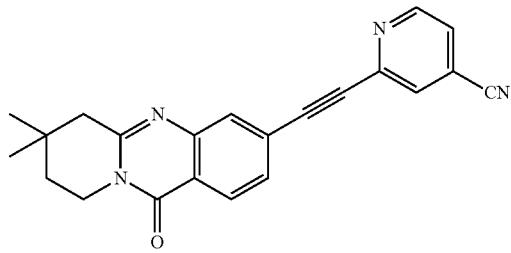

Example 2.25a
2-((7,7-dimethyl-11-oxo-7,8,9,11-tetrahydro-6H-pyrido[2,1-b]quinazolin-3-yl)ethynyl)isonicotinonitrile | Synthesized from 3-methylcyclopentenone, 2-amino-4-bromobenzoic acid, and 2-ethynylisonicotinonitrile according to General Experimentals G30, C2, B1, and A1. MS (ESI+): m/z 355 (M + H$^+$); $^1$H NMR (300 MHz, CD$_3$OD) δ 8.88-8.86 (d, J = 5.07 Hz, 1H), 8.41-8.39 (d, J = 8.28 Hz, 1H), 8.12 (s, 1H), 7.95-7.92 (d, J = 8.31 Hz, 1H), 7.89 (s, 1H), 7.83-7.81 (d, J = 5.10 Hz, 1H), 4.21-4.17 (t, J = 6.48 Hz, 2H), 3.07 (s, 2H), 2.01-1.97 (t, J = 6.48 Hz, 2H), 1.22 (s, 6H). mGluR5 PAM EC$_{50}$: ++++. |
| 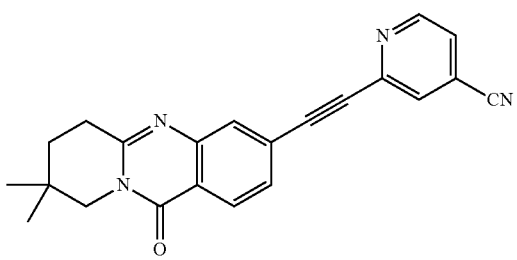

Example 2.25b
2-((8,8-dimethyl-11-oxo-7,8,9,11-tetrahydro-6H-pyrido[2,1-b]quinazolin-3-yl)ethynyl)isonicotinonitrile | Synthesized from 3-methylcyclopentenone, 2-amino-4-bromobenzoic acid, and 2-ethynylisonicotinonitrile according to General Experimentals G30, C2, B1, and A1. MS (ESI+): m/z 355 (M + H$^+$); $^1$H NMR (300 MHz, CD$_3$OD) δ 8.88-8.86 (d, J = 4.92 Hz, 1H), 8.41-8.38 (d, J = 8.31 Hz, 1H), 8.12 (s, 1H), 7.94-7.92 (d, J = 8.34 Hz, 1H), 7.89 (s, 1H), 7.82-7.81 (d, J = 3.87 Hz, 1H), 3.88 (s, 2H), 3.35-3.31 (m, 2H), 1.89-1.85 (t, J = 6.80 Hz, 2H), 1.19 (s, 6H). mGluR5 PAM EC$_{50}$: +++++. |

| Compound | Synthesis Method & Data |
|---|---|
| Example 2.26<br>3,3-dimethyl-8-(pyridin-2-ylethynyl)-2,3,13,13a-tetrahydro-1H-pyrrolo[1′,2′:4,5]pyrazino[2,1-b]quinazolin-11(5H)-one | Synthesized from 1-(tert-butoxycarbonyl)-5,5-dimethylpyrrolidine-2-carboxylic acid, 2-amino-4-bromobenzoic acid, and 2-ethynylpyridine according to General Experimentals G1, G17, G18, C5, B1, and A1. MS (ESI+): m/z 371 (M + H$^+$); mGluR5 PAM EC$_{50}$: ++. |
| Example 2.27<br>11-oxo-3-(pyridin-2-ylethynyl)-7,8,9,11-tetrahydro-6H-pyrido[2,1-b]quinazoline-8-carbonitrile | Synthesized from methyl 6-oxopiperidine-3-carboxylate, 2-amino-4-bromobenzoic acid, and 2-ethynylpyridine according to General Experimentals B1, G3, G4, and A1. MS (ESI+): m/z 327 (M + H$^+$); $^1$H NMR (300 MHz, DMSO-d$_6$) δ 8.67 (s, 1H), 8.20-8.17 (d, J = 7.83, 1H), 7.98-7.93 (m, 1H), 7.85 (s, 1H), 7.80-7.69 (m, 2H), 7.54-7.52 (m, 1H), 4.32-4.19 (m, 2H), 3.68-3.66 (m, 1H), 3.08-3.04 (t, J = 6.36 Hz, 2H), 2.34-2.27 (m, 1H), 2.15-2.10 (m, 1H). |
| Example 2.28<br>8-methyl-3-(pyridin-2-ylethynyl)-6H-pyrido[2,1-b]quinazolin-11(7H)-one | Synthesized from 5-hydroxypiperidin-2-one, 2-amino-4-bromobenzoic acid, and 2-ethynylpyridine according to General Experimentals F1, B1, F4, G16, G8, G14, and A1. MS (ESI+): m/z 314 (M + H$^+$); $^1$H NMR (300 MHz, CD$_3$OD) δ 8.88-8.86 (d, J = 5.55 Hz, 1H), 8.55-8.50 (t, J = 7.88 Hz, 1H), 8.41-8.38 (d, J = 8.28 Hz, 1H), 8.24-8.21 (d, J = 7.98 Hz, 1H), 8.00-7.97 (m, 2H), 7.91-7.88 (d, J = 8.22 Hz, 1H), 7.38 (s, 1H), 3.29-3.26 (m, 2H), 2.55-2.50 (t, J = 7.92 Hz, 2H), 2.01 (s, 3H). |
| Example 2.29<br>3,3-dimethyl-9-(pyridin-2-ylethynyl)-3,4-dihydro-[1,3]oxazino[2,3-b]quinazolin-6(2H)-one | Synthesized from ethyl 2-amino-4-bromobenzoate, 2-amino-4-bromobenzoic acid, and 2-ethynylpyridine according to General Experimentals B3 and A1. MS (ESI+): m/z 332 (M + H$^+$); $^1$H NMR (300 MHz, CD$_3$OD): δ 8.95 (d, J = 5.8 Hz, 1H), 8.71-8.66 (m, 1H), 8.39-8.34 (m, 2H), 8.15-8.10 (m, 1H), 7.92-7.89 (m, 2H), 4.58 (s, 2H), 3.93 (s, 2H), 1.27 (s, 6H). mGluR5 PAM EC$_{50}$: ++++. Fold shift at 1 μM: +++. |

| Compound | Synthesis Method & Data |
|---|---|
| 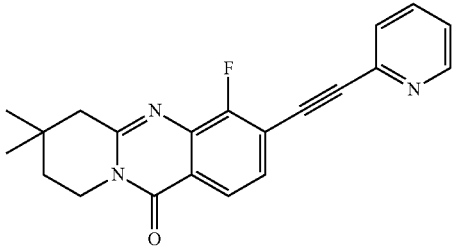

Example 2.30a
4-fluoro-7,7-dimethyl-3-(pyridin-2-ylethynyl)-8,9-dihydro-6H-pyrido[2,1-b]quinazolin-11(7H)-one and

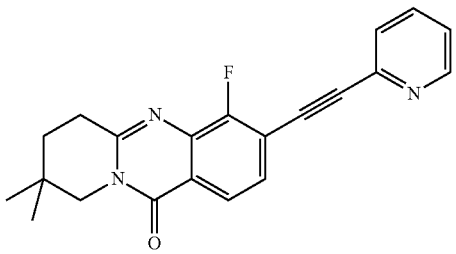

Example 2.30b
4-fluoro-8,8-dimethyl-3-(pyridin-2-ylethynyl)-8,9-dihydro-6H-pyrido[2,1-b]quinazolin-11(7H)-one | Synthesized from 3-methylcyclopentenone, 3-bromo-2-fluoroaniline, and 2-ethynylpyridine according to General Experimentals G30, C2, D1, B1, and A1. Mixture of Example 2.30a and Example 2.30b: MS (ESI+): m/z 348 (M + H $^+$); $^1$H NMR (300 MHz, CD$_3$OD) δ 8.62-8.61 (d, J = 4.74 Hz, 1H), 8.03-8.00 (d, J = 8.34 Hz, 1H), 7.96-7.91 (td, J = 7.77, 1.64 Hz, 1H), 7.76-7.74 (d, J = 7.86 Hz, 1H), 7.66-7.61 (m, 1H), 7.52-7.47 (m, 1H), 4.13-4.08 (t, J = 6.57 Hz, 0.5 H), 3.85 (s, 1.5H), 3.11-3.07 (t, J = 7.08 Hz, 1.5H), 2.86 (s, 0.5H), 1.92-1.89 (t, J = 6.54 Hz, 0.5H), 1.82-1.77 (t, J = 7.08 Hz, 1.5H), 1.15 (s, 1.5H), 1.12 (s, 4.5H).
Example 2.30a:
mGluR5 PAM EC$_{50}$: ++++.
Example 2.30b:
mGluR5 PAM EC$_{50}$: +++++. Fold shift at 1 μM: +++. |
| 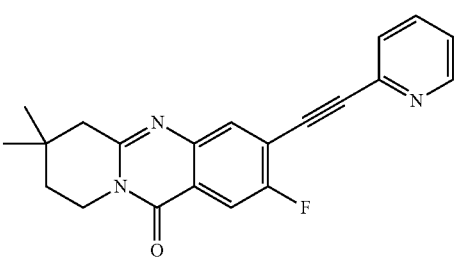

Example 2.31a
2-fluoro-7,7-dimethyl-3-(pyridin-2-ylethynyl)-8,9-dihydro-6H-pyrido[2,1-b]quinazolin-11(7H)-one | Synthesized from 3-methylcyclopentenone, 3-bromo-4-fluoroaniline, and 2-ethynylpyridine according to General Experimentals G30, C2, D1, B1, and A1. MS (ESI+): m/z 348 (M + H$^+$); $^1$H NMR (300 MHz, DMSO-d$_6$) δ 8.71 (brs, 1H), 7.98-7.91 (m, 3H), 7.79-7.77 (m, 1H), 7.51-7.49 (m, 1H), 3.99-3.95 (t, J = 6.45 Hz, 2H), 2.79 (s, 2H), 1.81-1.76 (t, J = 6.45 Hz, 2H), 1.05 (s, 6H). mGluR5 PAM EC$_{50}$: +++. |

-continued

| Compound | Synthesis Method & Data |
|---|---|
| Example 2.31b<br>2-fluoro-8,8-dimethyl-3-(pyridin-2-ylethynyl)-8,9-dihydro-6H-pyrido[2,1-b]quinazolin-11(7H)-one | Synthesized from 3-methylcyclopentenone, 3-bromo-4-fluoroaniline, and 2-ethynylpyridine according to General Experimentals G30, C2, D1, B1, and A1. MS (ESI+): m/z 348 (M + H$^+$); $^1$H NMR (30 MHz, DMSO-d$_6$) δ 8.68-8.67 (d, J = 4.80 Hz, 1H), 7.98-7.91 (m, 3H), 7.79-7.60 (m, 1H), 7.54-7.51 (m, 1H), 3.74 (s, 2H), 3.02-2.97 (t, J = 7,02 Hz, 2H), 1.70-1.65 (t, J = 6.99 Hz, 2H), 1.03 (s, 6H). |
| Example 2.32a<br>1-fluoro-7,7-dimethyl-3-(pyridin-2-ylethynyl)-8,9-dihydro-6H-pyrido[2,1-b]quinazolin-11(7H)-one | Synthesized from 3-methylcyclopentenone, 3-bromo-5-fluoroaniline, and 2-ethynylpyridine according to General Experimentals G30, C2, D1, B1, and A1. MS (ESI+): m/z 364 (M + H$^+$); $^1$H NMR (300 MHz, CD$_3$OD) δ 8.93-8.92 (d, J = 5.67 Hz, 1H), 8.66-8.61 (td, J = 7.93, 1.50 Hz, 1H), 8.34-8.31 (d, J = 7.98 Hz, 1H), 8.10-8.06 (td, J = 5.85, 1.08 Hz, 1H), 7.93-7.89 (dd, J = 8.73, 2.40 Hz, 1H), 7.61-7.58 (dd, J = 8.43, 2.40 Hz, 1 H), 4.20-4.16 (t, J = 6.42 Hz, 2H), 3.07 (s, 2H), 2.02-1.98 (t, J = 6.42 Hz, 2H), 1.22 (s, 6H). |
| Example 2.32b<br>1-fluoro-7,7-dimethyl-3-(pyridin-2-ylethynyl)-8,9-dihydro-6H-pyrido[2,1-b]quinazolin-11(8H)-one | Synthesized from 3-methylcyclopentenone, 3-bromo-5-fluoroaniline, and 2-ethynylpyridine according to General Experimentals G30, C2, D1, B1, E3, and A1. MS (ESI+): m/z 366 (M + H$^+$); $^1$H NMR (300 MHz, CD$_3$OD) δ 8.92-8.90 (d, J = 5.46 Hz, 1H), 8.69-8.64 (t, J = 7.92 Hz, 1H), 8.37-8.35 (d, J = 8.04 Hz, 1H), 8.11-8.06 (t, J = 6.33 Hz, 1H), 7.82-7.78 (dd, J = 8.64, 2.55, 1H), 7.67-7.63 (dd, J = 9.24, 2.46 Hz, 1H), 5.71-5.51 (dt, J = 47.70, 5.52 Hz, 1H), 4.02-3.92 (q, 2H), 2.26-2.21 (m, 1H), 2.17-2.13 (t, J = 5.10 Hz, 1H), 1.20 (s, 3H), 1.13 (s, 3H). |
| Example 2.33<br>1-chloro-7,7-dimethyl-3-(pyridin-2-ylethynyl)-8,9-dihydro-6H-pyrido[2,1-b]quinazolin-11(7H)-one | Synthesized from 3-methylcyclopentenone, 3-bromo-5-chloroaniline, and 2-ethynylpyridine according to General Experimentals G30, C2, D1, B1, and A1. MS (ESI+): mz 364 (M + H$^+$); $^1$H NMR (300 MHz, CD$_3$OD) δ 8.90-8.89 (d, J = 5.73 Hz, 1H), 8.59-8.55 (td, J = 8.66, 1.41 Hz, 1H), 8.30-8.28 (d, J = 7.98 Hz, 1H), 8.05-8.01 (m, 2H), 7.81 (s, 1H), 4.18-4.14 (t, J = 6.45 Hz, 2H), 3.00 (s, 2H), 2.00-1.95 (t, J = 6.43 Hz, 1H), 1.20 (s, 6H). |

| Compound | Synthesis Method & Data |
|---|---|
| 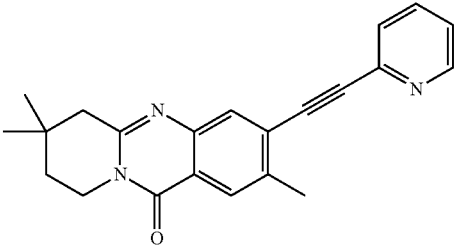

Example 2.34a
2,7,7-trimethyl-3-(pyridin-2-ylethynyl)-8,9-dihydro-6H-pyrido[2,1-b]quinazolin-11(7H)-one | Synthesized from 3-methylcyclopentenone, 3-bromo-4-methylaniline, and 2-ethynylpyridine according to General Experimentals G30, C2, D1, B1, and A1. MS (ESI+): m/z 344 (M + H$^+$); $^1$H NMR (300 MHz, CD$_3$OD) δ 8.86-8.84 (d, J = 5.70 Hz, 1H), 8.48-8.43 (td, J = 7.77, 1.43 Hz, 1H), 8.25 (s, 1H), 8.19-8.17 (d, J = 7.89 Hz, 1H), 8.10 (s, 1H), 7.94-7.90 (m, 1H), 4.20-4.15 (t, J = 6.56 Hz, 2H), 3.09 (s, 2H), 2.57 (s, 3H), 1.98-1.94 (t, J = 6.62 Hz, 2H), 1.20 (s, 5H). |
| 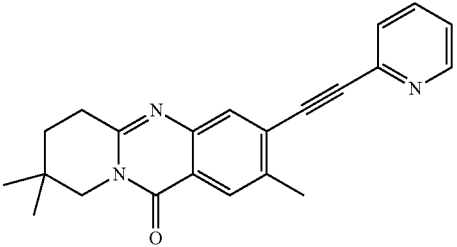

Example 2.34b
2,8,8-trimethyl-3-(pyridin-2-ylethynyl)-8,9-dihydro-6H-pyrido[2,1-b]quinazolin-11(7H)-one | Synthesized from 3-methylcyclopentenone, 3-bromo-4-methylaniline, and 2-ethynylpyridine according to General Experimentals G30, C2, D1, B1, and A1. MS (ESI+): m/z 344 (M + H$^+$); $^1$H NMR (300 MHz, CD$_3$OD) δ 8.91-8.89 (d, J = 6.21 Hz, 1H), 8.57-8.51 (td, J = 7.97, 1.50 Hz, 1H), 8.28-8.24 (m, 2H), 8.16 (s, 1H), 8.02-7.97 (t, J = 6.75 Hz, 1H), 3.91 (s, 2H), 3.44-3.39 (t, J = 6.87 Hz, 2H), 2.58 (s, 3H), 1.89-1.84 (t, J = 6.89 Hz, 2H), 1.17 (s, 6H). |
| 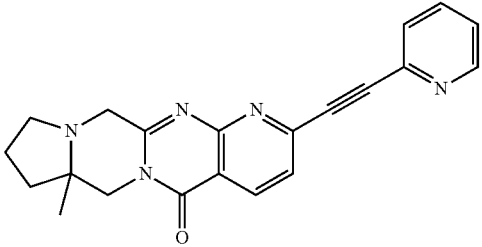

Example 2.35
7a-methyl-2-(pyridin-2-ylethynyl)-7,7a,8,9,10,12-hexahydro-5H-pyrido[2,3-d]pyrrolo[1',2':4,5]pyrazino[1,2-a]pyrimidin-5-one | Synthesized from pyrrolidine-2-carboxylic acid, 2-amino-6-bromonicotinic acid, and 2-ethynylpyridine according to General Experimentals F5, G1, G9, G17, G18, C5, B1, and A1. MS (ESI+): m/z 358 (M + H$^+$). |

| Compound | Synthesis Method & Data |
|---|---|
| Example 2.36<br>10a-methyl-3-(pyridin-2-ylethynyl)-9,10,10a,11-tetrahydro-6H-pyrido[2,3-d]pyrrolo[1',2':4,5]pyrazino[1,2-a]pyrimidin-13(8H)-one | Synthesized from pyrrolidine-2-carboxylic acid, 3-amino-5-bromopicolinic acid, and 2-ethynylpyridine according to General Experimentals F5, G1, G9, G17, G18, C5, B1, and A1. MS (ESI+): m/z 358 (M + H$^+$). |
| Example 2.37<br>8,8-dimethyl-3-(phenylethynyl)-8,9-dihydro-6H-pyrido[2,1-b]quinazolin-11(7H)-one | Synthesized from 3-methylcyclopentenone, 2-amino-4-bromobenzoic acid, and ethynylbenzene according to General Experimentals G30, C2, B1, and A1. MS (ESI+): m/z 329 (M + H$^+$). mGluR5 PAM EC$_{50}$: +++++, Fold shift at 1 μM: ++. |
| Example 2.38<br>8-fluoro-3-(pyridin-2-ylethynyl)-8-vinyl-8,9-dihydro-6H-pyrido[2,1-b]quinazolin-11(7H)-one | Synthesized from 5-hydroxypiperidin-2-one, 2-amino-4-bromobenzoic acid, and 2-ethynylpyridine according to General Experimentals F1, B1, F4, G16, G8, E1 and A1. MS (ESI+): m/z 346 (M + H$^+$). mGluR5 PAM EC$_{50}$: ++++. |
| Example 2.39<br>6-((8,8-dimethyl-11-oxo-7,8,9,11-tetrahydro-6H-pyrido[2,1-b]quinazolin-3-yl)ethynyl)nicotinonitrile | Synthesized from isobutyronitrile, 2-amino-4-bromobenzoic acid, ethynyltrimethylsilane, and 6-bromonicotinonitrile according to General Experimentals C6, B1, and A2. MS (ESI+): 355 (M + H$^+$); $^1$H NMR (300 MHz, CDCl$_3$): δ 8.92 (s, 1H), 8.29 (d, J = 8.2 Hz, 1H), 8.02-7.98 (dd, J = 8.2, 2.0 Hz, 1H), 7.86 (s, 1H), 7.68 (d, J = 8.2 Hz, 1H), 7.61 (d, J = 8.3 Hz, 1H), 3.84 (s, 2H), 3.07-3.02 (t, J = 7.1 Hz, 2H), 1.80-1.75 (t, J = 7.0 Hz, 2H), 1.13 (s, 6H). mGluR5 PAM EC$_{50}$: ++++. |

| Compound | Synthesis Method & Data |
|---|---|
| Example 2.40<br>3-((5-methoxypyridin-2-yl)ethynyl)-8,8-dimethyl-8,9-dihydro-6H-pyrido[2,1-b]quinazolin-11(7H)-one | Synthesized from isobutyronitrile, 2-amino-4-bromobenzoic acid, ethynyltrimethylsilane, and 2-bromo-5-methoxypyridine according to General Experimentals C6, B1, and A2. MS (ESI+): 360 (M + H$^+$); $^1$H NMR (300 MHz, CDCl$_3$) δ 8.36 (s, 1H), 8.24 (d, J = 8.2 Hz, 1H), 7.81 (s, 1H), 7.61-7.53 (m, 2H), 7.24-7.20 (dd, J = 8.6, 2.7 Hz, 1H), 3.92 (s, 3H), 3.82 (s, 2H), 3.06-3.02 (t, J = 7.1 Hz, 2H), 1.79-1.74 (t, J = 7.1 Hz, 2H), 1.12 (s, 6H). mGluR5 PAM EC$_{50}$: +++. |
| Example 2.41<br>8,8-dimethyl-3-((6-methylpyridin-2-yl)ethynyl)-8,9-dihydro-6H-pyrido[2,1-b]quinazolin-11(7H)-one | Synthesized from isobutyronitrile, 2-amino-4-bromobenzoic acid, and 2-ethynyl-6-methylpyridine according to General Experimentals C6, B1, and A1. MS (ESI+): 344 (M + H$^+$); $^1$H NMR (300 MHz, CDCl$_3$): δ 8.24 (d, J = 8.3 Hz, 1H), 7.84 (s, 1H), 7.64-7.59 (m, 2H), 7.42 (d, J = 7.7 Hz, 1H), 7.17 (d, J = 7.7 Hz, 1H), 3.83 (s, 2H), 3.06-3.01 (t, J = 7.1 Hz, 2H), 2.62 (s, 3H), 1.79-1.74 (t, J = 7.1 Hz, 2H), 1.12 (s, 6H). mGluR5 PAM EC$_{50}$: ++++. Fold shift at 1 μM: +++. |
| Example 2.42<br>3-((5-chloropyridin-2-yl)ethynyl)-8,8-dimethyl-8,9-dihydro-6H-pyrido[2,1-b]quinazolin-11(7H)-one | Synthesized from isobutyronitrile, 2-amino-4-bromobenzoic acid, ethynyltrimethylsilane, and 2-bromo-5-chloropyridine according to General Experimentals C6, B1, and A2. MS (ESI+): 364 (M + H$^+$); $^1$H NMR (300 MHz, CDCl$_3$) δ 8.62 (s, 1H), 8.27 (d, J = 8.2 Hz, 1H), 7.83 (s, 1H), 7.73-7.70 (dd, J = 8.3, 2.9 Hz, 1H), 7.61 (d, J = 8.2 Hz, 1H), 7.54 (d, J = 8.2 Hz, 1H), 3.84 (s, 2H), 3.06-3.02 (t, J = 7.1 Hz, 2H), 1.79-1.74 (t, J = 7.0 Hz, 2H), 1.12 (s, 6H). mGluR5 PAM EC$_{50}$: +++++. Fold shift at 1 μM: +++. |

| Compound | Synthesis Method & Data |
|---|---|
| Example 2.43<br>3-((5-fluoropyridin-2-yl)ethynyl)-8,8-dimethyl-8,9-dihydro-6H-pyrido[2,1-b]quinazolin-11(7H)-one | Synthesized from isobutyronitrile, 2-amino-4-bromobenzoic acid, ethynyltrimethylsilane, and 2-bromo-5-fluoropyridine according to General Experimentals C6, B1, and A2. MS (ESI+): 348 (M + H$^+$); $^1$H NMR (300 MHz, CDCl$_3$) δ 8.52 (d, J = 2.8 Hz, 1H), 8.26 (d, J = 8.2 Hz, 1H), 7.83 (s, 1H), 7.63-7.59 (m, 2H), 7.50-7.43 (dd, J = 9.2, 2.9 Hz, 1H), 3.84 (s, 2H), 3.06-3.02 (t, J = 7.1 Hz, 2H), 1.79-1.75 (t, J = 7.1 Hz, 2H), 1.12 (s, 6H). mGluR5 PAM EC$_{50}$: +++++. Fold shift at 1 μM: ++. |
| Example 2.44<br>8,8-dimethyl-3-(m-tolylethynyl)-8,9-dihydro-6H-pyrido[2,1-b]quinazolin-11(7H)-one | Synthesized from isobutyronitrile, 2-amino-4-bromobenzoic acid, and 1-ethynyl-3-methylbenzene according to General Experimentals C6, B1, and A1. MS (ESI+): 343 (M + H$^+$); $^1$H NMR (300 MHz, CDCl$_3$) δ 8.23 (d, J = 8.3 Hz, 1H), 7.76 (s, 1H), 7.56-7.53 (m, 1H), 7.40 (d, J = 9.7 Hz, 2H), 7.31-7.30 (m, 1H), 7.20 (d, J = 7.6 Hz, 1H), 3.84 (s, 2H), 3.06-3.02 (t, J = 7.1 Hz, 2H), 2.39 (s, 3H), 1.79-1.74 (t, J = 7.1 Hz, 2H), 1.12 (s, 6H). mGluR5 PAM EC$_{50}$: +++++. Fold shift at 1 μM: +++. |
| Example 2.45<br>3-((8,8-dimethyl-11-oxo-7,8,9,11-tetrahydro-6H-pyrido[2,1-b]quinazolin-3-yl)ethynyl)benzonitrile | Synthesized from isobutyronitrile, 2-amino-4-bromobenzoic acid, ethynyltrimethylsilane, and 3-bromobenzonitrile according to General Experimentals C6, B1, and A2. MS (ESI+): 354 (M + H$^+$); $^1$H NMR (300 MHz, CDCl$_3$): δ 8.28 (d, J = 8.2 Hz, 1h), 7.87 (s, 1H), 7.81-7.78 (m, 2H), 7.68-7.65 (m, 1H), 7.56-7.49 (m, 2H), 3.84 (s, 2H), 3.07-3.02 (t, J = 7.1 Hz, 2H), 1.84-1.75 (t, J = 7.1 Hz, 2H), 1.13 (s, 6H). mGluR5 PAM EC$_{50}$: ++++. Fold shift at 1 μM: ++. |

| Compound | Synthesis Method & Data |
|---|---|
| 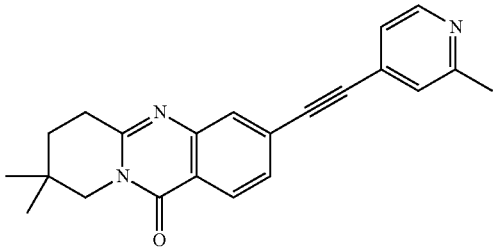<br>Example 2.46<br>8,8-dimethyl-3-((2-methylpyridin-4-yl)ethynyl)-8,9-dihydro-6H-pyrido[2,1-b]quinazolin-11(7H)-one | Synthsized from isobutyronitrile, 2-amino-4-bromobenzoic acid, ethynyltrimethylsilane, and 4-bromo-2-methylpyridine according to General Experimentals C6, B1, and A2. MS (ESI+): 344 (M + H$^+$); $^1$H NMR (300 MHz, CDCl$_3$) δ 8.54-8.53 (d, J = 5.04 Hz, 1H), 8.28-8.25 (d, J = 8.25 Hz, 1H), 7.79 (s, 1H), 7.57-7.54 (dd, J = 7.95, 1.50 Hz, 1H), 7.32 (s, 1H), 7.26-7.24 (d, J = 4.95 Hz, 1H), 3.84 (s, 2H), 3.07-3.02 (t, J = 7.11 Hz, 2H), 2.60 (s, 3H), 1.80-1.75 (t, J = 7.08 Hz, 2H), 1.13 (s, 6H). mGluR5 PAM EC$_{50}$: ++++. |
| 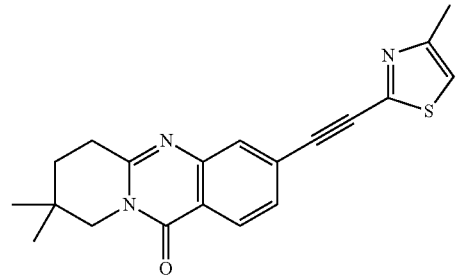<br>Example 2.47<br>8,8-dimethyl-3-((4-methylthiazol-2-yl)ethynyl)-8,9-dihydro-6H-pyrido[2,1-b]quinazolin-11(7H)-one | Synthesized from isobutyronitrile, 2-amino-4-bromobenzoic acid, ethynyltrimethylsilane, and 2-bromo-4-methylthiazole according to General Experimentals C6, B1, and A2. MS (ESI+): 350 (M + H$^+$); $^1$H NMR (300 MHz, CDCl$_3$) δ 8.27 (d, J = 8.3 Hz, 1H), 7.82 (s, 1H), 7.59 (d, J = 8.2 Hz, 1H), 7.01 (s, 1H), 3.83 (s, 2H), 3.06-3.01 (t, J = 7.1 Hz, 2H), 2.53 (s, 3H), 1.79-1.75 (t, J = 7.1 Hz, 2H), 1.12 (s, 6H). |
| 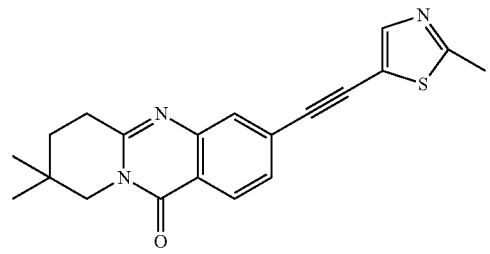<br>Example 2.49<br>8,8-dimethyl-3-((2-methylthiazol-5-yl)ethynyl)-8,9-dihydro-6H-pyrido[2,1-b]quinazolin-11(7H)-one | Synthesized from isobutyronitrile, 2-amino-4-bromobenzoic acid, ethynyltrimethylsilane, and 5-bromo-2-methylthiazole according to General Experimentals C6, B1, and A2. MS (ESI+): 350 (M + H$^+$); $^1$H NMR (300 MHz, CDCl$_3$): δ 8.24 (d, J = 8.1 Hz, 1H), 7.86 (s, 1H), 7.74 (s, 1H), 7.53-7.50 (dd, J = 8.2, 1.4 Hz, 1H), 3.84 (s, 2H), 3.06-3.01 (t, J = 7.1 Hz, 2H), 2.75 (s, 3H), 1.79-1.75 (t, J = 7.0 Hz, 2H), 1.13 (s, 6H). mGluR5 PAM EC$_{50}$: +++++. Fold shift at 1 μM: ++. |

| Compound | Synthesis Method & Data |
|---|---|
| Example 2.50<br>8,8-dimethyl-3-((5-methylthiazol-2-yl)ethynyl)-8,9-dihydro-6H-pyrido[2,1-b]quinazolin-11(7H)-one | Synthesized from isobutyronitrile, 2-amino-4-bromobenzoic acid, ethynyltrimethylsilane, and 2-bromo-5-methylthiazole according to General Experimentals C6, B1, and A2. MS (ESI+): 350 (M + H$^+$); $^1$H NMR (300 MHz, CDCl$_3$) δ 8.27 (d, J = 8.3 Hz, 1H), 7.81 (s, 1H), 7.60-7.56 (m, 2H), 3.83 (s, 2H), 3.06-3.01 (t, J = 7.1 Hz, 2h), 2.55 (s, 3H), 1.79-1.75 (t, J = 7.1 Hz, 2H), 1.12 (s, 6H). mGluR5 PAM EC$_{50}$: +++++. |
| Example 2.51<br>8,8-dimethyl-3-((3-methylisothiazol-5-yl)ethynyl)-8,9-dihydro-6H-pyrido[2,1-b]quinazolin-11(7H)-one | Synthesized from isobutyronitrile, 2-amino-4-bromobenzoic acid, ethynyltrimethylsilane, and 5-bromo-3-methylisothiazole according to General Experimentals C6, B1, and A2. MS (ESI+): 350 (M + H$^+$); $^1$H NMR (300 MHz, CDCl$_3$) δ 8.28-8.25 (d, J = 8.25 Hz, 1H), 7.77-7.760 (d, J = 1.14 Hz, 1H), 7.55-7.52 (dd, J = 8.25, 1.47 Hz, 1H), 7.20 (s, 1H), 3.84 (s, 2H), 3.07-3.02 (t, J = 7.11 Hz, 2H), 2.54 (s, 3H), 1.80-1.75 (t, J = 7.16 Hz, 2H), 1.13 (s, 6H). mGluR5 PAM EC$_{50}$: +++++. |
| Example 2.54<br>3-((5-fluoropyrimidin-2-yl)ethynyl)-8,8-dimethyl-8,9-dihydro-6H-pyrido[2,1-b]quinazolin-11(7H)-one | Synthesized from isobutyronitrile, 2-amino-4-bromobenzoic acid, ethynyltrimethylsilane, and 2-bromo-5-fluoropyrimidine according to General Experimentals C6, B1, and A2. MS (ESI+): 349 (M + H$^+$); $^1$H NMR (300 MHz, CDCl$_3$) δ 8.67 (s, 2H), 8.28 (d, J = 8.2 Hz, 1H), 7.90 (s, 1H), 7.65 (d, J = 8.31 Hz, 1H), 3.84 (s, 2H), 3.07-3.02 (t, J = 7.1 Hz, 2H), 1.81-1.77 (t, J = 7.1 Hz, 2H), 1.13 (s, 6H). mGluR5 PAM EC$_{50}$: +++. |

| Compound | Synthesis Method & Data |
|---|---|
| Example 2.55<br>8,8-dimethyl-3-(thiazolo[5,4-b]pyridin-2-ylethynyl)-8,9-dihydro-6H-pyrido[2,1-b]quinazolin-11(7H)-one | Synthesized from isobutyronitrile, 2-amino-4-bromobenzoic acid, ethynyltrimethylsilane, and 2-bromothiazolo[5,4-b]pyridine according to General Experimentals C6, B1, and A2. MS (ESI+): 387 (M + H$^+$); $^1$H NMR (300 MHz, CDCl$_3$) δ 8.80-8.60 (m, 1H), 8.37-8.30 (m, 2H), 7.90 (s, 1H), 7.67-7.64 (dd, J = 8.2, 1.4 Hz, 1H), 7.54-7.50 (m, 1H), 3.85 (s, 2H), 3.08-3.03 (t, J = 7.1 Hz, 2H), 1.81-1.76 (t, J = 7.1 Hz, 2H), 1.12 (s, 6H). |
| Example 2.58<br>3'-(pyridin-2-ylethynyl)-6',7'-dihydrospiro[oxetane-3,8'-pyrido[2,1-b]quinazolin]-11'(9'H)-one | Synthesized from tert-butyl 2-oxa-6-azaspiro[3.5]nonane-6-carboxylate, 2-amino-4-bromobenzoic acid, and 2-ethynylpyridine according to General Experimentals C4, F3, B1, and A1. mGluR5 PAM EC$_{50}$: ++++. Fold shift at 1 μM: +++. |
| Example 2.68<br>2,2-difluoro-3'-(pyridin-2-ylethynyl)-6',7'-dihydrospiro[cyclopropane-1,8'-pyrido[2,1-b]quinazolin]-11'(9'H)-one | Synthesized from tert-butyl 3-oxopiperidine-1-carboxylate, 2-amino-4-bromobenzoic acid, and 2-ethynylpyridine according to General Experimentals G22, G24, C4, F3, B1 and A1. MS (ESI+); 364 (M + H$^+$). $^1$H NMR (300 MHz, CD$_3$OD): δ 8.60 (d, J = 4.7 Hz, 1H), 8.24 (d, J = 8.2 Hz, 1H), 7.95-7.89 (m, 1H), 7.85-7.84 (d, J = 1.0 Hz, 1H), 7.75-7.67 (m, 2H), 7.50-7.45 (m, 1H), 4.28-4.11 (m, 2H), 3.21-3.11 (m, 2H), 2.24-2.01 (m, 2H), 1.64-1.48 (m, 2H). mGluR5 PAM EC$_{50}$: +++++. Fold shift at 1 μM: +++. |

| Compound | Synthesis Method & Data |
|---|---|
| 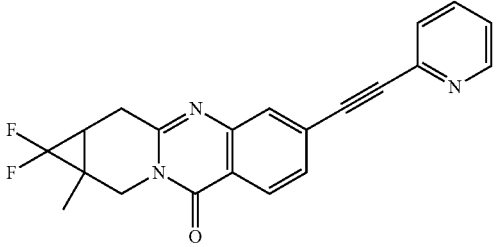<br>Example 2.69<br>1,1-difluoro-10a-methyl-5-(pyridin-2-ylethynyl)-1a,2,10,10a-tetrahydrocyclopropan[4,5]pyrido[2,1-b]quinazolin-8(1H)-one | Synthesized from benzyl 7,7-difluoro-1-methyl-3-azabicyclo[4.1.0]heptane-3-carboxylate, 2-amino-4-bromobenzoic acid, and 2-ethynylpyridine according to General Experimentals F7, F6, C4, F3, B1 and A1. MS (ESI+): 364 (M + H$^+$). $^1$H NMR (300 MHz, CDCl$_3$): δ 8.67 (d, J = 3.9 Hz, 1H), 8.27 (d, J = 8.3 Hz, 1H), 7.86 (d, J = 1.2 Hz, 1H), 7.71-7.59 (m, 3H), 7.33-7.28 (m, 1H), 5.10-5.04 (dd, J = 14.7, 3.6 Hz, 1H), 3.44 (d, J = 14.7 Hz, 1H), 3.37-3.28 (m, 1H), 2.77-2.69 (dd, J = 16.5, 7.2 Hz, 1H), 1.72-1.63 (m, 1H), 1.36 (d, J = 1.0 Hz, 3H), mGluR5 PAM EC$_{50}$: +++++. Fold shift at 1 μM: +++. |
| 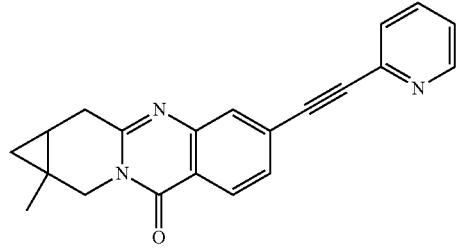<br>Example 2.70<br>10a-methyl-5-(pyridin-2-ylethynyl)-1a,2,10,10a-tetrahydrocyclopropan[4,5]pyrido[2,1-b]quinazolin-8(1H)-one | Synthesized from but-2-yn-1-ol, 3-bromoprop-1-ene, 2-amino-4-bromobenzoic acid, and 2-ethynylpyridine according to General Experimentals G21, H5, C2, B1, and A1. MS (ESI+): m/z 328 (M + H$^+$); $^1$H NMR (300 MHz, DMSO-d$_6$): δ 8.67 (d, J = 4.8 Hz, 1H), 8.17 (d, J = 8.2 Hz, 1H), 7.97-7.91 (t, J = 7.8 Hz, 1H), 7.84 (s, 1H), 7.77 (d, J = 7.8 Hz, 1H), 7.70-7.67 (dd, J = 8.2, 1.4 Hz, 1H), 7.52-7.48 (m, 1H), 4.44 (d, J = 13.9 Hz, 1H), 3.87 (d, J = 13.9 Hz, 1H), 3.41-3.34 (dd, J = 16.5, 3.9 Hz, 1H), 3.05-2.99 (dd, J = 16.5, 3.4 Hz, 1H), 1.24 (s, 3H), 1.21-1.18 (m, 1H), 0.53-0.47 (m, 2H). |
| 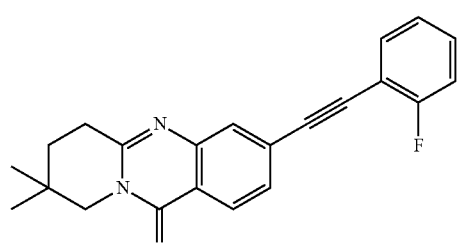<br>Example 2.73<br>3-((2-fluorophenyl)ethynyl)-8,8-dimethyl-8,9-dihydro-6H-pyrido[2,1-b]quinazolin-11(7H)-one | Synthesized from isobutyronitrile, 2-amino-4-bromobenzoic acid, and 1-ethynyl-2-fluorobenzene according to General Experimentals C6, B1, and A1. MS (ESI+): m/z 347 (M + H$^+$); $^1$H NMR (300 MHz, CDCl3) δ 8.27-8.24 (d, J = 8.25 Hz, 1H), 7.81 (s, 1H), 7.62-7.55 (m, 2H), 7.41-7.34 (m, 1H), 7.20-7.12 (m, 2H), 3.84 (s, 2H), 3.06-3.02 (t, J = 7.14 Hz, 2H), 1.79-1.75 (t, J = 6.99 Hz, 2H), 1.13 (s, 6H). mGluR5 PAM EC$_{50}$: ++++. |

| Compound | Synthesis Method & Data |
|---|---|
| Example 2.75<br>3-((4-fluorophenyl)ethynyl)-8,8-dimethyl-8,9-dihydro-6H-pyrido[2,1-b]quinazolin-11(7H)-one | Synthesized isobutyronitrile, 2-amino-4-bromobenzoic acid, ethynyltrimethylsilane, and 1-bromo-4-fluorobenzene according to General Experimentals C6, B1, and A2. MS (ESI+): 347 (M + H$^+$); $^1$H NMR (300 MHz, CDCl$_3$) δ 8.25 (d, J = 8.3 Hz, 1H), 7.76 (s, 1H), 7.59-7.53 (m, 3H), 7.12-7.06 (t, J = 8.6 Hz, 2 H), 3.84 (s, 2H), 3.06-3.02 (t, J = 7.1 Hz, 2H), 1.79-1.75 (t, J = 7.1 Hz, 2H), 1.13 (s, 6H). mGluR5 PAM EC$_{50}$: ++++. |
| Example 2.86<br>3-((3-fluoropyridin-2-yl)ethynyl)-8,8-dimethyl-8,9-dihydro-6H-pyrido[2,1-b]quinazolin-11(7H)-one | Synthesized from isobutyronitrile, 2-amino-4-bromobenzoic acid, ethynyltrimethylsilane, and 2-bromo-3-fluoropyridine according to General Experimentals C6, B1, and A2. MS (ESI+): 348 (M + H$^+$); $^1$H NMR (300 MHz, CDCl$_3$) δ 8.50-8.48 (m, 1H), 8.27 (d, J = 8.3 Hz, 1H), 7.88 (s, 1H), 7.63 (d, J = 8.2 Hz, 1H), 7.54-7.48 (td, J = 8.5, 1.2 Hz, 1H), 7.37-7.32 (m, 1H), 3.84 (s, 2H), 3.07-3.02 (t, J = 7.1 Hz, 2H), 1.80-1.75 (t, J = 7.1 Hz, 2H), 1.12 (s, 6H). mGluR5 PAM EC$_{50}$: +++++. |
| Example 2.87<br>3-((2-fluoropyridin-3-yl)ethynyl)-8,8-dimethyl-8,9-dihydro-6H-pyrido[2,1-b]quinazolin-11(7H)-one | Synthesized from isobutyronitrile, 2-amino-4-bromobenzoic acid, ethynyltrimethylsilane, and 3-bromo-2-fluoropyridine according to General Experimentals C6, B1, and A2. MS( (ESI+): 348 (M + H$^+$); $^1$H NMR (300 MHz, CDCl$_3$) δ 8.28-8.22 (m, 2H), 8.00-7.94 (m, 1H), 7.81 (s, 1H), 7.60-7.57 (m, 2H), 3.84 (s, 2H), 3.07-3.02 (t, J = 7.1 Hz, 2H), 1.80-1.75 (t, J = 7.1 Hz, 2H), 1.13 (s, 6H). mGluR5 PAM EC$_{50}$: +++++. |

| Compound | Synthesis Method & Data |
|---|---|
| Example 2.88<br>3-((6-fluoropyridin-3-yl)ethynyl)-8,8-dimethyl-8,9-dihydro-6H-pyrido[2,1-b]quinazolin-11(7H)-one | Synthesized from isobutyronitrile, 2-amino-4-bromobenzoic acid, ethynyltrimethylsilane, and 5-bromo-2-fluoropyridine according to General Experimentals C6, B1, and A2. MS (ESI+): 348 (M + H$^+$); $^1$H NMR (300 MHz, CDCl$_3$): δ 8.45 (s, 1H), 8.26 (d, J = 8.2 Hz, 1H), 7.99-7.93 (td, J = 8.3, 2.2 Hz, 1H), 7.78 (s, 1H), 7.56-7.53 (dd, J = 8.2, 1.3 Hz, 1H), 7.01-6.97 (dd, J = 8.2, 2.7 Hz, 1H), 3.84 (s, 2H), 3.07-3.02 (t, J = 7.1 Hz, 2H), 1.80-1.75 (t, J = 7.1 Hz, 2H), 1.13 (s, 6H). mGluR5 PAM EC$_{50}$: +++++. |
| Example 2.89<br>3-((5-fluoropyridin-3-yl)ethynyl)-8,8-dimethyl-8,9-dihydro-6H-pyrido[2,1-b]quinazolin-11(7H)-one | Synthesized from isobutyronitrile, 2-amino-4-bromobenzoic acid, ethynyltrimethylsilane, and 3-bromo-5-fluoropyridine according to General Experimentals C6, B1, and A2. MS (ESI+): 348 (M + H$^+$); $^1$H NMR (300 MHz, CDCl$_3$) δ 8.63 (s, 1H), 8.48 (s, 1H), 8.27 (d, J = 9.2 Hz, 1H), 7.79 (s, 1H), 7.60-7.55 (t, J = 8.7 Hz, 2H), 3.84 (s, 2H), 3.07-3.02 (t, J = 7.1 Hz, 2H), 1.79-1.75 (t, J = 7.0 Hz, 2H), 1.13 (s, 6H). mGluR5 PAM EC$_{50}$: +++++. |
| Example 2.90<br>3-((4-fluoropyridin-3-yl)ethynyl)-8,8-dimethyl-8,9-dihydro-6H-pyrido[2,1-b]quinazolin-11(7H)-one | Synthesized from isobutyronitrile, 2-amino-4-bromobenzoic acid, ethynyltrimethylsilane, and 3-bromo-4-fluoropyridine according to General Experimentals C6, B1, and A2. MS (ESI+): 348 (M + H$^+$); $^1$H NMR (300 MHz, CDCl$_3$): δ 8.80 (d, J = 9.4 Hz, 1H), 8.60-8.56 (m, 1H), 8.27 (d, J = 8.2 Hz, 1H), 7.83 (s, 1H), 7.60-7.57 (dd, J = 8.3, 1.4 Hz, 1H), 7.15-7.10 (m, 1H), 3.84 (s, 2H), 3.07-3.02 (t, J = 7.1 Hz, 2H), 1.80-1.75 (t, J = 7.1 Hz, 2H), 1.12 (s, 6H). mGluR5 PAM EC$_{50}$: +++++. |

-continued

| Compound | Synthesis Method & Data |
|---|---|
| Example 2.91<br>3-((3-fluoropyridin-4-yl)ethynyl)-8,8-dimethyl-8,9-dihydro-6H-pyrido[2,1-b]quinazolin-11(7H)-one | Synthesized from isobutyronitrile, 2-amino-4-bromobenzoic acid, ethynyltrimethylsilane, and HCl salt of 4-bromo-3-fluoropyridine according to General Experimentals C6, B1, and A2. MS (ESI+): 348 (M + H$^+$); $^1$H NMR (300 MHz, CDCl$_3$) δ 8.56 (s, 1H), 8.46-8.45 (d, J = 4.86 Hz, 1H), 8.30-8.27 (d, J = 8.25 Hz, 1H), 7.84 (s, 1H), 7.60-7.58 (d, J = 8.28 Hz, 1H), 7.48-7.44 (t, J = 6.15 Hz, 1H), 3.84 (s, 2H), 3.07-3.02 (t, J = 7.11 Hz, 2H), 1.80-1.75 (t, J = 7.08 Hz, 2H), 1.13 (s, 6H). mGluR5 PAM EC$_{50}$: +++++. |
| Example 2.92<br>3-((2-fluoropyridin-4-yl)ethynyl)-8,8-dimethyl-8,9-dihydro-6H-pyrido[2,1-b]quinazolin-11(7H)-one | Synthesized from isobutyronitrile, 2-amino-4-bromobenzoic acid, ethynyltrimethylsilane, and 4-bromo-2-fluoropyridine according to General Experimentals C6, B1, and A2. MS (ESI+): 348 (M + H$^+$); $^1$H NMR (300 MHz, CDCl$_3$) δ 8.30-8.25 (t, J = 8.4 Hz, 2H), 7.80 (s, 1H), 7.58-7.55 (dd, J = 8.2, 1.4 Hz, 1H), 7.35-7.32 (m ,1H), 7.09 (s, 1H), 3.84 (s, 2H), 3.07-3.02 (t, J = 7.1 Hz, 2H), 1.80-1.75 (t, J = 7.1 Hz, 2H), 1.13 (s, 6H). mGluR5 PAM EC$_{50}$: +++++. |
| Example 2.95<br>7-(chlorodifluoromethyl)-6-methyl-3-(pyridin-2-ylethynyl)-8,9-dihydro-6H-pyrido[2,1-b]quinazolin-11(7H)-one | Synthesized from benzyl 7,7-difluoro-1-methyl-3-azabicyclo[4.1.0]heptane-3-carboxylate, 2-amino-4-bromobenzoic acid, and 2-ethynylpyridine according to General Experimentals F7, F6, C4, F3, B1 and A1. MS (ESI+): 400, 402 (M + H$^+$). $^1$H NMR (300 MHz, CD$_3$OD): δ 8.61 (d, J = 4.8 Hz, 1H), 8.25 (d, J = 8.1 Hz, 1H), 7.96-7.88 (m, 2H), 7.75-7.68 (m, 2H), 7.51-7.46 (m, 1H), 4.64-4.57 (m, 1H), 3.94-3.84 (m, 1H), 3.43-3.38 (m, 1H), 3.09-2.91 (m, 1H), 2.52-2.42 (m, 1H), 2.08-1.95 (m, 1H), 1.63-1.60 (d, J = 7.4 Hz, 3H). |

| Compound | Synthesis Method & Data |
|---|---|
| Example 2.96<br>8-(fluoromethyl)-8-methyl-3-(pyridin-2-ylethynyl)-8,9-dihydro-6H-pyrido[2,1-b]quinazolin-11(7H)-one | Synthesized from 1-(tert-butoxycarbonyl)-3-methylpiperidine-3-carboxylic acid, 2-amino-4-bromobenzoic acid and 2-ethynylpyridine according to General Experimentals G1, C4, F3, B1, G31, E1 and A1. MS (ESI+): 348 (M + H$^+$); $^1$H NMR (300 MHz, CDCl$_3$) δ 8.68-8.67 (d, J = 4.35 Hz, 1H), 8.27-8.24 (d, J = 8.22 Hz, 1H), 7.85 (s, 1H), 7.77-7.71 (m, 1H), 7.66-7.59 (m, 2H), 7.33-7.30 (m, 1H), 4.67-4.62 (d, J = 13.80 Hz, 1H), 4.47-4.35 (dd, J = 19.73, 14.66 Hz, 1H), 3.12-3.05 (m, 2H), 2.14-2.05 (m, 2H), 1.97-1.84 (m, 2H), 1.51-1.44 (d, J = 21.90 Hz, 3H). mGluR5 PAM EC$_{50}$: +++++. Fold shift at 1 μM: +++. |
| Example 2.97<br>8-(methoxymethyl)-8-methyl-3-(pyridin-2-ylethynyl)-8,9-dihydro-6H-pyrido[2,1-b]quinazolin-11(7H)-one | Synthesized from 1-(tert-butoxycarbonyl)-3-methylpiperidine-3-carboxylic acid, 2-amino-4-bromobenzoic acid, and 2-ethynylpyridine according to General Experimentals G1, C4, F3, B1, G31, G13 and A1. MS (ESI+): 360 (M + H$^+$); $^1$H NMR (300 MHz, CDCl$_3$) δ 8.67-8.66 (dd, J = 4.83, 0.63 Hz, 1H), 8.27-8.24 (d, J = 8.25 Hz, 1H), 7.84 (d, 1H), 7.76-7.70 (dd, J = 7.80, 1.80 Hz, 1H), 7.63-7.58 (t, J = 7.77 Hz, 2H), 7.32-7.29 (m, 1H), 4.06-4.01 (d, J = 14.10 Hz, 1H), 3.93-3.83 (d, J = 13.80 Hz, 1H), 3.35 (s, 3H), 3.26-3.19 (m, 2H), 2.99-2.95 (t, J = 7.04 Hz, 2H), 2.01-1.92 (m, 1H), 1.68-1.59 (m, 1H), 1.07 (s, 3H). mGluR5 PAM EC$_{50}$: ++++. Fold shift at 1 μM: +++. |
| Example 2.98<br>1a-methyl-5-(pyridin-2-ylethynyl)-1a,2,10,10a-tetrahydrocyclopropan[4,5]pyrido[2,1-b]quinazolin-8(1H)-one | Synthesized from but-2-yn-1-ol, 3-bromoprop-1-ene, 2-amino-4-bromobenzoic acid and 2-ethynylpyridine according to General Experimentals G21, H5, C2, B1, and A1. MS (ESI+): m/z 328 (M + H$^+$); $^1$H NMR (300 MHz, DMSO-d$_6$): δ 8.68 (d, J = 4.5 Hz, 1H), 8.17 (d, J = 8.2 Hz, 1H), 7.99-7.93 (t, J = 7.8 Hz, 1H), 7.89 (s, 1H), 7.79 (d, J = 7.8 Hz, 1H), 7.70 (d, J = 8.3 Hz, 1H), 7.55-7.52 (m, 1H), 4.57-4.51 (dd, J = 14.2, 3.1 Hz, 1H), 4.07-4.02 (dd, J = 14.1, 3.0 Hz, 1H), 3.26-3.03 (m, 2H), 1.34-1.31 (m, 1H), 1.23 (s, 3H), 0.53-0.47 (m, 2H). mGluR5 PAM EC$_{50}$: +++++. Fold shift at 1 μM: +++. |

| Compound | Synthesis Method & Data |
|---|---|
| Example 2.99<br>8-(hydroxymethyl)-8-methyl-3-(pyridin-2-ylethynyl)-8,9-dihydro-6H-pyrido[2,1-b]quinazolin-11(7H)-one | Synthesized from 1-(tert-butoxycarbonyl)-3-methylpiperidine-3-carboxylic acid, 2-amino-4-bromobenzoic acid, and 2-ethynylpyridine according to General Experimentals G1, C4, F3, B1, G31 and A1. MS (ESI+): 346 (M + H+); $^1$H NMR (300 MHz, CDCl$_3$) δ 8.68 (brs, 1H), 8.27-8.25 (d, J = 8.16 Hz, 1H), 7.87 (s, 1H), 7.75-7.73 (m, 1H), 7.65-7.62 (d, J = 8.19 Hz, 2H), 7.37-7.31 (m, 1H), 4.26-4.22 (d, J = 13.84 Hz, 1H), 3.80-3.76 (d, J = 13.89 Hz, 1H), 3.44 (s, 2H), 3.03-2.98 (t, J = 7.01 Hz, 2H), 1.92-1.80 (m, 1H), 1.76-1.67 (m, 1H), 1.13 (s, 3H). mGluR5 PAM EC$_{50}$: +++. Fold shift at 1 μM: +++. |
| Example 2.100<br>3-((3-methoxypyridin-2-yl)ethynyl)-8,8-dimethyl-8,9-dihydro-6H-pyrido[2,1-b]quinazolin-11(7H)-one | Synthesized from isobutyronitrile, 2-amino-4-bromobenzoic acid, ethynyltrimethylsilane and 2-bromo-3-methoxypyridine according to General Experimentals C6, B1 and A2. MS (ESI+): 360 (M + H+); $^1$H NMR (300 MHz, CDCl$_3$) δ 8.26-8.24 (d, J = 8.31 Hz, 2H), 7.89 (s, 1H), 7.66-7.63 (d, J = 8.28 Hz, 1H), 7.32-7.29 (m, 2H), 3.97 (s, 3H), 3.84 (s, 2H), 3.08-3.03 (t, J = 7.10 Hz, 2H), 1.79-1.74 (t, J = 7.11 Hz, 2H), 1.12 (s, 6H). |
| Example 2.101<br>3-((6-methoxypyridin-2-yl)ethynyl)-8,8-dimethyl-8,9-dihydro-6H-pyrido[2,1-b]quinazolin-11(7H)-one | Synthesized from isobutyronitrile, 2-amino-4-bromobenzoic acid, ethynyltrimethylsilane and 2-bromo-6-methoxypyridine according to General Experimentals C6, B1 and A2. MS (ESI+): 360 (M + H+); $^1$H NMR (300 MHz, CDCl$_3$) δ 8.27-8.24 (d, J = 8.40 Hz, 1H), 7.87 (brs, 1H), 7.64-7.56 (m, 2H), 7.22-7.19 (d, J = 7.23 Hz, 1H), 6.79-6.76 (d, J = 8.40 Hz, 1H), 4.01 (s, 3H), 3.84 (s, 2H), 3.07 (brs, 2H), 1.80-1.75 (t, J = 6.95 Hz, 2H), 1.13 (s, 6H). mGluR5 PAM EC$_{50}$: +++. Fold shift at 1 μM: ++. |

| Compound | Synthesis Method & Data |
|---|---|
| Example 2.102<br>3-((4-methoxypyridin-2-yl)ethynyl)-8,8-dimethyl-8,9-dihydro-6H-pyrido[2,1-b]quinazolin-11(7H)-one | Synthesized from isobutyronitrile, 2-amino-4-bromobenzoic acid, ethynyltrimethylsilane and 2-bromo-4-methoxypyridine according to General Experimentals C6, B1 and A2. MS (ESI+): 360 (M + H$^+$); $^1$H NMR (300 MHz, CDCl$_3$) δ 8.48-8.46 (d, J = 5.76 Hz, 1H), 8.27-8.24 (d, J = 8.29 Hz, 1H), 7.85-7.84 (d, J = 1.02 Hz, 1H), 7.63-7.60 (dd, J = 8.24, 1.40 Hz, 1H), 7.14-7.13 (d, J = 2.43 Hz, 1H), 6.86-6.83 (dd, J = 5.81, 2.51 Hz, 1H), 3.92 (s, 3H), 3.84 (s, 2H), 3.07-3.02 (t, J = 7.13 Hz, 2H), 1.79-1.74 (t, J = 7.20 Hz, 2H), 1.12 (s, 6H). mGluR5 PAM EC$_{50}$: +++. Fold shift at 1 μM: +. |
| Example 2.103<br>1a-(hydroxymethyl)-8-(pyridin-2-ylethynyl)-1,2,3,10b-tetrahydrocyclopropan[3,4]pyrido[2,1-b]quinazolin-5(1aH)-one | Synthesized from dimethyl malonate, 1,4-dichlorobut-2-ene, 2-amino-4-bromobenzoic acid and 2-ethynylpyridine according to General Experimentals H18 and A1. MS (ESI+): 344 (M + H$^+$); $^1$H NMR (300 MHz, CDCl$_3$): δ 8.67 (d, J = 4.6 Hz, 1H), 8.22 (d, J = 8.2 Hz, 1H), 7.83 (s, 1H), 7.77-7.71 (td, J = 7.6, 1.7 Hz, 1H), 7.61-7.51 (m, 2H), 7.33-7.29 (m, 1H), 4.97-4.90 (m, 1H), 3.77 (d, J = 4.9 Hz, 2H), 3.27-3.6 (m, 1H), 2.40-2.30 (m, 2H), 2.11-2.04 (m, 1H), 1.33-1.24 (m, 2H). mGluR5 PAM EC$_{50}$: ++. |
| Example 2.104<br>(R)-8-(pyridin-2-ylethynyl)-2,3,13,13a-tetrahydro-1H-pyrrolo[1′,2′:4,5]pyrazino[2,1-b]quinazolin-11(5H)-one | Synthesized from (R)-tert-butyl 2-(aminomethyl)pyrrolidine-1-carboxylate, 2-amino-4-bromobenzoic acid and 2-ethynylpyridine according to General Experimentals H19, B1 and A1. MS (ESI+): m/z 343 (M + H$^+$); $^1$H NMR (300 MHz, DMSO-d$_6$) δ 8.69 (d, J = 4.7 Hz, 1H), 8.24 (d, J = 8.2 Hz, 1H), 8.02-7.94 (m, 2H), 7.82-7.80 (m, 2H), 7.56-7.52 (m, 1H), 4.62-4.44 (m, 3H), 4.29-4.20 (m, 2H), 3.72 (m, 1H), 3.11 (m, 1H), 2.26 (m, 1H), 2.00 (m, 1H), 1.80 (m, 2H). mGluR5 PAM EC$_{50}$: +++. |

| Compound | Synthesis Method & Data |
|---|---|
| Example 2.105<br>8,8-dimethyl-3-(pyridazin-3-ylethynyl)-8,9-dihydro-6H-pyrido[2,1-b]quinazolin-11(7H)-one | Synthesized from isobutyronitrile, 2-amino-4-bromobenzoic acid, ethynyltrimethylsilane and 3-bromopyridazine according to General Experimentals C6, B1 and A2. MS (ESI+): 331 (M + H$^+$); $^1$H NMR (300 MHz, CDCl$_3$) δ 9.21-9.19 (d, J = 3.54 Hz, 1H), 8.31-8.29 (d, J = 8.25 Hz, 1H), 7.94 (brs, 1H), 7.75-7.71 (m, 1H), 7.68-7.62 (m, 1H), 7.56-7.51 (m, 1H), 3.85 (s, 2H), 3.11 (brs, 2H), 1.81-1.76 (t, J = 7.05 Hz, 2H), 1.14 (s, 6H). mGluR5 PAM EC$_{50}$: +++. Fold shift at 1 μM: ++. |
| Example 2.106<br>3-ethynyl-8,8-dimethyl-8,9-dihydro-6H-pyrido[2,1-b]quinazolin-11(7H)-one | Synthesized from isobutyronitrile, 2-amino-4-bromobenzoic acid and ethynyltrimethylsilane according to General Experimentals C6, B1 and A2. MS (ESI+): m/z 253 (M + H$^+$); $^1$H NMR (300 MHz, CDCl$_3$) δ 8.30-8.18 (m, 1H), 7.80-7.70 (m, 1H), 7.50 (d, J = 8.3 Hz, 1H), 3.83 (s, 2H), 3.27 (s, 1H), 3.10-2.90 (m, 2H), 1.85-1.70 (m, 2H), 1.12 (s, 6H). |
| Example 3.1<br>8-fluoro-3-(pyridin-2-ylethynyl)-7,8,9,10-tetrahydroazepino[2,1-b]quinazolin-12(6H)-one | See PCT/US2010/061147. |
| Example 3.2<br>8-hydroxy-3-(pyridin-2-ylethynyl)-7,8,9,10-tetrahydroazepino[2,1-b]quinazolin-12(6H)-one | See PCT/US2010/061147. |

| Compound | Synthesis Method & Data |
|---|---|
| 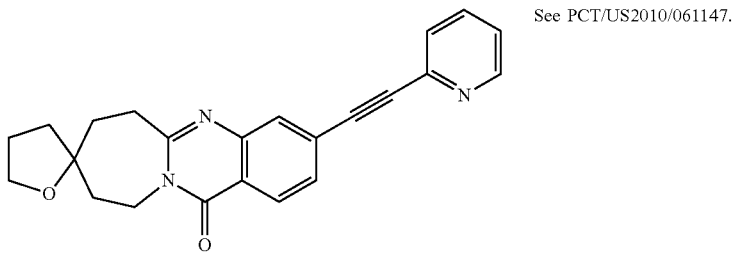<br>Example 3.3<br>3-(pyridin-2-ylethynyl)-<br>4',5',9,10-tetrahydro-3'H,6H-<br>spiro[azepino[2,1-b]quinazoline-<br>8,2'-furan]-12(7H)-one | See PCT/US2010/061147. |
| 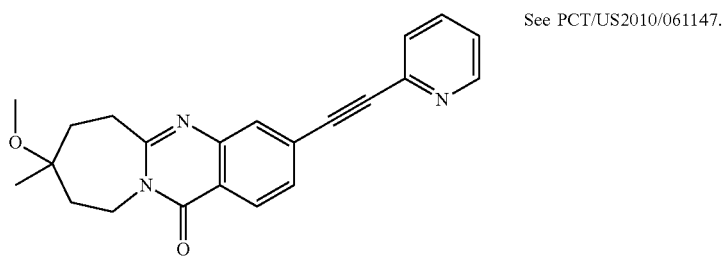<br>Example 3.4<br>8-methoxy-8-methyl-3-(pyridin-<br>2-ylethynyl)-7,8,9,10-<br>tetrahydroazepino[2,1-<br>b]quinazolin-12(6H)-one | See PCT/US2010/061147. |
| 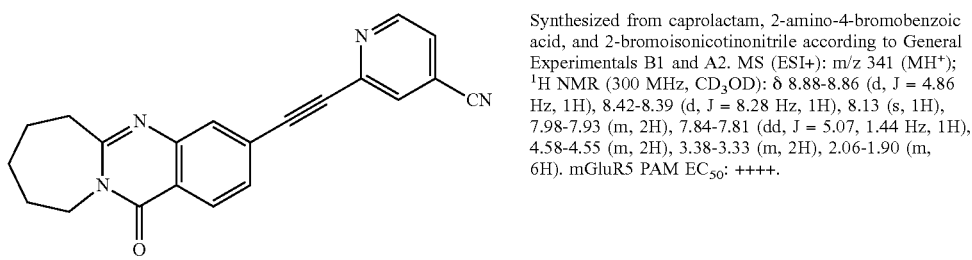<br>Example 3.5<br>2-((12-oxo-6,7,8,9,10,12-<br>hexahydroazepino[2,1-<br>b]quinazolin-3-<br>yl)ethynyl)isonicotinonitrile | Synthesized from caprolactam, 2-amino-4-bromobenzoic acid, and 2-bromoisonicotinonitrile according to General Experimentals B1 and A2. MS (ESI+): m/z 341 (MH$^+$); $^1$H NMR (300 MHz, CD$_3$OD): δ 8.88-8.86 (d, J = 4.86 Hz, 1H), 8.42-8.39 (d, J = 8.28 Hz, 1H), 8.13 (s, 1H), 7.98-7.93 (m, 2H), 7.84-7.81 (dd, J = 5.07, 1.44 Hz, 1H), 4.58-4.55 (m, 2H), 3.38-3.33 (m, 2H), 2.06-1.90 (m, 6H). mGluR5 PAM EC$_{50}$: ++++. |

| Compound | Synthesis Method & Data |
|---|---|
| 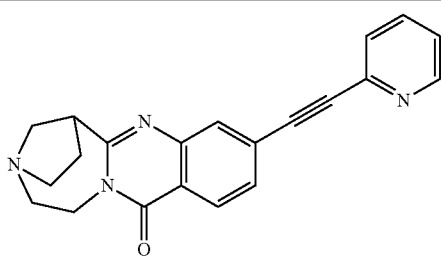<br>Example 3.6<br>9-(pyridin-2-ylethynyl)-1,2,5,6-tetrahydro-3,6-methano[1,4]diazocino[8,1-b]quinazolin-12(4H)-one | Synthesized from tert-butyl 4-oxopiperidine-1-carboxylate, 2-amino-4-bromobenzoic acid, and 2-ethynylpyridine according to General Experimentals C2, B1, F3, H3, and A1. MS (ESI+): m/z 343 (M + H$^+$); $^1$H NMR (300 MHz, CD$_3$OD) δ 8.95-8.93 (d, J = 5.61 Hz, 1H), 8.72-8.67 (t, J = 8.00 Hz, 1H), 8.38-8.34 (m, 2H), 8.15-8.10 (t, J = 6.90 Hz, 1H), 8.06 (s, 1H), 7.90-7.87 (d, J = 8.25 Hz, 1H), 5.74-5.68 (d, J = 12.26 Hz, 1H), 4.27-4.21 (t, J = 8.13 Hz, 1H), 4.15-4.05 (m, 1H), 3.94-3.72 (m, 5H), 3.61-3.53 (t, J = 12.58 Hz, 1H), 2.95-2.83 (m, 1H), 2.77-2.66 (m, 1H). mGluR5 PAM EC$_{50}$: ++. |
| 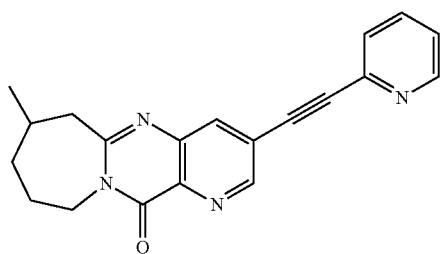<br>Example 3.7<br>7-methyl-3-(pyridin-2-ylethynyl)-7,8,9,10-tetrahydropyrido[3',2':4,5]pyrimido[1,2-a]azepin-12(6H)-one<br>and<br>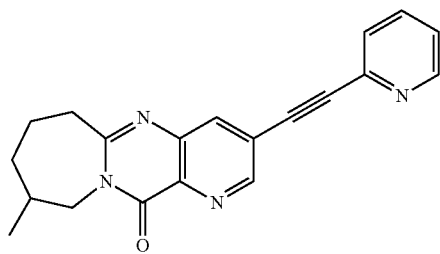<br>Example 3.28<br>9-methyl-3-(pyridin-2-ylethynyl)-7,8,9,10-tetrahydropyrido[3',2':4,5]pyrimido[1,2-a]azepin-12(6H)-one | Synthesized as a mixture from 4-methylcyclohexanone, 3-amino-5-bromopicolinic acid, and 2-ethynylpyridine according to General Experimentals C2, B2, and A1. MS (ESI+): m/z 331 (MH$^+$); $^1$H NMR (300 MHz, CDCl$_3$): δ 8.96 (d, J = 1.2 Hz, 1H), 8.68 (d, J = 4.8 Hz, 1H), 8.11-8.10 (m, 1H), 7.79-7.73 (m, 1H), 7.63-7.61 (m, 1H), 7.36-7.31 (m, 1H), 5.12-4.70 (m, 1H), 3.91-3.76 (m, 1H), 3.08-2.97 (m, 2H), 2.05-1.93 (m, 3H), 1.70-1.52 (m, 2H), 1.14-1.06 (m, 3H). mGluR5 PAM EC$_{50}$: +++. |

| Compound | Synthesis Method & Data |
|---|---|
| Example 3.8<br>3-(pyridin-2-ylethynyl)-7-(trifluoromethyl)-7,8,9,10-tetrahydropyrido[3',2':4,5]pyrimido[1,2-a]azepin-12(6H)-one | Synthesized from 3-(trifluoromethyl)cyclohexanone, 3-amino-5-bromopicolinic acid, and 2-ethynylpyridine according to General Experimentals C2, B1, and A1. MS (ESI+): m/z 385 (MH+). mGluR5 PAM $EC_{50}$: +++. |
| Example 3.9<br>3-(pyridin-2-ylethynyl)-8-(trifluoromethyl)-7,8,9,10-tetrahydropyrido[3',2':4,5]pyrimido[1,2-a]azepin-12(6H)-one | Synthesized from 4-(trifluoromethyl)cyclohexanone, 3-amino-5-bromopicolinic acid, and 2-ethynylpyridine according to General Experimentals C2, B1, and A1. MS (ESI+): m/z 385 (M + H+); $^1$H NMR (300 MHz, $CD_3OD$) δ 9.08 (s, 1H), 8.98-8.96 (d, J = 5.16 Hz, 1H), 8.71-8.66 (td, J = 7.98, 1.43 Hz, 1H), 8.48 (s, 1H), 8.39-8.36 (d, J = 7.98 Hz, 1H), 8.15-8.11 (t, J = 6.15 Hz, 1H), 5.38-5.31 (dd, J = 14.77, 6.93 Hz, 1H), 3.92-3.84 (dd, J = 14.70, 11.10 Hz, 1H), 3.51-3.33 (m, 2H), 2.88-2.78 (m, 1H), 2.46-2.42 (m, 2H), 1.86-1.64 (m, 2H). |
| Example 3.10<br>8-fluoro-8-methyl-3-(pyridin-2-ylethynyl)-7,8,9,10-tetrahydropyrido[3',2':4,5]pyrimido[1,2-a]azepin-12(6H)-one | Synthesized from azepan-4-one, 3-amino-5-bromopicolinic acid, and 2-ethynylpyridine according to General Experimentals F6, G8, E1, C4, F3, B1, and A1. MS (ESI+): m/z 349 (M + H+); $^1$H NMR (300 MHz, $CD_3OD$) δ 9.04 (s, 1H), 8.94-8.92 (d, J = 5.64 Hz, 1H), 8.65-8.60 (t, J = 7.89 Hz, 1H), 8.42 (s, 1H), 8.34-8.31 (d, J = 7.92 Hz, 1H), 8.10-8.06 (t, J = 6.60 Hz, 1H), 5.11-5.04 (dd, J = 15.16, 5.64 Hz, 1H), 4.14-4.06 (t, J = 7.35 Hz, 1H), 3.67-3.58 (t, J = 13.27 Hz, 1H), 3.02-2.95 (dd, J = 14.90, 7.16 Hz, 1H), 2.34-2.28 (m, 2H), 2.07-1.93 (m, 2H), 1.48-1.41 (d, J = 21.10 Hz, 3H). |

| Compound | Synthesis Method & Data |
|---|---|
| Example 3.11<br>8-methoxy-3-(pyridin-2-ylethynyl)-7,8,9,10-tetrahydroazepino[2,1-b]quinazolin-12(6H)-one | Synthesized from 1,4-dioxa-8-azaspiro[4.6]undecan-9-one, 2-amino-4-bromobenzoic acid, and 2-ethynylpyridine according to General Experimentals B1, F2, G7, G13, and A1. MS (ESI+): m/z 346 (M + H$^+$); $^1$H NMR (300 MHz, CDCl$_3$) δ 8.67-8.65 (d, J = 4.47 Hz, 1H), 8.25-8.22 (d, J = 8.22 Hz, 1H), 7.82 (s, 1H), 7.76-7.70 (td, J = 7.74, 1.68 Hz, 1H), 7.63-7.57 (t, J = 8.40 Hz, 2H), 7.32-7.30 (m, 1H), 4.70-4.63 (m, 1H), 4.26-4.18 (m, 1H), 3.65-3.63 (m, 1H), 3.42 (s, 3H), 3.39-3.35 (m, 1H), 2.88-2.81 (dd, J = 14.40, 8.40 Hz, 1H), 2.25-2.09 (m, 2H), 1.96-1.81 (m, 2H). |
| Example 3.12<br>4-fluoro-8-methyl-3-(pyridin-2-ylethynyl)-7,8,9,10-tetrahydroazepino[2,1-b]quinazolin-12(6H)-one | Synthesized from 4-methylcyclohexanone, 3-bromo-2-fluoroaniline, and 2-ethynylpyridine according to General Experimentals C2, D1, B1, and A1. MS (ESI+): m/z 348 (M + H$^+$); $^1$H NMR (300 MHz, CD$_3$OD) δ 8.92-8.90 (d, J = 5.13 Hz, 1H), 8.64-8.59 (t, J = 8.34 Hz, 1H), 8.31-8.29 (d, J = 8.13 Hz, 1H), 8.16-8.14 (d, J = 8.34 Hz, 1H), 8.09-8.05 (t, J = 7.17 Hz, 1H), 7.88-7.83 (t, J = 7.20 Hz, 1H), 5.19-5.12 (dd, J = 15.61, 6.30 Hz, 1H), 3.90-3.82 (t, J = 12.75 Hz, 1H), 3.61-3.45 (m, 1H), 2.15-2.01 (m, 3H), 1.47-1.29 (m, 3H), 1.05-1.03 (d, J = 6.60 Hz, 3H). |
| Example 3.13<br>8-ethyl-3-(pyridin-2-ylethynyl)-7,8,9,10-tetrahydroazepino[2,1-b]quinazolin-12(6H)-one | Synthesized from 4-ethylcyclohexanone, 2-amino-4-bromobenzoic acid, and 2-ethynylpyridine according to General Experimentals C2, B1, and A1. MS (ESI+): m/z 344 (M + H$^+$); $^1$H NMR (300 MHz, CDCl$_3$) δ 8.68-8.66 (d, J = 4.44 Hz, 1H), 8.26-8.23 (d, J = 8.22 Hz, 1H), 7.83 (s, 1H), 7.76-7.71 (td, J = 7.89, 1.71 Hz, 1H), 7.63-7.58 (t, J = 7.50 Hz, 1H), 7.33-7.30 (m, 1H), 5.24-5.17 (dd, J = 14.40, 6.60 Hz, 1H), 3.63-3.55 (dd, J = 14.40, 10.80 Hz, 1H), 3.18-2.99 (m, 2H), 2.19-2.14 (m, 2H), 1.44-1.18 (m, 4H), 0.96-0.92 (t, J = 7.43 Hz, 3H). |
| Example 3.14<br>8-ethyl-3-(pyridin-2-ylethynyl)-7,8,9,10-tetrahydropyrido[3',2':4,5]pyrimido[1,2-a]azepin-12(6H)-one | Synthesized from 4-ethylcyclohexanone, 3-amino-5-bromopicolinic acid, and 2-ethynylpyridine according to General Experimentals C2, B1, and A1. MS (ESI+): m/z 345 (M + H$^+$); $^1$H NMR (300 MHz, DMSO-d$_6$) δ 8.95-8.86 (m, 1H), 8.69 (broad, 1H), 8.24 (s, 1H), 8.02-7.97 (t, J = 7.68 Hz, 1H), 7.86-7.83 (d, J = 7.65 Hz, 1H), 7.58-7.54 (t, J = 6.00 Hz, 1H), 4.95-4.88 (dd, J = 14.40, 6.60 Hz, 1H), 3.75-3.71 (m, 1H), 3.22-3.13 (m, 1H), 3.03-2.96 (m, 1H), 2.06-1.98 (m, 2H), 1.63 (broad, 1H), 1.32-1.09 (m, 4H), 0.87-0.82 (t, J = 7.35 Hz, 3H). |

| Compound | Synthesis Method & Data |
|---|---|
| 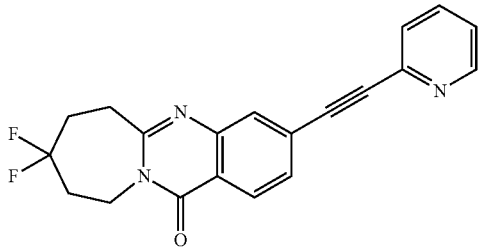<br><br>Example 3.15<br>8,8-difluoro-3-(pyridin-2-ylethynyl)-7,8,9,10-tetrahydroazepino[2,1-b]quinazolin-12(6H)-one | Synthesized from 1,4-dioxa-8-azaspiro[4.6]undecan-9-one, 2-amino-4-bromobenzoic acid, and 2-ethynylpyridine according to General Experimentals B1, F2, E2, and A1. MS (ESI+): m/z 352 (M + H$^+$); $^1$H NMR (300 MHz, CDCl$_3$) δ 8.69-8.67 (d, J = 4.95 Hz, 1H), 8.27-8.24 (d, J = 8.25 Hz, 1H), 7.88 (s, 1H), 7.77-7.71 (td, J = 7.71, 1.68 Hz, 1H), 7.68-7.65 (dd, J = 8.25, 1.35 Hz, 1H), 7.61-7.59 (d, J = 7.83 Hz, 1H), 7.34-7.29 (m, 1H), 4.49-4.46 (t, J = 4.41 Hz, 2H), 3.19-3.15 (t, J = 5.88 Hz, 2H), 2.42-2.22 (m, 4H). mGluR5 PAM EC$_{50}$: ++++, Fold shift at 10 μM: +++. |
| 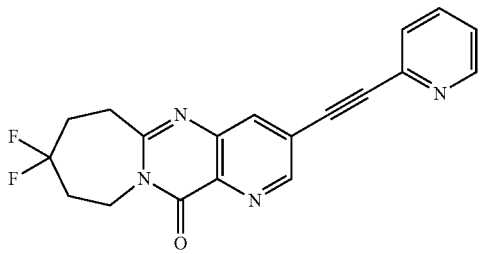<br><br>Example 3.16<br>8,8-difluoro-3-(pyridin-2-ylethynyl)-7,8,9,10-tetrahydropyrido[3',2':4,5]pyrimido[1,2-a]azepin-12(6H)-one | Synthesized from 1,4-dioxa-8-azaspiro[4.6]undecan-9-one, 3-amino-5-bromopicolinic acid, and 2-ethynylpyridine according to General Experimentals B1, F2, E2, and A1. MS (ESI+): m/z 353 (M + H$^+$); $^1$HNMR (300 MHz, CD$_3$OD) δ 9.06 (brs, 1H), 8.98-8.96 (d, J = 5.55 Hz, 1H), 8.73-8.67 (td, J = 7.98, 1.41 Hz, 1H), 8.47 (s, 1H), 8.40-8.37 (d, J = 8.01 Hz, 1H), 8.17-8.12 (m, 1H), 4.57-4.55 (m, 2H), 3.31-3.27 (m, 2H), 2.47-2.35 (m, 4H). mGluR5 PAM EC$_{50}$: ++. |
| 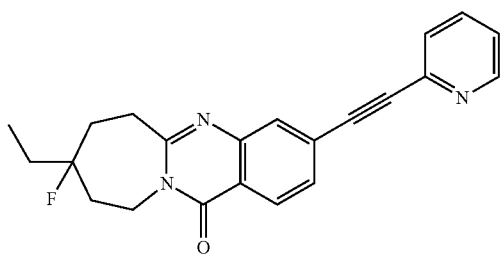<br><br>Example 3.17<br>8-ethyl-8-fluoro-3-(pyridin-2-ylethynyl)-7,8,9,10-tetrahydroazepino[2,1-b]quinazolin-12(6H)-one | Synthesized from azepan-4-one, 2-amino-4-bromobenzoic acid, and 2-ethynylpyridine according to General Experimentals F6, G8, E1, C4, F3, B1, and A1. MS (ESI+): m/z 362 (M + H$^+$); $^1$H NMR (300 MHz, CD$_3$OD) δ 8.90-8.88 (d, J = 5.13 Hz, 1H), 8.57-8.52 (t, J = 7.38 Hz, 1H), 8.45-8.42 (d, J = 8.43 Hz, 1H), 8.26-8.24 (d, J = 7.74 Hz, 1H), 8.07-7.98 (m, 3H), 5.17-5.10 (dd, J = 14.7, 5.10 Hz, 1H), 4.16-4.07 (t, J = 11.71 Hz, 1H), 3.78-3.69 (t, J = 14.46 Hz, 1H), 3.19-3.11 (dd, J = 15.60, 6.90 Hz, 1H), 2.46-2.26 (m, 2H), 2.20-1.91 (m, 2H), 1.82-1.68 (m, 2H), 1.03-0.98 (t, J = 7.50 Hz, 3H). mGluR5 PAM EC$_{50}$: ++++. |

| Compound | Synthesis Method & Data |
|---|---|
| Example 3.18<br>8-ethyl-8-fluoro-3-(pyridin-2-ylethynyl)-7,8,9,10-tetrahydropyrido[3',2':4,5]pyrimido[1,2-a]azepin-12(6H)-one | Synthesized from azepan-4-one, 3-amino-5-bromopicolinic acid, and 2-ethynylpyridine according to General Experimentals F6, G8, E1, C4, F3, B1, and A1. MS (ESI+): m/z 363 (M + H$^+$); $^1$H NMR (300 MHz, CD$_3$OD) δ 9.03 (brs, 1H), 8.92-8.91 (d, J = 5.25 Hz, 1H), 8.61-8.56 (t, J = 7.64 Hz, 1H), 8.40 (s, 1H), 8.30-8.28 (d, J = 8.46 Hz, 1H), 8.07-8.02 (t, J = 7.20 Hz, 1H), 5.14-5.07 (dd, J = 14.85, 6.15 Hz, 1H), 4.14-4.10 (t, J = 11.20 Hz, 1H), 3.67-3.58 (t, J = 13.93 Hz, 1H), 3.03-2.95 (dd, J = 17.90, 6.60 Hz, 1H), 2.34-2.29 (m, 2H), 2.05-1.85 (m, 2H), 1.78-1.69 (m, 2H), 1.02-0.97 (t, J = 7.52 Hz, 3H). mGluR5 PAM EC$_{50}$: +++. |
| Example 3.19<br>2-((8-methyl-12-oxo-6,7,8,9,10,12-hexahydroazepino[2,1-b]quinazolin-3-yl)ethynyl)isonicotinonitrile | Synthesized from 4-methylcyclohexanone, 2-amino-4-bromobenzoic acid, and 2-bromoisonicotinonitrile according to General Experimentals C2, B1, and A2. MS (ESI+): m/z 355 (M + H$^+$); $^1$H NMR (300 MHz, CD$_3$OD) δ 8.88-8.86 (d, J = 5.0 Hz, 1H), 8.41-8.39 (d, J = 8.3 Hz, 1H), 8.12 (s, 1H), 7.98-7.93 (m, 2H), 7.83-7.81 (dd, J = 5.1, 1.4 Hz, 1H), 5.23-5.17 (dd, J = 14.3, 6.4 Hz, 1H), 3.95-3.86 (m, 1H), 3.52-3.43 (m, 1H), 2.24-2.05 (m, 3H), 1.64-1.56 (m, 1H), 1.41-1.30 (m, 2H), 1.07-1.05 (d, J = 6.5 Hz, 3H). mGluR5 PAM EC$_{50}$: +++. |
| Example 3.20<br>9-methyl-2-(pyridin-2-ylethynyl)-8,9,10,11-tetrahydroazepino[1,2-b]isoquinolin-5(7H)-one | Synthesized from 4-methylcyclohexanone, 2-amino-4-bromobenzoic acid, and 2-ethynylpyridine according to General Experimentals C2, B4, B2, and A1. MS (ESI+): m/z 329 (M + H$^+$); $^1$H NMR (300 MHz, CD$_3$OD) δ 8.91 (d, J = 5.4 Hz, 1H), 8.69-8.65 (m, 1H), 8.37-8.30 (m, 2H), 8.13-8.08 (m, 1H), 7.97 (s, 1H), 7.73-7.70 (dd, J = 8.4, 1.5 Hz, 1H), 6.62 (s, 1H), 5.25-5.05 (m, 1H), 3.85-3.69 (m, 1H), 3.04-2.96 (m, 2H), 2.16-2.09 (m, 2H), 2.05-1.82 (m, 1H), 1.26-1.17 (m, 2H), 1.01 (d, J = 6.3 Hz, 3H). |

| Compound | Synthesis Method & Data |
|---|---|
| Example 3.21<br>2,8-dimethyl-3-(pyridin-2-ylethynyl)-7,8,9,10-tetrahydroazepino[2,1-b]quinazolin-12(6H)-one | Synthesized from 4-methylcyclohexanone, 3-bromo-4-methylaniline, and 2-ethynylpyridine according to General Experimentals D1, B1, and A1. MS (ESI+): m/z 344 (M + H$^+$); $^1$H NMR (300 MHz, CD$_3$OD) δ 8.92-8.90 (d, J = 5.70 Hz, 1H), 8.60-8.55 (td, J = 7.95, 1.49 Hz, 1H), 8.30-8.27 (m, 2H), 8.15-8.14 (m, 1H), 8.05-8.00 (m, 1H), 5.22-5.16 (dd, J = 14.74, 6.12 Hz, 1H), 5.11-5.05 (m, 1H), 3.94-3.86 (m, 1H), 3.63-3.56 (m, 1H), 2.59 (s, 3H), 2.18-2.11 (m, 3H), 1.54-1.49 (m, 1H), 1.38-1.33 (m, 1H), 1.08-1.05 (d, J = 6.54 Hz, 3H). |
| Example 3.22<br>1,8-dimethyl-3-(pyridin-2-ylethynyl)-7,8,9,10-tetrahydroazepino[2,1-b]quinazolin-12(6H)-one | Synthesized from 4-methylcyclohexanone, 3-bromo-5-methylaniline, and 2-ethynylpyridine according to General Experimentals D1, B1, and A1. MS (ESI+): m/z 344 (M + H$^+$); $^1$H NMR (300 MHz, CD$_3$OD) δ 8.92-8.90 (d, J = 5.13 Hz, 1H), 8.62-8.56 (td, J = 7.95, 1.46 Hz, 1H), 8.29-8.26 (d, J = 7.98 Hz, 1H), 8.07-8.03 (t, J = 7.02 Hz, 1H), 7.91 (s, 1H), 7.84 (s, 1H), 5.18-5.11 (dd, J = 15.00, 6.72 Hz, 1H), 3.91-3.82 (dd, J = 14.40, 11.10 Hz, 1H), 3.50-3.41 (t, J = 12.33 Hz, 1H), 3.27-3.22 (m, 1H), 2.92 (s, 3H), 2.23-2.04 (m, 3H), 1.64-1.52 (q, 1H), 1.41-1.31 (m, 1H), 1.07-1.04 (d, J = 6.42 Hz, 3H). mGluR5 PAM EC$_{50}$: +++. |
| Example 3.23<br>8-methoxy-3-(pyridin-2-ylethynyl)-7,8,9,10-tetrahydropyrido[3′,2′:4,5]pyrimido[1,2-a]azepin-12(6H)-one | Synthesized from 1,4-dioxa-8-azaspiro[4.6]undecan-9-one, 3-amino-5-bromopicolinic acid, and 2-ethynylpyridine according to General Experimentals B1, F2, G7, G13, and A1. MS (ESI+): m/z 347 (M + H$^+$); $^1$H NMR (300 MHz, CDCl$_3$) δ 8.67 (s, 1H), 8.40 (s, 1H), 7.82-7.72 (m, 3H), 7.61-7.55 (m, 1H), 4.93-4.87 (dd, J = 14.40, 6.90 Hz, 1H), 4.67 (s, 1H), 3.52-3.48 (m, 1H), 3.29-3.19 (m, 1H), 2.99 (s, 3H), 2.34 (s, 3H), 2.22-2.13 (m, 1H), 1.97-1.95 (m, 1H). mGluR5 PAM EC$_{50}$: ++. |

| Compound | Synthesis Method & Data |
|---|---|
| Example 3.24<br>9-fluoro-9-methyl-3-(pyridin-2-ylethynyl)-7,8,9,10-tetrahydroazepino[2,1-b]quinazolin-12(6H)-one | Synthesized from tert-butyl 3-oxoazepane-1-carboxylate, 2-amino-4-bromobenzoic acid, and 2-ethynylpyridine according to General Experimentals G8, E1, C4, B1, and A1. MS (ESI+): m/z 348 (M + H$^+$); $^1$H NMR (300 MHz, CD$_3$OD): δ 8.68-8.66 (d, J = 4.20 Hz, 1H), 8.27-8.24 (d, J = 78.22 Hz, 1H), 7.84 (s, 1H), 7.77-7.71 (td, J = 7.98, 1.74 Hz, 1H), 7.65-7.62 (dd, 8.25, 1.47 Hz, 1H), 7.61-7.58 (d, J = 7.80 Hz, 1H), 7.34-7.30 (m, 1H), 4.66-4.61 (m, 1H), 4.47-4.35 (m, 1H), 3.10-3.04 (m, 2H), 2.14-2.00 (m, 2H), 1.96-1.83 (m, 2H), 1.51-1.44 (d, J = 21.79 Hz, 3H). |
| Example 3.25<br>9-fluoro-9-methyl-3-(pyridin-2-ylethynyl)-7,8,9,10-tetrahydropyrido[3',2':4,5]pyrimido[1,2-a]azepin-12(6H)-one | Synthesized from tert-butyl 3-oxoazepane-1-carboxylate, 3-amino-5-bromopicolinic acid, and 2-ethynylpyridine according to General Experimentals G8, E1, C4, B1, and A1. MS (ESI+): m/z 349 (M + H$^+$); mGluR5 PAM EC$_{50}$: ++. |
| Example 3.26<br>9,9-difluoro-3-(pyridin-2-ylethynyl)-7,8,9,10-tetrahydropyrido[3',2':4,5]pyrimido[1,2-a]azepin-12(6H)-one | Synthesized from 1,4-dioxaspiro[4.5]decan-7-one, 3-amino-5-bromopicolinic acid, and 2-ethynylpyridine according to General Experimentals C2, B1, F2, E2, and A1. MS (ESI+): m/z 353 (M + H$^+$); mGluR5 PAM EC$_{50}$: +++. |

| Compound | Synthesis Method & Data |
|---|---|
| 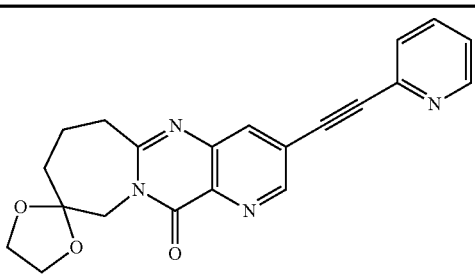<br>Example 3.29<br>3'-(pyridin-2-ylethynyl)-7',8'-dihydro-6'H-spiro[[1,3]dioxolane-2,9'-pyrido[3',2':4,5]pyrimido[1,2-a]azepin]-12'(10'H)-one | Synthesized form 1,4-dioxaspiro[4.5]decan-7-one, 3-amino-5-bromopicolinic acid, and 2-ethynylpyridine according to General Experimentals C2, B1, and A1. MS (ESI+): m/z 375 (M + H$^+$); |
| 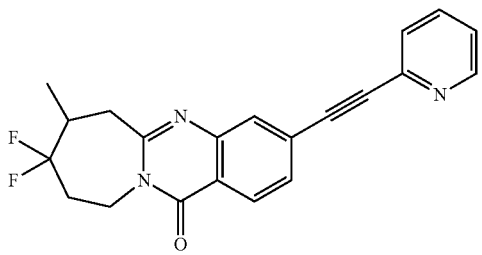<br>Example 3.30a<br>8,8-difluoro-7-methyl-3-(pyridin-2-ylethynyl)-7,8,9,10-tetrahydroazepino[2,1-b]quinazolin-12(6H)-one<br><br>and<br><br>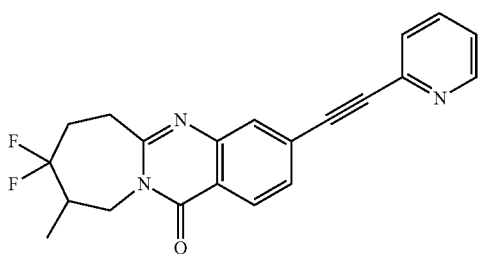<br>Example 3.30b<br>8,8-difluoro-9-methyl-3-(pyridin-2-ylethynyl)-7,8,9,10-tetrahydroazepino[2,1-b]quinazolin-12(6H)-one | Synthesized from 1,4-dioxaspiro[4.5]decan-8-one, 2-amino-4-bromobenzoic acid, and 2-ethynylpyridine according to General Experimentals G9, E2, F2, C2, B1, and A1. MS (ESI+): m/z 366 (M + H$^+$). |

| Compound | Synthesis Method & Data |
|---|---|
| 8,8-difluoro-7-methyl-3-(pyridin-2-ylethynyl)-7,8,9,10-tetrahydropyrido[3',2':4,5]pyrimido[1,2-a]azepin-12(6H)-one | Synthesized from 1,4-dioxaspiro[4.5]decan-8-one, 3-amino-5-bromopicolinic acid, and 2-ethynylpyridine according to General Experimentals G9, E2, F2, C2, B1, and A1. MS (ESI+): m/z 367 (M + H⁺); ¹H NMR (300 MHz, CDCl₃) δ 8.98 (d, J = 1.9 Hz, 1H), 8.68 (), 8.13 (s, 1H), 7.79-7.74 (m, 1H), 7.64-7.62 (m, 1H), 7.36-7.32 (m, 1H), 4.78-4.09 (m, 2H), 3.16-2.89 (m, 2H), 2.41-2.12 (m, 3H), 1.16 (d, J = 6.8 Hz, 1H), 1.11 (d, J = 6.8 Hz, 1H). |
| and | |
| 8,8-difluoro-9-methyl-3-(pyridin-2-ylethynyl)-7,8,9,10-tetrahydropyrido[3',2':4,5]pyrimido[1,2-a]azepin-12(6H)-one<br>Example 3.31 | |
| Example 3.32a<br>7-(pyridin-2-ylethynyl)-1,3a,4,12,13,13a-hexahydrofuro[3',4':4,5]azepino[2,1-b]quinazolin-10(3H)-one | Synthesized from tetrahydroisobenzofuran-1,3-dione, 2-amino-4-bromobenzoic acid, and 2-ethynylpyridine according to General Experimentals H2, C2, B1, and A1. MS (ESI+): m/z 358 (M + H⁺); ¹H NMR (300 MHz, CDCl₃) δ 8.67 (d, J = 4.5 Hz, 1H), 8.27-8.23 (dd, J = 8.2, 2.6 Hz, 1H), 7.84 (s, 1H), 7.77-7.71 (m, 1H), 7.65-7.58 (m, 2H), 7.33-7.31 (m, 1H), 4.84-4.70 (m, 1H), 4.15-4.06 (m, 1H), 4.05-3.95 (m, 2H), 3.86-3.70 (m, 2H), 3.37-3.17 (m, 1H), 3.09-3.04 (m, 1H), 2.64-2.51 (m, 2H), 2.12-1.97 (m, 2H). |
| and | |

| Compound | Synthesis Method & Data |
|---|---|
| 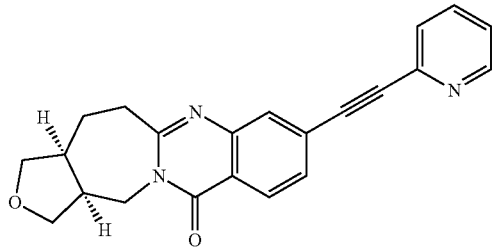<br><br>9-(pyridin-2-ylethynyl)-<br>1,3a,4,12,13,13a-<br>hexahydrofuro[3',4':5,6]azepino<br>[2,1-b]quinazolin-6(3H)-one<br>Example 3.32b | |
| 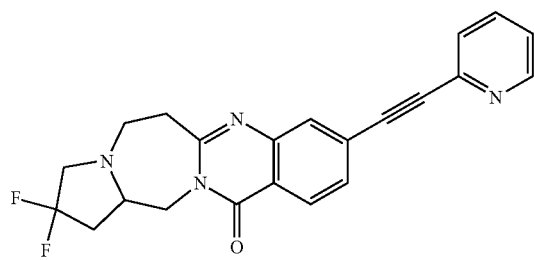<br><br>Example 3.33a<br>2,2-difluoro-9-(pyridin-2-ylethynyl)-2,3,5,6,14,14a-hexahydropyrrolo[2',1':3,4][1,4]diazepino[7,1-b]quinazolin-12(1H)-one<br><br>and | Synthesized from 1-(tert-butoxycarbonyl)-4-oxopyrrolidine-2-carboxylic acid, 2-amino-4-bromobenzoic acid, and 2-ethynylpyridine according to General Experimentals G1, E2, G2, G5, F3, G10, G11, G12, C2, B1, and A1. Example 3.33a. MS (ESI+): m/z 393 (M + H$^+$); $^1$H NMR (300 MHz, CD$_3$OD): δ 8.94-8.93 (d, J = 5.16 Hz, 1H), 8.71-8.65 (td, J = 7.97, 1.50 Hz, 1H), 8.40-8.33 (m, 2H), 8.14-8.08 (td, J = 5.91, 1.11 Hz, 1H), 8.06 (s, 1H), 7.91-7.88 (dd, J = 8.25, 1.47 Hz, 1h), 5.56-5.51 (d, J = 15.90 Hz, 1H), 4.28-4.16 (m, 2H), 3.99-3.92 (m, 2H), 3.81-3.66 (m, 2H), 3.52-3.42 (m, 2H), 3.11-2.97 (m, 1H), 2.76-2.67 (m, 1H).<br>mGluR5 PAM EC$_{50}$: +++. |
| 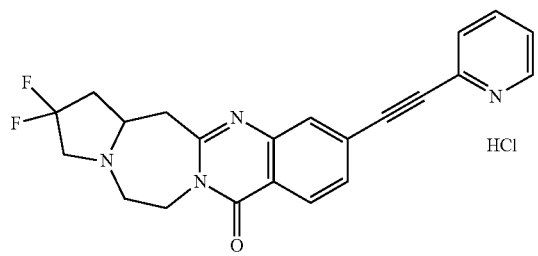<br><br>Example 3.33b<br>2,2-difluoro-11-(pyridin-2-ylethynyl)-2,3,5,6,14,14a-hexahydropyrrolo[1',2':4,5][1,4]diazepino[7,1-b]quinazolin-8(1H)-one | Example 3.33b. MS (ESI+): m/z 393 (M + H$^+$); $^1$H NMR (300 MHz, CD$_3$OD): δ 8.95-8.93 (d, J = 5.97 Hz, 1H), 8.72-8.66 (td, J = 7.99, 1.46 Hz, 1H), 8.39-8.34 (t, J = 8.04 Hz, 2H), 8.15-8.10 (t, J = 7.32 Hz, 1H), 8.06 (s, 1H), 7.90-7.87 (dd, J = 8.25, 1.38 Hz, 1H), 5.55-5.48 (dd, J = 16.39, 5.22 Hz, 1H), 4.28-4.14 (m, 2H), 4.13-3.91 (m, 3H), 3.78-3.65 (m, 1H), 3.53-3.37 (m, 2H), 3.11-2.97 (m, 1H), 2.83-2.62 (m, 1H). |

| Compound | Synthesis Method & Data |
|---|---|
| Example 3.34<br>14a-methyl-9-(pyridin-2-ylethynyl)-2,3,5,6,14,14a-hexahydropyrrolo[2',1':3,4][1,4]diazepino[7,1-b]quinazolin-12(1H)-one | Synthesized from 1-tert-butyl 2-methyl pyrrolidine-1,2-dicarboxylate, 2-amino-4-bromobenzoic acid, and 2-ethynylpyridine according to General Experimentals G9, G2, G5, F3, G10, G11, G12, C2, B1, and A1. MS (ESI+): m/z 371 (M + H$^+$); $^1$H NMR (300 MHz, CD$_3$OD) δ 8.92 (brs, 1H), 8.71-8.60 (t, J = 8.2 Hz, 1H), 8.41-8.29 (m, 2H), 8.16-8.05 (m, 2H), 7.87-7.84 (d, J = 8.1 Hz, 1H), 3.92-3.72 (m, 3H), 3.60-3.47 (m, 2H), 2.46-2.41 (m, 2H), 2.66 (brs, 3H), 1.59-1.47 (m, 2H), 1.35-1.30 (m, 1H), 1.21-1.14 (m, 2H). mGluR5 PAM EC$_{50}$: +. |
| Example 3.36a<br>8-fluoro-7-methyl-3-(pyridin-2-ylethynyl)-7,8,9,10-tetrahydroazepino[2,1-b]quinazolin-12(6H)-one | Synthesized as mixture of diasteriomers and enantiomers from methyl 5-oxozepane-4-carboxylate, 2-amino-4-bromobenzoic acid, and 2-ethynylpyridine according to General Experimentals F5, G9, G12, F5, G7, E1, C4, F3, B1, and A1. MS (ESI+): m/z 348 (M + H$^+$). |
| Example 3.36b<br>8-fluoro-9-methyl-3-(pyridin-2-ylethynyl)-7,8,9,10-tetrahydroazepino[2,1-b]quinazolin-12(6H)-one | |

| Compound | Synthesis Method & Data |
|---|---|
| 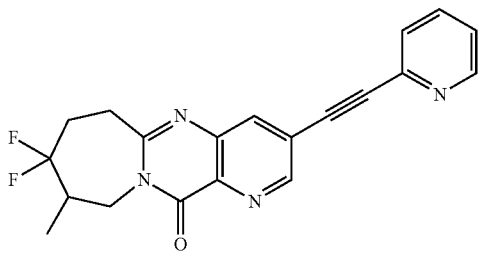<br>Example 3.37<br>8,8-difluoro-9-methyl-3-(pyridin-2-ylethynyl)-7,8,9,10-tetrahydropyrido[3',2':4,5]pyrimido[1,2-a]azepin-12(6H)-one | Synthesized from 1,4-dioxaspiro[4.5]decan-8-one, 3-amino-5-bromopicolinic acid, and 2-ethynylpyridine according to General Experimentals G9, E2, F2, C2, B1, and A1. MS (ESI+): m/z 367 (M + H$^+$). |
| 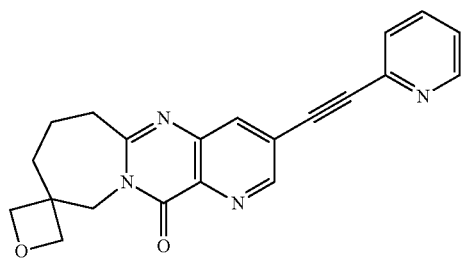<br>Example 3.38<br>3-(pyridin-2-ylethynyl)-7,8-dihydro-6H-spiro[azepino[2,1-b]quinazoline-9,3'-oxetan]-12(10H)-one | Synthesized from oxetan-3-one, nitromethane, (carbethoxymethylene)-triphenylphosphorane, 2-amino-4-bromobenzoic acid, and 2-ethynylpyridine according to General Experimentals H14 and A1. MS (ESI+): m/z 358 (M + H$^+$); $^1$H NMR (300 MHz, CDCl$_3$) δ 8.67 (d, J = 4.7 Hz, 1H), 8.27 (d, J = 8.2 Hz, 1H), 7.83 (s, 1H), 7.77-7.71 (m, 1H), 7.66-7.58 (m, 2H), 7.33-7.30 (m, 1H), 4.68 (s, 2H), 4.58 (d, J = 5.9 Hz, 2H), 4.30 (d, J = 5.9 Hz, 2H), 3.06-3.02 (m, 2H), 2.23-2.19 (m, 2H), 1.92-1.91 (m, 2H). mGluR5 PAM EC$_{50}$: ++++. |
| 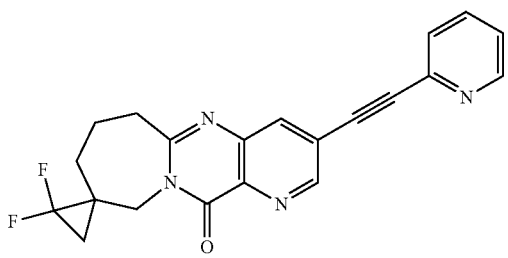<br>Example 3.40<br>2',2'-difluoro-3-(pyridin-2-ylethynyl)-7,8-dihydro-6H-spiro[azepino[2,1-b]quinazoline-9,1'-cyclopropan]-12(10H)-one | Synthesized from methyl(triphenyl)phosphonium bromide, tert-butyl 3-oxoazepane-1-carboxylate, 2-amino-4-bromobenzoic acid and 2-ethynylpyridine according to General Experimentals G22, G24, C4, F3, B1 and A1. MS (ESI+): 378 (M + H$^+$); $^1$H NMR (300 MHz, CDCl$_3$) δ 8.67 (d, J = 4.2 Hz, 1H), 8.22 (d, J = 8.2 Hz, 1H), 7.85 (s, 1H), 7.77-7.71 (td, J = 7.7, 1.6 Hz, 1H), 7.66-7.58 (m, 2H), 7.33-7.31 (m, 1H), 5.05 (d, J = 15.1 Hz, 1H), 3.97 (d, J = 15.0 Hz, 1H), 3.25-3.07 (m, 2H), 2.18-2.04 (m, 2H), 1.82-1.73 (m, 2H), 1.46-1.38 (m, 1H), 1.09-1.01 (m, 1H). mGluR5 PAM EC$_{50}$: ++++. Fold shift at 1 μM: +++. |

| Compound | Synthesis Method & Data |
|---|---|
| Example 3.42<br>8,8-dimethyl-3-(pyridin-2-ylethynyl)-9,10-dihydroazepino[2,1-b]quinazolin-12(8H)-one | Synthesized from 4,4-dimethylcyclohex-2-enone, 2-amino4-bromobenzonic and 2-ethynylpyridine according to General Experimentals C2, B1 and A1. MS (ESI+): 342 (M + H$^+$); $^1$H NMR (300 MHz, CDCl$_3$) δ 8.59-8.58 (d, J = 4.23 Hz, 1H), 8.18-8.15 (d, J = 8.22 Hz, 1H), 7.82 (s, 1H), 7.68-7.62 (m, 1H), 7.55-7.49 (t, J = 8.19 hz, 2H), 7.24-7.21 (m, 1H), 6.28-6.24 (d, J = 12.96 Hz, 1H), 6.03-5.99 (d, J = 12.96 Hz, 1H), 4.29-4.23 (m, 2H), 1.87-1.84 (m, 2H), 1.10 (s, 6H). mGluR5 PAM EC$_{50}$: +++. Fold shift at 1 μM: +++. |
| Example 4.1a<br>(E)-2-(2-(7,7-dimethyl-11-oxo-7,8,9,11-tetrahydro-6H-pyrido[2,1-b]quinazolin-3-yl)vinyl)isonicotinonitrile | Synthesized from 3-methylcyclopentenone, 2-amino-4-bromobenzoic acid, and 2-bromoisonicotinonitrile according to General Experimentals G30, C2, B1, and A1. MS (ESI+): m/z 357 (M + H$^+$); $^1$H NMR (300 MHz, CD$_3$OD) δ 8.85-8.84 (d, J = 5.19 Hz, 1H), 8.39-8.36 (d, J = 8.37 Hz, 1H), 8.11-7.96 (m, 3H), 7.81 (s, 1H), 7.69-7.60 (m, 2H), 4.22-4.18 (t, J = 6.42 Hz, 2H), 3.09 (s, 2H), 2.02-1.98 (t, J = 6.53 Hz, 2H), 1.23 (s, 6H). mGluR5 PAM EC$_{50}$: +. |
| Example 4.1b<br>(E)-2-(2-(8,8-dimethyl-11-oxo-7,8,9,11-tetrahydro-6H-pyrido[2,1-b]quinazolin-3-yl)vinyl)isonicotinonitrile | Synthesized from 3-methylcyclopentenone, 2-amino-4-bromobenzoic acid, and 2-bromoisonicotinonitrile according to General Experimentals G30, C2, B1, and A1, MS (ESI+): m/z 357 (M + H$^+$); $^1$H NMR (300 MHz, CD$_3$OD) δ 8.85-8.84 (d, J = 4.92 Hz, 1H), 8.38-8.35 (d, J = 8.58 Hz, 1H), 8.10-7.96 (m, 3H), 7.81 (s, 1H), 7.69-7.60 (m, 2H), 3.88 (s, 2H), 3.26-3.21 (m, 2H), 1.90-1.86 (t, J = 6.74 Hz, 2H), 1.97 (s, 6H). mGluR5 PAM EC$_{50}$: +. |
| Example 4.2<br>(E)-6-(2-(8,8-dimethyl-11-oxo-7,8,9,11-tetrahydro-6H-pyrido[2,1-b]quinazolin-3-yl)vinyl)nicotinonitrile | Synthesized from 3-methylcyclopentenone, 2-amino-4-bromobenzoic acid, and 6-bromonicotinonitrile according to General Experimentals G30, C2, B1, and A1. MS (ESI+): m/z 357 (M + H$^+$); $^1$H NMR (300 MHz, CD$_3$OD) δ 9.00 (s, 1H), 8.38-8.35 (d, J = 8.40 Hz, 1H), 8.30-8.27 (d, J = 8.22 Hz, 1H), 8.10-8.04 (m, 2H), 7.93-7.90 (d, J = 8.64 Hz, 2H), 7.69-7.64 (d, J = 16.03 Hz, 1H), 3.88 (s, 2H), 3.39-3.35 (m, 2H), 1.91-1.87 (t, J = 6.66 Hz, 2H), 1.20 (s, 6H). |

| Compound | Synthesis Method & Data |
|---|---|
| Example 4.3<br>(E)-8,8-dimethyl-3-(2-(4-methylthiazol-2-yl)vinyl)-8,9-dihydro-6H-pyrido[2,1-b]quinazolin-11(7H)-one | Synthesized from 3-methylcyclopentenone, 2-amino-4-bromobenzoic acid, and 2-bromo-4-methylthiazole according to General Experimentals G30, C2, B1, and A1. MS (ESI+): m/z 352 (M + H$^+$); $^1$H NMR (300 MHz, CDCl$_3$) δ 8.28-8.25 (d, J = 8.34 Hz, 1H), 7.71 (s, 1H), 7.63-7.61 (d, J = 8.43 Hz, 1H), 7.54-7.38 (q, 2H), 6.90 (s, 1H), 3.84 (s, 2H), 3.06-3.02 (t, J = 7.13 Hz, 2H), 2.51 (s, 3H), 1.79-1.75 (t, J = 7.11 Hz, 2H), 1.22 (s, 6H). mGluR5 PAM EC$_{50}$: ++++. |
| Example 4.4a<br>3-(2-chloro-2-(pyridin-2-yl)vinyl)-8,8-dimethyl-8,9-dihydro-6H-pyrido[2,1-b]quinazolin-11(7H)-one<br><br>and<br><br>Example 4.4b<br>(Z)-3-(1-chloro-2-(pyridin-2-yl)vinyl)-8,8-dimethyl-8,9-dihydro-6H-pyrido[2,1-b]quinazolin-11(7H)-one | Synthesized as a mixture of isomers by HCl addition to 8,8-dimethyl-3-(pyridin-2-ylethynyl)-8,9-dihydro-6H-pyrido[2.1-b]quinazolin-11(7H)-one, which was synthesized from 3-methylcyclopentenone, 2-amino-4-bromobenzoic acid, and 2-pyridyl acetylene according to General Experimentals G30, C2, B1, A1. The isomers were separated by column chromatography. Separated isomer 1: MS (ESI+): m/z 366 (M + H$^+$); mGluR5 PAM EC$_{50}$: +. Separated isomer 2: MS (ESI$^+$): m/z 366 (M + H$^+$); mGluR5 PAM EC$_{50}$: ++. |
| Example 4.5<br>8,8-dimethyl-3-(pyridin-2-ylmethoxy)-8,9-dihydro-6H-pyrido[2,1-b]quinazolin-11(7H)-one | Synthesized from isobutyronitrile, 2-amino-4-methoxybenzoic acid, and 2-(chloromethyl)pyridine according to General Experimentals C6, B1, G19, and G21.. MS (ESI+): m/z 336 (M + H$^+$). mGluR5 PAM EC$_{50}$: +++. |

| Compound | Synthesis Method & Data |
|---|---|
| Example 4.6<br>8,8-dimethyl-3-(1-(pyridin-2-yl)ethoxy)-8,9-dihydro-6H-pyrido[2,1-b]quinazolin-11(7H)-one | Synthesized from isobutyonitrile, 2-amino-4-methoxybenzoic acid, and 1-(pyridin-2-yl)ethanol according to General Experimentals C6, B1, G19, G20, and G21B. MS (ESI+): m/z 350 (M + H$^+$). |
| Example 4.7<br>N-(8,8-dimethyl-11-oxo-7,8,9,11-tetrahydro-6H-pyrido[2,1-b]quinazolin-3-yl)picolinamide | Synthesized from isobutyonitrile, 2-amino-4-nitrobenzoic acid, and picolinic acid according to General Experimentals C6, B5, G29 and G28. MS (ESI+): m/z 349 (M + H$^+$). mGluR5 PAM EC$_{50}$: ++. |
| Example 4.8<br>8,8-dimethyl-11-oxo-N-(pyridin-2-yl)-7,8,9,11-tetrahydro-6H-pyrido[2,1-b]quinazoline-3-carboxamide | Synthesized from isobutyronitrile, 2-aminoterephthalic acid, and pyridin-2-amine according to General Experimentals C6, B1 and G28. MS (ESI+): m/z 349 (M + H$^+$); $^1$H NMR (300 MHz, CD$_3$OD): δ 8.54-8.50 (m, 3H), 8.37 (d, J = 1.2 Hz, 1H), 8.30 (d, J = 8.4 Hz, 1H), 7.96 (d, J = 8.4 Hz, 1H), 7.74-7.70 (m, 1H), 3.91 (s, 2H), 3.38-3.33 (t, J = 6.9 Hz, 2H), 1.91-1.86 (t, J = 6.9 Hz, 2H), 1.20 (s, 6H). mGluR5 PAM EC$_{50}$: ++. |
| Example 4.9<br>8,8-dimethyl-11-oxo-N-(pyridin-4-yl)-7,8,9,11-tetrahydro-6H-pyrido[2,1-b]quinazoline-3-carboxamide | Synthesized from isobutyronitrile, 2-aminoterephthalic acid and pyridin-4-amine according to General Exaperimental C6, B1 and G28. MS (ESI+): m/z 349 (M + H$^+$); $^1$H NMR (300 MHz, DMSO-d$_6$): δ 8.80 (d, J = 6.9 Hz, 2H), 8.44 (d, J = 6.6 Hz, 2H), 8.35 (s, 1H), 8.28 (d, J = 8.4 Hz, 1H), 8.08 (d, J = 8.1 Hz, 1H), 3.92 (s, 2H), 3.04-2.99 (t, J = 6.8 Hz, 2H), 1.72-1.67 (t, J = 6.8 Hz, 2H), 1.04 (s, 6H). |

| Compound | Synthesis Method & Data |
|---|---|
| 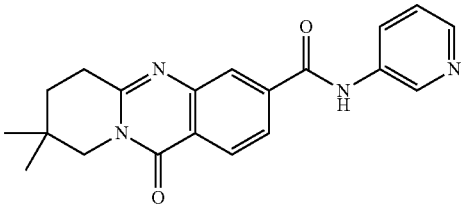<br>Example 4.10<br>8,8-dimethyl-11-oxo-N-(pyridin-3-yl)-7,8,9,11-tetrahydro-6H-pyrido[2,1-b]quinazoline-3-carboxamide | Synthesized from isobutyronitrile, 2-aminoterephthalic acid and pyridin-3-amine according to General Exaperimental C6, B1 and G28. MS (ESI+): m/z 349 (M + H$^+$); $^1$H NMR (300 MHz, CD$_3$OD): δ 9.65 (s, 1H), 8.86 (d, J = 8.7 Hz, 1H), 8.68 (d, J = 5.4 Hz, 1H), 8.50 (d, J = 8.4 Hz, 1H), 8.34 (s, 1H), 8.29 (d, J = 8.4 Hz, 1H), 8.18-8.13 (dd, J = 8.7, 5.7 Hz, 1H), 3.90 (s, 2H), 3.41-3.36 (t, J = 6.9 Hz, 2H), 1.91-1.86 (t, J = 6.9 Hz, 2H), 1.20 (s, 6H). |
| 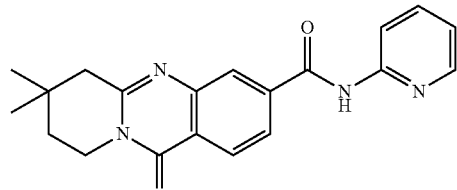<br>Example 4.11<br>7,7-dimethyl-11-oxo-N-(pyridin-2-yl)-7,8,9,11-tetrahydro-6H-pyrido[2,1-b]quinazoline-3-carboxamide | Synthesized from 3-methylcyclopent-2-enone, 2-aminoterephthalic acid and pyridin-2-amine according to General Exaperimental G30, C2, B1 and G28. MS (ESI+): m/z 349 (M + H$^+$); $^1$H NMR (300 MHz, CD$_3$OD): δ 8.55-8.52 (m, 3H), 8.38 (s, 1H), 8.30 (d, J = 8.4 Hz, 1H), 7.96 (d, J = 9.0 Hz, 1H), 7.75-7.70 (m, 1H), 4.23-4.18 (t, J = 6.3 Hz, 2H), 3.10 (s, 2H), 2.02-1.97 (t, J = 6.3 Hz, 2H), 1.23 (s, 6H). mGluR5 PAM EC$_{50}$: ++. Fold shift at 1 μM: +. |
| 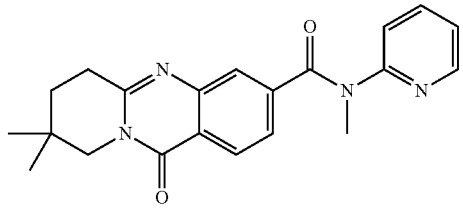<br>Example 4.12<br>N-8,8-trimethyl-11-oxo-N-(pyridin-2-yl)-7,8,9,11-tetrahydro-6H-pyrido[2,1-b]quinazoline-3-carboxamide | Synthesized from isobutyonitrile, 2-aminoterephthalic acid and N-methylpyridin-2-amine according to General Experimental C6, B1 and G28. MS (ESI+): m/z 363 (M + H$^+$); $^1$H NMR (300 MHz, CD$_3$OD): δ 8.32 (d, J = 3.9 Hz, 1H), 8.20 (d, J = 8.1 Hz, 1H), 7.82-7.80 (m, 1H), 7.64 (s, 1H), 7.61-7.58 (m, 1H), 7.39 (d, J = 8.4 Hz, 1H), 7.31-7.26 (m, 1H), 3.82 (s, 2H), 3.59 (s, 3H), 3.31-3.25 (t, J = 6.9 Hz, 2H), 1.86-1.81 (t, J = 6.9 Hz, 2H), 1.16 (s, 6H). |
| 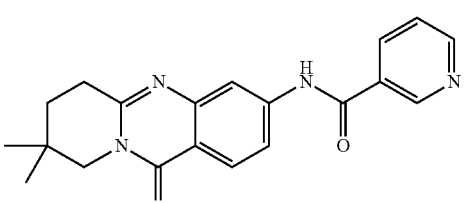<br>Example 4.14<br>N-(8,8-dimethyl-11-oxo-7,8,9,11-tetrahydro-6H-pyrido[2,1-b]quinazolin-3-yl)nicotinamide | Synthesized from isobutyronitrile, 2-amino-4-nitrobenzoic acid, and nicotinic acid according to General Experimentals C6, B1, G29, G26 and G27. MS (ESI+): m/z 349 (M + H$^+$); $^1$H NMR (300 MHz, CD$_3$OD): δ 9.42 (s, 1H), 9.03 (m, 2H), 8.66 (d, J = 1.8 Hz, 1H), 8.35 (d, J = 8.7 Hz, 1H), 8.18-8.15 (m, 1H), 7.89-7.85 (dd, J = 6.0, 1.8 Hz, 1H), 3.87 (s, 2H), 3.36-3.32 (t, J = 6.9 Hz, 2H), 1.89-1.84 (t, J = 6.9 Hz, 2H), 1.19 (s, 6H). |

| Compound | Synthesis Method & Data |
|---|---|
| Example 4.15<br>N-(8,8-dimethyl-11-oxo-7,8,9,11-tetrahydro-6H-pyrido[2,1-b]quinazolin-3-yl)isonicotinamide | Synthesized from isobutyonitrile, 2-amino-4-nitrobenzoic acid, and isonicotinic acid according to General Experimentals C6, B1, G29, G26 and G27. MS (ESI+): m/z 349 (M + H$^+$); $^1$H NMR (300 MHz, CD$_3$OD): δ 9.09 (d, J = 5.4 Hz, 2H), 8.65 (d, J = 1.8 Hz, 1H), 8.53 (d, J = 5.1 Hz, 2H), 8.37-8.34 (d, J = 8.7 Hz, 1H), 7.92-7.88 (dd, J = 8.7, 1.8 Hz, 1H), 3.88 (s, 2H), 3.36-3.33 (t, J = 6.9 Hz, 2H), 1.90-1.85 (t, J = 6.9 Hz, 2H), 1.19 (s, 6H). |
| Example 4.16<br>N-(8,8-dimethyl-11-oxo-7,8,9,11-tetrahydro-6H-pyrido[2,1-b]quinazolin-3-yl)-N-methylpicolinamide | Synthesized from isobutyronitrile, 2-amino-4-bromobenzoic acid, 33% methylamine in ethanol and picolinic acid according to General Experimentals C6, B1, G32, G26 and G27. MS (ESI+): m/z 363 (M + H$^+$); $^1$H NMR (300 MHz, DMSO-d$_6$): δ 8.30 (d, J = 4.8 Hz, 1H), 8.00 (d, J = 8.7 Hz, 1H), 7.91-7.86 (m, 1H), 7.70 (d, J = 8.5 Hz, 1H), 7.55 (s, 1H), 7.39-7.34 (m, 2H), 3.68 (s, 2H), 3.48 (s, 3H), 3.11-3.07 (t, J = 6.9 Hz, 2H), 1.69-1.64 (t, J = 6.9 Hz, 2H), 1.04 (s, 6H). |
| Example 4.17<br>2,2-dimethyl-9-oxo-N-(pyridin-2-yl)-1,2,3,9-tetrahydropyrrolo[2,1-b]quinazoline-6-carboxamide | Synthesized from 4,4-dimethylpyrrolidin-2-one, 2-aminoterephthalic acid and pyridin-2-amine according to General Exaperimental B1 and G28. MS (ESI+): m/z 335 (M + H$^+$); $^1$H NMR (300 MHz, CD$_3$OD): δ 8.56-8.47 (m, 3H), 8.36 (d, J = 1.2 Hz, 1H), 8.25 (d, J = 8.1 Hz, 1H), 7.90 (d, J = 8.4 Hz, 1H), 7.76-7.74 (m, 1H), 4.01 (s, 2H), 3.25 (s, 2H), 1.36 (s, 6H). mGluR5 PAM EC$_{50}$: +. |
| Example 4.18<br>N-(2,2-dimethyl-9-oxo-1,2,3,9-tetrahydropyrrolo[2,1-b]quinazolin-6-yl)picolinamide | Synthesized from 4,4-dimethylpyrrolidin-2-one, 2-amino-4-nitrobenzoic acid, and picolinic acid to General Experimentals B1, G29, G26 and G2. MS (ESI+): m/z 335 (M + H$^+$); $^1$H NMR (300 MHz, CD$_3$OD): δ 8.82 (d, J = 4.5 Hz, 1H), 8.71 (s, 1H), 8.40-8.32 (m, 2H), 8.24-8.18 (m, 1H), 8.01-7.98 (m, 1H), 7.81-7.77 (m, 1H), 4.13 (s, 2H), 3.42 (s, 2H), 1.40 (s, 6H). mGluR5 PAM EC$_{50}$: +. |

| Compound | Synthesis Method & Data |
|---|---|
| Example 5.1<br>8-methyl-3-(2-(4-methylthiazol-2-yl)vinyl)-7,8,9,10-tetrahydroazepino[2,1-b]quinazolin-12(6H)-one | Synthesized from 4-methylcyclohexanone, 2-amino-4-bromobenzoic acid, and 2-bromo-4-methylthiazole according to General Experimentals C2, B1, and A1. MS (ESI+): m/z 352 (M + H+); 1H NMR (300 MHz, CD3OD): δ 8.26-8.23 (d, J = 8.31 Hz, 1H), 7.70 (s, 1H), 7.63-7.61 (d, J = 8.37 Hz, 1H), 7.53-7.38 (q, 2H), 6.90 (s, 1H), 5.25-5.12 (m, 1H), 3.64-3.56 (m, 1H), 3.11-3.05 (m, 2H), 2.51 (s, 3H), 2.12-2.06 (m, 3H), 1.39 (s, 2H), 1.03-1.00 (d, J = 6.60 Hz, 3H). |
| Example 5.2<br>(E)-2-(2-(8-methyl-12-oxo-6,7,8,9,10,12-hexahydroazepino[2,1-b]quinazolin-3-yl)vinyl)isonicotinonitrile | Synthesized from 4-methylcyclohexanone, 2-amino-4-bromobenzoic acid, and 2-bromoisonicotinonitrile according to General Experimentals C2, B1, and A1. MS (ESI+): m/z 357 (M + H+); 1H NMR (300 MHz, CD3OD): δ 8.85-8.84 (d, J = 5.01 Hz, 1H), 8.38-8.35 (d, J = 8.40 Hz, 1H), 8.11-7.96 (m, 3H), 7.84 (s, 1H), 7.69-7.65 (m, 2H), 5.25-5.18 (m, 1H), 3.96-3.83 (m, 1H), 3.51-3.47 (m, 1H), 3.23-3.21 (m, 1H), 2.20-2.03 (m, 3H), 1.65-1.61 (m, 1H), 1.22-1.17 (m, 1H), 1.07-1.05 (d, J = 6.45 Hz, 3H). |
| Example 5.3a<br>(E)-8,8-difluoro-7-methyl-3-(2-(pyridin-2-yl)vinyl)-7,8,9,10-tetrahydroazepino[2,1-b]quinazolin-12(6H)-one | Synthesized from 1,4-dioxaspiro[4.5]decan-8-one, 2-amino-4-bromobenzoic acid, and 2-vinylpyridine according to General Experimentals G9, E2, F2, C2, B1, and A1. Mixture of Example 5.3a and Example 5.3b. MS (ESI+): m/z 368 (M + H+). |
| Example 5.3b<br>(E)-8,8-difluoro-9-methyl-3-(2-(pyridin-2-yl)vinyl)-7,8,9,10-tetrahydroazepino[2,1-b]quinazolin-12(6H)-one | |

| Compound | Synthesis Method & Data |
|---|---|
| Example 5.4<br>8,8-difluoro-12-oxo-N-(pyridin-2-yl)-6,7,8,9,10,12-hexahydroazepino[2,1-b]quinazoline-3-carboxamide | Synthesized from 1,4-dioxaspiro[4.5]decan-8-one, 2-aminoterephthalic acid, and pyridin-2-amine according to General Exaperimental E2, F2, C2, B1 and G28. MS (ESI+): m/z 371 (M + H⁺); $^1$H NMR (300 MHz, DMSO-d$_6$): δ 11.47 (s, 1H), 8.45 (d, J = 3.6 Hz, 1H), 8.27-8.18 (m, 3H), 8.10-8.00 (m, 2H), 7.33-7.28 (m, 1H), 4.42-4.38 (m, 2H), 3.18-3.14 (m, 2H), 2.36-2.27 (m, 4H). mGluR5 PAM EC$_{50}$: +. |
| Example 5.5<br>N-(8,8-difluoro-12-oxo-6,7,8,9,10,12-hexahydroazepino[2,1-b]quinazolin-3-yl)picolinamide | Synthesized from 1,4-dioxaspiro[4.5]decan-8-one, 2-amino-4-nitrobenzoic acid and picolinic acid according to General Experimentals E2, F2, C2, B1, G29, G26 and G27. MS (ESI+): m/z 371 (M + H⁺); $^1$H NMR (300 MHz, DMSO-d$_6$): δ 11.30 (s, 1H), 8.79 (d, J = 4.5 Hz, 1H), 8.57 (s, 1H), 8.22-8.08 (m, 4H), 7.76-7.71 (m, 1H), 4.42-4.37 (m, 2H), 3.41-3.33 (m, 2H), 2.49-2.35 (m, 4H). |
| Example 6.1<br>8,8-dimethyl-3-(pyridin-2-yloxy)-8,9-dihydro-6H-pyrido[2,1-b]quinazolin-11(7H)-one | Synthesized from isobutyonitrile, 2-amino-4-methoxybenzoic acid, and 2-iodopyridine according to General Experimentals C6, B1, G19 and G21. MS (ESI+): 322 (M + H⁺). $^1$H NMR (300 MHz, CD$_3$OD): δ 8.36 (d, J = 8.7 Hz, 1H), 8.28-8.27 (m, 1H), 8.03-7.99 (t, J = 7.3 Hz, 1H), 7.51-7.47 (dd, J = 6.0, 2.1 Hz, 1H), 7.42 (s, 1H), 7.35-7.31 (m, 1H), 7.25-7.22 (d, J = 8.1 Hz, 1H), 3.88 (s, 2H), 3.29-3.24 (t, J = 6.8 Hz, 2H), 1.89-1.84 (t, J = 6.8 Hz, 2H), 1.19 (s, 6H). |
| Example 6.2<br>8,8-dimethyl-3-(pyridin-2-ylamino)-8,9-dihydro-6H-pyrido[2,1-b]quinazolin-11(7H)-one | Synthesized from isobutyronitrile, 2-amino-4-bromobenzoic acid, and pyridin-2-amine according to General Experimentals C6, B1 and G32. MS (ESI+): 321 (M + H⁺); $^1$H NMR (300 MHz, CD$_3$OD): δ 8.35-8.23 (m, 3H), 7.99-7.93 (t, J = 8.4 Hz, 1H), 7.60-7.56 (dd, J = 8.7, 2.1 Hz, 1H), 7.24 (d, J = 8.4 Hz, 1H), 7.18-7.13 (m, 1H), 3.86 (s, 2H), 3.27-3.21 (t, J = 6.9 Hz, 2H), 1.88-1.83 (t, J = 6.9 Hz, 2H), 1.18 (s, 6H). mGluR5 PAM EC$_{50}$: +. |

| Compound | Synthesis Method & Data |
|---|---|
| 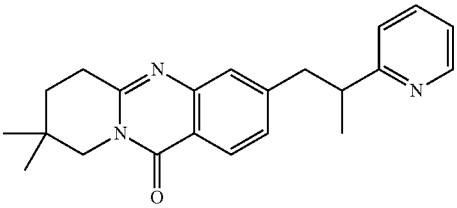<br>Example 6.3<br>8,8-dimethyl-3-(2-(pyridin-2-yl)propyl)-8,9-dihydro-6H-pyrido[2,1-b]quinazolin-11(7H)-one | Synthesized from isobutyronitrile, 2-amino-4-bromobenzoic acid, and 2-(prop-1-en-2-yl)pyridine according to General Experimentals C6, B1, A1 and G33. MS (ESI+): 348 (M + H$^+$); $^1$H NMR (300 MHz, CDCl$_3$): δ 8.58 (d, J = 4.1 Hz, 1H), 8.11 (d, J = 8.1 Hz, 1H), 7.54-7.51 (m, 1H), 7.38 (s, 1H), 7.17-7.11 (m, 2H), 7.03 (d, J = 7.8 Hz, 1H), 3.81 (s, 2H), 3.28-3.24 (m, 2H), 3.05-2.98 (m, 3H), 1.77-1.72 (t, J = 7.0 Hz, 2H), 1.33 (d, J = 6.5 Hz, 3H), 1.10 (s, 6H). |
| 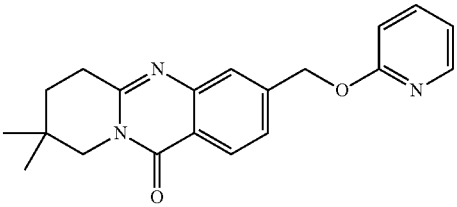<br>Example 6.4<br>8,8-dimethyl-3-((pyridin-2-yloxy)methyl)-8,9-dihydro-6H-pyrido[2,1-b]quinazolin-11(7H)-one | Synthesized from isobutyronitrile, dimethyl 2-aminoterephthalate, sodium acetate, 2-chloropyridine and 18-crown-6 according to General Experimentals G31, C6, B1, G1, G2 and G21. MS (ESI+): m/z 336 (M + H$^+$); $^1$H NMR (300 MHz, CD$_3$OD): δ 8.33 (d, J = 8.3 Hz, 1H), 8.26-8.24 (m, 1H), 8.08-8.02 (td, J = 8.1, 1.8 Hz, 1H), 7.84 (d, J = 8.3 Hz, 1H), 7.79 (s, 1H), 7.27-7.20 (m, 2H), 5.71 (s, 2H), 3.87 (s, 2H), 3.34-3.29 (t, J = 6.9 Hz, 2H), 1.89-1.84 (t, J = 6.9 Hz, 2H), 1.18 (s, 6H). mGluR5 PAM EC$_{50}$: ++. |
| 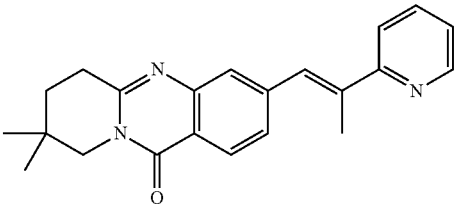<br>Example 6.5<br>(E)-8,8-dimethyl-3-(2-(pyridin-2-yl)prop-1-en-1-yl)-8,9-dihydro-6H-pyrido[2,1-b]quinazolin-11(7H)-one | Synthesized from isobutyronitrile, 2-amino-4-bromobenzoic acid and 2-(prop-1-en-2-yl)pyridine according to General Experimentals C6, B1 and A1. MS (ESI+): 346 (M + H$^+$); $^1$H NMR (300 MHz, CD$_3$OD): δ 8.86-8.83 (dd, J = 6.0, 1.0 Hz, 1H), 8.73-8.67 (td, J = 8.1, 1.5 Hz, 1H), 8.45-8.40 (m, 2H), 8.11-8.06 (m, 1H), 7.90-7.86 (m, 2H), 7.64 (s, 1H), 3.85 (s, 2H), 3.41-3.36 (t, J = 6.8 Hz, 2H), 2.53 (d, J = 1.20 Hz, 3H), 1.92-1.87 (t, J = 6.8 Hz, 2H), 1.20 (s, 6H). mGluR5 PAM EC$_{50}$: ++. |
| 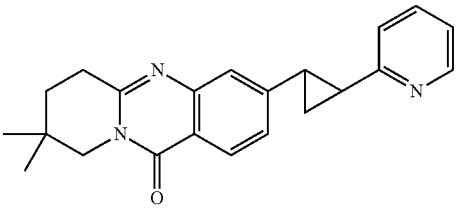<br>Example 6.6<br>8,8-dimethyl-3-(2-(pyridin-2-yl)cyclopropyl)-8,9-dihydro-6H-pyrido[2,1-b]quinazolin-11(7H)-one | Synthesized from isobutyronitrile, 2-amino-4-bromobenzoic acid and 2-vinylpyridine according to General Experimentals C6, B1, A1 and G23. MS (ESI+): 346 (M + H$^+$); $^1$H NMR (300 MHz, CD$_3$OD): δ 8.70 (d, J = 5.1 Hz, 1H), 8.55-8.50 (t, J = 8.1 Hz, 1H), 8.30 (d, J = 8.7 Hz, 1H), 7.93-7.90 (m, 2H), 7.62-7.59 (m, 2H), 3.87 (s, 2H), 3.32-3.27 (t, J = 6.9 Hz, 2H), 3.10-3.03 (m, 1H), 2.90-2.88 (m, 1H), 2.17-2.10 (m, 2H), 1.89-1.84 (t, J = 6.9 Hz, 2H), 1.18 (s, 6H). |

| Compound | Synthesis Method & Data |
|---|---|
| Example 6.7<br>8,8-dimethyl-3-(2-(pyridin-2-yl)acetyl)-8,9-dihydro-6H-pyrido[2,1-b]quinazolin-11(7H)-one | Synthesized from isobutyronitrile, 2-amino-4-bromobenzoic acid and 2-ethynylpyridine according to General Experimentals C6, B1, A1 and G34. MS (ESI+): 348 (M + H$^+$). $^1$H NMR (300 MHz, CD$_3$OD): δ 8.96 (d, J = 5.8 Hz, 1H), 8.69-8.67 (m, 1H), 8.56-8.53 (m, 1H), 8.40-8.37 (m, 2H), 8.15-8.06 (m, 2H), 3.91-3.88 (s, 2H), 3.38-3.33 (t, J = 6.6 Hz, 2H), 1.92-1.87 (t, J = 6.6 Hz, 2H), 1.20 (s, 6H). Note: The protons of COCH$_2$ exchanged with deuterium in the NMR sample. mGluR5 PAM EC$_{50}$: +++. |
| Example 6.8<br>8,8-dimethyl-3-(2-(pyridin-2-yl)propanoyl)-8,9-dihydro-6H-pyrido[2,1-b]quinazolin-11(7H)-one | Synthesized from isobutyronitrile, 2-amino-4-bromobenzoic acid, 2-ethynylpyridine and MeI according to General Experimentals C6, B1, A1, G34 and G9. MS (ESI+): 362 (M + H$^+$); $^1$H NMR (300 MHz, DMSO-d$_6$): δ 8.54 (d, J = 4.4 Hz, 1H), 8.19-8.16 (m, 2H), 8.04-7.93 (m, 2H), 7.71-7.68 (d, J = 8.1 Hz, 1H), 7.44-7.41 (m, 1H), 5.33-5.31 (m, 1H), 3.73 (s, 2H), 3.02-2.97 (t, J = 7.0 Hz, 2H), 1.69-1.64 (t, J = 7.0 Hz, 2H), 1.53-1.51 (d, J = 6.8 Hz, 3H), 1.02 (s, 6H). |
| Example 6.9<br>3-(1-chloro-2-hydroxy-1-(pyridin-2-yl)propan-2-yl)-8,8-dimethyl-8,9-dihydro-6H-pyrido[2,1-b]quinazolin-11(7H)-one | Synthesized from isobutyronitrile, 2-amino-4-bromobenzoic acid and 2-ethynylpyridine according to General Experimentals C6, B1, A1, G34 and G8. Converted to HCl salt. MS (ESI+): 398, 401 (M + H$^+$); $^1$H NMR (300 MHz, D$_2$O): δ 8.62 (d, J = 5.5 Hz, 1H), 8.33-8.28 (m, 1H), 8.23 (d, J = 8.4 Hz, 1H), 7.90-7.87 (m, 1H), 7.84-7.80 (m, 1H), 7.73-7.70 (m, 2H), 5.69 (s, 1H), 3.80 (s, 2H), 3.27-3.22 (t, J = 6.7 Hz, 2H), 1.80-1.75 (t, J = 6.7 Hz, 2H), 1.56 (s, 3H), 1.06 (s, 6H). |
| Example 6.10<br>8,8-dimethyl-3-(3-(pyridin-2-yl)propyl)-8,9-dihydro-6H-pyrido[2,1-b]quinazolin-11(7H)-one | Synthesized from isobutyronitrile, dimethyl 2-aminoterephthalate, 2-ethynylpyridine and 6M HCl according to General Experimentals G31, C6, B1, G1, G2, G16, G38, G33, G14 and G33. MS (ESI+): 348 (M + H$^+$); $^1$H NMR (300 MHz, CD$_3$OD) δ 8.77-8.75 (d, J = 5.58 Hz, 1H), 8.61-8.55 (t, J = 7.65 Hz, 1H), 8.28-8.25 (d, J = 8.10 Hz, 1H), 8.07-8.05 (d, J = 8.01 Hz, 1H), 7.98-7.94 (t, J = 6.60 Hz, 1H), 7.68-7.65 (m, 2H), 3.86 (s, 2H), 3.38-3.36 (m, 2H), 3.23-3.18 (t, J = 7.50 Hz, 2H), 3.05-3.00 (t, J = 7.80 Hz, 2H), 2.31-2.21 (m, 2H), 1.90-1.85 (t, J = 6.54 Hz, 2H), 1.18 (s, 6H). |

| Compound | Synthesis Method & Data |
|---|---|
| 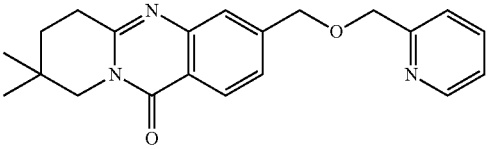<br>Example 6.11<br>8,8-dimethyl-3-((pyridin-2-ylmethoxy)methyl)-8,9-dihydro-6H-pyrido[2,1-b]quinazolin-11(7H)-one | Synthesized from isobutyronitrile, dimethyl 2-aminoterephthalate and pyridin-2-ylmethanol according to General Experimentals G31, C6, B1 and G21. MS (ESI+): 350 (M + H$^+$); $^1$H NMR (300 MHz, CD$_3$OD) δ 8.86-8.84 (d, J = 6.03 Hz, 1H), 8.67-8.61 (td, J = 7.91, 1.45 Hz, 1H), 8.37-8.34 (d, J = 8.61 Hz, 1H), 8.14-8.11 (d, J = 7.98 Hz, 1H), 8.07-8.03 (t, J = 6.90 Hz, 1H), 7.81-7.79 (m, 2H), 5.11 (s, 2H), 5.03 (s, 2H), 3.88 (s, 2H), 3.35-3.34 (m, 2H), 1.89-1.84 (t, J = 6.82 Hz, 2h), 1.18 (s, 6H). |
| 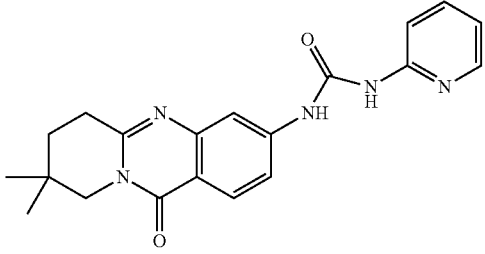<br>Example 6.12<br>1-(8,8-dimethyl-11-oxo-7,8,9,11-tetrahydro-6H-pyrido[2,1-b]quinazolin-3-yl)-3-(pyridin-2-yl)urea | Synthesized from isobutyonittile, 2-amino-4-nitrobenzoic acid, picolinic acid and sodium azide according to General Experimentals C6, B1, G29 and H17. MS (ESI+): m/z 364 (M + H$^+$); $^1$H NMR (300 MHz, DMSO-d$_6$): δ 11.33 (s, 1H), 9.99 (s, 1H), 8.32 (d, J = 4.1 Hz, 1H), 8.23 (s, 1H), 8.15 (d, J = 8.7 Hz, 1H), 7.89-7.83 (td, J = 8.1, 1.8 Hz, 1H), 7.70-7.60 (m, 2H), 7.14-7.10 (m, 1H), 3.71 (s, 2H), 3.21-3.16 (t, J = 6.9 Hz, 2H), 1.73-1.68 (t, J = 6.9 Hz, 2H), 1.08 (s, 6H). mGluR5 PAM EC$_{50}$: +. |
| 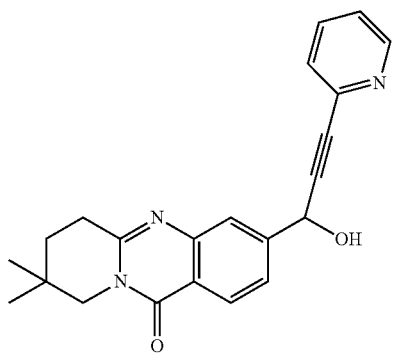<br>Example 6.13<br>3-(1-hydroxy-3-(pyridin-2-yl)prop-2-yn-1-yl)-8,8-dimethyl-8,9-dihydro-6H-pyrido[2,1-b]quinazolin-11(7H)-one | Synthesized from isobutyonitrile, dimethyl 2-aminoterephthalate and 2-ethynylpyridine according to General Experimentals G31, C6, B1, G1, G2, G16 and G38. MS (ESI+): 360 (M + H$^+$); $^1$H NMR (300 MHz, CDCl$_3$) δ 8.56-8.55 (d, J = 3.27 Hz, 1H), 8.21-8.18 (d, J = 8.25 Hz, 1H), 7.95 (s, 1H), 7.68-7.60 (m, 2H), 7.42-7.39 (d, J = 7.68 Hz, 1H), 7.24-7.20 (m, 1H), 5.89 (s, 1H), 3.78 (s, 2H), 3.02-2.97 (t, J = 7.01 Hz, 2H), 1.72-1.67 (t, J = 6.99 Hz, 2H), 1.07 (s, 6H). |

| Compound | Synthesis Method & Data |
|---|---|
| Example 6.14<br>3-(1-fluoro-3-(pyridin-2-yl)prop-2-yn-1-yl)-8,8-dimethyl-8,9-dihydro-6H-pyrido[2,1-b]quinazolin-11(7H)-one | Synthesized from isobutyronitrile, dimethyl 2-aminoterephthalate and 2-ethynylpyridine according to General Experimentals G31, C6, B1, G1, G2, G16, G38 and E1. MS (ESI+): 362 (M + H$^+$); $^1$H NMR (300 MHz, CDCl$_3$) δ 8.62 (s, 1H), 8.35-8.32 (d, J = 8.25 Hz, 1H), 7.86 (s, 1H), 7.72-7.65 (m, 2H), 7.54-7.51 (d, J = 7.62 Hz, 1H), 7.32-7.30 (d, J = 6.24 Hz, 1H), 6.51-6.35 (d, J = 59.40 Hz, 1H), 3.84 (s, 2H), 3.06-3.01 (t, J = 7.10 Hz, 2H), 1.78-1.74 (t, J = 7.07 Hz, 2H), 1.11 (s, 6H). |
| Example 6.15<br>2,2-dimethyl-9-oxo-N'-picolinoyl-1,2,3,9-tetrahydropyrrolo[2,1-b]quinazoline-6-carbohydrazide | Synthesized from 4,4-dimethylpyrrolidin-2-one, 2-amino-4-(methoxycarbonyl)benzoic acid and picolinoyl choride according to General Experimentals C1 and H6. MS (ESI+): m/z 378 (M + H$^+$); $^1$H NMR (300 MHz, CDCl$_3$) δ 8.64 (d, J = 4.1 Hz, 1H), 8.38 (d, J = 8.3 Hz, 1H), 8.22-8.20 (m, 2H), 7.96-7.87 (m, 2H), 7.53-.49 (m, 1H), 4.00 (s, 2H), 3.00 (s, 2H), 1.29 (s, 6H). |
| Example 6.16<br>8-methyl-12-oxo-N'-picolinoyl-6,7,8,9,10,12-hexahydroazepino[2,1-b]quinazoline-3-carbohydrazide | Synthesized from 5-methylazepan-2-one, 2-amino-4-(methoxycarbonyl)benzoic acid and picolinoyl chloride according to General Experimentals C1 and H6. MS (ESI+): m/z 392 (M + H$^+$); $^1$H NMR (300 MHz, CDCl$_3$) δ 8.64 (d, J = 4.3 Hz, 1H), 8.36 (d, J = 8.2 Hz, 1H), 8.20 (d, J = 7.7 Hz, 1H), 8.13 (s, 1H), 7.95-7.88 (m, 2H), 7.53-7.49 (m, 1H), 5.22-5.16 (dd, J = 14.0, 6.7 Hz, 1H), 3.68-3.59 (m, 1H), 3.17-3.07 (m, 2H), 2.32-2.10 (m, 5H), 1.03 (d, J = 6.6 Hz, 3H). |
| Example 6.17<br>8,8-dimethyl-3-(1-phenyl-2,5-dihydro-1H-pyrrol-3-yl)-8,9-dihydro-6H-pyrido[2,1-b]quinazolin-11(7H)-one | Synthesized from isobutyonitrile, 2-amino-4-bromobenzonic acid, tert-butyl 3-oxopyrrolidine-1-carboxylate, bis(pinacolato)diboron and 2-bromobenzene according to General Experimentals C6, B1, A8, A4, F3 and G32. MS (ESI+): m/z 372 (M + H$^+$); $^1$H NMR (300 MHz, CDCl$_3$) δ 8.26 (d, J = 8.9 Hz, 1H), 7.63-7.61 (m, 2H), 7.34-7.29 (t, J = 7.8 Hz, 2H), 6.78-6.73 (t, J = 7.3 Hz, 1H), 6.63 (d, J = 8.0 Hz, 2H), 6.56 (s, 1H), 4.58-4.55 (m, 2H), 4.41-4.31 (m, 2H), 3.84 (s, 2H), 3.07-3.02 (t, J = 7.1 Hz, 2H) 1.80-1.75 (t, J = 7.1 Hz, 2H), 1.13 (s, 6H). |

| Compound | Synthesis Method & Data |
|---|---|
| 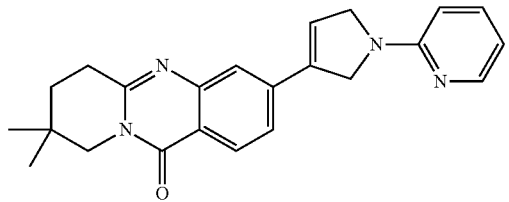

Example 6.18
8,8-dimethyl-3-(1-(pyridin-2-yl)-2,5-dihydro-1H-pyrrol-3-yl)-8,9-dihydro-6H-pyrido[2,1-b]quinazolin-11(7H)-one | Synthesized from isobutyronitrile, 2-amino-4-bromobenzonic acid, tert-butyl 3-oxopyrrolidine-1-carboxylate, bis(pinacolato)diboron and 2-bromopyridine according to General Experimentals C6, B1, A8, A4, F3 and G32. MS (ESI+): m/z 373 (M + H$^+$); $^1$H NMR (300 MHz, CD$_3$OD) δ 8.38 (d, J = 8.4 Hz, 1H), 8.16-8.11 (t, J = 7.4 Hz, 1H), 8.06-7.99 (m, 2H), 7.82 (s, 1H), 7.33-7.30 (m, 1H), 7.10-7.05 (t, J = 6.6 Hz, 1H), 6.96 (s, 1H), 4.99 (s, 2H), 4.75 (s, 2H), 3.89 (s, 2H), 3.42-3.37 (t, J = 6.8 Hz, 2H), 1.91-1.87 (t, J = 6.8 Hz, 2H), 1.20 (s, 6H). |
| 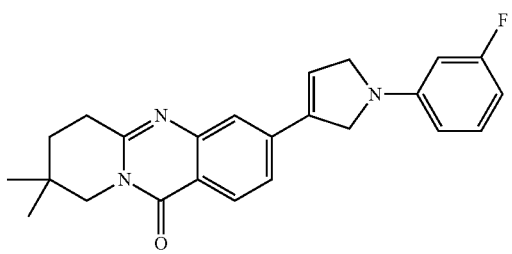

Example 6.19
3-(1-(3-fluorophenyl)-2,5-dihydro-1H-pyrrol-3-yl)-8,8-dimethyl-8,9-dihydro-6H-pyrido[2,1-b]quinazolin-11(7H)-one | Synthesized from isobutyronitrile, 2-amino-4-bromobenzonic acid, tert-butyl 3-oxopyrrolidine-1-carboxylate, bis(pinacolato)diboron and 1-bromo-3-fluorobenzene according to General Experimentals C6, B1, A8, A4, F3 and G32. MS (ESI+): m/z 390 (M + H$^+$); $^1$H NMR (300 MHz, CDCl$_3$) δ 8.27 (d, J = 8.8 Hz, 1H), 7.62-7.60 (m, 2H), 7.24-7.19 (m, 1H), 6.56-6.55 (m, 1H), 6.47-6.28 (m, 3H), 4.56-4.54 (m, 2H), 4.36-4.35 (m, 2H), 3.85 (s, 2H), 3.07-3.02 (t, J = 7.1 Hz, 2H) 1.80-1.75 (t, J = 7.1 Hz, 2H), 1.13 (s, 6H). |
| 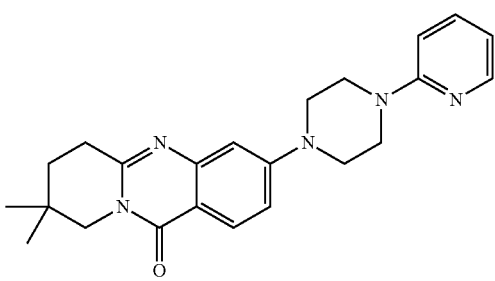

Example 6.20
8,8-dimethyl-3-(4-(pyridin-2-yl)piperazin-1-yl)-8,9-dihydro-6H-pyrido[2,1-b]quinazolin-11(7H)-one | Synthesized from isobutyronitrile, 2-amino-4-bromobenzonic acid, tert-butyl piperazine-1-carboxylate and 2-bromopyridine according to General Experimentals C6, B1, G32, F3 and G32. MS (ESI+): m/z 390 (M + H$^+$); $^1$H NMR (300 MHz, CD$_3$OD) δ 8.17-8.09 (m, 2H), 8.02 (d, J = 6.3 Hz, 1H), 7.43 (d, J = 9.3 Hz, 1H), 7.33-7.29 (dd, J = 9.2, 2.3 Hz, 1H), 7.10-7.05 (t, J = 6.7 Hz, 1H), 6.85 (s, 1H), 4.04-4.01 (m, 4H), 3.93-3.90 (m, 4H), 3.83 (s, 2H), 3.31-3.27 (m, 2H), 1.87-1.83 (t, J = 6.8 Hz, 2H), 1.17 (s, 6H). |

| Compound | Synthesis Method & Data |
|---|---|
| Example 6.21<br>8,8-dimethyl-3-(4-(pyridin-2-yl)-1H-imidazol-2-yl)-8,9-dihydro-6H-pyrido[2,1-b]quinazolin-11(7H)-one | Synthesized from isobutyonitrile, 2-aminoterephthalic acid, HBr salt of 2-bromo-1-(pyridin-2-yl)ethanone and $CH_3COONH_4$ according to General Experimentals C6, B1 and H13. MS (ESI+): 372 (M + H$^+$); $^1$H NMR (300 MHz, $CD_3OD$): δ 8.71 (d, J = 5.8 Hz, 1H), 8.57-8.43 (m, 4H), 8.39-8.32 (m, 2H), 7.88-7.83 (t, J = 7.2 Hz, 1H), 3.90 (s, 2H), 3.37-3.32 (t, J = 6.9 Hz, 2H), 1.90-1.85 (t, J = 6.9 Hz, 2H), 1.19 (s, 6H). mGluR5 PAM EC$_{50}$: +. |
| Example 6.22<br>8,8-dimethyl-3-(1-(pyridin-2-yl)-1H-imidazol-4-yl)-8,9-dihydro-6H-pyrido[2,1-b]quinazolin-11(7H)-one | Synthesized from isobutyonitrile, 2-amino-4-bromobenzonic acid, bis(pinacolato)diboron, 2-bromopyridine and 4-bromo-1H-imidazole according to General Experimentals G32, C6, B1 and A4. MS (ESI+): 372 (M + H$^+$); $^1$H NMR (300 MHz, $CD_3OD$): δ 8.86 (s, 1H), 8.66 (s, 1H), 8.58 (d, J = 3.9 Hz, 1H), 8.30 (d, J = 9.0 Hz, 1H), 8.09-8.03 (m, 3H), 7.86-7.83 (d, J = 8.1 Hz, 1H), 7.48-7.44 (m, 1H), 3.88 (s, 2H), 3.23-3.18 (t, J = 6.9 Hz, 2H), 1.87-1.82 (t, J = 6.9 Hz, 2H), 1.16 (s, 6H). |
| Example 6.23<br>8,8-dimethyl-3-(4-(pyridin-2-yl)-1H-imidazol-1-yl)-8,9-dihydro-6H-pyrido[2,1-b]quinazolin-11(7H)-one | Synthesized from isobutyronitrile, 2-amino-4-bromobenzonic acid,, picolinaldehyde and TosMIC according to General Experimentals H13, C6, B1 and G32. MS (ESI+): m/z 372 (M + H$^+$); $^1$H NMR (300 MHz, $CD_3OD$): δ 9.01 (s, 1H), 8.40 (s, 1H), 8.30 (d, J = 8.7 Hz, 1H), 7.99 (s, 1H), 7.90-7.83 (td, J = 7.7, 1.8, 1H), 7.63-7.61 (m, 2H), 7.48-7.44 (dd, J = 8.7, 1.8 Hz, 1H), 7.39-7.34 (m, 1H), 3.87 (s, 2H), 3.07-3.02 (t, J = 6.9 Hz, 2H), 1.82-1.77 (t, J = 6.9 Hz, 2H), 1.12 (s, 6H). |

| Compound | Synthesis Method & Data |
|---|---|
| 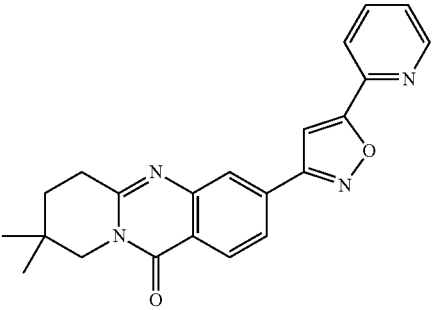<br>Example 6.24<br>8,8-dimethyl-3-(5-(pyridin-2-yl)isoxazol-3-yl)-8,9-dihydro-6H-pyrido[2,1-b]quinazolin-11(7H)-one | Synthesized from dimethyl 2-aminoterephthalate, isobutyronitrile, 2-ethynylpyridine and according to General Experimentals G31, C6, B1, G1, G2, G16 and H16. MS (ESI+): m/z 373 (M + H$^+$); $^1$H NMR (300 MHz, CD$_3$OD): δ 8.89 (d, J = 5.4 Hz, 1H), 8.51 (d, J = 8.7 Hz, 1H), 8.45-8.42 (m, 2H), 8.34-8.32 (m, 2H), 8.00 (s, 1H), 7.89-7.85 (m, 1H), 3.91 (s, 2H), 3.42-3.37 (t, J = 6.6 Hz, 2H), 1.93-1.88 (t, J = 6.6 Hz, 2H), 1.19 (s, 6H). |
| 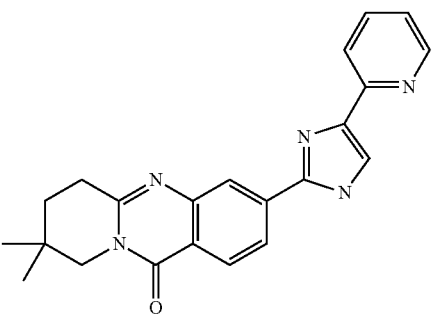<br>Example 6.25<br>8,8-dimethyl-3-(5-(pyridin-2-yl)oxazol-2-yl)-8,9-dihydro-6H-pyrido[2,1-b]quinazolin-11(7H)-one | Synthesized from isobutyronitrile, 2-amino-4-bromobenzonic acid,, picolinaldehyde, TosMIC and chlorotributylstannane tributyltin chloride according to General Experimentals H12, G37, C6, B1 and A5. MS (ESI+): m/z 373 (M + H$^+$); $^1$H NMR (300 MHz, CD$_3$OD): δ 8.81 (d, J = 5.7 Hz, 1H), 8.53-8.49 (m, 3H), 8.39-8.27 (m, 3H), 7.80-7.76 (t, J = 6.3 Hz, 1H), 3.91 (s, 2H), 3.41-3.36 (t, J = 6.9 Hz, 2H), 1.93-1.88 (t, J = 6.9 Hz, 2H), 1.21 (s, 6H). mGluR5 PAM EC$_{50}$: ++. |
| 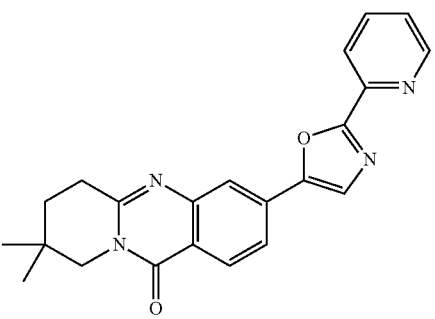<br>Example 6.26<br>8,8-dimethyl-3-(2-(pyridin-2-yl)oxazol-5-yl)-8,9-dihydro-6H-pyrido[2,1-b]quinazolin-11(7H)-one | Synthesized from isobutyronitrile, 2-amino-4-bromobenzonic acid, bis(pinacolato)diboron, picolinaldehyde and 2-aminoethanol according to General Experimentals H11, C6, B1 and A4. MS (ESI+): m/z 373 (M + H$^+$); $^1$H NMR (300 MHz, CD$_3$OD): δ 8.84 (brs, 1H), 8.46-8.44 (m, 2H), 8.30-8.24 (m, 4H), 7.80-7.76 (m, 1H), 3.90 (s, 2H), 3.40-3.35 (t, J = 6.9 Hz, 2H), 1.92-1.87 (t, J = 6.9 Hz, 2H), 1.18 (s, 6H). |

-continued

| Compound | Synthesis Method & Data |
|---|---|
| Example 6.27<br>8,8-dimethyl-3-(5-(pyriidn-2-yl)thiazol-2-yl)-8,9-dihydro-6H-pyrido[2,1-b]quinazolin-11(7H)-one | Synthesized from isobutyronitrile, 2-amino-4-bromobenzoic acid, bis(pinacolato)diboron, 2-bromothiazole and 2-iodopyridine according to General Experimentals C6, B1, A4 and A7. MS (ESI+) : m/z 389 (M + H$^+$); $^1$H NMR (300 MHz, DMSO-d$_6$): δ 8.73 (s, 1H), 8.63 (d, J = 4.5 Hz, 1H), 8.28-8.22 (m, 2H), 8.15-8.10 (m, 2H), 7.97-7.92 (t, J = 8.1 Hz, 1H), 7.42-7.37 (m, 1H), 3.76 (s, 2H), 3.10-3.05 (t, J = 6.9 Hz, 2H), 1.73-1.68 (t, J = 6.9 Hz, 2H), 1.06 (s, 6H). |
| Example 6.28<br>8,8-dimethyl-3-(2-(pyridin-2-yl)thiazol-5-yl)-8,9-dihydro-6H-pyrido[2,1-b]quinazolin-11(7H)-one | Synthesized from isobutyronitrile, 2-amino-4-bromobenzonic acid, bis(pinacolato)diboron, 5-bromothiazole and 2-iodopyridine according to General Experimentals C6, B1, A4 and A7. MS (ESI+): m/z 389 (M + H$^+$); $^1$H NMR (300 MHz, DMSO-d$_6$): δ 8.68 (d, J = 4.8 Hz, 1H), 8.63 (s, 1H), 8.19-8.16 (m, 2H), 8.03-7.88 (m, 3H), 7.56-7.52 (m, 1H), 3.76 (s, 2H), 3.03-2.97 (t, J = 6.9 Hz, 2H), 1.72-1.67 (t, J = 6.9 Hz, 2H), 1.03 (s, 6H). mGluR5 PAM EC$_{50}$: +. |
| Example 6.29<br>8,8-dimethyl-3-(4-(pyridin-2-yl)thiazol-2-yl)-8,9-dihydro-6H-pyrido[2,1-b]quinazolin-11(7H)-one | Synthesized from isobutyronitrile, 2-amino-4-bromobenzonic acid, bis(pinacolato)diboron and 2-bromo-1-(pyridin-2-yl)ethanone according to General Experimentals H10, C6, B1 and A4. MS (ESI+): m/z 389 (M + H$^+$); $^1$H NMR (300 MHz, CD$_3$OD): δ 9.01 (s, 1H), 8.89 (d, J = 5.5 Hz, 1H), 8.74-8.68 (m, 2H), 8.51-8.44 (m, 3H), 8.10-8.05 (m, 1H), 3.91 (s, 2H), 3.41-3.36 (t, J = 6.9 Hz, 2H), 1.92-1.87 (t, J = 6.9 Hz, 2H), 1.20 (s, 6H). |

-continued

| Compound | Synthesis Method & Data |
|---|---|
| 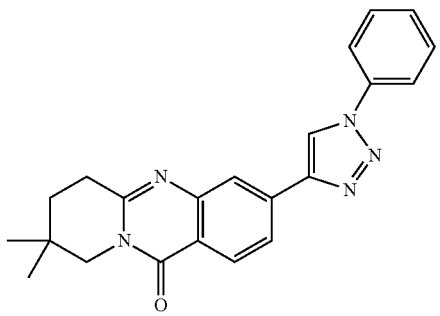<br>Example 6.30<br>8,8-dimethyl-3-(1-phenyl-1H-1,2,3-triazol-4-yl)-8,9-dihydro-6H-pyrido[2,1-b]quinazolin-11(7H)-one | Synthesized as a mixture from isobutyronitrile, 2-amino-4-bromobenzonic acid ethynyltrimethylsilane and chlorobenzene according to General Experimentals C6, B1, A2, G36 and H9. MS (ESI+): m/z 372 (M + H$^+$); $^1$H NMR (300 MHz, DMSO-d$_6$): δ 9.57 (s, 1H), 8.29-8.23 (m, 2H), 8.13-8.09 (m, 1H), 7.99-7.96 (m, 2H), 7.69-7.64 (t, J = 7.8 Hz, 2H), 7.58-7.55 (m, 1H), 3.77-3.75 (m, 2H), 3.09-3.04 (m, 2H), 1.74-1.68 (m, 2H), 1.06-1.03 (m, 6H). |
| 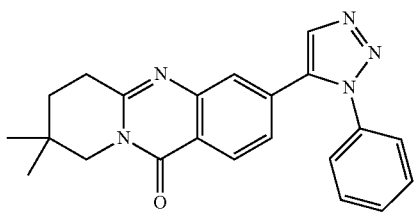<br>Example 6.31<br>8,8-dimethyl-3-(1-phenyl-1H-1,2,3-triazol-5-yl)-8,9-dihydro-6H-pyrido[2,1-b]quinazolin-11(7H)-one | |
| 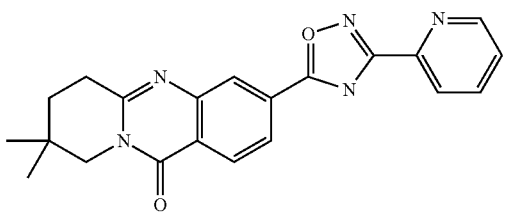<br>Example 6.32<br>8,8-dimethyl-3-(3-(pyridin-2-yl)-1,2,4-oxadiazol-5-yl)-8,9-dihydro-6H-pyrido[2,1-b]quinazolin-11(7H)-one | Synthesized from isobutyronitrile, 2-aminoterephthalic acid and picolinonitrile according to General Experimentals C6, B1, G35 and H8. MS (ESI+): 374 (M + H$^+$); $^1$H NMR (300 MHz, CD$_3$OD): δ 8.91-8.89 (d, J = 5.0 Hz, 1H), 8.62-8.51 (m, 4H), 8.41-8.35 (m, 1H), 7.93-7.88 (m, 1H), 3.92 (s, 2H), 3.42-3.37 (t, J = 6.7 Hz, 2H), 1.93-1.88 (t, J = 6.7 Hz, 2H), 1.21 (s, 6H). |

| Compound | Synthesis Method & Data |
|---|---|
| Example 6.33<br>2,2-dimethyl-6-(5-(pyridin-2-yl)-1,3,4-oxadiazol-2-yl)-2,3-dihydropyrrolo[2,1-b]quinazolin-9(1H)-one | Synthesized from 4,4-dimethylpyrrolidin-2-one, 2-amino-4-(methoxycarbonyl)benzoic acid and picolinoyl chloride according to General Experimentals B1 and H6. MS (ESI+): 360 (M + H$^+$); $^1$H NMR (300 MHz, CD$_3$OD): δ 8.86 (brs, 1H), 8.53-8.41 (m, 4H), 8.19-8.14 (t, J = 8.4 Hz, 1H), 7.73 (s, 1H), 4.09 (s, 2H), 3.24 (s, 2H), 1.33 (s, 6H). |
| Example 6.34<br>3-(5-(pyridin-2-yl)-1,3,4-oxadiazol-2-yl)-8,9-dihydro-6H-pyrido[2,1-b]quinazolin-11(7H)-one | Synthesized from piperidin-2-one, 2-amino-4-(methoxycarbonyl)benzoic acid and picolinoyl chloride according to General Experimentals B1 and H6. MS (ESI+): m/z 346 (M + H$^+$); $^1$H NMR (300 MHz, CD$_3$OD): δ 8.85 (d, J = 4.8 Hz, 1H), 8.60-8.40 (m, 4H), 8.19-8.16 (t, J = 6.3 Hz, 1H), 7.75-7.71 (m, 1H), 4.19-4.15 (t, J = 5.9 Hz, 2H), 3.55-3.51 (t, J = 5.9 Hz, 2H), 2.24-2.06 (m, 4H). |
| Example 6.35<br>8,8-dimethyl-3-(5-(pyridin-2-yl)-1,3,4-oxadiazol-2-yl)-8,9-dihydro-6H-pyrido[2,1-b]quinazolin-11(7H)-one | Synthsized from isobutyronitrile, 2-amino-4-(methoxycarbonyl)benzoic acid and picolinoyl chlorde according to General Experimentals B1 and H6. MS (ESI+): m/z 374 (M + H$^+$); $^1$H NMR (300 MHz, CD$_3$OD): δ 8.86 (d, J = 4.9 Hz, 1H), 8.59-8.42 (m, 4H), 8.20-8.14 (td, J = 7.8, 1.6 Hz, 1H), 7.76-7.72 (m, 1H), 3.92 (s, 2H), 3.42-3.37 (t, J = 6.8 Hz, 2H), 1.93-1.89 (t, J = 6.8 Hz, 2H), 1.22 (s, 6H). mGluR5 PAM EC$_{50}$: ++. |

| Compound | Synthesis Method & Data |
|---|---|
| Example 6.36<br>3-(5-(pyridin-2-yl)-1,3,4-oxadiazol-2-yl)-7,8,9,10-tetrahydroazepino[2,1-b]quinazolin-12(6H)-one | Synthesized from azepan-2-one, 2-amino-4-(methoxycarbonyl)benzoic acid and picolinoyl chlorde according to General Experimentals B1 and H6.<br>MS (ESI+): m/z 360 (M + H$^+$); $^1$H NMR (300 MHz, CD$_3$OD): δ 8.88 (brs, 1H), 8.60-8.56 (m, 4H), 8.21-8.16 (t, J = 7.8 Hz, 1H), 7.76 (brs, 1H), 4.61-4.58 (m, 2H), 3.55-3.52 (m, 2H), 2.58-1.92 (m, 6H). |
| Example 6.37<br>8-methyl-3-(5-(pyridin-2-yl)-1,3,4-oxadiazol-2-yl)-7,8,9,10-tetrahydroazepino[2,1-b]quinazolin-12(6H)-one | Synthesized from 5-methylazepan-2-one, 2-amino-4-(methoxycarbonyl)benzoic acid and picolinoyl chloride according to General Experimentals B1 and H6.<br>MS (ESI+): m/z 374 (M + H$^+$); $^1$H NMR (300 MHz, CD$_3$OD): δ 8.58 (brs, 1H), 8.55-8.46 (m, 4H), 8.23-8.18 (t, J = 7.8 Hz, 1H), 7.78 (s, 1H), 5.25-5.18 (dd, J = 14.7, 6.0 Hz, 1H), 4.00-3.91 (m, 1H), 3.57-3.49 (m, 1H), 2.26-2.10 (m, 3H), 1.64-1.60 (m, 1H), 1.45-1.31 (m, 2H), 1.07 (d, J = 7.5 Hz, 3H). |
| Example 6.38<br>8,8-dimethyl-3-(5-(pyridin-2-yl)-1,3,4-thiadiazol-2-yl)-8,9-dihydro-6H-pyrido[2,1-b]quinazolin-11(7H)-one | Synthesized from isobutyonitrile, 2-amino-4-(methoxycarbonyl)benzoic acid, picolinoyl chloride and P$_2$S$_5$ according to General Experimentals H6 and H7.<br>MS (ESI+): m/z 390 (M + H$^+$); $^1$H NMR (300 MHz, CD$_3$OD): δ 8.77 (d, J = 4.8 Hz, 1H), 8.36-8.27 (m, 3H), 8.20-8.06 (m, 2H), 7.66-7.62 (m, 1H), 3.80 (s, 2H), 3.07-3.03 (t, J = 6.8 Hz, 2H), 1.73-1.68 (t, J = 6.8 Hz, 2H), 1.05 (s, 6H). mGluR5 PAM EC$_{50}$: ++. |

| Compound | Synthesis Method & Data |
|---|---|
| 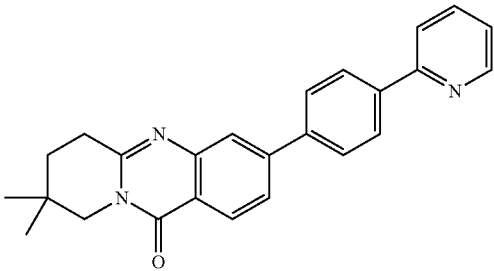<br>Example 6.39<br>8,8-dimethyl-3-(4-(pyridin-2-yl)phenyl)-8,9-dihydro-6H-pyrido[2,1-b]quinazolin-11(7H)-one | Synthesized from isobutyronitrile, 2-amino-4-bromobenzoic acid, bis(pinacolato)diboron and 2-(4-bromophenyl)pyridine according to General Experimentals C6, B1 and A4. MS (ESI+): m/z 382 (M + H$^+$); $^1$H NMR (300 MHz, CD$_3$OD): δ 8.91 (d, J = 4.9 Hz, 1H), 8.76-8.70 (td, J = 7.8, 1.5 Hz, 1H), 8.51-8.47 (t, J = 5.1 Hz, 2H), 8.21-8.07 (m, 6H), 8.01 (d, J = 1.4 Hz, 1H), 3.92 (s, 2H), 3.41-3.36 (t, J = 6.9 Hz, 2H), 1.93-1.88 (t, J = 6.9 Hz, 2H), 1.21 (s, 6H). |
| 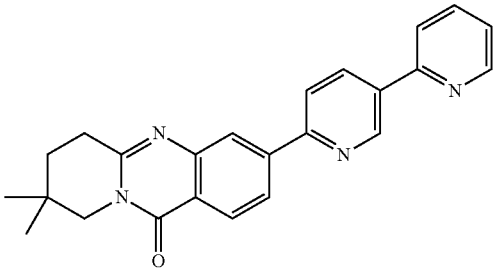<br>Example 6.40<br>3-([2,3'-pyridin]-6'-yl)-8,8-dimethyl-8,9-dihydro-6H-pyrido[2,1-b]quinazolin-11(7H)-one | Synthesized from isobutyronitrile, 2-amino-4-bromobenzoic acid, bis(pinacolato)diboron, 6-bromopyridin-3-ylboronic acid and 2-iodopyridine according to General Experimentals C6, B1 and A4. MS (ESI+): m/z 383 (M + H$^+$); $^1$H NMR (300 MHz, CD$_3$OD): δ 9.37 (d, J = 1.9 Hz, 1H), 8.99 (d, J = 5.8 Hz, 1H), 8.80-8.74 (td, J = 7.9, 1.5 Hz, 1H), 8.67-8.47 (m, 6H), 8.18-8.13 (m, 1H), 3.92 (s, 2H), 3.41-3.36 (t, J = 6.9 Hz, 2H), 1.93-1.88 (t, J = 6.9 Hz, 2H), 1.21 (s, 6H). |
| 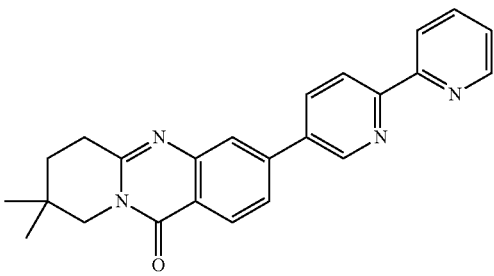<br>Example 6.41<br>3-([2,2'-pyridin]-5-yl)-8,8-dimethyl-8,9-dihydro-6H-pyrido[2,1-b]quinazolin-11(7H)-one | Synthesized from isobutyronitrile, 2-amino-4-bromobenzoic acid, bis(pinacolato)diboron, 5-bromo-2-chloropyridine and 2-(tributylstannyl)pyridine according to General Experimentals C6, B1, A4 and A5. MS (ESI+): m/z 383 (M + H$^+$); $^1$H NMR (300 MHz, CD$_3$OD): δ 9.35 (s, 1H), 8.96 (d, J= 5.4 Hz, 1H), 8.90 (d, J = 8.4 Hz, 1H), 8.81-8.75 (t, J = 7.5 Hz, 1H), 8.70-8.62 (m, 2H), 8.53 (d, J = 8.4 Hz, 1H), 8.21-8.13 (m, 3H), 3.92 (s, 2H), 3.41-3.36 (t, J = 6.9 Hz, 2H), 1.93-1.88 (t, J = 6.9 Hz, 2H), 1.21 (s, 6H). |

| Compound | Synthesis Method & Data |
|---|---|
| Example 6.42<br>8,8-dimethyl-3-(5-(pyridin-2-yl)pyrimidin-2-yl)-8,9-dihydro-6H-pyrido[2,1-b]quinazolin-11(7H)-one | Synthesized from isobutyronitrile, 2-amino-4-bromobenzoic acid, bis(pinacolato)diboron, pyridin-2-ylzinc(II) bromide and 2-chloro-5-iodopyrimidine according to General Experimentals C6, B1, A6 and A4. MS (ESI+): m/z 384 (M + H$^+$); $^1$H NMR (300 MHz, DMSO-d$_6$): δ 9.67 (s, 2H), 8.91 (s, 1H), 8.80 (d, J = 4.2 Hz, 1H), 8.68-8.65 (dd, J = 8.4, 1.3 Hz, 1H), 8.39-8.36 (d, J = 8.5 Hz, 1H), 8.26 (d, J = 7.9 Hz, 1H), 8.09-8.03 (td, J = 7.8, 1.6 Hz, 1H), 7.57-7.54 (m, 1H), 3.77 (s, 2H), 3.29-3.24 (t, J = 6.9 Hz, 2H), 1.77-1.72 (t, J = 6.9 Hz, 2H), 1.09 (s, 6H). mGluR5 PAM EC$_{50}$: +. |
| Example 6.43<br>8,8-dimethyl-3-(6-(pyridin-2-yl)pyridazin-3-yl)-8,9-dihydro-6H-pyrido[2,1-b]quinazolin-11(7H)-one | Synthesized from isobutyronitrile, 2-amino-4-bromobenzoic acid, 3-chloro-6-iodopyridazine and 2-(tributylstannyl)pyridine according to General Experimentals C6, B1, A4 and A5. MS (ESI+): m/z 384 (M + H$^+$); $^1$H NMR (300 MHz, CD$_3$OD): δ 8.99 (d, J = 5.4 Hz, 1H), 8.90-8.84 (m, 2H), 8.72-8.67 (m, 3H), 8.57 (s, 2H), 8.14-8.12 (m, 1H), 3.93 (s, 2H), 3.43-3.38 (t, J = 6.9 Hz, 2H), 1.94-1.89 (t, J = 6.9 Hz, 2H), 1.22 (s, 6H). |
| Example 6.44<br>8,8-dimethyl-3-(2-(pyridin-2-yl)pyrimidin-5-yl)-8,9-dihydro-6H-pyrido[2,1-b]quinazolin-11(7H)-one | Synthesized from isobutyronitrile, 2-amino-4-bromobenzoic acid, 5-bromo-2-chloropyrimidine and 2-(tributylstannyl)pyridine according to General Experimentals C6, B1, A4 and A5. MS (ESI+): m/z 384 (M + H$^+$); $^1$H NMR (300 MHz, DMSO-d$_6$): δ 9.67 (s, 2H), 8.91 (s, 1H), 8.80 (d, J = 4.2 Hz, 1H), 8.68-8.65 (dd, J = 8.4, 1.3 Hz, 1H), 8.39-8.36 (d, J = 8.5 Hz, 1H), 8.26 (d, J = 7.9 Hz, 1H), 8.09-8.03 (td, J = 7.8, 1.6 Hz, 1H), 7.57-7.54 (m, 1H), 3.77 (s, 2H), 3.29-3.24 (t, J = 6.9 Hz, 2H), 1.77-1.72 (t, J = 6.9 Hz, 2H), 1.09 (s, 6H). |

Example S. General Method for Separation of Isomers

Chiral separations of enantiomers from racemic compounds were performed on chiral columns with isocratic Supercritical Fluid Chromatography (SFC) technology. The chiral columns used for preparative separations were chosen from 3.0×25.0 cm RegisPack®, or 3.0×25.0 cm (S,S) Whelk-O1 columns, both from Regis Technologies, Morton Grove, Ill., or 2.1×25.0 cm LUX Cellulose 2 column from Phenomenex, Torrance, Calif., or 3.0×25.0 cm 2-Ethylpyridine from Princeton Chromatography, Cranbury, N.J., or 2.0×25 cm Pyridyl Amide from ES Industries, West Berlin, N.J. The chiral columns used for analytical separations were chosen from 4.6×100 mm RegisPack® or 4.6×100 mm (S,S) Whelk-O1 columns, both from Regis Technologies, Morton Grove, Ill., or 4.6×100 mm LUX Cellulose 2 column from Phenomenex, Torrance, Calif., or 4.6×100 mm Pyridyl Amide from ES Industries, West Berlin, N.J. The supercritical fluid (SF) was carbon dioxide (CO$_2$). The co-solvent used with CO$_2$ was a mixture of isopropanol or acetonitrile with or without methanol, and sometimes, with a small percentage of isopropylamine. For a compound separated from preparative column, the first peak (faster moving) was labeled as fraction 1, and the second peak (slower moving) was labeled as fraction 2. The enantiomeric purity of each fraction was analyzed on analytical columns and the retention time (Rt) and the percentage of enantiomeric excess (% ee) were recorded. Unless otherwise indicated, the absolute chemistry of the enantiomers was assigned arbitrarily.

Example PS. General Preparative Separation Method

Preparative Separation Method PS(I):
Column: 3.0×25.0 cm RegisPack®. $CO_2$ co-solvent: isopropanol with 10-90% methanol and 0.1-1% isopropylamine. Isocratic method: 20-70% co-solvent at 50-80 mL/min. System pressure: 100-150 bar. Column temperature: 25° C.
Preparative Separation Method PS(II):
Column: 3.0×25.0 cm RegisPack®. $CO_2$ co-solvent: isopropanol with 0.1-1% isopropylamine. Isocratic method: 20-50% co-solvent at 50-80 mL/min. System pressure 100-150 bar. Column temperature: 25° C.
Preparative Separation Method PS(III):
Column: 3.0×25.0 cm (S,S) Whelk-O1 Regis Pack. $CO_2$ co-solvent: isopropanol with 25-50% methanol with 0-1% isopropylamine. Isocratic method: 20-50% co-solvent at 50-80 mL/min. System pressure: 100-150 bar. Column temperature: 25° C.
Preparative Separation Method PS(IV):
Column: 3.0×25.0 cm (S,S) Whelk-O1 Regis Pack. $CO_2$ co-solvent: isopropanol with 0.5-1% isopropylamine. Isocratic method: 20-50% co-solvent at 50-80 mL/min. System pressure: 100-150 bar. Column temperature: 25° C.
Preparative Separation Method PS(V):
Column: 2.1×25.0 cm LUX Cellulose 2 from Phenomenex, Torrance, Calif. $CO_2$ co-solvent: methanol with 0.5-1% isopropylamine. Isocratic method: 20-50% co-solvent at 50-80 mL/min. System pressure: 100-150 bar. Column temperature: 25° C.
Preparative Separation Method PS(VI)):
Column: 2.1×25.0 cm LUX Cellulose 2 from Phenomenex, Torrance, Calif. $CO_2$ co-solvent: acetonitrile with 10-25% methanol and 0.1-1% isopropylamine. Isocratic method: 20-60% co-solvent at 50-80 mL/min. System pressure: 100-150 bar. Column temperature: 25° C.
Preparative Separation Method PS(VII):
Column: 3.0×25.0 cm 2-Ethylpyridine from Princeton Chromatography, Cranbury, N.J. $CO_2$ co-solvent: isopropanol with 0.1-1% isopropylamine. Isocratic method: 20% co-solvent at 80 mL/min. System pressure 100-bar. Column temperature: 25° C.
Preparative Separation Method PS(VIII):
Column: 2.0×25 cm Pyridyl Amide from ES Industries, West Berlin, N.J. $CO_2$ co-solvent: isopropanol with 10-90% methanol and 0.1-1% isopropylamine. Isocratic method: 10% co-solvent at 80 mL/min. System pressure: 100-150 bar. Column temperature: 25° C.

Preparative Separation Method PS(IX):
Column: 3.0×25.0 cm RegisPack®. $CO_2$ co-solvent: ethanol. Isocratic method: 30% co-solvent at 80 mL/min. System pressure: 100 bar. Column temperature: 25° C.

Example AS. General Analytical Separation Method

Analytical Separation Method AS(I):
Column: 4.6×100 mm RegisPack®. $CO_2$ co-solvent: isopropanol with 10-90% methanol and 0.1-0.5% isopropylamine. Isocratic method: 20-70% co-solvent at 4 mL/min. System Pressure 70-150 bar. Column Temperature: 25° C.
Analytical Separation Method AS(II):
Column: 4.6×100 mm RegisPack®. $CO_2$ co-solvent: isopropanol with 0.1-1% isopropylamine. Isocratic method: 20-50% co-solvent at 50-80 mL/min. System pressure 70-150 bar. Column temperature: 25° C.
Analytical Separation Method AS(III):
Column: 4.6×100 mm (S,S) Whelk-O1. $CO_2$ co-solvent: isopropanol with 25-50% methanol and 0.1-1% isopropylamine. Isocratic method: 20-50% co-solvent at 4 mL/min. System Pressure: 70-150 bar. Column Temperature: 25° C.
Analytical Separation Method AS(IV):
Column: 4.6×100 mm (S,S) Whelk-O1. $CO_2$ co-solvent: isopropanol with 0.1-1% isopropylamine. Isocratic method: 20-50% co-solvent at 4 mL/min. System Pressure: 70-150 bar. Column Temperature: 25° C.
Analytical Separation Method AS(V):
Column: 4.6×100 mm LUX Cellulose 2 from Phenomenex, Torrance, Calif. $CO_2$ co-solvent: methanol with 0.1-1% isopropylamine. Isocratic method: 20-50% co-solvent at 4 mL/min. System pressure: 70-150 bar. Column temperature: 25° C.
Analytical Separation Method AS(VI):
Column: 4.6×100 mm LUX Cellulose 2 from Phenomenex, Torrance, Calif. $CO_2$ co-solvent: acetonitrile with 10-25% methanol and 0.1-1% isopropylamine. Isocratic method: 50-65% co-solvent at 4 mL/min. System pressure: 100-125 bar. Column temperature: 25° C.
Analytical Separation Method AS(VII):
Column: 4.6×100 mm 2-Ethylpyridine from Princeton Chromatography, Cranbury, N.J. $CO_2$ co-solvent: isopropanol with 0.1% isopropylamine. Isocratic method: 15% co-solvent at 4 mL/min. System pressure 100 bar. Column temperature: 25° C.
Analytical Separation Method AS(VIII):
Column: 4.6×100 mm Pyridyl Amide from ES Industries, West Berlin, N.J. $CO_2$ co-solvent: isopropanol with 10-90% methanol and 0.1-1% isopropylamine. Isocratic method: 5% co-solvent at 4 mL/min. System pressure: 100 bar. Column temperature: 25° C.
Analytical Separation Method AS(IX):
Column: 4.6×100 mm cm RegisPack®. $CO_2$ co-solvent: ethanol with 1% isopropylamine. Isocratic method: 25% co-solvent at 80 mL/min. System pressure: 100 bar. Column temperature: 25° C.

| Structure/Compound # | Separation method & data |
|---|---|
| Example 1.1a and Example 1.1b | Separated by preparative separation method PS(I) and analyzed by analytical separation method AS(I).<br>Faster moving enantiomer (fraction 1, Example 1.1a): Rt = 2.0 min, 100% ee.<br>Slower moving enantiomer (fraction 2, Example 1.1b): Rt = 3.1 min, 99.0% ee. mGluR5 PAM EC$_{50}$: ++. |
| Example 1.2a and Example1.2b | Separated by preparative separation method PS(II) and analyzed by analytical separation method AS(II).<br>Faster moving enantiomer (fraction 1, Example 1.2a): Rt = 2.0 min, 100% ee. mGluR5 PAM EC$_{50}$: ++++.<br>Slower moving enantiomer (fraction 2, Example 1.2b): Rt = 3.1 min, 99.0% ee. mGluR5 PAM EC$_{50}$: +. |
| Example 1.3a and Example1.3b | Separated by preparative separation method PS(III) and analyzed by analytical separation method AS(III).<br>Faster moving enantiomer (fraction 1, Example 1.3a): Rt = 2.5 min, 97.6% ee. mGluR5 PAM EC$_{50}$: +++++.<br>Slower moving enantiomer (fraction 2, Example 1.3b): Rt = 3.6 min, 95.4% ee. mGluR5 PAM EC$_{50}$: ++. |
| Example 1.8a and Example1.8b | Separated by preparative separation method PS(IV) and analyzed by analytical separation method AS(IV).<br>Faster moving enantiomer (fraction 1, Example 1.8a): Rt = 2.0 min, 99.2% ee. mGluR5 PAM EC$_{50}$: ++++.<br>Fold shift at 1 μM: +++.<br>Slower moving enantiomer (fraction 2, Example 1.8b): Rt = 2.9 min, 99.5% ee. mGluR5 PAM EC$_{50}$: +++.<br>Fold shift at 1 μM: +. |
| Example 1.9a and Example1.9b | Separated by preparative separation method PS(II) and analyzed by analytical separation method AS(II).<br>Faster moving enantiomer (fraction 1, Example 1.9a): Rt = 2.4 min, 100% ee. mGluR5 PAM EC$_{50}$: +++.<br>Slower moving enantiomer (fraction 2, Example 1.9b): Rt = 3.2 min, 98.8% ee. mGluR5 PAM EC$_{50}$: +. |

| Structure/Compound # | Separation method & data |
|---|---|
| 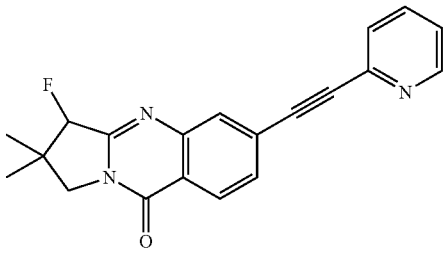 [SMILES: CC1(C)Cn2c(nc3cc(C#Cc4ccccn4)ccc3c2=O)C1F]<br>Example 1.11a and Example1.11b | Separated by preparative separation method PS(I) and analyzed by analytical separation method AS(I).<br>Faster moving enantiomer (fraction 1, Example 1.11a): Rt = 1.1 min, 98.1% ee. mGluR5 PAM $EC_{50}$: +++++.<br>Slower moving enantiomer (fraction 2, Example 1.11b): Rt = 1.6 min, 100% ee. mGluR5 PAM $EC_{50}$: ++++. |
| 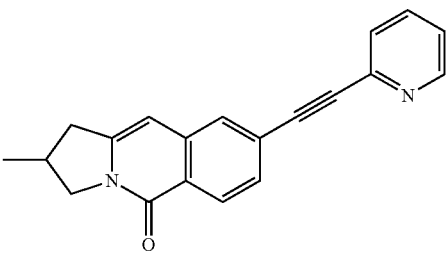 [SMILES: CC1Cc2cc3cc(C#Cc4ccccn4)ccc3c(=O)n2C1]<br>Example 1.13a and Example 1.13b | Separated by preparative separation method PS(II) and analyzed by analytical separation method AS(II).<br>Faster moving enantiomer (fraction 1, Example 1.13a): Rt = 2.4 min, 100% ee. mGluR5 PAM $EC_{50}$: +++.<br>Slower moving enantiomer (fraction 2, Example 1.13b): Rt = 3.0 min, 100% ee. |
| 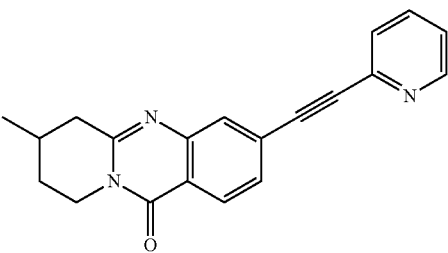<br>Example 2.1a and Example 2.1b | Separated by preparative separation method PS(I) and analyzed by analytical separation method AS(I).<br>Faster moving enantiomer (fraction 1, Example 2.1a): Rt = 2.5 min, 98.2% ee. mGluR5 PAM $EC_{50}$: ++++.<br>Slower moving enantiomer (fraction 2, Example 2.1b): Rt = 3.4 min, 96.4% ee. mGluR5 PAM $EC_{50}$: Fold shift at 1 μM: ++. |
| 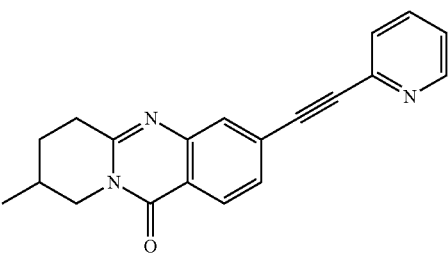 [SMILES: CC1CCc2nc3cc(C#Cc4ccccn4)ccc3c(=O)n2C1]<br>Example 2.2a and Example 2.2b | Separated by preparative separation method PS(I) and analyzed by analytical separation method AS(I).<br>Faster moving enantiomer (fraction 1, Example 2.2a): Rt = 2.0 min, 97.8% ee.<br>Slower moving enantiomer (fraction 2, Example 2.2b): Rt = 2.6 min, 97.3% ee. mGluR5 PAM $EC_{50}$: ++++. |
| 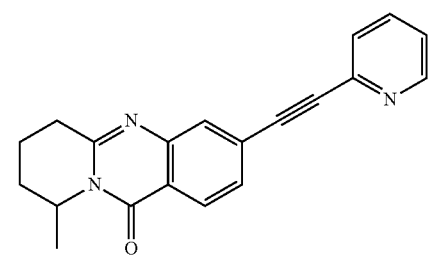 [SMILES: CC1CCCc2nc3cc(C#Cc4ccccn4)ccc3c(=O)n21]<br>Example 2.3a and Example 2.3b | Separated by preparative separation method PS(I) and analyzed by analytical separation method AS(I).<br>Faster moving enantiomer (fraction 1, Example 2.3a): Rt = 1.8 min, 98.8% ee.<br>Slower moving enantiomer (fraction 2, Example 2.3b): Rt = 1.9 min, 99.0% ee. mGluR5 PAM $EC_{50}$: +++++. |

| Structure/Compound # | Separation method & data |
|---|---|
| Example 2.4a and Example 2.4b | Separated by preparative separation method PS(II) and analyzed by analytical separation method AS(II).<br>Faster moving enantiomer (fraction 1, Example 2.4a): Rt = 4.4 min, 100% ee.<br>Slower moving enantiomer (fraction 2, Example 2.4b): Rt = 4.8 min, 100% ee. mGluR5 PAM $EC_{50}$: +++++. |
| Example 2.5a and Example 2.5b | Separated by preparative separation method PS(I) and analyzed by analytical separation method AS(I).<br>Faster moving enantiomer (fraction 1, Example 2.5a): Rt = 1.6 min, 100% ee. mGluR5 PAM $EC_{50}$: +++. Fold shift at 10 µM: +++.<br>Slower moving enantiomer (fraction 2, Example 2.5b): Rt = 2.0 min, 98.1% ee. mGluR5 PAM $EC_{50}$: +++. Fold shift at 10 µM: +++. |
| Example 2.6a and Example 2.6b | Separated by preparative separation method PS(II) and analyzed by analytical separation method AS(II).<br>Faster moving enantiomer (fraction 1, Example 2.6a): Rt = 2.0 min, 100% ee.<br>Slower moving enantiomer (fraction 2, Example 2.6b): Rt = 2.9 min, 100% ee. |
| Example 2.7a and Example 2.7b | Separated by preparative separation method PS(I) and analyzed by analytical separation method AS(I).<br>Faster moving enantiomer (fraction 1, Example 2.7a): Rt = 1.2 min, 100% ee. mGluR5 PAM $EC_{50}$: +++.<br>Slower moving enantiomer (fraction 2, Example 2.7b): Rt = 2.4 min, 97.2% ee. mGluR5 PAM $EC_{50}$: +++++. |
| Example 2.8a and Example 2.8b | Separated by preparative separation method PS(I) and analyzed by analytical separation method AS(I).<br>Faster moving enantiomer (fraction 1, Example 2.8a): Rt = 1.3 min, 100% ee. mGluR5 PAM $EC_{50}$: ++. Fold shift at 10 µM: ++.<br>Slower moving enantiomer (fraction 2, Example 2.8b): Rt = 3.2 min, 99.6% ee. mGluR5 PAM $EC_{50}$: +++. Fold shift at 1 µM: +++. |

-continued

| Structure/Compound # | Separation method & data |
|---|---|
| 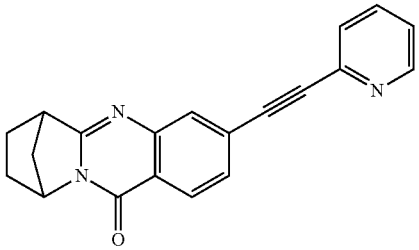 [SMILES: O=c1c2ccc(C#Cc3ccccn3)cc2nc2n1C1CCC2C1]<br>Example 2.9a and Example 2.9b | Separated by preparative separation method PS(I) and analyzed by analytical separation method AS(I).<br>Faster moving enantiomer (fraction 1, Example 2.9a): Rt = 1.7 min, 100% ee. mGluR5 PAM $EC_{50}$: ++++. Fold shift at 1 µM: +.<br>Slower moving enantiomer (fraction 2, Example 2.9b): Rt = 2.4 min, 98.0% ee. mGluR5 PAM $EC_{50}$: ++++. Fold shift at 1 µM: ++. |
| 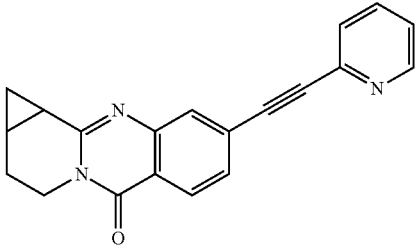 [SMILES: O=c1c2ccc(C#Cc3ccccn3)cc2nc2n1CCC1CC21]<br>Example 2.10a and Example 2.10b | Separated by preparative separation method PS(I) and analyzed by analytical separation method AS(I).<br>Faster moving enantiomer (fraction 1, Example 2.10a): Rt = 3.2 min, 100% ee. mGluR5 PAM $EC_{50}$: +++. mGluR5 Fold shift at 1 µM: ++.<br>Slower moving enantiomer (fraction 2, Example 2.10b): Rt = 5.1 min, 100% ee. |
| 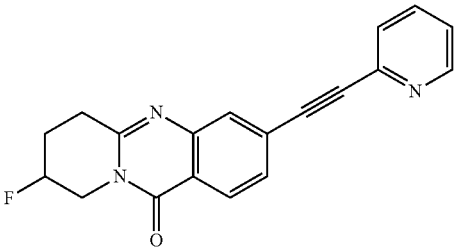 [SMILES: O=c1c2ccc(C#Cc3ccccn3)cc2nc2n1CC(F)CC2]<br>Example 2.11a and Example 2.11b | Separated by preparative separation method PS(I) and analyzed by analytical separation method AS(I).<br>Faster moving enantiomer (fraction 1, Example 2.11a): Rt = 2.7 min, 98.8% ee.<br>Slower moving enantiomer (fraction 2, Example 2.11b): Rt = 3.7 min, 96.0% ee. |
| 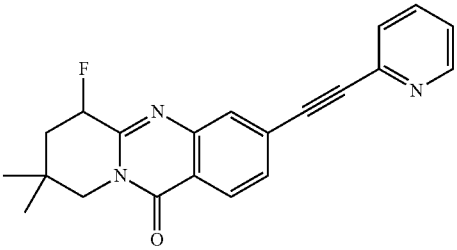 [SMILES: CC1(C)CC(F)c2nc3cc(C#Cc4ccccn4)ccc3c(=O)n2C1]<br>Example 2.12a and Example 2.12b | Separated by preparative separation method PS(I) and analyzed by analytical separation method AS(I).<br>Faster moving enantiomer (fraction 1, Example 2.12a): Rt = 1.2 min, 100% ee. mGluR5 PAM $EC_{50}$: +++++. Fold shift at 10 µM: +++.<br>Slower moving enantiomer (fraction 2, Example 2.12b): Rt = 2.1 min, 100% ee. mGluR5 PAM $EC_{50}$: +++++. Fold shift at 10 µM: +. |
| 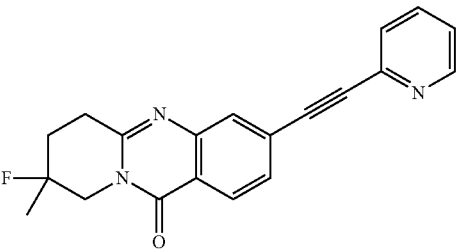 [SMILES: CC1(F)CCc2nc3cc(C#Cc4ccccn4)ccc3c(=O)n2C1]<br>Example 2.13a and Example 2.13b | Separated by preparative separation method PS(I) and analyzed by analytical separation method AS(I).<br>Faster moving enantiomer (fraction 1, Example 2.13a): Rt = 2.2 min, 100% ee. mGluR5 PAM $EC_{50}$: ++++. Fold shift at 10 µM: +++.<br>Slower moving enantiomer (fraction 2, Example 2.13b): Rt = 3.1 min, 98.4% ee. mGluR5 PAM $EC_{50}$: ++++. Fold shift at 10 µM: +++. |

-continued

| Structure/Compound # | Separation method & data |
|---|---|
| 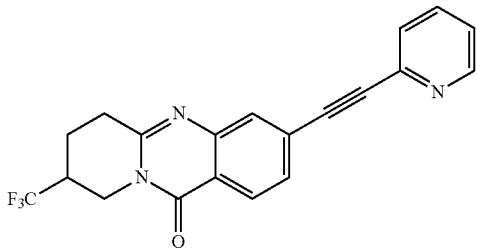 [SMILES: O=c1c2ccc(C#Cc3ccccn3)cc2nc2n1CC(C(F)(F)F)CC2]<br>Example 2.14a and Example 2.14b | Separated by preparative separation method PS(II) and analyzed by analytical separation method AS(II).<br>Faster moving enantiomer (fraction 1, Example 2.14a): Rt = 1.7 min, 100% ee. mGluR5 PAM $EC_{50}$: ++++.<br>Slower moving enantiomer (fraction 2, Example 2.14b): Rt = 3.4 min, 98.0 ee%. mGluR5 PAM $EC_{50}$: +++++. |
| 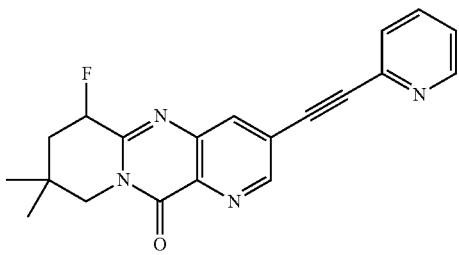<br>Example 2.15a and Example 2.15b | Separated by preparative separation method PS(V) and analyzed by analytical separation method AS(V).<br>Faster moving enantiomer (fraction 1, Example 2.15a): Rt = 2.2 min, 98.0% ee. mGluR5 PAM $EC_{50}$: +++.<br>Slower moving enantiomer (fraction 2, Example 2.15b): Rt = 2.9 min, 99.4% ee. mGluR5 PAM $EC_{50}$: +++. |
| 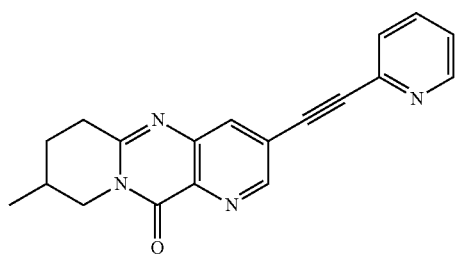<br>Example 2.16a and Example 2.16b<br>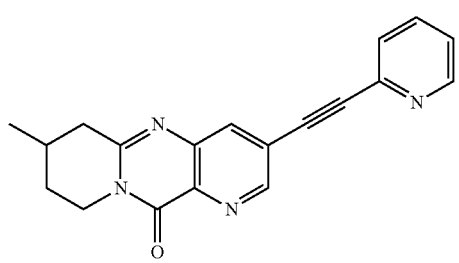 [SMILES: CC1CCn2c(nc3cc(C#Cc4ccccn4)cnc3c2=O)C1]<br>Example 2.17a and Example 2.17b | The regioisomers 1 (racemate) and 2 (racemate) were first separated by achiral preparative separation method PS(VII) and analyzed by achiral analytical separation method AS(VII). The regiochemistry was assigned arbitrarily.<br>Then separation of enantiomers Example 2.16a and 2.16b from regioisomer 1 was carried by preparative separation method PS(VI) and analyzed by analytical separation method AS(VI).<br>Faster moving enantiomer (fraction 1, Example 2.16a): Rt = 4.8 min, 100% ee.<br>Slower moving enantiomer (fraction 2, Example 2.16b): Rt = 6.1 min, 95.0% ee. mGluR5 PAM $EC_{50}$: ++.<br>The separation of enantiomers Example 2.17a and 2.17 b from regioisomer 2 was carried by preparative separation method PS(I) and analyzed by analytical separation method AS(I).<br>Faster moving enantiomer (fraction 1, Example 2.17a): Rt = 3.2 min, 100% ee.<br>Slower moving enantiomer (fraction 2, Example 2.17b): Rt = 3.4 min, 98.4% ee. mGluR5 PAM $EC_{50}$: +. |

| Structure/Compound # | Separation method & data |
|---|---|
| 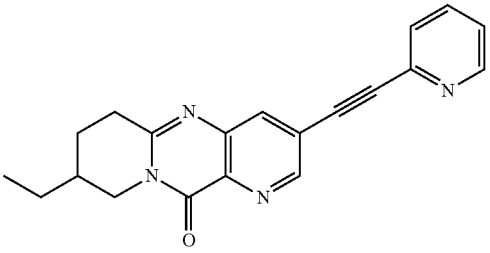 [SMILES: CCC1CCc2nc3cc(C#Cc4ccccn4)cnc3c(=O)n2C1]<br>Example 2.22a and Example 2.22b | The regioisomers 1 (racemate) and 2 (racemate) were first separated by achiral preparative separation method PS(VII) and analyzed by achiral analytical separation method AS(VII) to give fraction 1 (arbitrarily assigned as regioisomer 1) and fraction 2 arbitrarily assigned as regioisomer 2).<br>The enantiomers from fraction 1 (regioisomer 1, regiochemistry is arbitrarily assigned) were separated by preparative separation method PS(II) and analyzed by analytical separation method AS(II).<br>Faster moving enantiomer (fraction 1, Example 2.22c Rt = 1.2 min, 97.0% ee. mGluR5 PAM $EC_{50}$: ++++.<br>Slower moving enantiomer (fraction 2, Example 2.22b): Rt = 1.8 min, 100% ee. mGluR5 PAM $EC_{50}$: ++. |
| 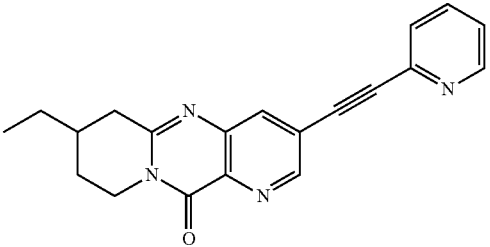 [SMILES: CCC1CCn2c(nc3cc(C#Cc4ccccn4)cnc3c2=O)C1]<br>Example 22.2c and Example 2.22d | |
| 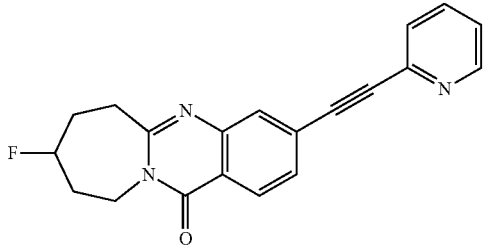 [SMILES: O=c1c2ccc(C#Cc3ccccn3)cc2nc2n1CCC(F)CC2]<br>Example 3.1a and Example 3.1b | Separated by preparative separation method PS(I) and analyzed by analytical separation method AS(I).<br>Faster moving enantiomer (fraction 1, Example 3.1a): Rt = 8.8 min, 100% ee. mGluR5 PAM $EC_{50}$: +++.<br>Slower moving enantiomer (fraction 2, Example 3.1b): Rt = 10.4 min, 100% ee. mGluR5 PAM $EC_{50}$: ++++. |
| 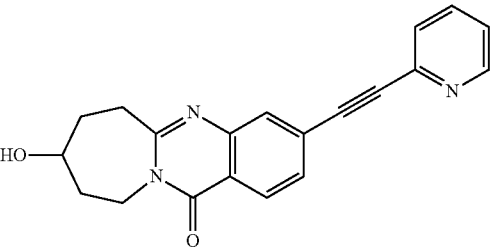 [SMILES: O=c1c2ccc(C#Cc3ccccn3)cc2nc2n1CCC(O)CC2]<br>Example 3.2a and Example 3.2b | Separated by preparative separation method PS(II) and analyzed by analytical separation method AS(II).<br>Faster moving enantiomer (fraction 1, Example 3.2a): Rt = 1.2 min, 100% ee. mGluR5 PAM $EC_{50}$: +.<br>Slower moving enantiomer (fraction 2, Example 3.2b): Rt = 1.9 min, 98.6% ee. mGluR5 PAM $EC_{50}$: +++. |
| 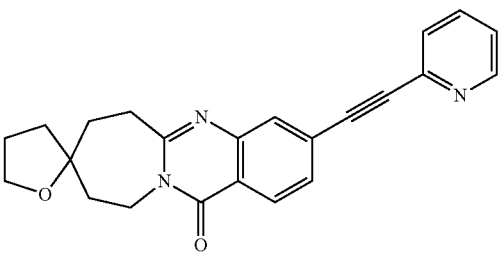 [SMILES: O=c1c2ccc(C#Cc3ccccn3)cc2nc2n1CCC1(CCCO1)CC2]<br>Example 3.3a and Example 3.3b | Separated by preparative separation method PS(I) and analyzed by analytical separation method AS(I).<br>Faster moving enantiomer (fraction 1, Example 3.3a): Rt = 2.1 min, 100% ee. mGluR5 PAM $EC_{50}$: +++. Fold shift at 10 μM: +++.<br>Slower moving enantiomer (fraction 2, Example 3.3b): Rt = 2.8 min, 95.0% ee. mGluR5 PAM $EC_{50}$: ++. Fold shift at 10 μM: +++. |

| Structure/Compound # | Separation method & data |
|---|---|
| Example 3.4a and Example 3.4b | Separated by preparative separation method PS(I) and analyzed by analytical separation method AS(I).<br>Faster moving enantiomer (fraction 1, Example 3.4a): Rt = 2.1 min, 96.5% ee. mGluR5 PAM $EC_{50}$: +++. Fold shift at 10 µM: +++.<br>Slower moving enantiomer (fraction 2, Example 3.4b): Rt = 2.8 min, 98.8% ee. mGluR5 PAM $EC_{50}$: +++. Fold shift at 10 µM: ++. |
| Example 3.9a and Example 3.9b | Separated by preparative separation method PS(II) and analyzed by analytical separation method AS(II).<br>Faster moving enantiomer (fraction 1, Example 3.9a): Rt = 2.8 min, 100% ee. mGluR5 PAM $EC_{50}$: +++.<br>Slower moving enantiomer (fraction 2, Example 3.9b): Rt = 3.9 min, 100% ee. mGluR5 PAM $EC_{50}$: +++. |
| Example 3.10a and Example 3.10b | Separated by preparative separation method PS(II) and analyzed by analytical separation method AS(II).<br>Faster moving enantiomer (fraction 1, Example 3.10a): Rt = 0.8 min, 97.6% ee. mGluR5 PAM $EC_{50}$: ++.<br>Slower moving enantiomer (fraction 2, Example 3.10b): Rt = 2.1 min; 99.2% ee. mGluR5 PAM $EC_{50}$: +++. Fold shift at 1 µM: +++. |
| Example 3.11a and Example 3.11b | Separated by preparative separation method PS(II) and analyzed by analytical separation method AS(II).<br>Faster moving enantiomer (fraction 1, Example 3.11a): Rt = 0.9 min, 100% ee.<br>Slower moving enantiomer (fraction 2, Example 3.11b): Rt = 2.3 min; 99.8% ee. mGluR5 PAM $EC_{50}$: ++++. Fold shift at 1 µM: ++. |
| Example 3.12a and Example 3.12b | Separated by preparative separation method PS(II) and analyzed by analytical separation method AS(II).<br>Faster moving enantiomer (fraction 1, Example 3.12a): Rt = 1.5 min, 100% ee. mGluR5 PAM $EC_{50}$: +++++.<br>Slower moving enantiomer (fraction 2, Example 3.12b): Rt = 2.2 min, 99.5% ee. mGluR5 PAM $EC_{50}$: ++++. |

| Structure/Compound # | Separation method & data |
|---|---|
| Example 3.13a and Example 3.13b | Separated by preparative separation method PS(I) and analyzed by analytical separation method PS(I). Faster moving enantiomer (fraction 1, Example 3.13a): Rt = 1.8 min, 98.6% ee. mGluR5 PAM EC$_{50}$: +++++. Fold shift at 1 μM: +++. Slower moving enantiomer (fraction 2, Example 3.13b): Rt = 2.6 min, 98.8% ee. mGluR5 PAM EC$_{50}$: ++++. Fold shift at 1 μM: +++. |
| Example 3.14a and Example 3.14b | Separated by preparative separation method PS(II) and analyzed by analytical separation method AS(II). Faster moving enantiomer (fraction 1, Example 3.14a): Rt = 1 min, 100% ee. mGluR5 PAM EC$_{50}$: +++. Fold shift at 1 μM: +++. Slower moving enantiomer (fraction 2, Example 3.14b): Rt = 3.3 min, 99.6% ee. mGluR5 PAM EC$_{50}$: +++. Fold shift at 1 μM: +++. |
| Example 3.20a and Example 3.20b | Separated by preparative separation method PS(II) and analyzed by analytical separation method AS(II). Faster moving enantiomer (fraction 1, Example 3.20a): Rt = 1 min, 100% ee. mGluR5 PAM EC$_{50}$: +++++. Fold shift at 10 μM: +++. Slower moving enantiomer (fraction 2, Example 3.20b): Rt = 3.3 min, 99.6% ee. |
| Example 3.24a and Example 3.24b | Separated by preparative separation method PS(I) and analyzed by analytical separation method AS(I). Faster moving enantiomer (fraction 1, Example 3.24a): Rt = 1.4 min, 99.1% ee. mGluR5 PAM EC$_{50}$: +++++. Fold shift at 1 μM: +++. Slower moving enantiomer (fraction 2, Example 3.24b): Rt = 2.0 min, 99.2% ee. mGluR5 PAM EC$_{50}$: +++++. Fold shift at 1 μM: +++. |
| Example 3.30c and Example 3.30d | The regioisomers and enantiomers were separated by two chiral chromatographies. The regiochemistry was assigned arbitrarily. Enantiomers 3.30a and 3.30b were separated from regioisomers 1 by preparative separation method PS(I) and analyzed by analytical separation method AS(I). Faster moving enantiomer (fraction 1, Example 3.30c): Rt = 3.3 min, 100% ee. mGluR5 PAM EC$_{50}$: ++++. Fold shift at 10 μM: +++. Slower moving enantiomer (fraction 2, Example 3.30d): Rt = 4.1 min, 98.4% ee. mGluR5 PAM EC$_{50}$: ++++. Fold shift at 10 μM: +. |

| Structure/Compound # | Separation method & data |
|---|---|
| 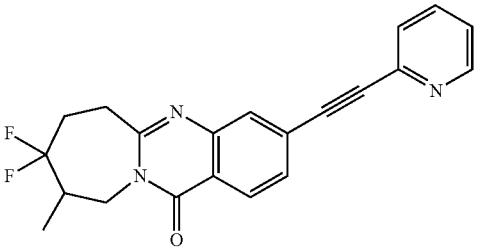 [SMILES: CC1Cn2c(nc3cc(C#Cc4ccccn4)ccc3c2=O)CCC1(F)F]<br>Example 3.30e and Example 3.30f | Enantiomers 3.30c and 3.30d were separated from regioisomer 2 by preparative separation method PS(II) and analyzed by analytical separation method AS(II). The regiochemistry was assigned arbitrarily.<br>Faster moving enantiomer (fraction 1, Example 3.30e): Rt = 1.2 min, 100% ee.<br>Slower moving enantiomer (fraction 2, Example 3.30f): Rt = 2.0 min, 98.4% ee. mGluR5 PAM EC$_{50}$: ++++. Fold shift at 10 μM: ++. |
| 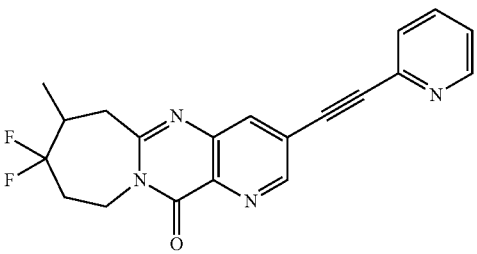 [SMILES: CC1Cc2nc3cc(C#Cc4ccccn4)cnc3c(=O)n2CCC1(F)F]<br>Example 3.31c and Example 3.31d<br><br>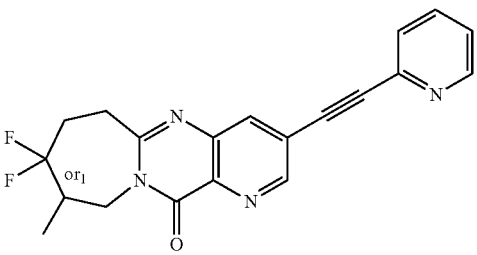<br>Example 3.31e and Example 3.31f | The two regioisomers were separated by chromatography on achiral column by preparative separation method PS(VIII) and analytical separation method AS(VIII) to give regioisomer 1 and regioisomer 2 (The regiochemistry was assigned arbitrarily).<br>The separation of enantiomers from regioisomer 1 (Example 3.31a) was carried by preparative separation method PS(IX) and analyzed by analytical separation method AS(IX) to provide Example 3.31c and 3.31d (The absolute stereochemistry was arbitrarily assigned).<br>Faster moving enantiomer (fraction 1, Example 3.31c): Rt = 2.8 min, 96.6% ee. mGluR5 PAM EC$_{50}$: +++.<br>Slower moving enantiomer (fraction 2, Example 3.31d): Rt = 3.2 min, 99.6% ee. mGluR5 PAM EC$_{50}$: +++. Fold shift at 1 μM: +++.<br>The separation of enantiomers from regioisomer 2 (example 3.31b was carried out by preparative separation method PS(II) and analyzed by analytical separation method AS(II) to give Example 3.31e, and 3.31f (The absolute stereochemistry was arbitrarily assigned).<br>Faster moving enantiomer (fraction 1, Example 3.31e): Rt = 1.4 min, 100% ee. mGluR5 PAM EC$_{50}$: +++. Fold shift at 1 μM: +++.<br>Slower moving enantiomer (fraction 2, Example 3.31f): Rt = 3.1 min, 100% ee. mGluR5 PAM EC$_{50}$: +++. |
| 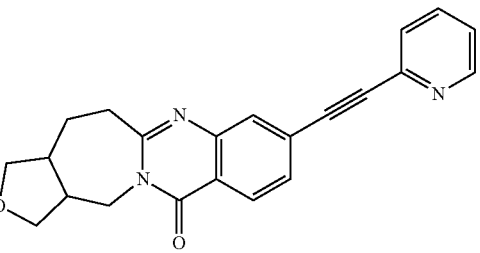<br>Example 3.32c and Example 3.32d<br><br>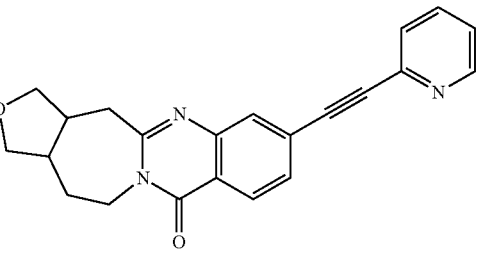<br>Example 3.32e and Example 3.32f<br>The regiochemistry and absolute stereochemistry were arbitrarily assigned. | Preparative separation method PS(II) generated two fractions (Fractions 1 and 2). Fraction 1 contained three peaks, while fraction 2 was a single peak. Fraction 1 was then put through preparative separation method PS(VI) where the three peaks were resolved (Fractions 3, 4 and 5). The collected fractions were analyzed by analytical separation methods AS(II) and AS(VI).<br>Fraction 1, Example 3.32c: Rt from analytical separation methods AS(II) and AS(VI): 3.4 min and 3.1 min, respectively, 95.6% ee.<br>Fraction 2, Example3.2d: Rt from analytical separation methods AS(II) and AS(VI): 1.8 min and 3.1 min, respectively, 100% ee. mGluR5 PAM EC$_{50}$: +++.<br>Fraction 3, Example 3.2e: Rt from analytical separation methods AS(II) and AS(VI): 1.8 min and 3.7 min, respectively, 100% ee. mGluR5 PAM EC$_{50}$: +++.<br>Fraction 4, Example 3.2f: Rt from analytical separation methods AS(II) and AS(VI): 1.8 min and 4.1 min, respectively, 97.8% ee. mGluR5 PAM EC$_{50}$: +++++. |

Prophetic Compounds

| Compound | Synthesis Method & Data |
|---|---|
| 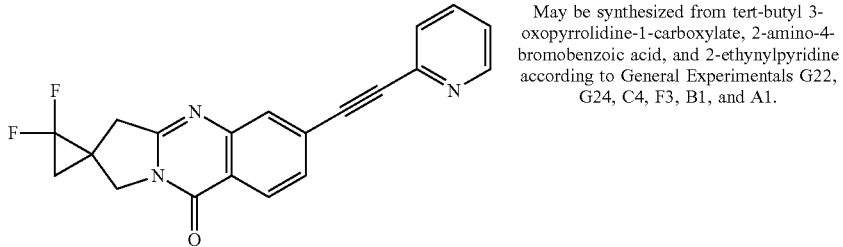<br>Example 1.21<br>2,2-difluoro-6'-(pyridin-2-ylethynyl)-1'H-spiro<br>[cyclopropane-1,2'-pyrrolo[2,1-b]quinazolin]-<br>9'(3'H)-one | May be synthesized from tert-butyl 3-oxopyrrolidine-1-carboxylate, 2-amino-4-bromobenzoic acid, and 2-ethynylpyridine according to General Experimentals G22, G24, C4, F3, B1, and A1. |
| 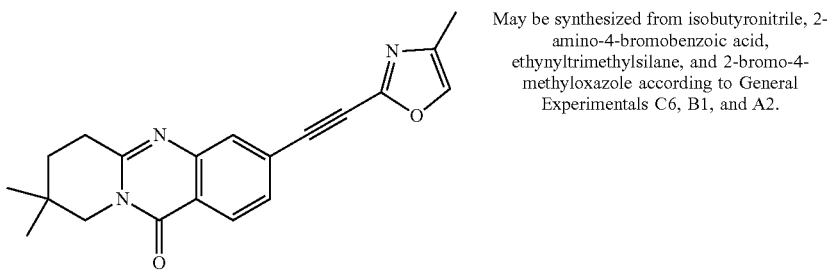<br>Example 2.48<br>8,8-dimethyl-3-((4-methyloxazol-2-yl)<br>ethynyl)-8,9-dihydro-6H-pyrido[2,1-b]<br>quinazolin-11(7H)-one | May be synthesized from isobutyronitrile, 2-amino-4-bromobenzoic acid, ethynyltrimethylsilane, and 2-bromo-4-methyloxazole according to General Experimentals C6, B1, and A2. |
| 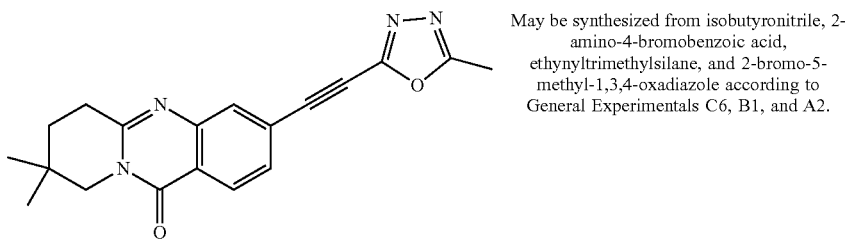<br>Example 2.52<br>8,8-dimethyl-3-((5-methyl-1,3,4-oxadiazol-2-yl)<br>ethynyl)-8,9-dihydro-6H-pyrido[2,1-b]<br>quinazolin-11(7H)-one | May be synthesized from isobutyronitrile, 2-amino-4-bromobenzoic acid, ethynyltrimethylsilane, and 2-bromo-5-methyl-1,3,4-oxadiazole according to General Experimentals C6, B1, and A2. |
| 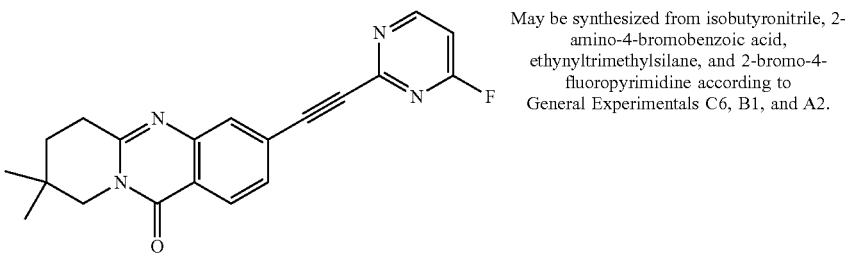<br>Example 2.53<br>3-((4-fluoropyrimidin-2-yl)ethynyl)-8,8-<br>dimethyl-8,9-dihydro-6H-pyrido[2,1-b]<br>quinazolin-11(7H)-one | May be synthesized from isobutyronitrile, 2-amino-4-bromobenzoic acid, ethynyltrimethylsilane, and 2-bromo-4-fluoropyrimidine according to General Experimentals C6, B1, and A2. |

| Compound | Synthesis Method & Data |
|---|---|
| Example 2.56<br>3-((5,6-dihydro-4H-cyclopental[d]thiazol-2-yl)ethynyl)-8,8-dimethyl-8,9-dihydro-6H-pyrido[2,1-b]quinazolin-11(7H)-one | May be synthesized from isobutyronitrile, 2-amino-4-bromobenzoic acid, ethynyltrimethylsilane, and 2-bromo-5,6-dihydro-4H-cyclopenta[d]thiazole according to General Experimental C6, B1, and A2. |
| Example 2.57<br>8,8-dimethyl-3-((4,5,6,7-tetrahydrobenzo[d]thiazol-2-yl)ethynyl)-8,9-dihydro-6H-pyrido[2,1-b]quinazolin-11(7H)-one | May be synthesized from isobutyronitrile, 2-amino-4-bromobenzoic acid, ethynyltrimethylsilane, and 2-bromo-4,5,6,7-tetrahydrobenzo[d]thiazole according to General Experimentals C6, B1, and A2. |
| Example 2.59<br>3'-(pyridin-2-ylethynyl)-6',7'-dihydrospiro[oxetane-2,8'-pyrido[2,1-b]quinazolin]-11'(9'H)-one | May be synthesized from tert-butyl 1-oxa-6-azaspiro[3.5]nonane-6-carboxylate, 2-amino-4-bromobenzoic acid, and 2-ethynylpyridine according to General Experimentals C4, F3, B1, and A1. |
| Example 2.60<br>3'-(pyridin-2-ylethynyl)-6',7'-dihydrospiro[cyclopropane-1,8'-pyrido[2,1-b]quinazolin]-11'(9'H)-one | May be synthesized from cyclopropanecarbonitrile, ethyl acrylate, 2-amino-4-bromobenzoic acid, and 2-ethynylpyridine according to General Experimental C6, B1, and A1 or from tert-butyl 5-azaspiro[2.5]octane-5-carboxylate, 2-amino-4-bromobenzoic acid, and 2-ethynylpyridine according to General Experimentals C4, F3, B1, and A1. |

-continued

| Compound | Synthesis Method & Data |
|---|---|
| Example 2.61<br>1'-methyl-3-(pyridin-2-ylethynyl)-6,7-dihydrospiro[pyrido[2,1-b]quinazoline-8,2'-pyrrolidin]-11(9H)-one | May be synthesized from tert-butyl 1-methyl-1,7-diazaspiro[4.5]decane-7-carboxylate, 2-amino-4-bromobenzoic acid, and 2-ethynylpyridine according to General Experimentals C4, F3, B1, and A1. |
| Example 2.62<br>3-(pyridin-2-ylethynyl)-6,7-dihydrospiro[pyrido[2,1-b]quinazoline-8,2'-pyrrolidin]-11(9H)-one | May be synthesized from 1-((9H-fluoren-9-yl)methyl) 7-tert-butyl 1,7-diazaspiro[4.5]decane-1,7-dicarboxylate, 2-amino-4-bromobenzoic acid, and 2-ethynylpyridine according to General Experimentals C4, F3, F4, B1, and A1. |
| Example 2.63<br>8-methyl-3-(pyridin-2-ylethynyl)-8-(trifluoromethyl)-8,9-dihydro-6H-pyrido[2,1-b]quinazolin-11(7H)-one | May be synthesized from 3,3,3-trifluoro-2-methylpropanenitrile (prepared from methylation of 3,3,3-trifluoropropanenitrile by deprotonation with LDA and methylation with MeI), ethyl acrylate, 2-amino-4-bromobenzoic acid, and 2-ethynylpyridine according to General Experimentals C6, B1, and A1. |
| Example 2.64<br>8,8-bis(fluoromethyl)-3-(pyridin-2-ylethynyl)-8,9-dihydro-6H-pyrido[2,1-b]quinazolin-11(7H)-one | May be synthesized from dimethyl malonate, (Z)-1,4-dichlorobut-2-ene, 2-amino-4-bromobenzoic acid, and 2-ethynylpyridine according to General Experimentals H4, B1, and A1. |

| Compound | Synthesis Method & Data |
|---|---|
| 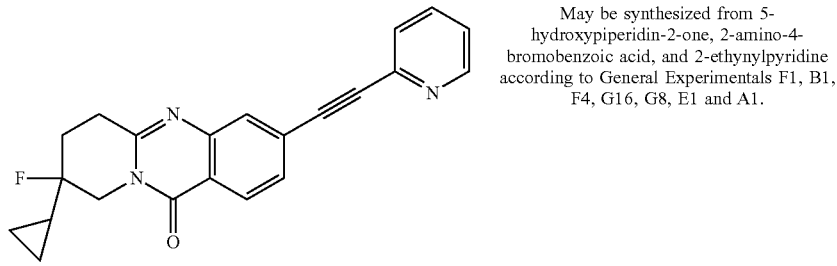

Example 2.65
8-cyclopropyl-8-fluoro-3-(pyridin-2-ylethynyl)-8,9-dihydro-6H-pyrido[2,1-b]quinazolin-11(7H)-one | May be synthesized from 5-hydroxypiperidin-2-one, 2-amino-4-bromobenzoic acid, and 2-ethynylpyridine according to General Experimentals F1, B1, F4, G16, G8, E1 and A1. |
| 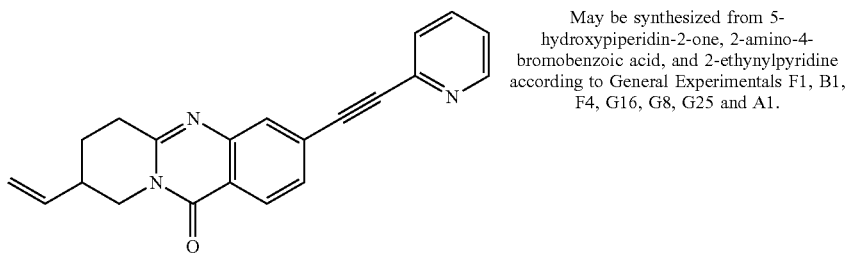

Example 2.66
3-(pyridin-2-ylethynyl)-8-vinyl-8,9-dihydro-6H-pyrido[2,1-b]quinazolin-11(7H)-one | May be synthesized from 5-hydroxypiperidin-2-one, 2-amino-4-bromobenzoic acid, and 2-ethynylpyridine according to General Experimentals F1, B1, F4, G16, G8, G25 and A1. |
| 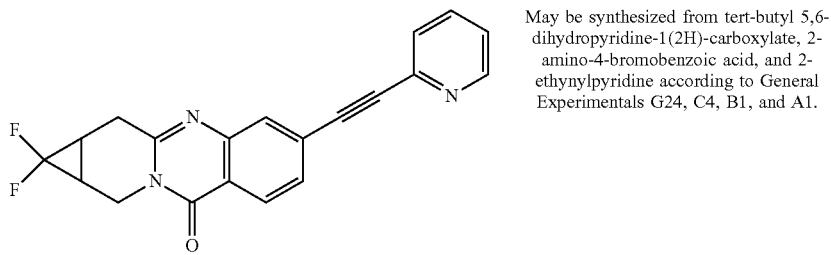

Example 2.67
1,1-difluoro-5-(pyridin-2-ylethynyl)-1a,2,10,10a-tetrahydrocyclopropa[4,5]pyrido[2,1-b]quinazolin-8(1H)-one | May be synthesized from tert-butyl 5,6-dihydropyridine-1(2H)-carboxylate, 2-amino-4-bromobenzoic acid, and 2-ethynylpyridine according to General Experimentals G24, C4, B1, and A1. |
| 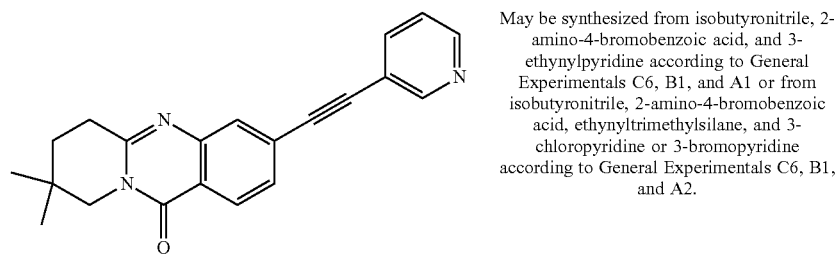

Example 2.71
8,8-dimethyl-3-(pyridin-3-ylethynyl)-8,9-dihydro-6H-pyrido[2,1-b]quinazolin-11(7H)-one | May be synthesized from isobutyronitrile, 2-amino-4-bromobenzoic acid, and 3-ethynylpyridine according to General Experimentals C6, B1, and A1 or from isobutyronitrile, 2-amino-4-bromobenzoic acid, ethynyltrimethylsilane, and 3-chloropyridine or 3-bromopyridine according to General Experimentals C6, B1, and A2. |

| Compound | Synthesis Method & Data |
|---|---|
| Example 2.72<br>8,8-dimethyl-3-(pyridin-4-ylethynyl)-8,9-dihydro-6H-pyrido[2,1-b]quinazolin-11(7H)-one | May be synthesized from isobutyronitrile, 2-amino-4-bromobenzoic acid, and 4-ethynylpyridine according to General Experimentals C6, B1, and A1 or from isobutyronitrile, 2-amino-4-bromobenzoic acid, ethynyltrimethylsilane, and 4-chloropyridine or 4-bromopyridine according to General Experimentals C6, B1, and A2. |
| Example 2.74<br>3-((3-fluorophenyl)ethynyl)-8,8-dimethyl-8,9-dihydro-6H-pyrido[2,1-b]quinazolin-11(7H)-one | May be synthesized from isobutyronitrile, 2-amino-4-bromobenzoic acid, and 1-ethynyl-3-fluorobenzene according to General Experimentals C6, B1, and A1 or from isobutyronitrile, 2-amino-4-bromobenzoic acid, ethynyltrimethylsilane, and 1-bromo-3-fluorobenzene or 1-chloro-3-fluorobenzene according to General Experimentals C6, B1, and A2. |
| Example 2.76<br>3-((2,3-difluorophenyl)ethynyl)-8,8-dimethyl-8,9-dihydro-6H-pyrido[2,1-b]quinazolin-11(7H)-one | May be synthesized from isobutyronitrile, 2-amino-4-bromobenzoic acid, and 1-ethynyl-2,3-difluorobenzene according to General Experimentals C6, B1, and A1 or from isobutyronitrile, 2-amino-4-bromobenzoic acid, ethynyltrimethylsilane, and 1-bromo-2,3-difluorobenzene or 1-chloro-2,3-difluorobenzene according to General Experimentals C6, B1, and A2. |
| Example 2.77<br>3-((2,4-difluorophenyl)ethynyl)-8,8-dimethyl-8,9-dihydro-6H-pyrido[2,1-b]quinazolin-11(7H)-one | May be synthesized from isobutyronitrile, 2-amino-4-bromobenzoic acid, and 1-ethynyl-2,4-difluorobenzene according to General Experimentals C6, B1, and A1 or from isobutyronitrile, 2-amino-4-bromobenzoic acid, ethynyltrimethylsilane, and 1-bromo-2,4-difluorobenzene or 1-chloro-2,4-difluorobenzene according to General Experimentals C6, B1, and A2. |

| Compound | Synthesis Method & Data |
|---|---|
| 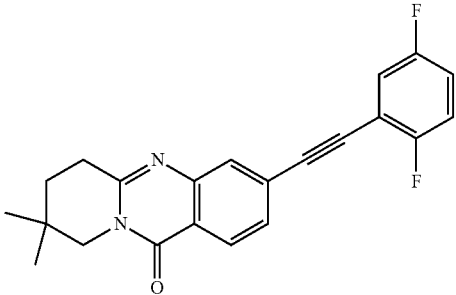<br>Example 2.78<br>3-((2,5-difluorophenyl)ethynyl)-8,8-dimethyl-8,9-dihydro-6H-pyrido[2,1-b]quinazolin-11(7H)-one | May be synthesized from isobutyronitrile, 2-amino-4-bromobenzoic acid, and 2-ethynyl-1,4-difluorobenzene according to General Experimentals C6, B1, and A1 or from isobutyronitrile, 2-amino-4-bromobenzoic acid, ethynyltrimethylsilane, and 2-bromo-1,4-difluorobenzene or 2-chloro-1,4-difluorobenzene according to General Experimentals C6, B1, and A2. |
| 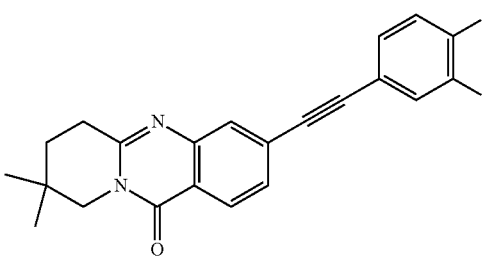<br>Example 2.79<br>3-((3,4-difluorophenyl)ethynyl)-8,8-dimethyl-8,9-dihydro-6H-pyrido[2,1-b]quinazolin-11(7H)-one | May be synthesized from isobutyronitrile, 2-amino-4-bromobenzoic acid, and 4-ethynyl-1,2-difluorobenzene according to General Experimentals C6, B1, and A1 or from isobutyronitrile, 2-amino-4-bromobenzoic acid, ethynyltrimethylsilane, and 4-bromo-1,2-difluorobenzene or 4-chloro-1,2-difluorobenzene according to General Experimentals C6, B1, and A2. |
| 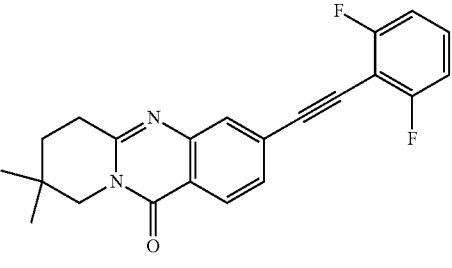<br>Example 2.80<br>3-((2,6-difluorophenyl)ethynyl)-8,8-dimethyl-8,9-dihydro-6H-pyrido[2,1-b]quinazolin-11(7H)-one | May be synthesized from isobutyronitrile, 2-amino-4-bromobenzoic acid, and 2-ethynyl-1,3-difluorobenzene according to General Experimentals C6, B1, and A1 or from isobutyronitrile, 2-amino-4-bromobenzoic acid, ethynyltrimethylsilane, and 2-chloro-1,3-difluorobenzene or 2-bromo-1,3-difluorobenzene according to General Experimentals C6, B1, and A2. |
| 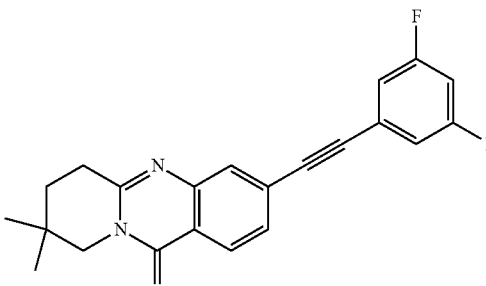<br>Example 2.81<br>3-((3,5-difluorophenyl)ethynyl)-8,8-dimethyl-8,9-dihydro-6H-pyrido[2,1-b]quinazolin-11(7H)-one | May be synthesized from isobutyronitrile, 2-amino-4-bromobenzoic acid, and 1-ethynyl-3,5-difluorobenzene according to General Experimentals C6, B1, and A1 or from isobutyronitrile, 2-amino-4-bromobenzoic acid, ethynyltrimethylsilane, and 1-bromo-3,5-difluorobenzene or 1-chloro-3,5-difluorobenzene according to General Experimentals C6, B1, and A2. |

| Compound | Synthesis Method & Data |
|---|---|
| 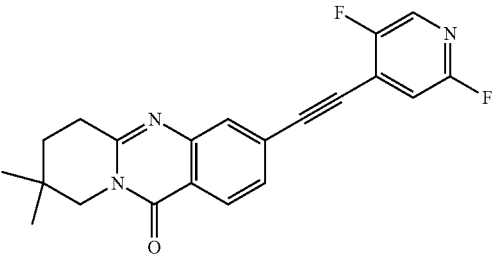<br>Example 2.82<br>3-((2,5-difluoropyridin-4-yl)ethynyl)-8,8-dimethyl-8,9-dihydro-6H-pyrido[2,1-b]quinazolin-11(7H)-one | May be synthesized from isobutyronitrile, 2-amino-4-bromobenzoic acid, and 4-ethynyl-2,5-difluoropyridine according to General Experimentals C6, B1, and A1 or from isobutyronitrile, 2-amino-4-bromobenzoic acid, ethynyltrimethylsilane, and 4-bromo-2,5-difluoropyridine or 4-chloro-2,5-difluoropyridine according to General Experimentals C6, B1, and A2. |
| 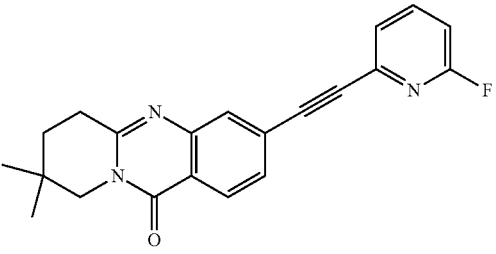<br>Example 2.83<br>3-((6-fluoropyridin-2-yl)ethynyl)-8,8-dimethyl-8,9-dihydro-6H-pyrido[2,1-b]quinazolin-11(7H)-one | May be synthesized from isobutyronitrile, 2-amino-4-bromobenzoic acid, and 2-ethynyl-6-fluoropyridine according to General Experimentals C6, B1, and A1 or from isobutyronitrile, 2-amino-4-bromobenzoic acid, ethynyltrimethylsilane, and 2-chloro-6-fluoropyridine or 2-bromo-6-fluoropyridine according to General Experimentals C6, B1, and A2. |
| 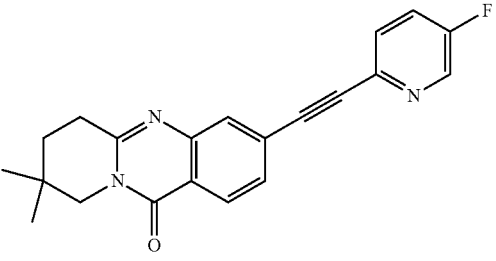<br>Example 2.84<br>3-((5-fluoropyridin-2-yl)ethynyl)-8,8-dimethyl-8,9-dihydro-6H-pyrido[2,1-b]quinazolin-11(7H)-one | May be synthesized from isobutyronitrile, 2-amino-4-bromobenzoic acid, and 2-ethynyl-5-fluoropyridine according to General Experimentals C6, B1, and A1 or from isobutyronitrile, 2-amino-4-bromobenzoic acid, ethynyltrimethylsilane, and 2-chloro-5-fluoropyridine or 2-bromo-5-fluoropyridine according to General Experimentals C6, B1, and A2. |
| 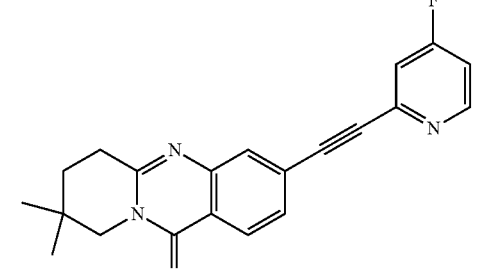<br>Example 2.85<br>3-((4-fluoropyridin-2-yl)ethynyl)-8,8-dimethyl-8,9-dihydro-6H-pyrido[2,1-b]quinazolin-11(7H)-one | May be synthesized from isobutyronitrile, 2-amino-4-bromobenzoic acid, and 2-ethynyl-4-fluoropyridine according to General Experimentals C6, B1, and A1 or from isobutyronitrile, 2-amino-4-bromobenzoic acid, ethynyltrimethylsilane, and 2-chloro-4-fluoropyridine or 2-bromo-4-fluoropyridine according to General Experimentals C6, B1, and A2. |

| Compound | Synthesis Method & Data |
|---|---|
| Example 2.93<br>3-((2,4-difluoropyridin-3-yl)ethynyl)-8,8-dimethyl-8,9-dihydro-6H-pyrido[2,1-b]quinazolin-11(7H)-one | May be synthesized from isobutyronitrile, 2-amino-4-bromobenzoic acid, and 3-ethynyl-2,4-difluoropyridine according to General Experimentals C6, B1, and A1 or from isobutyronitrile, 2-amino-4-bromobenzoic acid, ethynyltrimethylsilane, and 3-chloro-2,4-difluoropyridine or 3-bromo-2,4-difluoropyridine according to General Experimentals C6, B1, and A2. |
| Example 2.94<br>3-((2,3-difluoropyridin-4-yl)ethynyl)-8,8-dimethyl-8,9-dihydro-6H-pyrido[2,1-b]quinazolin-11(7H)-one | May be synthesized from isobutyronitrile, 2-amino-4-bromobenzoic acid, and 4-ethynyl-2,3-difluoropyridine according to General Experimentals C6, B1, and A1 or from isobutyronitrile, 2-amino-4-bromobenzoic acid, ethynyltrimethylsilane, and 4-chloro-2,3-difluoropyridine or 4-bromo-2,3-difluoropyridine according to General Experimentals C6, B1, and A2. |
| Example 3.39<br>10-(pyridin-2-ylethynyl)-4,5-dihydro-1H-2,5-methano[1,4]diazepino[2,1-b]quinazolin-7(3H)-one | May be synthesized from tert-butyl, 1,4-diazabicyclo[3.2.1]octane-4-carboxylate, 2-amino-4-bromobenzoic acid, and 2-ethynylpyridine according to General Experimentals C4, F3, B1, and A1. |
| Example 3.41<br>8-fluoro-3-(pyridin-2-ylethynyl)-7,8-dihydor-6H-spiro[azepino[2,1-b]quinazoline-9,1'-cyclopropan]-12(10H)-one | May be synthesized from tert-butyl 3-oxoazepane-1-carboxylate, 2-amino-4-bromobenzoic acid, and 2-ethynylpyridine according to General Experimentals E4, G22, G23, C4, F3, B1, and A1. |

| Compound | Synthesis Method & Data |
|---|---|
| 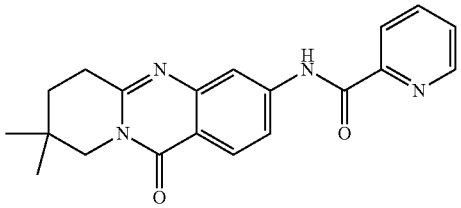

Example 4.13
N-(8,8-dimethyl-11-oxo-7,8,9,11-tetrahydro-6H-pyrido[2,1-b]quinazolin-3-yl)picolinamide | May be synthesized from isobutyronitrile, 2-amino-4-nitrobenzoic acid, and picolinic acid according to General Experimentals C6, B5, G29 and G28. |

It will be understood that the invention has been described by way of example only and modifications may be made whilst remaining within the scope and the spirit of the invention.

The invention claimed is:

1. A compound of formula (I) or a pharmaceutically acceptable salt thereof:

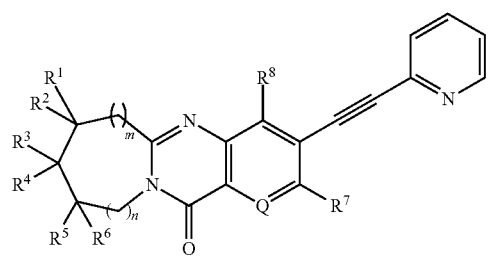

(I)

wherein
Q is $CR^9$ or N;
m and n are both 0;
X is F, Cl, Br, or I;
$R^1$, $R^2$, $R^3$, $R^4$, $R^5$, $R^6$, $R^7$, and $R^8$ are each independently hydrogen, X, alkyl, heteroalkyl, or alkenyl; or any two of $R^1$, $R^2$, $R^3$, $R^4$, $R^5$ and $R^6$ together with the atoms to which they are attached, form a cycloalkyl ring; and
$R^9$ is hydrogen or alkyl;
provided that:
at least one of $R^1$, $R^2$, $R^3$, $R^4$, $R^5$, $R^6$, $R^7$, and $R^8$ is either X, or alkyl or heteroalkyl substituted with at least one X; or a cycloalkyl ring formed by any two of $R^1$, $R^2$, $R^3$, $R^4$, $R^5$ and $R^6$ together with the atoms to which they are attached is substituted with at least one X;
and at least one of $R^3$ and $R^4$ is not hydrogen.

2. A compound of formula (II) or a pharmaceutically acceptable salt thereof:

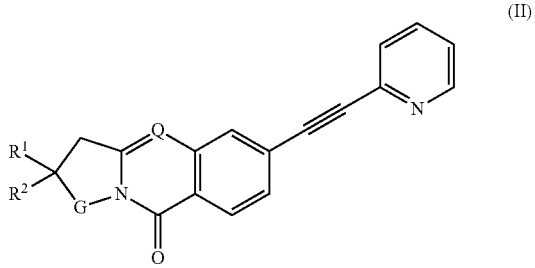

(II)

wherein
Q is $CR^7$ or N;
G is $CH_2$ or O;
$R^1$ and $R^2$ are independently hydrogen, alkyl, cyano, or heteroalkyl; or $R^1$ and $R^2$ together with the atom to which they are attached form a cycloalkyl or heterocycloalkyl ring; and
$R^7$ is selected from hydrogen and alkyl
provided that
when Q is N and G is $CH_2$, then at least one of $R^1$ and $R^2$ is not hydrogen;
when Q is N, G is $CH_2$, and one of $R^1$ and $R^2$ is methyl, then the other of $R^1$ and $R^2$ is not hydrogen or methyl;
when Q is N, G is $CH_2$, and one of $R^1$ and $R^2$ is hydroxymethyl or methoxymethyl, then the other of $R^1$ and $R^2$ is not hydrogen; and
when Q is N, G is $CH_2$, and $R^1$ and $R^2$ together with the atom to which they are attached form a heterocycloalkyl ring, then $R^1$ and $R^2$ together are not —$(CH_2)_2O(CH_2)_2$—.

3. A compound of formula (IV) or a pharmaceutically acceptable salt thereof:

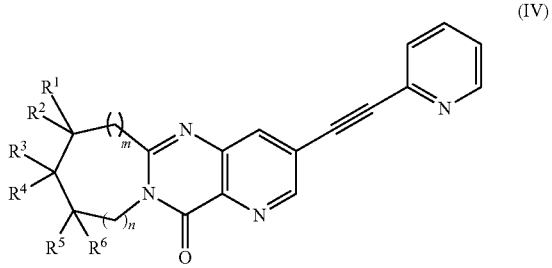

(IV)

wherein
  m and n are both 0;
  R¹, R², R³, R⁴, R⁵, and R⁶ are each independently hydrogen, alkyl, or heteroalkyl; or
  R¹ and R², R³ and R⁴, or R⁵ and R⁶ together with the atom to which they are bonded form a cycloalkyl or heterocycloalkyl ring;
provided that
  at least one of R¹, R², R³, R⁴, R⁵, and R⁶ is not hydrogen;
  when m and n are both 0 and both R¹ and R⁴ are methyl, then at least one of R¹, R², R⁵ and R⁶ is not hydrogen; and
  when m and n are both 0, one of R⁵ and R⁶ is hydroxymethyl or methoxymethyl, and the other of R⁵ and R⁶ is hydrogen, then at least one of R¹, R², R³, and R⁴ is not hydrogen.

4. A compound of formula (V) or a pharmaceutically acceptable salt thereof:

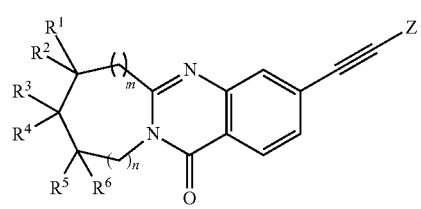

(V)

wherein
  m and n are both 0;
  Z is

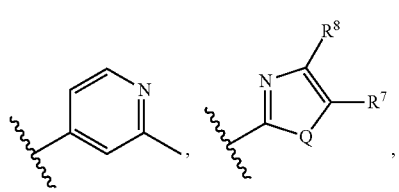

, or

R¹, R², R³, R⁴, R⁵, and R⁶ are each independently hydrogen or alkyl;
Q is O or S;
R⁷ and R⁸ are hydrogen or alkyl; or R⁷ and R⁸ together with the atoms to which they are attached form a cyclolalkyl, heterocycloalkyl, aryl, or heteroaryl ring.

5. A compound selected from:

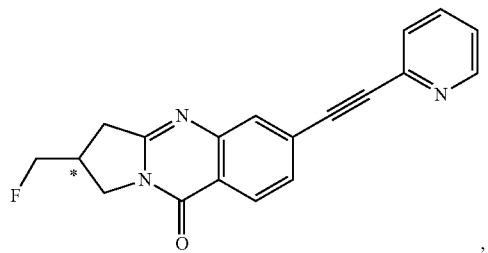

,

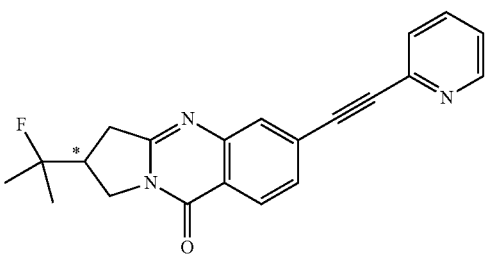

,

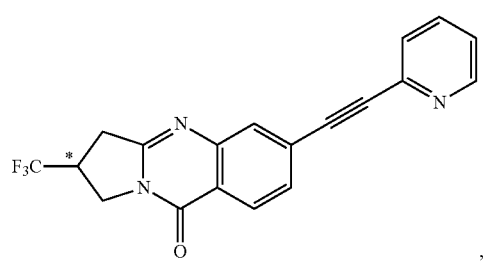

,

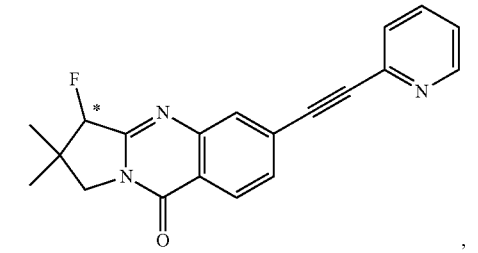

,

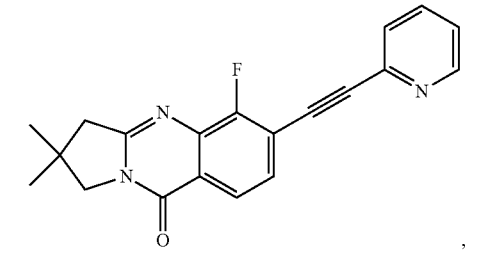

,

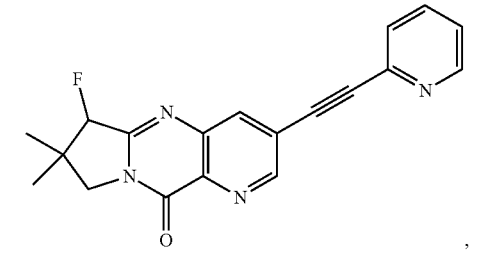

,

357
-continued
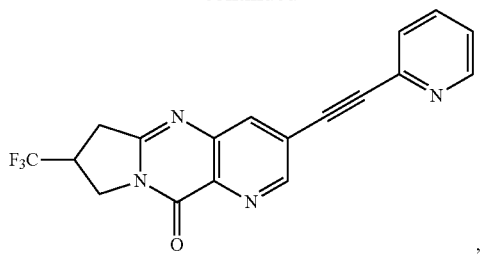
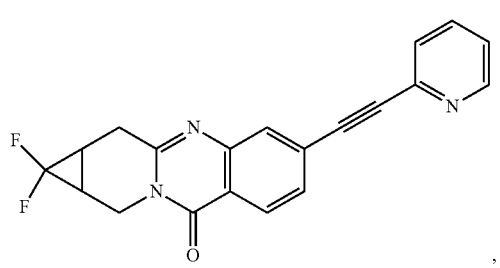
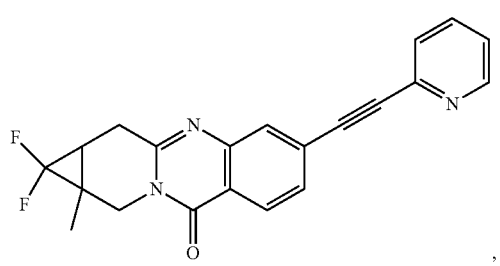
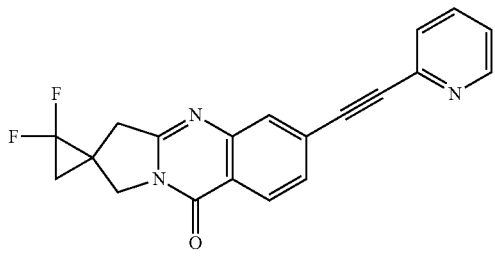
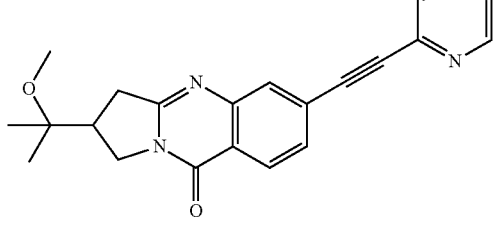
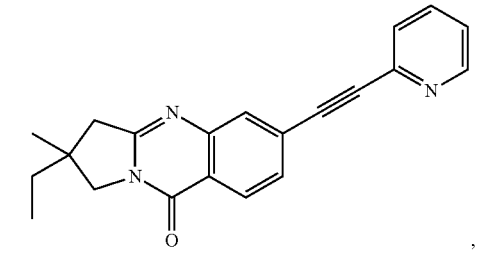
358
-continued
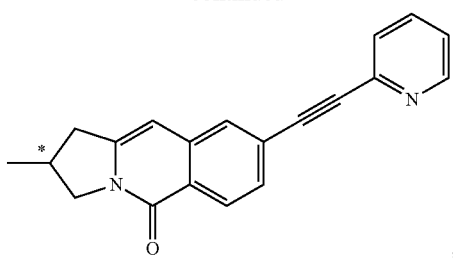
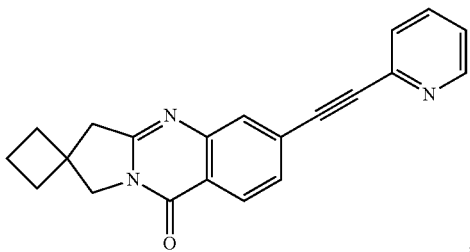
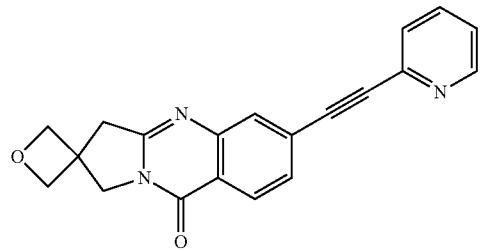
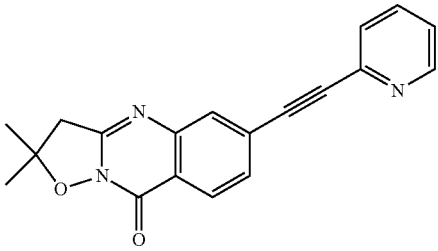
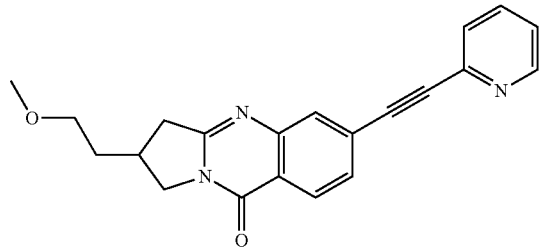
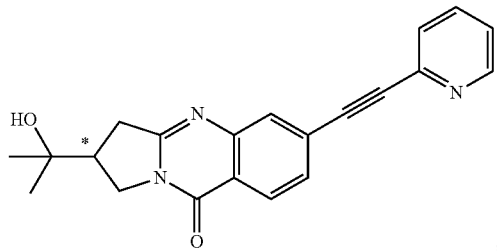

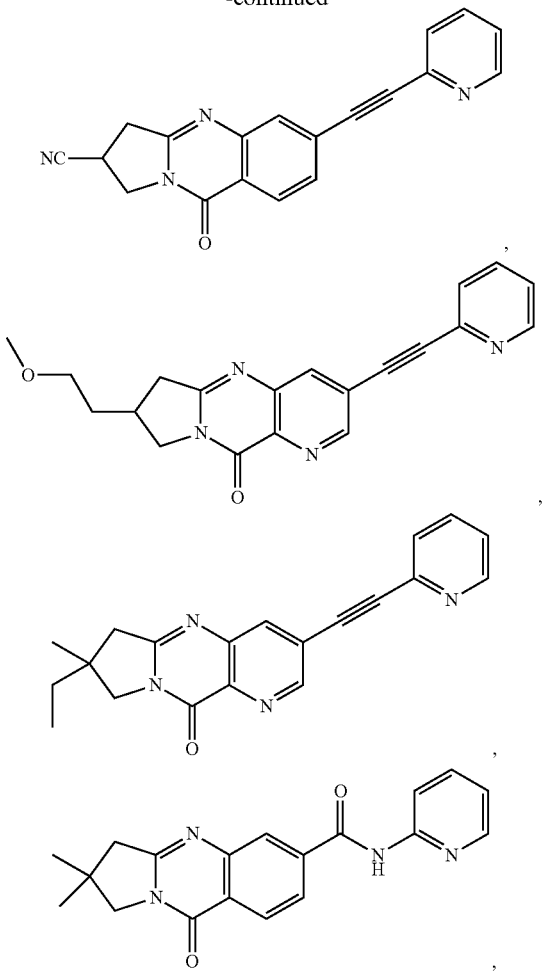

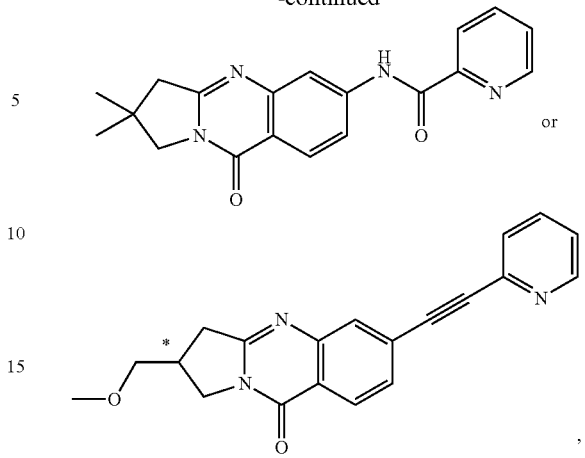

or a pharmaceutically acceptable salt thereof.

6. A pharmaceutical composition, comprising a therapeutically effective amount of a compound according to claim 1, or a pharmaceutically acceptable salt thereof, and a pharmaceutically acceptable carrier.

7. A method of treating psychosis, comprising the step of administering a therapeutically effective amount of a compound according to claim 1, or a pharmaceutically acceptable salt thereof, to a subject in need thereof.

8. A method of treating schizophrenia, comprising the step of administering a therapeutically effective amount of a compound according to claim 1, or a pharmaceutically acceptable salt thereof, to a subject in need thereof.

9. A method of treating Alzheimer's disease, comprising the step of administering a therapeutically effective amount of a compound according to claim 1, or a pharmaceutically acceptable salt thereof, to a subject in need thereof.

* * * * *

UNITED STATES PATENT AND TRADEMARK OFFICE
CERTIFICATE OF CORRECTION

PATENT NO. : 10,196,399 B2
APPLICATION NO. : 15/625604
DATED : February 5, 2019
INVENTOR(S) : Michele L. R. Heffernan et al.

Page 1 of 1

It is certified that error appears in the above-identified patent and that said Letters Patent is hereby corrected as shown below:

In the Claims

At Column 355, Line 13, Claim 3 "both R1 and R4 are methyl" should be replaced with "both R3 and R4 are methyl."

Signed and Sealed this
Nineteenth Day of March, 2019

Andrei Iancu
*Director of the United States Patent and Trademark Office*